US006054431A

United States Patent [19]

Horwitz et al.

[11] Patent Number: 6,054,431

[45] Date of Patent: *Apr. 25, 2000

[54] ANTI-GRAM-POSITIVE BACTERIAL METHODS AND MATERIALS

[75] Inventors: Arnold Horwitz, Los Angeles; Lewis H. Lambert, Jr., Fremont; Roger G. Little, II, Benicia, all of Calif.

[73] Assignee: XOMA Corporation, Berkeley, Calif.

[ * ] Notice: This patent is subject to a terminal disclaimer.

[21] Appl. No.: 09/119,263

[22] Filed: Jul. 20, 1998

Related U.S. Application Data

[63] Continuation of application No. 08/758,116, Nov. 25, 1996, Pat. No. 5,783,561, which is a continuation of application No. 08/372,783, Jan. 13, 1995, Pat. No. 5,578,572, which is a continuation-in-part of application No. 08/274,299, Jul. 11, 1994, abandoned, which is a continuation-in-part of application No. 08/209,762, Mar. 11, 1994, Pat. No. 5,733,872, which is a continuation-in-part of application No. 08/183,222, Jan. 14, 1994, abandoned.

[51] Int. Cl.[7] .......................... A61K 38/00; A61K 31/43; C07K 1/00

[52] U.S. Cl. .............................. 514/12; 514/21; 514/192; 424/114; 530/350

[58] Field of Search .................................... 514/8, 12, 14, 514/21, 152, 192, 2, 198, 199; 530/350; 424/114

[56] References Cited

U.S. PATENT DOCUMENTS

| | | | |
|---|---|---|---|
| 5,089,274 | 2/1992 | Marra et al. . | |
| 5,171,739 | 12/1992 | Scott . | |
| 5,198,541 | 3/1993 | Elsbach et al. . | |
| 5,234,912 | 8/1993 | Marra et al. . | |
| 5,308,834 | 5/1994 | Scott et al. . | |
| 5,334,584 | 8/1994 | Scott et al. . | |
| 5,348,942 | 9/1994 | Little, II et al. . | |
| 5,783,561 | 7/1998 | Horwitz | 514/12 |

FOREIGN PATENT DOCUMENTS

| | | |
|---|---|---|
| WO 89/01486 | 2/1989 | WIPO . |
| WO 90/09183 | 8/1990 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/201290 | 9/1994 | WIPO . |
| WO 94/20532 | 9/1994 | WIPO . |

OTHER PUBLICATIONS

Bamberger, et al. "Microbial Etiology and Clinical Characteristics of Distributive Shock", *Clinical Infectious Diseases,* 18:726–30, (1994).

Bone, "Gram–positive Organisms and Sepsis", *Arch. Intern. Med.,* 154(1):26–34 (Jan. 10, 1994).

Bone, "How Gram–Positive Organisms Cause Sepsis", *J. Critical Care,* 8(1):51–59 (Mar. 1993).

Dahmash, et al., "Septic shock in critically ill patients: aetiology, management and outcome", *J. Infection 26:*159–170 (1993).

Dal Nogare, "Southwestern Internal Medicine Conference: Septic Shock", *Am. J. Med. Sciences,* 302 (1):50–65 (Jul. 1991).

Davies, "Inactivation of Antibiotics and the Dissemination of Resistance Genes", *Science,* 264:375–381 (Apr. 15, 1994).

Eliopoulos and Moellering, "Antimicrobial Combinations", in *Antibiotics in Laboratory Medicine,* 3rd ed., pp. 432–492, (Lorian ed., Baltimore, MD) (1991).

Elsbach, "Antibiotics from within: Antibacterials from Human and Animal Sources", *Trends. Biotech,* 8(1):26–30 (Jan. 1990).

Elsbach and Weiss, "Oxygen–Independent Antimicrobial Systems of Phagocytes," in *Inflammation: Basic Principles and Clinical Correlates,* pp. 603–636, (Gallin et al eds., Raven Press, Ltd.) (1992).

Elsbach and Weiss, "Oxygen–Independent Bactericidal Systems of Polymorphonuclear Leukocytes", in *Advances in Inflammation Research,* vol. 2, pp. 95–113 (Weissmann ed., Raven Press, Ltd.) (1981).

Elsbach et al., "Separation and Purification of a Potent Bactericidal/Permeability–Increasing Protein and a Closely Associated Phospholipase $A_2$ from Rabbit Polymorphonuclear Leukocytes", *J. Biol. Chem.,* 254(21):11000–11009 (Nov. 10, 1979).

Fry et al. "Nosocomial Blood–borne Infection Secondary to Intravascular Devices", *Am. J. Surg.,* 167(2):268–272 (Feb. 1994).

Gabay, "Ubiquitous Natural Antibiotics", *Science,* 264:373–374 (Apr. 15, 1994).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.,* 60(11):4754–4761 (Nov. 1992).

Gray et al., "Bactericidal Activity of Synthetic Peptides Based on the Structure of the 55–Kilodalton Bactericidal Protein from Human Neutrophils", *Infect. Immun.,* 60(7): 2732–2739 (Jul. 1994).

Gray et al., "Cloning of the cDNA of a Human Neutrophil Bactericidal Protein", *J. Biol. Chem.,* 264(16):9505–9509 (Jun. 5, 1989).

(List continued on next page.)

*Primary Examiner*—Keith D. MacMillan
*Assistant Examiner*—P. Ponnalun
*Attorney, Agent, or Firm*—Marshall, O'Toole, Gerstein, Murray & Borun

[57] ABSTRACT

The present invention relates to methods of treating gram-positive bacterial infections by administration of a BPI protein product alone, or in combination with an antibiotic. BPI protein product alone has a bactericidal or growth inhibitory effect on selected gram-positive organisms. BPI protein product also increases the susceptibility of gram-positive organisms to antibiotics and can even reverse resistance of gram-positive organisms to antibiotic.

14 Claims, 32 Drawing Sheets

OTHER PUBLICATIONS

Hackshaw, et al., "Naloxone in septic shock", *Critical Care Med.,* 18(1):47–51 (1990).

Heumann et al., "Gram–Positive Cell Walls Stimulate Synthesis of Tumor Necrosis Factor Alpha and Interleukin–6 by Human Monocytes", *Infect. Immun.,* 62(7):2715–2721 (Jul. 1994).

Johansson et al., "Septicemia in Granulocytopenic Patients: A Shift in Bacterial Etiology", *Scand J. Infect. Dis,* 24:357–360 (1992).

Kadurugamuwa et al., "Interaction of Gentamicin with the A Band and B Band Lipopolysaccharides of *Pseudomonas aeruginosa* and Its Possible Lethal Effect", Antimicrobial Agents and Chemotherapy, 37(4):715–721 (Apr. 1993).

Kessler et al., "Bacteremia in Patients on Chronic Hemodialysis", *Nephron,* 64(1):95–100 (1993).

Kingman, "Resistance a European Problem, Too", *Science,* 264:363–365 (Apr. 15, 1994).

Lautenschlager, et al. "Course and Outcome of Bacteremia Due to *Staphylococcus aureus*: Evaluation of Different Clinical Case Definitions", *Clinical Infectious Diseases,* 16:567–73 (1993).

Levy et al., "Antibacterial 15–kDa Protein Isoforms (p15s) are Members of a Novel Family of Leukocyte Proteins", *J. Biol. Chem.,* 268(8):6058–6068 (Mar. 16, 1993).

Mannion et al., "Preferential Binding of the Neutrophil Cytoplasmic Granule–Derived Bactericidal/Permeability Increasing Protein to Target Bacteria", *J. Clin. Invest.,* 142(8):2807–2812 (Apr. 15, 1989).

Mannion et al., "Separation of Sublethal and Lethal Effects of Polymorphonuclear Leukocytes on *Escherichia coli", J. Clin. Invest.,* 86:631–641 (Aug. 1990).

Mannion et al., "Separation of Sublethal and Lethal Effects of the Bactericidal/Permeability Increasing Protein on *Escherichia coli", J. Clin. Invest.,* 85:853–860 (Mar. 1990).

Moon et al., "Monoclonal Antibodies Provide Protection Against Acular *Pseudomonas aeruginosa* Infection", *Invest Ophthalmol & Vis Sci.,* 29(8):1277–1284 (1988).

Nikaido, "Prevention of Drug Access to Bacterial Targets: Permeability Barriers and Active Efflux", *Science,* 264:382–387 (Apr. 15, 1994).

Ooi et al., "A 25–kDa $NH_2$–terminal Fragment Carries All the Antibacterial Activities of the Human Neutrophil 6–kDa Bactericidal/Permeability–Increasing Protein", *J. Biol. Chem.,* 262(31):14891–14894 (1987).

Ooi et al., Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils, *J. Exp. Med.,* 174:649–655 (Sep. 1991).

Ooi et al., "Isolation of Two Isoforms of a Novel 15–kDa Protein from Rabbit Polymorphonuclear Leukocytes that Modulate the Antibacterial Actions of Other Leukocyte Proteins," *J. Biol. Chem.,* 265:15956–15962 (1990).

Spratt, "Resistance to Antibiotics Mediated by Target Alterations", *Science,* 264:388–393 (Apr. 15, 1994).

Stratton, "In Vitro Testing: Correlations Between Bacterial Susceptibility, Body Fluid Levels and Effectiveness of Antibacterial Therapy", in *Antibiotics in Laboratory Medicine,* pp. 849–879 (Lorian ed., Williams & Wilkins) (1991).

Sugar et al., "Treatment of Experimental Pseudomonas Corneal Ulcers with Enoxacin, a Quinolone Antibiotic", *Arch Ophthalmol.,* 104:1230–1232 (Aug. 1986).

Taber et al., "Bacterial Uptake of Aminoglycoside Antibiotics", *Microbiological Reviews,* 51(4):439–457 (Dec. 1987).

Travis, "Reviving the Antibiotic Miracle", *Science,* 264:360–362 (Apr. 15, 1994).

Vaara, "Agents that Increase the Permeability of the Outer Membrane", *Microbiological Reviews,* 56(3):395–411 (Sep. 1992).

Veld et al., "Effects of the Bactericidal/Permeability–Increasing Protein of Polymorphonuclear Leukocytes on Isolated Bacterial Cytoplasmic Membrane Vesicles", *Infect. Immun.,* 56(5):1203–1208 (May 1988).

Vindenes et al., "The Frequency of Bacteremia and Fungemia Following Wound Cleaning and Excision in Patients with Large Burns", *J. Trauma,* 35(5):742–749 (Nov. 1993).

Watanakunakorn et al., "Alpha–hemolytic Streptococcal Bacteremia: A Review of 203 Episodes during 1980–1991", *Scand. J. Infect. Dis.,*25(4):403–408 (1993).

Watanakunakorn et al., "Pneumococcal Bacteremia in Three Community Teaching Hospitals From 1980 to 1989", *Chest,* 103(4):1152–56 (1993).

Weiss and Olsson, "Cellular and Subcellular Localization of the Bactericidal/Permeability–Increasing Protein of Neutrophils", *Blood,* 69(2):652–659 (Feb. 1987).

Weiss et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.,* 90:1122–1130 (Sep. 1992).

Weiss et al., "Resistance of Gram–negative Bacteria to Purified Bactericidal Leukocyte Proteins", *J. Clin. Invest.,* 65:619–628 (Mar. 1980).

Weiss et al., "The Role of Lipopolysaccharides in the Action of the Bactericidal/Permeability–Increasing Neutrophil Protein on the Bacterial Envelope", *J. Immunol.,* 132(6):3109–3115 (Jun. 1984).

Growth

Chloramphenicol

Ciprofloxacin

Vancomycin

SEQUENCE LISTING (1) GENERAL INFORMATION:

(iii) NUMBER OF SEQUENCES: 237

(2) INFORMATION FOR SEQ ID NO:1:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "Domain I"

(xi) SEQUENCE DESCRIPTION: SEQ ID NO:1:

```
Ala Ser Gln Gln Gly Thr Ala Ala Leu Gln Lys Glu Leu Lys Arg Ile
1               5                   10                  15

Lys Ile Pro Asp Tyr Ser Asp Ser Phe Lys Ile Lys His
            20                  25
```

(2) INFORMATION FOR SEQ ID NO:2:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.14"

(xi) SEQUENCE DESCRIPTION: SEQ ID NO:2:

```
Gly Thr Ala Ala Leu Gln Lys Glu Leu Lys Arg Ile Lys Ile Pro Asp
1               5                   10                  15

Tyr Ser Asp Ser Phe Lys Ile Lys His Leu Gly Lys Gly His
            20                  25                  30
```

(2) INFORMATION FOR SEQ ID NO:3:

(i) SEQUENCE CHARACTERISTICS:
(A) LENGTH: 22 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.4"

(xi) SEQUENCE DESCRIPTION: SEQ ID NO:3:

```
Leu Gln Lys Glu Leu Lys Arg Ile Lys Ile Pro Asp Tyr Ser Asp Ser
1               5                   10                  15

Phe Lys Ile Lys His Leu
            20
```

(2) INFORMATION FOR SEQ ID NO:4:

(i) SEQUENCE CHARACTERISTICS:
(A) LENGTH: 15 amino acids
(B) TYPE: amino acid

-continued (D) TOPOLOGY: linear (ii) MOLECULE TYPE: peptide (ix) FEATURE:
(A) NAME/KEY: misc_feature
(D) OTHER INFORMATION: "XMP.1"

(xi) SEQUENCE DESCRIPTION: SEQ ID NO:4:

```
Gln Gln Gly Thr Ala Ala Leu Gln Lys Glu Leu Lys Arg Ile Lys
1               5                   10                  15
```

(2) INFORMATION FOR SEQ ID NO:5:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.54"

(xi) SEQUENCE DESCRIPTION: SEQ ID NO:5:

```
Gly Thr Ala Ala Leu Gln Lys Glu Leu Lys Arg Ile Lys Ile Pro
1               5                   10                  15
```

(2) INFORMATION FOR SEQ ID NO:6:

(i) SEQUENCE CHARACTERISTICS:
(A) LENGTH: 35 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "Domain II"

(xi) SEQUENCE DESCRIPTION: SEQ ID NO:6:

```
Ser Ser Gln Ile Ser Met Val Pro Asn Val Gly Leu Lys Phe Ser Ile
1               5                   10                  15

Ser Asn Ala Asn Ile Lys Ile Ser Gly Lys Trp Lys Ala Gln Lys Arg
            20                  25                  30

Phe Leu Lys
        35
```

(2) INFORMATION FOR SEQ ID NO:7:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.2"

(xi) SEQUENCE DESCRIPTION: SEQ ID NO:7:

```
Ile Lys Ile Ser Gly Lys Trp Lys Ala Gln Lys Arg Phe Leu Lys
1               5                   10                  15
```

(2) INFORMATION FOR SEQ ID NO:8:

-continued (i) SEQUENCE CHARACTERISTICS:
(A) LENGTH: 10 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.8”

(xi) SEQUENCE DESCRIPTION: SEQ ID NO:8:

```
Lys Trp Lys Ala Gln Lys Arg Phe Leu Lys
1               5                   10
```

(2) INFORMATION FOR SEQ ID NO:9:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.58”

(xi) SEQUENCE DESCRIPTION: SEQ ID NO:9:

```
Cys Ile Lys Ile Ser Gly Lys Trp Lys Ala Gln Lys Arg Phe Leu Lys
1               5                   10                  15
```

(2) INFORMATION FOR SEQ ID NO:10:

(i) SEQUENCE CHARACTERISTICS:
(A) LENGTH: 17 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.65 oxidized”

(xi) SEQUENCE DESCRIPTION: SEQ ID NO:10:

```
Cys Ile Lys Ile Ser Gly Lys Trp Lys Ala Gln Lys Arg Phe Leu Lys
1               5                   10                  15

Cys
```

(2) INFORMATION FOR SEQ ID NO:11:

(i) SEQUENCE CHARACTERISTICS:
(A) LENGTH: 27 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.3”

(xi) SEQUENCE DESCRIPTION: SEQ ID NO:11:

```
Asn Val Gly Leu Lys Phe Ser Ile Ser Asn Ala Asn Ile Lys Ile Ser
1               5                   10                  15

Gly Lys Trp Lys Ala Gln Lys Arg Phe Leu Lys
            20                  25
```

-continued (2) INFORMATION FOR SEQ ID NO:12:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "Domain III"

(xi) SEQUENCE DESCRIPTION: SEQ ID NO:12:

```
Val His Val His Ile Ser Lys Ser Lys Val Gly Trp Leu Ile Gln Leu
1               5                   10                  15

Phe His Lys Lys Ile Glu Ser Ala Leu Arg Asn Lys
            20                  25
```

(2) INFORMATION FOR SEQ ID NO:13:

(i) SEQUENCE CHARACTERISTICS:
(A) LENGTH: 13 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.11"

(xi) SEQUENCE DESCRIPTION: SEQ ID NO:13:

```
Lys Ser Lys Val Trp Leu Ile Gln Leu Phe His Lys Lys
1               5                   10
```

(2) INFORMATION FOR SEQ ID NO:14:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.12"

(xi) SEQUENCE DESCRIPTION: SEQ ID NO:14:

```
Ser Val His Val His Ile Ser Lys Ser Lys Val Gly Trp Leu Ile Gln
1               5                   10                  15

Leu Phe His Lys Lys Ile Glu Ser Ala Leu Arg Asn Lys
            20                  25
```

(2) INFORMATION FOR SEQ ID NO:15:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.13"

(xi) SEQUENCE DESCRIPTION: SEQ ID NO:15:

```
Lys Ser Lys Val Gly Trp Leu Ile Gln Leu Phe His Lys Lys
```

-continued 1 5 10

(2) INFORMATION FOR SEQ ID NO:16:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.15"

(xi) SEQUENCE DESCRIPTION: SEQ ID NO:16:

Ala Lys Ile Ser Gly Lys Trp Lys Ala Gln Lys Arg Phe Leu Lys
1 5 10 15

(2) INFORMATION FOR SEQ ID NO:17:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.16"

(xi) SEQUENCE DESCRIPTION: SEQ ID NO:17:

Ile Ala Ile Ser Gly Lys Trp Lys Ala Gln Lys Arg Phe Leu Lys
1 5 10 15

(2) INFORMATION FOR SEQ ID NO:18:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.17"

(xi) SEQUENCE DESCRIPTION: SEQ ID NO:18:

Ile Lys Ala Ser Gly Lys Trp Lys Ala Gln Lys Arg Phe Leu Lys
1 5 10 15

(2) INFORMATION FOR SEQ ID NO:19:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.18"

(xi) SEQUENCE DESCRIPTION: SEQ ID NO:19:

Ile Lys Ile Ala Gly Lys Trp Lys Ala Gln Lys Arg Phe Leu Lys
1 5 10 15

-continued (2) INFORMATION FOR SEQ ID NO:20:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.19"

(xi) SEQUENCE DESCRIPTION: SEQ ID NO:20:

```
Ile Lys Ile Ser Ala Lys Trp Lys Ala Gln Lys Arg Phe Leu Lys
1               5                   10                  15
```

(2) INFORMATION FOR SEQ ID NO:21:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.20"

(xi) SEQUENCE DESCRIPTION: SEQ ID NO:21:

```
Ile Lys Ile Ser Gly Ala Trp Lys Ala Gln Lys Arg Phe Leu Lys
1               5                   10                  15
```

(2) INFORMATION FOR SEQ ID NO:22:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.21"

(xi) SEQUENCE DESCRIPTION: SEQ ID NO:22:

```
Ile Lys Ile Ser Gly Lys Ala Lys Ala Gln Lys Arg Phe Leu Lys
1               5                   10                  15
```

(2) INFORMATION FOR SEQ ID NO:23:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.22"

(xi) SEQUENCE DESCRIPTION: SEQ ID NO:23:

```
Ile Lys Ile Ser Gly Lys Trp Ala Ala Gln Lys Arg Phe Leu Lys
1               5                   10                  15
```

(2) INFORMATION FOR SEQ ID NO:24:

(i) SEQUENCE CHARACTERISTICS:

-continued (A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.23"

(xi) SEQUENCE DESCRIPTION: SEQ ID NO:24:

Ile Lys Ile Ser Gly Lys Trp Lys Ala Ala Lys Arg Phe Leu Lys
1 5 10 15

(2) INFORMATION FOR SEQ ID NO:25:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.24"

(xi) SEQUENCE DESCRIPTION: SEQ ID NO:25:

Ile Lys Ile Ser Gly Lys Trp Lys Ala Gln Ala Arg Phe Leu Lys
1 5 10 15

(2) INFORMATION FOR SEQ ID NO:26:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.25"

(xi) SEQUENCE DESCRIPTION: SEQ ID NO:26:

Ile Lys Ile Ser Gly Lys Trp Lys Ala Gln Lys Ala Phe Leu Lys
1 5 10 15

(2) INFORMATION FOR SEQ ID NO:27:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.26"

(xi) SEQUENCE DESCRIPTION: SEQ ID NO:27:

Ile Lys Ile Ser Gly Lys Trp Lys Ala Gln Lys Arg Ala Leu Lys
1 5 10 15

(2) INFORMATION FOR SEQ ID NO:28:

(i) SEQUENCE CHARACTERISTICS:
(A) LENGTH: 15 amino acids
(B) TYPE: amino acid
(D) TOPOLOGY: linear -continued (ii) MOLECULE TYPE: peptide (ix) FEATURE:
(A) NAME/KEY: misc_feature
(D) OTHER INFORMATION: "XMP.27"

(xi) SEQUENCE DESCRIPTION: SEQ ID NO:28:

```
Ile Lys Ile Ser Gly Lys Trp Lys Ala Gln Lys Arg Phe Ala Lys
1               5                   10                  15
```

(2) INFORMATION FOR SEQ ID NO:29:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.28"

(xi) SEQUENCE DESCRIPTION: SEQ ID NO:29:

```
Ile Lys Ile Ser Gly Lys Trp Lys Ala Gln Lys Arg Phe Leu Ala
1               5                   10                  15
```

(2) INFORMATION FOR SEQ ID NO:30:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.59"

(xi) SEQUENCE DESCRIPTION: SEQ ID NO:30:

```
Ile Lys Ile Ser Gly Ala Trp Ala Ala Gln Lys Arg Phe Leu Lys
1               5                   10                  15
```

(2) INFORMATION FOR SEQ ID NO:31:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.45"

(xi) SEQUENCE DESCRIPTION: SEQ ID NO:31:

```
Ile Lys Ile Ser Gly Lys Trp Lys Ala Ala Ala Arg Phe Leu Lys
1               5                   10                  15
```

(2) INFORMATION FOR SEQ ID NO:32:

(i) SEQUENCE CHARACTERISTICS:
(A) LENGTH: 15 amino acids
(B) TYPE: amino acid
(D) TOPOLOGY: linear (ii) MOLECULE TYPE: peptide -continued (ix) FEATURE:
(A) NAME/KEY: misc_feature
(D) OTHER INFORMATION: “XMP.60”

(xi) SEQUENCE DESCRIPTION: SEQ ID NO:32:

Ile Ala Ile Ser Gly Lys Trp Lys Ala Gln Lys Arg Phe Leu Ala
1 5 10 15

(2) INFORMATION FOR SEQ ID NO:33:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.31”

(xi) SEQUENCE DESCRIPTION: SEQ ID NO:33:

Ala Ser Lys Val Gly Trp Leu Ile Gln Leu Phe His Lys Lys
1 5 10

(2) INFORMATION FOR SEQ ID NO:34:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.32”

(xi) SEQUENCE DESCRIPTION: SEQ ID NO:34:

Lys Ala Lys Val Gly Trp Leu Ile Gln Leu Phe His Lys Lys
1 5 10

(2) INFORMATION FOR SEQ ID NO:35:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.33”

(xi) SEQUENCE DESCRIPTION: SEQ ID NO:35:

Lys Ser Ala Val Gly Trp Leu Ile Gln Leu Phe His Lys Lys
1 5 10

(2) INFORMATION FOR SEQ ID NO:36:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.34”

-continued (xi) SEQUENCE DESCRIPTION: SEQ ID NO:36:

Lys Ser Lys Ala Gly Trp Leu Ile Gln Leu Phe His Lys Lys
1 5 10

(2) INFORMATION FOR SEQ ID NO:37:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.35”

(xi) SEQUENCE DESCRIPTION: SEQ ID NO:37:

Lys Ser Lys Val Ala Trp Leu Ile Gln Leu Phe His Lys Lys
1 5 10

(2) INFORMATION FOR SEQ ID NO:38:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.36”

(xi) SEQUENCE DESCRIPTION: SEQ ID NO:38:

Lys Ser Lys Val Gly Ala Leu Ile Gln Leu Phe His Lys Lys
1 5 10

(2) INFORMATION FOR SEQ ID NO:39:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.37”

(xi) SEQUENCE DESCRIPTION: SEQ ID NO:39:

Lys Ser Lys Val Gly Trp Ala Ile Gln Leu Phe His Lys Lys
1 5 10

(2) INFORMATION FOR SEQ ID NO:40:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.38”

(xi) SEQUENCE DESCRIPTION: SEQ ID NO:40:

-continued

```
Lys Ser Lys Val Gly Trp Leu Ala Gln Leu Phe His Lys Lys
1               5                   10


(2) INFORMATION FOR SEQ ID NO:41:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.39"

    (xi) SEQUENCE DESCRIPTION: SEQ ID NO:41:

Lys Ser Lys Val Gly Trp Leu Ile Ala Leu Phe His Lys Lys
1               5                   10


(2) INFORMATION FOR SEQ ID NO:42:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.40"

    (xi) SEQUENCE DESCRIPTION: SEQ ID NO:42:

Lys Ser Lys Val Gly Trp Leu Ile Gln Ala Phe His Lys Lys
1               5                   10


(2) INFORMATION FOR SEQ ID NO:43:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.41"

    (xi) SEQUENCE DESCRIPTION: SEQ ID NO:43:

Lys Ser Lys Val Gly Trp Leu Ile Gln Leu Ala His Lys Lys
1               5                   10


(2) INFORMATION FOR SEQ ID NO:44:

     (i) SEQUENCE CHARACTERISTICS:
          (A) LENGTH: 14 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.42"

    (xi) SEQUENCE DESCRIPTION: SEQ ID NO:44:

Lys Ser Lys Val Gly Trp Leu Ile Gln Leu Phe Ala Lys Lys
1               5                   10
```

-continued (2) INFORMATION FOR SEQ ID NO:45:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.43"

(xi) SEQUENCE DESCRIPTION: SEQ ID NO:45:

```
Lys Ser Lys Val Gly Trp Leu Ile Gln Leu Phe His Ala Lys
1               5                   10
```

(2) INFORMATION FOR SEQ ID NO:46:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.44"

(xi) SEQUENCE DESCRIPTION: SEQ ID NO:46:

```
Lys Ser Lys Val Gly Trp Leu Ile Gln Leu Phe His Lys Ala
1               5                   10
```

(2) INFORMATION FOR SEQ ID NO:47:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.56"

(xi) SEQUENCE DESCRIPTION: SEQ ID NO:47:

```
Ile Lys Ile Ser Gly Lys Trp Lys Ala Lys Gln Arg Phe Leu Lys
1               5                   10                  15
```

(2) INFORMATION FOR SEQ ID NO:48:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.61"

(xi) SEQUENCE DESCRIPTION: SEQ ID NO:48:

```
Ile Lys Ile Ser Gly Lys Phe Lys Ala Gln Lys Arg Phe Leu Lys
1               5                   10                  15
```

(2) INFORMATION FOR SEQ ID NO:49:

-continued (i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.66"

(ix) FEATURE:
(A) NAME/KEY: Modified-site
(B) LOCATION: 7
(D) OTHER INFORMATION: /label= D-Trp
/note= "The amino acid at position 7 is D-tryptophan"

(xi) SEQUENCE DESCRIPTION: SEQ ID NO:49:

```
Ile Lys Ile Ser Gly Lys Trp Lys Ala Gln Lys Arg Phe Leu Lys
1               5                   10                  15
```

(2) INFORMATION FOR SEQ ID NO:50:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.67"

(ix) FEATURE:
(A) NAME/KEY: Modified-site
(B) LOCATION: 6..8
(D) OTHER INFORMATION: /label= Substituted-Ala
/note= "The alanine at position 7 is beta-1-naphthyl-substituted"

(xi) SEQUENCE DESCRIPTION: SEQ ID NO:50:

```
Ile Lys Ile Ser Gly Lys Ala Lys Ala Gln Lys Arg Phe Leu Lys
1               5                   10                  15
```

(2) INFORMATION FOR SEQ ID NO:51:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.9"

(xi) SEQUENCE DESCRIPTION: SEQ ID NO:51:

```
Lys Arg Phe Leu Lys Lys Trp Lys Ala Gln Lys Arg Phe Leu Lys
1               5                   10                  15
```

(2) INFORMATION FOR SEQ ID NO:52:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.30"

(xi) SEQUENCE DESCRIPTION: SEQ ID NO:52:

Lys Trp Lys Ala Gln Lys Arg Phe Leu Lys Lys Ser Lys Val Gly Trp
1 5 10 15

Leu Ile Gln Leu Phe His Lys Lys
20

(2) INFORMATION FOR SEQ ID NO:53:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.63"

(xi) SEQUENCE DESCRIPTION: SEQ ID NO:53:

Ile Lys Ile Ser Gly Lys Trp Lys Ala Gln Lys Arg Phe Leu Lys Lys
1 5 10 15

Ser Lys Val Gly Trp Leu Ile Gln Leu Phe His Lys Lys
20 25

(2) INFORMATION FOR SEQ ID NO:54:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.7"

(xi) SEQUENCE DESCRIPTION: SEQ ID NO:54:

Lys Trp Lys Ala Gln Lys Arg Phe Leu Lys Lys Trp Lys Ala Gln Lys
1 5 10 15

Arg Phe Leu Lys
20

(2) INFORMATION FOR SEQ ID NO:55:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.10.1"

(xi) SEQUENCE DESCRIPTION: SEQ ID NO:55:

Lys Arg Phe Leu Lys Lys Trp Lys Ala Gln Lys Arg Phe Leu Lys Lys
1 5 10 15

Trp Lys Ala Gln Lys Arg Phe Leu Lys
20 25

(2) INFORMATION FOR SEQ ID NO:56:

-continued (i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.29"

(xi) SEQUENCE DESCRIPTION: SEQ ID NO:56:

```
Lys Ser Lys Val Gly Trp Leu Ile Gln Leu Phe His Lys Lys Lys Ser
1               5                   10                  15

Lys Val Gly Trp Leu Ile Gln Leu Phe His Lys Lys
            20                  25
```

(2) INFORMATION FOR SEQ ID NO:57:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.46"

(xi) SEQUENCE DESCRIPTION: SEQ ID NO:57:

```
Lys Trp Lys Ala Ala Ala Arg Phe Leu Lys Lys Trp Lys Ala Gln Lys
1               5                   10                  15

Arg Phe Leu Lys
            20
```

(2) INFORMATION FOR SEQ ID NO:58:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.47"

(xi) SEQUENCE DESCRIPTION: SEQ ID NO:58:

```
Lys Trp Lys Ala Gln Lys Arg Phe Leu Lys Lys Trp Lys Ala Ala Ala
1               5                   10                  15

Arg Phe Leu Lys
            20
```

(2) INFORMATION FOR SEQ ID NO:59:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.48"

(xi) SEQUENCE DESCRIPTION: SEQ ID NO:59:

-continued

```
Lys Trp Lys Ala Ala Ala Arg Phe Leu Lys Lys Trp Lys Ala Ala Ala
1               5                   10                  15

Arg Phe Leu Lys
            20
```

(2) INFORMATION FOR SEQ ID NO:60:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.69"

(xi) SEQUENCE DESCRIPTION: SEQ ID NO:60:

```
Lys Trp Lys Ala Ala Ala Arg Phe Leu Lys Lys Trp Lys Ala Ala Ala
1               5                   10                  15

Arg Phe Leu Lys Lys Trp Lys Ala Ala Ala Arg Phe Leu Lys
            20                  25                  30
```

(2) INFORMATION FOR SEQ ID NO:61:

(i) SEQUENCE CHARACTERISTICS:
(A) LENGTH: 21 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.55"

(xi) SEQUENCE DESCRIPTION: SEQ ID NO:61:

```
Gly Trp Leu Ile Gln Leu Phe His Lys Lys Ile Glu Ser Ala Leu Arg
1               5                   10                  15

Asn Lys Met Asn Ser
            20
```

(2) INFORMATION FOR SEQ ID NO:62:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.73"

(xi) SEQUENCE DESCRIPTION: SEQ ID NO:62:

```
Ile Lys Ile Ser Gly Lys Trp Lys Ala Gln Phe Arg Phe Leu Lys
1               5                   10                  15
```

(2) INFORMATION FOR SEQ ID NO:63:

(i) SEQUENCE CHARACTERISTICS:
(A) LENGTH: 15 amino acids
(B) TYPE: amino acid
(D) TOPOLOGY: linear (ii) MOLECULE TYPE: peptide -continued (ix) FEATURE:
(A) NAME/KEY: misc_feature
(D) OTHER INFORMATION: “XMP.70”

(ix) FEATURE:
(A) NAME/KEY: Modified-site
(B) LOCATION: 8..10
(D) OTHER INFORMATION: /label= Substituted-Ala
/note= “The alanine at position 7 is
beta-3-pyridyl-substituted”

(xi) SEQUENCE DESCRIPTION: SEQ ID NO:63:

```
Ile Lys Ile Ser Gly Lys Ala Lys Ala Gln Lys Arg Phe Leu Lys
1               5                   10                  15
```

(2) INFORMATION FOR SEQ ID NO:64:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.71”

(ix) FEATURE:
(A) NAME/KEY: Modified-site
(B) LOCATION: 13..15
(D) OTHER INFORMATION: /label= Substituted-Ala
/note= “The alanine at position 13 is
beta-3-pyridyl-substituted”

(xi) SEQUENCE DESCRIPTION: SEQ ID NO:64:

```
Ile Lys Ile Ser Gly Lys Trp Lys Ala Gln Lys Arg Ala Leu Lys
1               5                   10                  15
```

(2) INFORMATION FOR SEQ ID NO:65:

(i) SEQUENCE CHARACTERISTICS:
(A) LENGTH: 26 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.10.2”

(xi) SEQUENCE DESCRIPTION: SEQ ID NO:65:

```
Gln Lys Arg Phe Leu Lys Lys Trp Lys Ala Gln Lys Arg Phe Leu Lys
1               5                   10                  15

Lys Trp Lys Ala Gln Lys Arg Phe Leu Lys
            20                  25
```

(2) INFORMATION FOR SEQ ID NO:66:

(i) SEQUENCE CHARACTERISTICS:
(A) LENGTH: 17 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.72”

-continued (ix) FEATURE:
(A) NAME/KEY: Modified-site
(B) LOCATION: 1..3
(D) OTHER INFORMATION: /label= D-alanine
/note= "The position 1 and position 2 alanine residues are both D-alanine"

(xi) SEQUENCE DESCRIPTION: SEQ ID NO:66:

```
Ala Ala Ile Lys Ile Ser Gly Lys Trp Lys Ala Gln Lys Arg Phe Leu
1               5                   10                  15

Lys
```

(2) INFORMATION FOR SEQ ID NO:67:

(i) SEQUENCE CHARACTERISTICS:
(A) LENGTH: 22 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.5"

(xi) SEQUENCE DESCRIPTION: SEQ ID NO:67:

```
Val His Val His Ile Ser Lys Ser Lys Val Gly Trp Leu Ile Gln Leu
1               5                   10                  15

Phe His Lys Lys Ile Glu
            20
```

(2) INFORMATION FOR SEQ ID NO:68:

(i) SEQUENCE CHARACTERISTICS:
(A) LENGTH: 17 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.65 reduced"

(ix) FEATURE:
(A) NAME/KEY: Disulfide-bond
(B) LOCATION: 1..17

(xi) SEQUENCE DESCRIPTION: SEQ ID NO:68:

```
Cys Ile Lys Ile Ser Gly Lys Trp Lys Ala Gln Lys Arg Phe Leu Lys
1               5                   10                  15

Cys
```

(2) INFORMATION FOR SEQ ID NO:69:

(i) SEQUENCE CHARACTERISTICS:
(A) LENGTH: 487 amino acids
(B) TYPE: amino acid
(D) TOPOLOGY: linear (ii) MOLECULE TYPE: protein (ix) FEATURE:
(A) NAME/KEY: misc_feature
(D) OTHER INFORMATION: "rBPI"

(xi) SEQUENCE DESCRIPTION: SEQ ID NO:69:

```
Met Arg Glu Asn Met Ala Arg Gly Pro Cys Asn Ala Pro Arg Trp Val
-31 -30                 -25                 -20
```

-continued

```
Ser Leu Met Val Leu Val Ala Ile Gly Thr Ala Val Thr Ala Ala Val
-15                 -10                 -5                   1

Asn Pro Gly Val Val Val Arg Ile Ser Gln Lys Gly Leu Asp Tyr Ala
                5                   10                  15

Ser Gln Gln Gly Thr Ala Ala Leu Gln Lys Glu Leu Lys Arg Ile Lys
        20                  25                  30

Ile Pro Asp Tyr Ser Asp Ser Phe Lys Ile Lys His Leu Gly Lys Gly
    35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400
```

-continued

```
Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
        420                 425                 430

Gln Leu Tyr Asn Val Val Leu Gln Pro His Gln Asn Phe Leu Leu Phe
    435                 440                 445

Gly Ala Asp Val Val Tyr Lys
450                 455
```

(2) INFORMATION FOR SEQ ID NO:70:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.74"

(xi) SEQUENCE DESCRIPTION: SEQ ID NO:70:

```
Lys Ser Lys Val Gly Trp Leu Ile Gln Leu Phe His Lys Lys Lys Trp
1               5                   10                  15

Lys Ala Gln Lys Arg Phe Leu Lys
            20
```

(2) INFORMATION FOR SEQ ID NO:71:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.76"

(ix) FEATURE:
(A) NAME/KEY: Modified-site
(B) LOCATION: 10..12
(D) OTHER INFORMATION: /label= D-Phe
/note= "The amino acid at position 11 is D-phenylalanine"

(xi) SEQUENCE DESCRIPTION: SEQ ID NO:71:

```
Ile Lys Ile Ser Gly Lys Trp Lys Ala Gln Phe Arg Phe Leu Lys
1               5                   10                  15
```

(2) INFORMATION FOR SEQ ID NO:72:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.77"

(xi) SEQUENCE DESCRIPTION: SEQ ID NO:72:

```
Ile Lys Ile Ser Gly Lys Trp Lys Ala Gln Trp Arg Phe Leu Lys
1               5                   10                  15
```

-continued (2) INFORMATION FOR SEQ ID NO:73:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.79"

(xi) SEQUENCE DESCRIPTION: SEQ ID NO:73:

```
Ile Lys Ile Ser Gly Lys Trp Lys Ala Lys Lys Arg Phe Leu Lys
1               5                   10                  15
```

(2) INFORMATION FOR SEQ ID NO:74:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.80"

(ix) FEATURE:
(A) NAME/KEY: Modified-site
(B) LOCATION: 10..12
(D) OTHER INFORMATION: /label= Substituted-Ala
/note= "The alanine at position 11 is
beta-1-naphthyl-substituted"

(xi) SEQUENCE DESCRIPTION: SEQ ID NO:74:

```
Ile Lys Ile Ser Gly Lys Trp Lys Ala Gln Ala Arg Phe Leu Lys
1               5                   10                  15
```

(2) INFORMATION FOR SEQ ID NO:75:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.81"

(xi) SEQUENCE DESCRIPTION: SEQ ID NO:75:

```
Ile Lys Ile Ser Gly Lys Trp Lys Ala Phe Lys Arg Phe Leu Lys
1               5                   10                  15
```

(2) INFORMATION FOR SEQ ID NO:76:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.82"

(xi) SEQUENCE DESCRIPTION: SEQ ID NO:76:

-continued

Lys Ser Lys Val Gly Trp Leu Ile Gln Leu Trp His Lys Lys
1 5 10

(2) INFORMATION FOR SEQ ID NO:77:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.83"

(ix) FEATURE:
(A) NAME/KEY: Modified-site
(B) LOCATION: 10..12
(D) OTHER INFORMATION: /label= Substituted-Ala
/note= "The alanine at position 6 is
beta-1-naphthyl-substituted"

(xi) SEQUENCE DESCRIPTION: SEQ ID NO:77:

Lys Ser Lys Val Gly Ala Lys Ile Gln Leu Phe His Lys Lys
1 5 10

(2) INFORMATION FOR SEQ ID NO:78:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.84"

(ix) FEATURE:
(A) NAME/KEY: Modified-site
(B) LOCATION: 6..8
(D) OTHER INFORMATION: /label= Substituted-Ala
/note= "The alanine at position 7 is
beta-1-naphthyl-substituted"

(xi) SEQUENCE DESCRIPTION: SEQ ID NO:78:

Ile Lys Ile Ser Gly Lys Ala Lys Ala Gln Phe Arg Phe Leu Lys
1 5 10 15

(2) INFORMATION FOR SEQ ID NO:79:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.85"

(xi) SEQUENCE DESCRIPTION: SEQ ID NO:79:

Lys Ser Lys Val Leu Trp Leu Ile Gln Leu Phe His Lys Lys
1 5 10

(2) INFORMATION FOR SEQ ID NO:80:

(i) SEQUENCE CHARACTERISTICS:

-continued (A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.86"

(xi) SEQUENCE DESCRIPTION: SEQ ID NO:80:

Lys Ser Lys Val Gly Trp Leu Ile Leu Leu Phe His Lys Lys
1 5 10

(2) INFORMATION FOR SEQ ID NO:81:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.87"

(xi) SEQUENCE DESCRIPTION: SEQ ID NO:81:

Lys Ser Lys Val Gly Trp Leu Ile Gln Leu Phe Leu Lys Lys
1 5 10

(2) INFORMATION FOR SEQ ID NO:82:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.88"

(xi) SEQUENCE DESCRIPTION: SEQ ID NO:82:

Ile Lys Ile Ser Gly Lys Trp Lys Ala Phe Phe Arg Phe Leu Lys
1 5 10 15

(2) INFORMATION FOR SEQ ID NO:83:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.98"

(ix) FEATURE:
(A) NAME/KEY: Modified-site
(B) LOCATION: 2
(D) OTHER INFORMATION: /label= Substituted-Trp
/note= "The alanine at position 2 is
beta-1-naphthyl-substituted"

(xi) SEQUENCE DESCRIPTION: SEQ ID NO:83:

Lys Trp Lys Ala Gln Phe Arg Phe Leu Lys Lys Ser Lys Val Gly Trp
1 5 10 15

-continued

Leu Ile Phe Leu Phe His Lys Lys
20

(2) INFORMATION FOR SEQ ID NO:84:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.89"

(ix) FEATURE:
(A) NAME/KEY: Modified-site
(B) LOCATION: 6..8
(D) OTHER INFORMATION: /label= Substituted-Ala
/note= "The alanine at position 7 is
beta-1-naphthyl-substituted"

(xi) SEQUENCE DESCRIPTION: SEQ ID NO:84:

Ile Lys Ile Ser Gly Lys Ala Lys Ala Phe Lys Arg Phe Leu Lys
1 5 10 15

(2) INFORMATION FOR SEQ ID NO:85:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.90"

(ix) FEATURE:
(A) NAME/KEY: Modified-site
(B) LOCATION: 6..8
(D) OTHER INFORMATION: /label= Substituted-Ala
/note= "The alanine at position 7 is
beta-1-naphthyl-substituted"

(xi) SEQUENCE DESCRIPTION: SEQ ID NO:85:

Ile Lys Ile Ser Gly Lys Ala Lys Ala Phe Phe Arg Phe Leu Lys
1 5 10 15

(2) INFORMATION FOR SEQ ID NO:86:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.91"

(xi) SEQUENCE DESCRIPTION: SEQ ID NO:86:

Lys Ser Lys Val Gly Trp Leu Ile Phe Leu Phe His Lys Lys
1 5 10

(2) INFORMATION FOR SEQ ID NO:87:

(i) SEQUENCE CHARACTERISTICS:
(A) LENGTH: 14 amino acids

-continued (B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.92"

(xi) SEQUENCE DESCRIPTION: SEQ ID NO:87:

```
Lys Ser Lys Val Gly Trp Leu Ile Lys Leu Phe His Lys Lys
1               5                   10
```

(2) INFORMATION FOR SEQ ID NO:88:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.93"

(ix) FEATURE:
(A) NAME/KEY: Modified-site
(B) LOCATION: 6..8
(D) OTHER INFORMATION: /label= Substituted-Ala
/note= "The alanine at position 7 is
beta-1-naphthyl-substituted"

(xi) SEQUENCE DESCRIPTION: SEQ ID NO:88:

```
Ile Lys Ile Ser Gly Lys Ala Lys Ala Gln Phe Arg Phe Leu Lys Lys
1               5                   10                  15

Ser Lys Val Gly Trp Leu Ile Gln Leu Phe His Lys Lys
            20                  25
```

(2) INFORMATION FOR SEQ ID NO:89:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.94"

(xi) SEQUENCE DESCRIPTION: SEQ ID NO:89:

```
Lys Ser Lys Val Gly Trp Leu Ile Gln Leu Phe Phe Lys Lys
1               5                   10
```

(2) INFORMATION FOR SEQ ID NO:90:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.95"

(xi) SEQUENCE DESCRIPTION: SEQ ID NO:90:

```
Lys Ser Lys Val Phe Trp Leu Ile Gln Leu Phe His Lys Lys
```

-continued 1 5 10

(2) INFORMATION FOR SEQ ID NO:91:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.96"

(xi) SEQUENCE DESCRIPTION: SEQ ID NO:91:

Lys Ser Lys Val Gly Trp Leu Ile Gln Leu Phe His Lys Phe
1 5 10

(2) INFORMATION FOR SEQ ID NO:92:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.97"

(xi) SEQUENCE DESCRIPTION: SEQ ID NO:92:

Lys Ser Lys Val Lys Trp Leu Ile Gln Leu Phe His Lys Lys
1 5 10

(2) INFORMATION FOR SEQ ID NO:93:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.99"

(xi) SEQUENCE DESCRIPTION: SEQ ID NO:93:

Lys Trp Lys Ala Gln Trp Arg Phe Leu Lys Lys Trp Lys Ala Gln Trp
1 5 10 15

Arg Phe Leu Lys Lys Trp Lys Ala Gln Trp Arg Phe Leu Lys
20 25 30

(2) INFORMATION FOR SEQ ID NO:94:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.100"

(xi) SEQUENCE DESCRIPTION: SEQ ID NO:94:

Lys Ser Lys Val Lys Trp Leu Ile Lys Leu Phe His Lys Lys

-continued

```
1               5                   10


(2) INFORMATION FOR SEQ ID NO:95:

     (i) SEQUENCE CHARACTERISTICS:
          (A) LENGTH: 28 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.101"

    (xi) SEQUENCE DESCRIPTION: SEQ ID NO:95:

Lys Ser Lys Val Lys Trp Leu Ile Lys Leu Phe Phe Lys Phe Lys Ser
1               5                   10                  15

Lys Val Lys Trp Leu Ile Lys Leu Phe Phe Lys Phe
            20                  25


(2) INFORMATION FOR SEQ ID NO:96:

     (i) SEQUENCE CHARACTERISTICS:
          (A) LENGTH: 24 amino acids
          (B) TYPE: amino acid
          (D) TOPOLOGY: linear

    (ii) MOLECULE TYPE: peptide

    (ix) FEATURE:
          (A) NAME/KEY: misc_feature
          (D) OTHER INFORMATION: "XMP.102"

    (xi) SEQUENCE DESCRIPTION: SEQ ID NO:96:

Lys Trp Lys Ala Gln Phe Arg Phe Leu Lys Lys Ser Lys Val  Gly Trp
1               5                   10                  15

Leu Ile Leu Leu Phe His Lys Lys
            20


(2) INFORMATION FOR SEQ ID NO:97:

     (i) SEQUENCE CHARACTERISTICS:
          (A) LENGTH: 1443 base pairs
          (B) TYPE: nucleic acid
          (C) STRANDEDNESS: single
          (D) TOPOLOGY: linear

    (ii) MOLECULE TYPE: DNA

    (ix) FEATURE:
          (A) NAME/KEY: CDS
          (B) LOCATION: 1..1443

    (ix) FEATURE:
          (A) NAME/KEY: mat_peptide
          (B) LOCATION: 76..1443

    (ix) FEATURE:
          (A) NAME/KEY: misc_feature
          (D) OTHER INFORMATION: "rLBP"

    (xi) SEQUENCE DESCRIPTION: SEQ ID NO:97:

ATG GGG GCC TTG GCC AGA GCC CTG CCG TCC ATA CTG CTG GCA TTG CTG       48
Met Gly Ala Leu Ala Arg Ala Leu Pro Ser Ile Leu Leu Ala Leu Leu
-25                 -20                 -15                 -10

CTT ACG TCC ACC CCA GAG GCT CTG GGT GCC AAC CCC GGC TTG GTC GCC       96
Leu Thr Ser Thr Pro Glu Ala Leu Gly Ala Asn Pro Gly Leu Val Ala
                -5                   1               5
```

-continued

```
AGG ATC ACC GAC AAG GGA CTG CAG TAT GCG GCC CAG GAG GGG CTA TTG      144
Arg Ile Thr Asp Lys Gly Leu Gln Tyr Ala Ala Gln Glu Gly Leu Leu
         10                  15                  20

GCT CTG CAG AGT GAG CTG CTC AGG ATC ACG CTG CCT GAC TTC ACC GGG      192
Ala Leu Gln Ser Glu Leu Leu Arg Ile Thr Leu Pro Asp Phe Thr Gly
     25                  30                  35

GAC TTG AGG ATC CCC CAC GTC GGC CGT GGG CGC TAT GAG TTC CAC AGC      240
Asp Leu Arg Ile Pro His Val Gly Arg Gly Arg Tyr Glu Phe His Ser
 40                  45                  50                  55

CTG AAC ATC CAC AGC TGT GAG CTG CTT CAC TCT GCG CTG AGG CCT GTC      288
Leu Asn Ile His Ser Cys Glu Leu Leu His Ser Ala Leu Arg Pro Val
                 60                  65                  70

CCT GGC CAG GGC CTG AGT CTC AGC ATC TCC GAC TCC TCC ATC CGG GTC      336
Pro Gly Gln Gly Leu Ser Leu Ser Ile Ser Asp Ser Ser Ile Arg Val
             75                  80                  85

CAG GGC AGG TGG AAG GTG CGC AAG TCA TTC TTC AAA CTA CAG GGC TCC      384
Gln Gly Arg Trp Lys Val Arg Lys Ser Phe Phe Lys Leu Gln Gly Ser
         90                  95                 100

TTT GAT GTC AGT GTC AAG GGC ATC AGC ATT TCG GTC AAC CTC CTG TTG      432
Phe Asp Val Ser Val Lys Gly Ile Ser Ile Ser Val Asn Leu Leu Leu
    105                 110                 115

GGC AGC GAG TCC TCC GGG AGG CCC ACA GTT ACT GCC TCC AGC TGC AGC     480
Gly Ser Glu Ser Ser Gly Arg Pro Thr Val Thr Ala Ser Ser Cys Ser
120                 125                 130                 135

AGT GAC ATC GCT GAC GTG GAG GTG GAC ATG TCG GGA GAC TTG GGG TGG      528
Ser Asp Ile Ala Asp Val Glu Val Asp Met Ser Gly Asp Leu Gly Trp
                140                 145                 150

CTG TTG AAC CTC TTC CAC AAC CAG ATT GAG TCC AAG TTC CAG AAA GTA      576
Leu Leu Asn Leu Phe His Asn Gln Ile Glu Ser Lys Phe Gln Lys Val
            155                 160                 165

CTG GAG AGC AGG ATT TGC GAA ATG ATC CAG AAA TCG GTG TCC TCC GAT      624
Leu Glu Ser Arg Ile Cys Glu Met Ile Gln Lys Ser Val Ser Ser Asp
        170                 175                 180

CTA CAG CCT TAT CTC CAA ACT CTG CCA GTT ACA ACA GAG ATT GAC AGT      672
Leu Gln Pro Tyr Leu Gln Thr Leu Pro Val Thr Thr Glu Ile Asp Ser
    185                 190                 195

TTC GCC GAC ATT GAT TAT AGC TTA GTG GAA GCC CCT CGG GCA ACA GCC      720
Phe Ala Asp Ile Asp Tyr Ser Leu Val Glu Ala Pro Arg Ala Thr Ala
200                 205                 210                 215

CAG ATG CTG GAG GTG ATG TTT AAG GGT GAA ATC TTT CAT CGT AAC CAC      768
Gln Met Leu Glu Val Met Phe Lys Gly Glu Ile Phe His Arg Asn His
                220                 225                 230

CGT TCT CCA GTT ACC CTC CTT GCT GCA GTC ATG AGC CTT CCT GAG GAA      816
Arg Ser Pro Val Thr Leu Leu Ala Ala Val Met Ser Leu Pro Glu Glu
            235                 240                 245

CAC AAC AAA ATG GTC TAC TTT GCC ATC TCG GAT TAT GTC TTC AAC ACG      864
His Asn Lys Met Val Tyr Phe Ala Ile Ser Asp Tyr Val Phe Asn Thr
        250                 255                 260

GCC AGC CTG GTT TAT CAT GAG GAA GGA TAT CTG AAC TTC TCC ATC ACA      912
Ala Ser Leu Val Tyr His Glu Glu Gly Tyr Leu Asn Phe Ser Ile Thr
    265                 270                 275

GAT GAG ATG ATA CCG CCT GAC TCT AAT ATC CGA CTG ACC ACC AAG TCC      960
Asp Glu Met Ile Pro Pro Asp Ser Asn Ile Arg Leu Thr Thr Lys Ser
280                 285                 290                 295

TTC CGA CCC TTC GTC CCA CGG TTA GCC AGG CTC TAC CCC AAC ATG AAC     1008
Phe Arg Pro Phe Val Pro Arg Leu Ala Arg Leu Tyr Pro Asn Met Asn
                300                 305                 310

CTG GAA CTC CAG GGA TCA GTG CCC TCT GCT CCG CTC CTG AAC TTC AGC     1056
Leu Glu Leu Gln Gly Ser Val Pro Ser Ala Pro Leu Leu Asn Phe Ser
            315                 320                 325
```

-continued

```
CCT GGG AAT CTG TCT GTG GAC CCC TAT ATG GAG ATA GAT GCC TTT GTG     1104
Pro Gly Asn Leu Ser Val Asp Pro Tyr Met Glu Ile Asp Ala Phe Val
        330                 335                 340

CTC CTG CCC AGC TCC AGC AAG GAG CCT GTC TTC CGG CTC AGT GTG GCC     1152
Leu Leu Pro Ser Ser Ser Lys Glu Pro Val Phe Arg Leu Ser Val Ala
    345                 350                 355

ACT AAT GTG TCC GCC ACC TTG ACC TTC AAT ACC AGC AAG ATC ACT GGG     1200
Thr Asn Val Ser Ala Thr Leu Thr Phe Asn Thr Ser Lys Ile Thr Gly
360                 365                 370                 375

TTC CTG AAG CCA GGA AAG GTA AAA GTG GAA CTG AAA GAA TCC AAA GTT     1248
Phe Leu Lys Pro Gly Lys Val Lys Val Glu Leu Lys Glu Ser Lys Val
                380                 385                 390

GGA CTA TTC AAT GCA GAG CTG TTG GAA GCG CTC CTC AAC TAT TAC ATC     1296
Gly Leu Phe Asn Ala Glu Leu Leu Glu Ala Leu Leu Asn Tyr Tyr Ile
            395                 400                 405

CTT AAC ACC TTC TAC CCC AAG TTC AAT GAT AAG TTG GCC GAA GGC TTC     1344
Leu Asn Thr Phe Tyr Pro Lys Phe Asn Asp Lys Leu Ala Glu Gly Phe
        410                 415                 420

CCC CTT CCT CTG CTG AAG CGT GTT CAG CTC TAC GAC CTT GGG CTG CAG     1392
Pro Leu Pro Leu Leu Lys Arg Val Gln Leu Tyr Asp Leu Gly Leu Gln
    425                 430                 435

ATC CAT AAG GAC TTC CTG TTC TTG GGT GCC AAT GTC CAA TAC ATG AGA     1440
Ile His Lys Asp Phe Leu Phe Leu Gly Ala Asn Val Gln Tyr Met Arg
440                 445                 450                 455

GTT                                                                 1443
Val
```

(2) INFORMATION FOR SEQ ID NO:98:

(i) SEQUENCE CHARACTERISTICS:
(A) LENGTH: 481 amino acids
(B) TYPE: amino acid
(D) TOPOLOGY: linear (ii) MOLECULE TYPE: protein (ix) FEATURE:
(A) NAME/KEY: misc_feature
(D) OTHER INFORMATION: "rLBP"

(xi) SEQUENCE DESCRIPTION: SEQ ID NO:98:

```
Met Gly Ala Leu Ala Arg Ala Leu Pro Ser Ile Leu Leu Ala Leu Leu
-25                 -20                 -15                 -10

Leu Thr Ser Thr Pro Glu Ala Leu Gly Ala Asn Pro Gly Leu Val Ala
                 -5                   1               5

Arg Ile Thr Asp Lys Gly Leu Gln Tyr Ala Ala Gln Glu Gly Leu Leu
        10                  15                  20

Ala Leu Gln Ser Glu Leu Leu Arg Ile Thr Leu Pro Asp Phe Thr Gly
     25                  30                  35

Asp Leu Arg Ile Pro His Val Gly Arg Gly Arg Tyr Glu Phe His Ser
 40                  45                  50                  55

Leu Asn Ile His Ser Cys Glu Leu Leu His Ser Ala Leu Arg Pro Val
                 60                  65                  70

Pro Gly Gln Gly Leu Ser Leu Ser Ile Ser Asp Ser Ser Ile Arg Val
            75                  80                  85

Gln Gly Arg Trp Lys Val Arg Lys Ser Phe Phe Lys Leu Gln Gly Ser
        90                  95                 100

Phe Asp Val Ser Val Lys Gly Ile Ser Ile Ser Val Asn Leu Leu Leu
    105                 110                 115
```

-continued

```
Gly Ser Glu Ser Ser Gly Arg Pro Thr Val Thr Ala Ser Ser Cys Ser
120                 125                 130                 135

Ser Asp Ile Ala Asp Val Glu Val Asp Met Ser Gly Asp Leu Gly Trp
                140                 145                 150

Leu Leu Asn Leu Phe His Asn Gln Ile Glu Ser Lys Phe Gln Lys Val
            155                 160                 165

Leu Glu Ser Arg Ile Cys Glu Met Ile Gln Lys Ser Val Ser Ser Asp
        170                 175                 180

Leu Gln Pro Tyr Leu Gln Thr Leu Pro Val Thr Thr Glu Ile Asp Ser
    185                 190                 195

Phe Ala Asp Ile Asp Tyr Ser Leu Val Glu Ala Pro Arg Ala Thr Ala
200                 205                 210                 215

Gln Met Leu Glu Val Met Phe Lys Gly Glu Ile Phe His Arg Asn His
                220                 225                 230

Arg Ser Pro Val Thr Leu Leu Ala Ala Val Met Ser Leu Pro Glu Glu
            235                 240                 245

His Asn Lys Met Val Tyr Phe Ala Ile Ser Asp Tyr Val Phe Asn Thr
        250                 255                 260

Ala Ser Leu Val Tyr His Glu Glu Gly Tyr Leu Asn Phe Ser Ile Thr
    265                 270                 275

Asp Glu Met Ile Pro Pro Asp Ser Asn Ile Arg Leu Thr Thr Lys Ser
280                 285                 290                 295

Phe Arg Pro Phe Val Pro Arg Leu Ala Arg Leu Tyr Pro Asn Met Asn
                300                 305                 310

Leu Glu Leu Gln Gly Ser Val Pro Ser Ala Pro Leu Leu Asn Phe Ser
            315                 320                 325

Pro Gly Asn Leu Ser Val Asp Pro Tyr Met Glu Ile Asp Ala Phe Val
        330                 335                 340

Leu Leu Pro Ser Ser Ser Lys Glu Pro Val Phe Arg Leu Ser Val Ala
    345                 350                 355

Thr Asn Val Ser Ala Thr Leu Thr Phe Asn Thr Ser Lys Ile Thr Gly
360                 365                 370                 375

Phe Leu Lys Pro Gly Lys Val Lys Val Glu Leu Lys Glu Ser Lys Val
                380                 385                 390

Gly Leu Phe Asn Ala Glu Leu Leu Glu Ala Leu Leu Asn Tyr Tyr Ile
            395                 400                 405

Leu Asn Thr Phe Tyr Pro Lys Phe Asn Asp Lys Leu Ala Glu Gly Phe
        410                 415                 420

Pro Leu Pro Leu Leu Lys Arg Val Gln Leu Tyr Asp Leu Gly Leu Gln
    425                 430                 435

Ile His Lys Asp Phe Leu Phe Leu Gly Ala Asn Val Gln Tyr Met Arg
440                 445                 450                 455

Val
```

(2) INFORMATION FOR SEQ ID NO:99:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.57"

-continued (xi) SEQUENCE DESCRIPTION: SEQ ID NO:99:

Cys Ile Lys Ile Ser Gly Lys Trp Lys Ala Gln Lys Arg Pro Leu Cys
1 5 10 15

(2) INFORMATION FOR SEQ ID NO:100:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.75"

(xi) SEQUENCE DESCRIPTION: SEQ ID NO:100:

Ile Lys Lys Arg Ala Ile Ser Phe Leu Gly Lys Lys Trp Gln Lys
1 5 10 15

(2) INFORMATION FOR SEQ ID NO:101:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.282"

(xi) SEQUENCE DESCRIPTION: SEQ ID NO:101:

Lys Trp Lys Ala Phe Phe Arg Phe Leu Lys Lys Trp Lys Ala Phe Phe
1 5 10 15

Arg Phe Leu Lys
20

(2) INFORMATION FOR SEQ ID NO:102:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.103"

(xi) SEQUENCE DESCRIPTION: SEQ ID NO:102:

Ile Lys Ile Ser Gly Lys Trp Lys Ala Trp Lys Arg Phe Leu Lys Lys
1 5 10 15

(2) INFORMATION FOR SEQ ID NO:103:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.104"

-continued (xi) SEQUENCE DESCRIPTION: SEQ ID NO:103:

Lys Ser Lys Val Gly Trp Leu Ile Ser Leu Phe His Lys Lys
1 5 10

(2) INFORMATION FOR SEQ ID NO:104:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.105"

(ix) FEATURE:
(A) NAME/KEY: Modified-site
(B) LOCATION: 13
(C) OTHER INFORMATION: /label= Substituted-Ala
/note= "The alanine at position 13 is beta-1-naphthyl-substituted."

(xi) SEQUENCE DESCRIPTION: SEQ ID NO:104:

Ile Lys Ile Ser Gly Lys Trp Lys Ala Trp Lys Arg Ala Leu Lys Lys
1 5 10 15

(2) INFORMATION FOR SEQ ID NO:105:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.106"

(xi) SEQUENCE DESCRIPTION: SEQ ID NO:105:

Lys Ser Lys Val Gly Trp Leu Ile Thr Leu Phe His Lys Lys
1 5 10

(2) INFORMATION FOR SEQ ID NO:106:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.107"

(xi) SEQUENCE DESCRIPTION: SEQ ID NO:106:

Lys Ser Lys Val Gly Trp Leu Ile Gln Leu Phe Trp Lys Lys
1 5 10

(2) INFORMATION FOR SEQ ID NO:107:

(i) SEQUENCE CHARACTERISTICS:
(A) LENGTH: 14 amino acids
(B) TYPE: amino acid
(D) TOPOLOGY: linear (ii) MOLECULE TYPE: peptide -continued (ix) FEATURE:
(A) NAME/KEY: misc_feature
(D) OTHER INFORMATION: "XMP.108"

(xi) SEQUENCE DESCRIPTION: SEQ ID NO:107:

Lys Ser Lys Val Gly Trp Leu Ile Gln Leu Phe His Lys Trp
1 5 10

(2) INFORMATION FOR SEQ ID NO:108:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.109"

(ix) FEATURE:
(A) NAME/KEY: Modified-site
(B) LOCATION: 11
(C) OTHER INFORMATION: /label= Substituted-Ala
/note= "The alanine at position 11 is beta-1-naphthyl-substituted."

(xi) SEQUENCE DESCRIPTION: SEQ ID NO:108:

Lys Ser Lys Val Gly Trp Leu Ile Gln Leu Ala His Lys Lys
1 5 10

(2) INFORMATION FOR SEQ ID NO:109:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.110"

(ix) FEATURE:
(A) NAME/KEY: Modified-site
(B) LOCATION: 12
(C) OTHER INFORMATION: /label= Substituted-Ala
/note= "The alanine at position 12 is beta-1-naphthyl-substituted."

(xi) SEQUENCE DESCRIPTION: SEQ ID NO:109:

Lys Ser Lys Val Gly Trp Leu Ile Gln Leu Phe Ala Lys Lys
1 5 10

(2) INFORMATION FOR SEQ ID NO:110:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.111"

(ix) FEATURE:
(A) NAME/KEY: Modified-site
(B) LOCATION: 14
(C) OTHER INFORMATION: /label= Substituted-Ala -continued /note= "The alanine at position 14 is beta-1-naphthyl-substituted."

(xi) SEQUENCE DESCRIPTION: SEQ ID NO:110:

Lys Ser Lys Val Gly Trp Leu Ile Gln Leu Phe His Lys Ala
1 5 10

(2) INFORMATION FOR SEQ ID NO:111:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.112"

(ix) FEATURE:
(A) NAME/KEY: Modified-site
(B) LOCATION: 7
(C) OTHER INFORMATION: /label= Substituted-Ala
/note= "The alanine at position 7 is beta-1-naphthyl-substituted."

(ix) FEATURE:
(A) NAME/KEY: Modified-site
(B) LOCATION: 11
(C) OTHER INFORMATION: /label= Substituted-Ala
/note= "The alanine at position 11 is beta-1-naphthyl-substituted."

(xi) SEQUENCE DESCRIPTION: SEQ ID NO:111:

Ile Lys Ile Ser Gly Lys Ala Lys Ala Gln Ala Arg Phe Leu Lys
1 5 10 15

(2) INFORMATION FOR SEQ ID NO:112:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.113"

(xi) SEQUENCE DESCRIPTION: SEQ ID NO:112:

Lys Ser Lys Val Gly Trp Leu Ile Gln Phe Phe His Lys Lys
1 5 10

(2) INFORMATION FOR SEQ ID NO:113:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.114"

(xi) SEQUENCE DESCRIPTION: SEQ ID NO:113:

Lys Trp Gln Leu Arg Ser Lys Gly Lys Ile Lys Ile Phe Lys Ala
1 5 10 15

-continued (2) INFORMATION FOR SEQ ID NO:114:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.116"

(ix) FEATURE:
(A) NAME/KEY: Modified-site
(B) LOCATION: 6
(C) OTHER INFORMATION: /label= Substituted-Ala
/note= "The alanine at position 6 is beta-1-naphthyl-substituted."

(xi) SEQUENCE DESCRIPTION: SEQ ID NO:114:

```
Lys Ser Lys Val Lys Ala Leu Ile Gln Leu Phe His Lys Lys
1               5                   10
```

(2) INFORMATION FOR SEQ ID NO:115:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.119"

(ix) FEATURE:
(A) NAME/KEY: Modified-site
(B) LOCATION: 7
(C) OTHER INFORMATION: /label= Substituted-Ala
/note= "The alanine at position 7 is beta-1-naphthyl-substituted."

(ix) FEATURE:
(A) NAME/KEY: Modified-site
(B) LOCATION: 10
(C) OTHER INFORMATION: /label= Substituted-Ala
/note= "The alanine at position 10 is beta-1-naphthyl-substituted."

(xi) SEQUENCE DESCRIPTION: SEQ ID NO:115:

```
Ile Lys Ile Ser Gly Lys Ala Lys Ala Ala Lys Arg Phe Leu Lys
1               5                   10                  15
```

(2) INFORMATION FOR SEQ ID NO:116:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.120"

(xi) SEQUENCE DESCRIPTION: SEQ ID NO:116:

```
Ile Lys Ile Ser Gly Lys Trp Lys Ala Gln Lys Arg Lys Leu Lys
1               5                   10                  15
```

-continued (2) INFORMATION FOR SEQ ID NO:117:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.121"

(ix) FEATURE:
(A) NAME/KEY: Modified-site
(B) LOCATION: 10
(C) OTHER INFORMATION: /label= Substituted-Ala
/note= "The alanine at position 10 is beta-1-naphthyl-substituted."

(ix) FEATURE:
(A) NAME/KEY: Modified-site
(B) LOCATION: 11
(C) OTHER INFORMATION: /label= Substituted-Ala
/note= "The alanine at position 11 is beta-1-naphthyl-substituted."

(xi) SEQUENCE DESCRIPTION: SEQ ID NO:117:

```
Ile Lys Ile Ser Gly Lys Trp Lys Ala Ala Ala Arg Phe Leu Lys
1               5                   10                  15
```

(2) INFORMATION FOR SEQ ID NO:118:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.122"

(ix) FEATURE:
(A) NAME/KEY: Modified-site
(B) LOCATION: 7
(C) OTHER INFORMATION: /label= Substituted-Ala
/note= "The alanine at position 7 is beta-1-naphthyl-substituted."

(ix) FEATURE:
(A) NAME/KEY: Modified-site
(B) LOCATION: 10
(C) OTHER INFORMATION: /label= Substituted-Ala
/note= "The alanine at position 10 is beta-1-naphthyl-substituted."

(ix) FEATURE:
(A) NAME/KEY: Modified-site
(B) LOCATION: 11
(C) OTHER INFORMATION: /label= Substituted-Ala
/note= "The alanine at position 11 is beta-1-naphthyl-substituted."

(xi) SEQUENCE DESCRIPTION: SEQ ID NO:118:

```
Ile Lys Ile Ser Gly Lys Ala Lys Ala Ala Ala Arg Phe Leu Lys
1               5                   10                  15
```

(2) INFORMATION FOR SEQ ID NO:119:

(i) SEQUENCE CHARACTERISTICS:
(A) LENGTH: 14 amino acids
(B) TYPE: amino acid
(D) TOPOLOGY: linear -continued (ii) MOLECULE TYPE: peptide (ix) FEATURE:
(A) NAME/KEY: misc_feature
(D) OTHER INFORMATION: “XMP.123”

(ix) FEATURE:
(A) NAME/KEY: Modified-site
(B) LOCATION: 9
(C) OTHER INFORMATION: /label= Substituted-Phe
/note= “The phenylalanine at position 9 is
p-amino-substituted.”

(xi) SEQUENCE DESCRIPTION: SEQ ID NO:119:

```
Lys Ser Lys Val Gly Trp Leu Ile Phe Leu Phe His Lys Lys
1               5                   10
```

(2) INFORMATION FOR SEQ ID NO:120:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.124”

(xi) SEQUENCE DESCRIPTION: SEQ ID NO:120:

```
Lys Ser Lys Val Lys Trp Leu Ile Gln Leu Trp His Lys Lys
1               5                   10
```

(2) INFORMATION FOR SEQ ID NO:121:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.125”

(xi) SEQUENCE DESCRIPTION: SEQ ID NO:121:

```
Lys Ser Lys Val Gly Trp Leu Ile Tyr Leu Phe His Lys Lys
1               5                   10
```

(2) INFORMATION FOR SEQ ID NO:122:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.126”

(ix) FEATURE:
(A) NAME/KEY: Modified-site
(B) LOCATION: 6
(C) OTHER INFORMATION: /label= D-Trp
/note= “The amino acid at position 6 is
D-tryptophan.”

(xi) SEQUENCE DESCRIPTION: SEQ ID NO:122:

-continued

Lys Ser Lys Val Gly Trp Leu Ile Gln Leu Phe His Lys Lys
1 5 10

(2) INFORMATION FOR SEQ ID NO:123:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.127"

(xi) SEQUENCE DESCRIPTION: SEQ ID NO:123:

Lys Ser Lys Val Gly Phe Leu Ile Gln Leu Phe His Lys Lys
1 5 10

(2) INFORMATION FOR SEQ ID NO:124:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.128"

(ix) FEATURE:
(A) NAME/KEY: Modified-site
(B) LOCATION: 6
(C) OTHER INFORMATION: /label= D-Phe
/note= "The amino acid at position 6 is
D-phenylalanine."

(xi) SEQUENCE DESCRIPTION: SEQ ID NO:124:

Lys Ser Lys Val Gly Phe Leu Ile Gln Leu Pro His Lys Lys
1 5 10

(2) INFORMATION FOR SEQ ID NO:125:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.129"

(ix) FEATURE:
(A) NAME/KEY: Modified-site
(B) LOCATION: 6
(C) OTHER INFORMATION: /label= Substituted-Ala
/note= "The alanine at position 6 is
D-1-beta-1-naphthyl-
substituted."

(xi) SEQUENCE DESCRIPTION: SEQ ID NO:125:

Lys Ser Lys Val Gly Ala Leu Ile Gln Leu Phe His Lys Lys
1 5 10

(2) INFORMATION FOR SEQ ID NO:126:

-continued (i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.130”

(ix) FEATURE:
(A) NAME/KEY: Modified-site
(B) LOCATION: 6
(C) OTHER INFORMATION: /label= Substituted-Ala
/note= “The alanine at position 6 is
2-beta-1-naphthyl-
substituted.”

(xi) SEQUENCE DESCRIPTION: SEQ ID NO:126:

Lys Ser Lys Val Gly Ala Leu Ile Gln Leu Phe His Lys Lys
1 5 10

(2) INFORMATION FOR SEQ ID NO:127:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.131”

(ix) FEATURE:
(A) NAME/KEY: Modified-site
(B) LOCATION: 6
(C) OTHER INFORMATION: /label= Substituted-Ala
/note= “The alanine at position 6 is
D-2-beta-1-naphthyl-
substituted.”

(xi) SEQUENCE DESCRIPTION: SEQ ID NO:127:

Lys Ser Lys Val Gly Ala Leu Ile Gln Leu Phe His Lys Lys
1 5 10

(2) INFORMATION FOR SEQ ID NO:128:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: “XMP.132”

(ix) FEATURE:
(A) NAME/KEY: Modified-site
(B) LOCATION: 6
(C) OTHER INFORMATION: /label= Substituted-Ala
/note= “The alanine at position 6 is
pyridyl-substituted.”

(xi) SEQUENCE DESCRIPTION: SEQ ID NO:128:

Lys Ser Lys Val Gly Ala Leu Ile Gln Leu Phe His Lys Lys
1 5 10

(2) INFORMATION FOR SEQ ID NO:129:

-continued (i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.133"

(ix) FEATURE:
(A) NAME/KEY: Modified-site
(B) LOCATION: 6
(C) OTHER INFORMATION: /label= Substituted-Phe
/note= "The phenylalanine at position 6 is
para-amino-
substituted."

(xi) SEQUENCE DESCRIPTION: SEQ ID NO:129:

Lys Ser Lys Val Gly Phe Leu Ile Gln Leu Phe His Lys Lys
1 5 10

(2) INFORMATION FOR SEQ ID NO:130:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.134"

(ix) FEATURE:
(A) NAME/KEY: Modified-site
(B) LOCATION: 5
(C) OTHER INFORMATION: /label= Substituted-Phe
/note= "The phenylalanine at position 5 is
para-amino-substituted."

(xi) SEQUENCE DESCRIPTION: SEQ ID NO:130:

Lys Ser Lys Val Phe Trp Leu Ile Gln Leu Phe His Lys Lys
1 5 10

(2) INFORMATION FOR SEQ ID NO:131:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.135"

(xi) SEQUENCE DESCRIPTION: SEQ ID NO:131:

Lys Ser Lys Val Gly Lys Leu Ile Gln Leu Pro His Lys Lys
1 5 10

(2) INFORMATION FOR SEQ ID NO:132:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.136"

(xi) SEQUENCE DESCRIPTION: SEQ ID NO:132:

Ile Lys Ile Ser Gly Lys Trp Lys Ala Gln Glu Arg Phe Leu Lys
1 5 10 15

(2) INFORMATION FOR SEQ ID NO:133:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.137"

(xi) SEQUENCE DESCRIPTION: SEQ ID NO:133:

Cys Lys Ser Lys Val Gly Trp Leu Ile Gln Leu Phe His Lys Lys Cys
1 5 10 15

(2) INFORMATION FOR SEQ ID NO:134:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.138"

(xi) SEQUENCE DESCRIPTION: SEQ ID NO:134:

Lys Ser Lys Val Lys Phe Leu Ile Gln Leu Phe His Lys Lys
1 5 10

(2) INFORMATION FOR SEQ ID NO:135:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.139"

(xi) SEQUENCE DESCRIPTION: SEQ ID NO:135:

Lys Ser Lys Val Gly Tyr Leu Ile Gln Leu Phe His Lys Lys
1 5 10

(2) INFORMATION FOR SEQ ID NO:136:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: misc_feature -continued (D) OTHER INFORMATION: "XMP.140"

(ix) FEATURE:
(A) NAME/KEY: Modified-site
(B) LOCATION: 1
(C) OTHER INFORMATION: /label= Substituted-Ala
/note= "The alanine at position 1 is
beta-1-naphthyl-substituted."

(ix) FEATURE:
(A) NAME/KEY: Modified-site
(B) LOCATION: 2
(C) OTHER INFORMATION: /label= Substituted-Ala
/note= "The alanine at position 2 is
beta-1-naphthyl-substituted."

(xi) SEQUENCE DESCRIPTION: SEQ ID NO:136:

```
Ala Ala Arg Phe Leu Lys Phe
1               5
```

(2) INFORMATION FOR SEQ ID NO:137:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.141"

(xi) SEQUENCE DESCRIPTION: SEQ ID NO:137:

```
Ile Lys Ile Ser Gly Lys Trp Lys Ala Gln Lys Arg Trp Leu Lys
1               5                   10                  15
```

(2) INFORMATION FOR SEQ ID NO:138:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.142"

(xi) SEQUENCE DESCRIPTION: SEQ ID NO:138:

```
Lys Ser Lys Val Gly Trp Leu Ile Gln Trp Phe His Lys Lys
1               5                   10
```

(2) INFORMATION FOR SEQ ID NO:139:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.143"

(ix) FEATURE:
(A) NAME/KEY: Modified-site
(B) LOCATION: 10
(C) OTHER INFORMATION: /label= Substituted-Ala
/note= "The alanine at position 10 is
beta-1-naphthyl-substituted."

-continued (xi) SEQUENCE DESCRIPTION: SEQ ID NO:139:

Lys Ser Lys Val Gly Trp Leu Ile Gln Ala Phe His Lys Lys
1 5 10

(2) INFORMATION FOR SEQ ID NO:140:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.144"

(ix) FEATURE:
(A) NAME/KEY: Modified-site
(B) LOCATION: 6
(C) OTHER INFORMATION: /label= Substituted-Ala
/note= "The alanine at position 6 is
cyclohexyl-substituted."

(xi) SEQUENCE DESCRIPTION: SEQ ID NO:140:

Lys Ser Lys Val Gly Ala Leu Ile Gln Leu Phe His Lys Lys
1 5 10

(2) INFORMATION FOR SEQ ID NO:141:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.145"

(xi) SEQUENCE DESCRIPTION: SEQ ID NO:141:

Lys Trp Lys Ala Ala Ala Arg Phe Leu Lys Lys Ser Lys Val Gly Trp
1 5 10 15

Leu Ile Gln Leu Phe His Lys Lys
20

(2) INFORMATION FOR SEQ ID NO:142:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.146"

(ix) FEATURE:
(A) NAME/KEY: Modified-site
(B) LOCATION: 12
(C) OTHER INFORMATION: /label= Substituted-Ala
/note= "The alanine at position 12 is
beta-1-naphthyl-substituted."

(ix) FEATURE:
(A) NAME/KEY: Modified-site
(B) LOCATION: 14
(C) OTHER INFORMATION: /label= Substituted-Ala -continued /note= "The alanine at position 14 is
beta-1-naphthyl-substituted."

(xi) SEQUENCE DESCRIPTION: SEQ ID NO:142:

```
Lys Ser Lys Val Gly Trp Leu Ile Gln Leu Phe Ala Lys Ala
1               5                   10
```

(2) INFORMATION FOR SEQ ID NO:143:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.147"

(xi) SEQUENCE DESCRIPTION: SEQ ID NO:143:

```
Ile Lys Ile Ser Gly Lys Trp Lys Ala Glu Lys Lys Phe Leu Lys
1               5                   10                  15
```

(2) INFORMATION FOR SEQ ID NO:144:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.148"

(ix) FEATURE:
(A) NAME/KEY: Modified-site
(B) LOCATION: 6
(C) OTHER INFORMATION: /label= Substituted-Ala
/note= "The alanine at position 6 is
beta-1-naphthyl-substituted."

(ix) FEATURE:
(A) NAME/KEY: Modified-site
(B) LOCATION: 12
(C) OTHER INFORMATION: /label= Substituted-Ala
/note= "The alanine at position 12 is
beta-1-naphthyl-substituted."

(xi) SEQUENCE DESCRIPTION: SEQ ID NO:144:

```
Lys Ser Lys Val Gly Ala Leu Ile Gln Leu Phe Ala Lys Lys
1               5                   10
```

(2) INFORMATION FOR SEQ ID NO:145:

(i) SEQUENCE CHARACTERISTICS:
(A) LENGTH: 1813 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 31..1491

(ix) FEATURE:
(A) NAME/KEY: mat_peptide
(B) LOCATION: 124..1491

-continued

```
    (ix) FEATURE:
          (A) NAME/KEY: misc_feature
          (D) OTHER INFORMATION: "rBPI"

    (xi) SEQUENCE DESCRIPTION: SEQ ID NO:145:

CAGGCCTTGA GGTTTTGGCA GCTCTGGAGG ATG AGA GAG AAC ATG GCC AGG GGC      54
                                 Met Arg Glu Asn Met Ala Arg Gly
                                 -31 -30                 -25

CCT TGC AAC GCG CCG AGA TGG GTG TCC CTG ATG GTG CTC GTC GCC ATA      102
Pro Cys Asn Ala Pro Arg Trp Val Ser Leu Met Val Leu Val Ala Ile
            -20                 -15                 -10

GGC ACC GCC GTG ACA GCG GCC GTC AAC CCT GGC GTC GTG GTC AGG ATC      150
Gly Thr Ala Val Thr Ala Ala Val Asn Pro Gly Val Val Val Arg Ile
        -5                  1               5

TCC CAG AAG GGC CTG GAC TAC GCC AGC CAG CAG GGG ACG GCC GCT CTG      198
Ser Gln Lys Gly Leu Asp Tyr Ala Ser Gln Gln Gly Thr Ala Ala Leu
 10                  15                  20                  25

CAG AAG GAG CTG AAG AGG ATC AAG ATT CCT GAC TAC TCA GAC AGC TTT      246
Gln Lys Glu Leu Lys Arg Ile Lys Ile Pro Asp Tyr Ser Asp Ser Phe
                 30                  35                  40

AAG ATC AAG CAT CTT GGG AAG GGG CAT TAT AGC TTC TAC AGC ATG GAC      294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTG CCC AAT      342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG      390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC      438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT      486
Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC      534
Asn Pro Thr Ser Gly Lys Pro Thr Ile Thr Cys Ser Ser Cys Ser Ser
            125                 130                 135

CAC ATC AAC AGT GTC CAC GTG CAC ATC TCA AAG AGC AAA GTC GGG TGG      582
His Ile Asn Ser Val His Val His Ile Ser Lys Ser Lys Val Gly Trp
        140                 145                 150

CTG ATC CAA CTC TTC CAC AAA AAA ATT GAG TCT GCG CTT CGA AAC AAG      630
Leu Ile Gln Leu Phe His Lys Lys Ile Glu Ser Ala Leu Arg Asn Lys
    155                 160                 165

ATG AAC AGC CAG GTC TGC GAG AAA GTG ACC AAT TCT GTA TCC TCC AAG      678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT      726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT      774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC      822
Glu Thr Leu Asp Val Gln Met Lys Gly Glu Phe Tyr Ser Glu Asn His
        220                 225                 230

CAC AAT CCA CCT CCC TTT GCT CCA CCA GTG ATG GAG TTT CCC GCT GCC      870
His Asn Pro Pro Pro Phe Ala Pro Pro Val Met Glu Phe Pro Ala Ala
    235                 240                 245

CAT GAC CGC ATG GTA TAC CTG GGC CTC TCA GAC TAC TTC TTC AAC ACA      918
```

-continued

```
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA      966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC     1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG     1062
Phe Gly Thr Phe Leu Pro Glu Val Ala Lys Lys Phe Pro Asn Met Lys
        300                 305                 310

ATA CAG ATC CAT GTC TCA GCC TCC ACC CCG CCA CAC CTG TCT GTG CAG     1110
Ile Gln Ile His Val Ser Ala Ser Thr Pro Pro His Leu Ser Val Gln
    315                 320                 325

CCC ACC GGC CTT ACC TTC TAC CCT GCC GTG GAT GTC CAG GCC TTT GCC     1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC     1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA     1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT     1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA     1350
Gly Pro Phe Pro Val Glu Leu Leu Gln Asp Ile Met Asn Tyr Ile Val
    395                 400                 405

CCC ATT CTT GTG CTG CCC AGG GTT AAC GAG AAA CTA CAG AAA GGC TTC     1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG     1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA         1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC   1551

ACCGGCTGCC TTTCCCCAGG GAATCCTCTC CAGATCTTAA CCAAGAGCCC CTTGCAAACT   1611

TCTTCGACTC AGATTCAGAA ATGATCTAAA CACGAGGAAA CATTATTCAT TGGAAAAGTG   1671

CATGGTGTGT ATTTTAGGGA TTATGAGCTT CTTTCAAGGG CTAAGGCTGC AGAGATATTT   1731

CCTCCAGGAA TCGTGTTTCA ATTGTAACCA AGAAATTTCC ATTTGTGCTT CATGAAAAAA   1791

AACTTCTGGT TTTTTTCATG TG                                            1813
```

(2) INFORMATION FOR SEQ ID NO:146:

(i) SEQUENCE CHARACTERISTICS:
(A) LENGTH: 487 amino acids
(B) TYPE: amino acid
(D) TOPOLOGY: linear (ii) MOLECULE TYPE: protein (xi) SEQUENCE DESCRIPTION: SEQ ID NO:146:

```
Met Arg Glu Asn Met Ala Arg Gly Pro Cys Asn Ala Pro Arg Trp Val
-31 -30                 -25                 -20

Ser Leu Met Val Leu Val Ala Ile Gly Thr Ala Val Thr Ala Ala Val
```

-continued

```
-15                 -10                 -5                   1

Asn Pro Gly Val Val Val Arg Ile Ser Gln Lys Gly Leu Asp Tyr Ala
             5                  10                  15

Ser Gln Gln Gly Thr Ala Ala Leu Gln Lys Glu Leu Lys Arg Ile Lys
         20                  25                  30

Ile Pro Asp Tyr Ser Asp Ser Phe Lys Ile Lys His Leu Gly Lys Gly
     35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415
```

-continued

```
Asn Glu Lys Leu Gln Lys Gly Phe Pro Leu Pro Thr Pro Ala Arg Val
        420                 425                 430

Gln Leu Tyr Asn Val Val Leu Gln Pro His Gln Asn Phe Leu Leu Phe
    435                 440                 445

Gly Ala Asp Val Val Tyr Lys
450                 455
```

(2) INFORMATION FOR SEQ ID NO:147:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.149"

(xi) SEQUENCE DESCRIPTION: SEQ ID NO:147:

```
Lys Trp Lys Val Phe Lys Lys Ile Glu Lys Lys Ser Lys Val Gly Trp
1               5                   10                  15

Leu Ile Gln Leu Phe His Lys Lys
            20
```

(2) INFORMATION FOR SEQ ID NO:148:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.150"

(xi) SEQUENCE DESCRIPTION: SEQ ID NO:148:

```
Lys Trp Ala Phe Ala Lys Lys Gln Lys Lys Arg Leu Lys Arg Gln Trp
1               5                   10                  15

Leu Lys Lys Phe
            20
```

(2) INFORMATION FOR SEQ ID NO:149:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.153"

(xi) SEQUENCE DESCRIPTION: SEQ ID NO:149:

```
Lys Trp Lys Ala Gln Lys Arg Phe Leu Lys Lys Trp Lys Ala Gln Lys
1               5                   10                  15

Arg Phe Leu Lys Lys Trp Lys Ala Gln Lys Arg Phe Leu Lys
            20                  25                  30
```

(2) INFORMATION FOR SEQ ID NO:150:

-continued (i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.154"

(ix) FEATURE:
(A) NAME/KEY: Modified-site
(B) LOCATION: 5
(C) OTHER INFORMATION: /label= Substituted-Ala
/note= "Position 5 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(xi) SEQUENCE DESCRIPTION: SEQ ID NO:150:

```
Lys Trp Lys Ala Ala Ala Arg Phe Leu Lys Lys Trp Lys Ala Gln Lys
1               5                   10                  15

Arg Phe Leu Lys
            20
```

(2) INFORMATION FOR SEQ ID NO:151:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.155"

(ix) FEATURE:
(A) NAME/KEY: Modified-site
(B) LOCATION: 15
(C) OTHER INFORMATION: /label= Substituted-Ala
/note= "Position 15 is
beta-1-naphthyl-substituted."

(ix) FEATURE:
(A) NAME/KEY: Modified-site
(B) LOCATION: 16
(C) OTHER INFORMATION: /label= Substituted-Ala
/note= "Position 16 is
beta-1-naphthyl-substituted."

(xi) SEQUENCE DESCRIPTION: SEQ ID NO:151:

```
Lys Trp Lys Ala Gln Lys Arg Phe Leu Lys Lys Trp Lys Ala Ala Ala
1               5                   10                  15

Arg Phe Leu Lys
            20
```

(2) INFORMATION FOR SEQ ID NO:152:

(i) SEQUENCE CHARACTERISTICS:
(A) LENGTH: 20 amino acids
(B) TYPE: amino acid
(D) TOPOLOGY: linear (ii) MOLECULE TYPE: peptide -continued (ix) FEATURE:
(A) NAME/KEY: misc_feature
(D) OTHER INFORMATION: "XMP.156"

(ix) FEATURE:
(A) NAME/KEY: Modified-site
(B) LOCATION: 5
(C) OTHER INFORMATION: /label= Substituted-Ala
/note= "Position 5 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 15
(C) OTHER INFORMATION: /label= Substituted-Ala
/note= "Position 15 is
beta-1-naphthyl-substituted."

(ix) FEATURE:
(A) NAME/KEY: Modified-site
(B) LOCATION: 16
(C) OTHER INFORMATION: /label= Substituted-Ala
/note= "Position 16 is
beta-1-naphthyl-substituted."

(xi) SEQUENCE DESCRIPTION: SEQ ID NO:152:

```
Lys Trp Lys Ala Ala Ala Arg Phe Leu Lys Lys Trp Lys Ala Ala Ala
1               5                   10                  15

Arg Phe Leu Lys
            20
```

(2) INFORMATION FOR SEQ ID NO:153:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.157"

(ix) FEATURE:
(A) NAME/KEY: Modified-site
(B) LOCATION: 5
(C) OTHER INFORMATION: /label= Substituted-Ala
/note= "Position 5 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 15
(C) OTHER INFORMATION: /label= Substituted-Ala
/note= "Position 15 is
beta-1-naphthyl-substituted."

(ix) FEATURE:
(A) NAME/KEY: Modified-site
(B) LOCATION: 16
(C) OTHER INFORMATION: /label= Substituted-Ala -continued /note= "Position 16 is beta-1-naphthyl-substituted."

(ix) FEATURE:
(A) NAME/KEY: Modified-site
(B) LOCATION: 25
(C) OTHER INFORMATION: /label= Substituted-Ala
/note= "Position 25 is beta-1-naphthyl-substituted."

(ix) FEATURE:
(A) NAME/KEY: Modified-site
(B) LOCATION: 26
(C) OTHER INFORMATION: /label= Substituted-Ala
/note= "Position 26 is beta-1-naphthyl-substituted."

(xi) SEQUENCE DESCRIPTION: SEQ ID NO:153:

```
Lys Trp Lys Ala Ala Ala Arg Phe Leu Lys Lys Trp Lys Ala Ala Ala
1               5                   10                  15

Arg Phe Leu Lys Lys Trp Lys Ala Ala Ala Arg Phe Leu Lys
            20                  25                  30
```

(2) INFORMATION FOR SEQ ID NO:154:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.158"

(ix) FEATURE:
(A) NAME/KEY: Modified-site
(B) LOCATION: 10
(C) OTHER INFORMATION: /label= Substituted-Ala
/note= "Position 10 is beta-1-naphthyl-substituted."

(ix) FEATURE:
(A) NAME/KEY: Modified-site
(B) LOCATION: 11
(C) OTHER INFORMATION: /label= Substituted-Ala
/note= "Position 11 is beta-1-naphthyl-substituted."

(xi) SEQUENCE DESCRIPTION: SEQ ID NO:154:

```
Ile Lys Ile Ser Gly Lys Trp Lys Ala Ala Ala Arg Phe Leu Lys Lys
1               5                   10                  15

Ser Lys Val Gly Trp Leu Ile Gln Leu Phe His Lys Lys
            20                  25
```

(2) INFORMATION FOR SEQ ID NO:155:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.159"

(ix) FEATURE:
(A) NAME/KEY: Modified-site
(B) LOCATION: 2
(C) OTHER INFORMATION: /label= Substituted-Ala -continued /note= "Position 2 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(xi) SEQUENCE DESCRIPTION: SEQ ID NO:155:

```
Lys Ala Lys Ala Gln Ala Arg Phe Leu Lys Lys Ser Lys Val Gly Trp
1               5                   10                  15

Leu Ile Gln Leu Trp His Lys Lys
            20
```

(2) INFORMATION FOR SEQ ID NO:156:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.160"

(ix) FEATURE:
(A) NAME/KEY: Modified-site
(B) LOCATION: 2
(C) OTHER INFORMATION: /label= Substituted-Ala
/note= "Position 2 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(ix) FEATURE:
(A) NAME/KEY: Modified-site
(B) LOCATION: 16
(C) OTHER INFORMATION: /label= Substituted-Ala
/note= "Position 16 is
beta-1-naphthyl-substituted."

(xi) SEQUENCE DESCRIPTION: SEQ ID NO:156:

```
Lys Ala Lys Ala Gln Ala Arg Phe Leu Lys Lys Ala Lys Ala Gln Ala
1               5                   10                  15

Arg Phe Leu Lys
            20
```

(2) INFORMATION FOR SEQ ID NO:157:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.161"

(xi) SEQUENCE DESCRIPTION: SEQ ID NO:157:

```
Lys Ser Lys Val Lys Ala Leu Ile Gln Leu Phe His Lys Lys
1               5                   10
```

(2) INFORMATION FOR SEQ ID NO:158:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.162"

(xi) SEQUENCE DESCRIPTION: SEQ ID NO:158:

```
Lys Trp Lys Ala Gln Trp Arg Phe Leu Lys Lys Ser Lys Val Gly Trp
1               5                   10                  15

Leu Ile Gln Leu Phe His Lys Lys
            20
```

(2) INFORMATION FOR SEQ ID NO:159:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.163"

(xi) SEQUENCE DESCRIPTION: SEQ ID NO:159:

```
Lys Trp Lys Ala Gln Trp Arg Phe Leu Lys Lys Trp Lys Ala Gln Trp
1               5                   10                  15

Arg Phe Leu Lys
            20
```

(2) INFORMATION FOR SEQ ID NO:160:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.164"

(ix) FEATURE:
(A) NAME/KEY: Modified-site
(B) LOCATION: 5
(C) OTHER INFORMATION: /label= Substituted-Ala
/note= "Position 5 is
beta-1-naphthyl-substituted."

(ix) FEATURE:
(A) NAME/KEY: Modified-site
(B) LOCATION: 15
(C) OTHER INFORMATION: /label= Substituted-Ala
/note= "Position 15 is
beta-1-naphthyl-substituted."

-continued (xi) SEQUENCE DESCRIPTION: SEQ ID NO:160:

Lys Trp Lys Ala Ala Lys Arg Phe Leu Lys Lys Trp Lys Ala Ala Lys
1 5 10 15

Arg Phe Leu Lys
20

(2) INFORMATION FOR SEQ ID NO:161:

(i) SEQUENCE CHARACTERISTICS:
(A) LENGTH: 20 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.165"

(ix) FEATURE:
(A) NAME/KEY: Modified-site
(B) LOCATION: 2
(C) OTHER INFORMATION: /label= Substituted-Ala
/note= "Position 2 is
beta-1-naphthyl-substituted."

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(xi) SEQUENCE DESCRIPTION: SEQ ID NO:161:

Lys Ala Lys Ala Gln Phe Arg Phe Leu Lys Lys Ala Lys Ala Gln Phe
1 5 10 15

Arg Phe Leu Lys
20

(2) INFORMATION FOR SEQ ID NO:162:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.166"

(xi) SEQUENCE DESCRIPTION: SEQ ID NO:162:

Lys Ser Lys Val Gly Val Leu Ile Gln Leu Phe His Lys Lys
1 5 10

(2) INFORMATION FOR SEQ ID NO:163:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.167"

(xi) SEQUENCE DESCRIPTION: SEQ ID NO:163:

-continued

Lys Trp Lys Ala Gln Lys Arg Phe
1 5

(2) INFORMATION FOR SEQ ID NO:164:

(i) SEQUENCE CHARACTERISTICS:
(A) LENGTH: 14 amino acids
(B) TYPE: amino acid
(D) TOPOLOGY: circular (ii) MOLECULE TYPE: peptide (ix) FEATURE:
(A) NAME/KEY: misc_feature
(D) OTHER INFORMATION: "XMP.168"

(xi) SEQUENCE DESCRIPTION: SEQ ID NO:164:

Cys Lys Trp Lys Ala Gln Lys Arg Phe Leu Lys Met Ser Cys
1 5 10

(2) INFORMATION FOR SEQ ID NO:165:

(i) SEQUENCE CHARACTERISTICS:
(A) LENGTH: 10 amino acids
(B) TYPE: amino acid
(D) TOPOLOGY: circular (ii) MOLECULE TYPE: peptide (ix) FEATURE:
(A) NAME/KEY: misc_feature
(D) OTHER INFORMATION: "XMP.169"

(xi) SEQUENCE DESCRIPTION: SEQ ID NO:165:

Cys Lys Trp Lys Ala Gln Lys Arg Phe Cys
1 5 10

(2) INFORMATION FOR SEQ ID NO:166:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.221"

(ix) FEATURE:
(A) NAME/KEY: Modified-site
(B) LOCATION: 13
(C) OTHER INFORMATION: /label= Substituted-Ala
/note= "Position 13 is
beta-1-naphthyl-substituted."

(xi) SEQUENCE DESCRIPTION: SEQ ID NO:166:

Ile Lys Ile Ser Gly Lys Trp Lys Ala Gln Lys Arg Ala Leu Lys
1 5 10 15

(2) INFORMATION FOR SEQ ID NO:167:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.222"

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 14
(C) OTHER INFORMATION: /label= Substituted-Ala
/note= "Position 14 is
beta-1-naphthyl-substituted."

(xi) SEQUENCE DESCRIPTION: SEQ ID NO:167:

Lys Ser Lys Val Gly Ala Leu Ile Gln Leu Phe His Lys Ala
1               5                   10

(2) INFORMATION FOR SEQ ID NO:168:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.223"

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(xi) SEQUENCE DESCRIPTION: SEQ ID NO:168:

Lys Ser Lys Val Gly Ala Leu Ile Gln Ala Phe His Lys Lys
1               5                   10

(2) INFORMATION FOR SEQ ID NO:169:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.224"

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 9

-continued (C) OTHER INFORMATION: /label= Substituted-Phe
/note= "Position 9 is
para-amino-substituted."

(xi) SEQUENCE DESCRIPTION: SEQ ID NO:169:

Lys Ser Lys Val Gly Ala Leu Ile Phe Leu Phe His Lys Lys
1 5 10

(2) INFORMATION FOR SEQ ID NO:170:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.225"

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 5
(C) OTHER INFORMATION: /label= Substituted-Phe
/note= "Position 5 is
para-amino-substituted."

(xi) SEQUENCE DESCRIPTION: SEQ ID NO:170:

Lys Ser Lys Val Phe Ala Leu Ile Gln Leu Phe His Lys Lys
1 5 10

(2) INFORMATION FOR SEQ ID NO:171:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.226"

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(xi) SEQUENCE DESCRIPTION: SEQ ID NO:171:

Lys Ser Lys Val Gly Ala Leu Ile Gln Leu Trp His Lys Lys
1 5 10

(2) INFORMATION FOR SEQ ID NO:172:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.227"

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(ix) FEATURE:
(A) NAME/KEY: Modified-site
(B) LOCATION: 14
(C) OTHER INFORMATION: /label= Substituted-Ala
/note= "Position 14 is
beta-1-naphthyl-substituted."

(xi) SEQUENCE DESCRIPTION: SEQ ID NO:172:

```
Lys Ser Lys Val Gly Trp Leu Ile Gln Ala Phe His Lys Ala
1               5                   10
```

(2) INFORMATION FOR SEQ ID NO:173:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.228"

(ix) FEATURE:
(A) NAME/KEY: Modified-site
(B) LOCATION: 9
(C) OTHER INFORMATION: /label= Substituted-Phe
/note= "Position 9 is
para-amino-substituted."

(ix) FEATURE:
(A) NAME/KEY: Modified-site
(B) LOCATION: 14
(C) OTHER INFORMATION: /label= Substituted-Ala
/note= "Position 14 is
beta-1-naphthyl-substituted."

(xi) SEQUENCE DESCRIPTION: SEQ ID NO:173:

```
Lys Ser Lys Val Gly Trp Leu Ile Phe Leu Phe His Lys Ala
1               5                   10
```

(2) INFORMATION FOR SEQ ID NO:174:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.229"

(ix) FEATURE:
(A) NAME/KEY: Modified-site
(B) LOCATION: 5
(C) OTHER INFORMATION: /label= Substituted-Ala
/note= "Position 5 is
para-amino-substituted."

(ix) FEATURE:
(A) NAME/KEY: Modified-site
(B) LOCATION: 14

-continued (C) OTHER INFORMATION: /label= Substituted-Ala
/note= "Position 14 is
beta-1-naphthyl-substituted."

(xi) SEQUENCE DESCRIPTION: SEQ ID NO:174:

Lys Ser Lys Val Phe Trp Leu Ile Gln Leu Phe His Lys Ala
1 5 10

(2) INFORMATION FOR SEQ ID NO:175:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.230"

(ix) FEATURE:
(A) NAME/KEY: Modified-site
(B) LOCATION: 14
(C) OTHER INFORMATION: /label= Substituted-Ala
/note= "Position 14 is
beta-1-naphthyl-substituted."

(xi) SEQUENCE DESCRIPTION: SEQ ID NO:175:

Lys Ser Lys Val Gly Trp Leu Ile Gln Leu Trp His Lys Ala
1 5 10

(2) INFORMATION FOR SEQ ID NO:176:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.231"

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(xi) SEQUENCE DESCRIPTION: SEQ ID NO:176:

Lys Ser Lys Val Gly Trp Leu Ile Gln Ala Phe Ala Lys Lys
1 5 10

(2) INFORMATION FOR SEQ ID NO:177:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.232"

(ix) FEATURE:
(A) NAME/KEY: Modified-site
(B) LOCATION: 9
(C) OTHER INFORMATION: /label= Substituted-Phe
/note= "Position 9 is
para-amino-substituted."

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(xi) SEQUENCE DESCRIPTION: SEQ ID NO:177:

```
Lys Ser Lys Val Gly Trp Leu Ile Phe Leu Phe Ala Lys Lys
1               5                   10
```

(2) INFORMATION FOR SEQ ID NO:178:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.233"

(ix) FEATURE:
(A) NAME/KEY: Modified-site
(B) LOCATION: 5
(C) OTHER INFORMATION: /label= Substituted-Phe
/note= "Position 5 is
para-amino-substituted."

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(xi) SEQUENCE DESCRIPTION: SEQ ID NO:178:

```
Lys Ser Lys Val Phe Trp Leu Ile Gln Leu Phe Ala Lys Lys
1               5                   10
```

(2) INFORMATION FOR SEQ ID NO:179:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.234"

(ix) FEATURE:
(A) NAME/KEY: Modified-site
(B) LOCATION: 12
(C) OTHER INFORMATION: /label= Substituted-Ala
/note= "Position 12 is
beta-1-naphthyl-substituted."

(xi) SEQUENCE DESCRIPTION: SEQ ID NO:179:

```
Lys Ser Lys Val Gly Trp Leu Ile Gln Leu Trp Ala Lys Lys
```

-continued 1 5 10

(2) INFORMATION FOR SEQ ID NO:180:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.235"

(ix) FEATURE:
(A) NAME/KEY: Modified-site
(B) LOCATION: 9
(C) OTHER INFORMATION: /label= Substituted-Phe
/note= "Position 9 is
para-amino-substituted."

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(xi) SEQUENCE DESCRIPTION: SEQ ID NO:180:

Lys Ser Lys Val Gly Trp Leu Ile Phe Ala Phe His Lys Lys
1 5 10

(2) INFORMATION FOR SEQ ID NO:181:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.236"

(ix) FEATURE:
(A) NAME/KEY: Modified-site
(B) LOCATION: 5
(C) OTHER INFORMATION: /label= Substituted-Phe
/note= "Position 5 is
para-amino-substituted."

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(xi) SEQUENCE DESCRIPTION: SEQ ID NO:181:

Lys Ser Lys Val Phe Trp Leu Ile Gln Ala Phe His Lys Lys
1 5 10

(2) INFORMATION FOR SEQ ID NO:182:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:

-continued (A) NAME/KEY: misc_feature
(D) OTHER INFORMATION: "XMP.237"

(ix) FEATURE:
(A) NAME/KEY: Modified-site
(B) LOCATION: 10
(C) OTHER INFORMATION: /label= Substituted-Ala
/note= "Position 10 is
beta-1-naphthyl-substituted."

(xi) SEQUENCE DESCRIPTION: SEQ ID NO:182:

```
Lys Ser Lys Val Gly Trp Leu Ile Gln Ala Trp His Lys Lys
1               5                   10
```

(2) INFORMATION FOR SEQ ID NO:183:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.238"

(ix) FEATURE:
(A) NAME/KEY: Modified-site
(B) LOCATION: 5
(C) OTHER INFORMATION: /label= Substituted-Phe
/note= "Position 5 is
para-amino-substituted."

(ix) FEATURE:
(A) NAME/KEY: Modified-site
(B) LOCATION: 9
(C) OTHER INFORMATION: /label= Substituted-Phe
/note= "Position 9 is
para-amino-substituted."

(xi) SEQUENCE DESCRIPTION: SEQ ID NO:183:

```
Lys Ser Lys Val Phe Trp Leu Ile Phe Leu Phe His Lys Lys
1               5                   10
```

(2) INFORMATION FOR SEQ ID NO:184:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.239"

(ix) FEATURE:
(A) NAME/KEY: Modified-site
(B) LOCATION: 9
(C) OTHER INFORMATION: /label= Substituted-Phe
/note= "Position 9 is
para-amino-substituted."

(xi) SEQUENCE DESCRIPTION: SEQ ID NO:184:

```
Lys Ser Lys Val Gly Trp Leu Ile Phe Leu Trp His Lys Lys
1               5                   10
```

(2) INFORMATION FOR SEQ ID NO:185:

(i) SEQUENCE CHARACTERISTICS:
(A) LENGTH: 14 amino acids

-continued (B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.240"

(ix) FEATURE:
(A) NAME/KEY: Modified-site
(B) LOCATION: 5
(C) OTHER INFORMATION: /label= Substituted-Phe
/note= "Position 5 is
para-amino-substituted."

(xi) SEQUENCE DESCRIPTION: SEQ ID NO:185:

```
Lys Ser Lys Val Phe Trp Leu Ile Gln Leu Trp His Lys Lys
1               5                   10
```

(2) INFORMATION FOR SEQ ID NO:186:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.247"

(ix) FEATURE:
(A) NAME/KEY: Modified-site
(B) LOCATION: 2
(C) OTHER INFORMATION: /label= Substituted-Ala
/note= "Position 2 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(xi) SEQUENCE DESCRIPTION: SEQ ID NO:186:

```
Lys Ala Lys Ala Gln Ala Arg Phe Leu Lys Lys Ser Lys Val Gly Trp
1               5                   10                  15

Leu Ile Leu Leu Phe His Lys Lys
            20
```

(2) INFORMATION FOR SEQ ID NO:187:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.245"

(xi) SEQUENCE DESCRIPTION: SEQ ID NO:187:

```
Lys Trp Lys Ala Gln Phe Arg Phe Leu Lys Lys Ser Lys Val Gly Trp
1               5                   10                  15

Leu Ile Gln Leu Trp His Lys Lys
            20
```

-continued (2) INFORMATION FOR SEQ ID NO:188:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.246"

(ix) FEATURE:
(A) NAME/KEY: Modified-site
(B) LOCATION: 16
(C) OTHER INFORMATION: /label= Substituted-Ala
/note= "Position 16 is
D-beta-2-naphthyl-substituted."

(xi) SEQUENCE DESCRIPTION: SEQ ID NO:188:

```
Lys Trp Lys Ala Gln Phe Arg Phe Leu Lys Lys Ser Lys Val Gly Ala
1               5                   10                  15

Leu Ile Gln Leu Phe His Lys Lys
            20
```

(2) INFORMATION FOR SEQ ID NO:189:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.248"

(ix) FEATURE:
(A) NAME/KEY: Modified-site
(B) LOCATION: 2
(C) OTHER INFORMATION: /label= Substituted-Ala
/note= "Position 2 is
beta-1-naphthyl-substituted."

(ix) FEATURE:
(A) NAME/KEY: Modified-site
(B) LOCATION: 6
(C) OTHER INFORMATION: /label= Substituted-Ala
/note= "Position 6 is
beta-1-naphthyl-substituted."

(ix) FEATURE:
(A) NAME/KEY: Modified-site
(B) LOCATION: 16
(C) OTHER INFORMATION: /label= Substituted-Ala
/note= "Position 16 is
D-beta-2-naphthyl-substituted."

(xi) SEQUENCE DESCRIPTION: SEQ ID NO:189:

```
Lys Ala Lys Ala Gln Ala Arg Phe Leu Lys Lys Ser Lys Val Gly Ala
1               5                   10                  15

Leu Ile Gln Leu Phe His Lys Lys
            20
```

(2) INFORMATION FOR SEQ ID NO:190:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.242"

(ix) FEATURE:
(A) NAME/KEY: Modified-site
(B) LOCATION: 6
(C) OTHER INFORMATION: /label= Substituted-Ala
/note= "Position 6 is
D-beta-2-naphthyl-substituted."

(xi) SEQUENCE DESCRIPTION: SEQ ID NO:190:

```
Lys Ser Lys Val Gly Ala Leu Ile Leu Leu Phe His Lys Lys
1               5                   10
```

(2) INFORMATION FOR SEQ ID NO:191:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.272"

(xi) SEQUENCE DESCRIPTION: SEQ ID NO:191:

```
Lys Ser Lys Val Gly Trp Leu Ile Leu Leu Phe His Lys Lys Lys Ser
1               5                   10                  15

Lys Val Gly Trp Leu Ile Leu Leu Phe His Lys Lys
            20                  25
```

(2) INFORMATION FOR SEQ ID NO:192:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.275"

(xi) SEQUENCE DESCRIPTION: SEQ ID NO:192:

```
Lys Ser Lys Val Gly Trp Leu Ile Phe Leu Phe His Lys Lys Lys Ser
1               5                   10                  15

Lys Val Gly Trp Leu Ile Phe Leu Phe His Lys Lys
            20                  25
```

(2) INFORMATION FOR SEQ ID NO:193:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.270"

(xi) SEQUENCE DESCRIPTION: SEQ ID NO:193:

-continued

Lys Ser Lys Val Gly Trp Leu Ile Leu Leu Phe His Lys Lys Lys Ser
1 5 10 15

Lys Val Gly Trp Leu Ile Gln Leu Phe His Lys Lys
20 25

(2) INFORMATION FOR SEQ ID NO:194:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.271"

(xi) SEQUENCE DESCRIPTION: SEQ ID NO:194:

Lys Ser Lys Val Gly Trp Leu Ile Gln Leu Phe His Lys Lys Lys Ser
1 5 10 15

Lys Val Gly Trp Leu Ile Leu Leu Phe His Lys Lys
20 25

(2) INFORMATION FOR SEQ ID NO:195:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.273"

(xi) SEQUENCE DESCRIPTION: SEQ ID NO:195:

Lys Ser Lys Val Gly Trp Leu Ile Phe Leu Phe His Lys Lys Lys Ser
1 5 10 15

Lys Val Gly Trp Leu Ile Gln Leu Phe His Lys Lys
20 25

(2) INFORMATION FOR SEQ ID NO:196:

(i) SEQUENCE CHARACTERISTICS:
(A) LENGTH: 28 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.274"

(xi) SEQUENCE DESCRIPTION: SEQ ID NO:196:

Lys Ser Lys Val Gly Trp Leu Ile Gln Leu Phe His Lys Lys Lys Ser
1 5 10 15

Lys Val Gly Trp Leu Ile Phe Leu Phe His Lys Lys
20 25

(2) INFORMATION FOR SEQ ID NO:197:

(i) SEQUENCE CHARACTERISTICS:
(A) LENGTH: 24 amino acids
(B) TYPE: amino acid
(D) TOPOLOGY: linear -continued (ii) MOLECULE TYPE: peptide (ix) FEATURE:
(A) NAME/KEY: misc_feature
(D) OTHER INFORMATION: "XMP.276"

(xi) SEQUENCE DESCRIPTION: SEQ ID NO:197:

```
Lys Trp Lys Ala Gln Phe Arg Phe Leu Lys Lys Ser Lys Val Gly Trp
1               5                   10                  15

Leu Ile Phe Leu Phe His Lys Lys
            20
```

(2) INFORMATION FOR SEQ ID NO:198:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.241"

(xi) SEQUENCE DESCRIPTION: SEQ ID NO:198:

```
Lys Ser Lys Val Gly Trp Leu Ile Leu Leu Trp His Lys Lys
1               5                   10
```

(2) INFORMATION FOR SEQ ID NO:199:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.243"

(ix) FEATURE:
(A) NAME/KEY: Modified-site
(B) LOCATION: 6
(C) OTHER INFORMATION: /label= Substituted-Ala
/note= "Position 6 is
D-beta-2-naphthyl-substituted."

(xi) SEQUENCE DESCRIPTION: SEQ ID NO:199:

```
Lys Ser Lys Val Gly Ala Leu Ile Gln Leu Trp His Lys Lys
1               5                   10
```

(2) INFORMATION FOR SEQ ID NO:200:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.244"

(ix) FEATURE:
(A) NAME/KEY: Modified-site
(B) LOCATION: 6
(C) OTHER INFORMATION: /label= Substituted-Ala
/note= "Position 6 is -continued D-beta-2-naphthyl-substituted."

(xi) SEQUENCE DESCRIPTION: SEQ ID NO:200:

```
Lys Ser Lys Val Gly Ala Leu Ile Leu Leu Trp His Lys Lys
1               5                   10
```

(2) INFORMATION FOR SEQ ID NO:201:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.249"

(xi) SEQUENCE DESCRIPTION: SEQ ID NO:201:

```
Lys Ser Lys Val Gly Gly Leu Ile Gln Leu Phe His Lys Lys
1               5                   10
```

(2) INFORMATION FOR SEQ ID NO:202:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.250"

(xi) SEQUENCE DESCRIPTION: SEQ ID NO:202:

```
Lys Ser Lys Val Gly Leu Leu Ile Gln Leu Phe His Lys Lys
1               5                   10
```

(2) INFORMATION FOR SEQ ID NO:203:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.251"

(xi) SEQUENCE DESCRIPTION: SEQ ID NO:203:

```
Lys Ser Lys Val Gly Ile Leu Ile Gln Leu Phe His Lys Lys
1               5                   10
```

(2) INFORMATION FOR SEQ ID NO:204:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.252"

(ix) FEATURE:

(A) NAME/KEY: Modified-site
(B) LOCATION: 6
(D) OTHER INFORMATION: /label= D-Ala
/note= "The amino acid at position 6 is
D-alanine"

(xi) SEQUENCE DESCRIPTION: SEQ ID NO:204:

Lys Ser Lys Val Gly Ala Leu Ile Gln Leu Phe His Lys Lys
1 5 10

(2) INFORMATION FOR SEQ ID NO:205:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.253"

(ix) FEATURE:
(A) NAME/KEY: Modified-site
(B) LOCATION: 6
(D) OTHER INFORMATION: /label= D-Val
/note= "The amino acid at position 6 is
D-valine"

(xi) SEQUENCE DESCRIPTION: SEQ ID NO:205:

Lys Ser Lys Val Gly Val Leu Ile Gln Leu Phe His Lys Lys
1 5 10

(2) INFORMATION FOR SEQ ID NO:206:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.254"

(ix) FEATURE:
(A) NAME/KEY: Modified-site
(B) LOCATION: 6
(D) OTHER INFORMATION: /label= beta-Ala
/note= "The amino acid at position 6 is
beta-alanine"

(xi) SEQUENCE DESCRIPTION: SEQ ID NO:206:

Lys Ser Lys Val Gly Ala Leu Ile Gln Leu Phe His Lys Lys
1 5 10

(2) INFORMATION FOR SEQ ID NO:207:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.255"

(ix) FEATURE:
(A) NAME/KEY: Modified-site

-continued (B) LOCATION: 6
(D) OTHER INFORMATION: /label= delta-aba
/note= "The amino acid at position 6 is
delta-aminobutyric acid"

(xi) SEQUENCE DESCRIPTION: SEQ ID NO:207:

Lys Ser Lys Val Gly Xaa Leu Ile Gln Leu Phe His Lys Lys
1 5 10

(2) INFORMATION FOR SEQ ID NO:208:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.256"

(ix) FEATURE:
(A) NAME/KEY: Modified-site
(B) LOCATION: 6
(D) OTHER INFORMATION: /label= gaba
/note= "The amino acid at position 6 is
gamma-aminobutyric acid"

(xi) SEQUENCE DESCRIPTION: SEQ ID NO:208:

Lys Ser Lys Val Gly Xaa Leu Ile Gln Leu Phe His Lys Lys
1 5 10

(2) INFORMATION FOR SEQ ID NO:209:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.257"

(ix) FEATURE:
(A) NAME/KEY: Modified-site
(B) LOCATION: 6
(D) OTHER INFORMATION: /label= d-methyl-A
/note= "The amino acid at position 6 is
delta-Methyl-alanine"

(xi) SEQUENCE DESCRIPTION: SEQ ID NO:209:

Lys Ser Lys Val Gly Ala Leu Ile Gln Leu Phe His Lys Lys
1 5 10

(2) INFORMATION FOR SEQ ID NO:210:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.258"

(ix) FEATURE:
(A) NAME/KEY: Modified-site
(B) LOCATION: 6

-continued (D) OTHER INFORMATION: /label= t-butyl-G
/note= "The amino acid at position 6 is
tert-butyl-glycine"

(xi) SEQUENCE DESCRIPTION: SEQ ID NO:210:

Lys Ser Lys Val Gly Gly Leu Ile Gln Leu Phe His Lys Lys
1 5 10

(2) INFORMATION FOR SEQ ID NO:211:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.259"

(ix) FEATURE:
(A) NAME/KEY: Modified-site
(B) LOCATION: 6
(D) OTHER INFORMATION: /label= N-methyl-G
/note= "The amino acid at position 6 is
N-Methyl-glycine"

(xi) SEQUENCE DESCRIPTION: SEQ ID NO:211:

Lys Ser Lys Val Gly Gly Leu Ile Gln Leu Phe His Lys Lys
1 5 10

(2) INFORMATION FOR SEQ ID NO:212:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.260"

(ix) FEATURE:
(A) NAME/KEY: Modified-site
(B) LOCATION: 6
(D) OTHER INFORMATION: /label= N-methyl-V
/note= "The amino acid at position 6 is
N-Methyl-valine"

(xi) SEQUENCE DESCRIPTION: SEQ ID NO:212:

Lys Ser Lys Val Gly Val Leu Ile Gln Leu Phe His Lys Lys
1 5 10

(2) INFORMATION FOR SEQ ID NO:213:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.261"

(ix) FEATURE:
(A) NAME/KEY: Modified-site
(B) LOCATION: 6
(D) OTHER INFORMATION: /label= N-methyl-L -continued /note= "The amino acid at position 6 is N-Methyl-leucine"

(xi) SEQUENCE DESCRIPTION: SEQ ID NO:213:

```
Lys Ser Lys Val Gly Leu Leu Ile Gln Leu Phe His Lys Lys
1               5                   10
```

(2) INFORMATION FOR SEQ ID NO:214:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.262"

(xi) SEQUENCE DESCRIPTION: SEQ ID NO:214:

```
Lys Ser Lys Val Gly Trp Leu Ile Asn Leu Phe His Lys Lys
1               5                   10
```

(2) INFORMATION FOR SEQ ID NO:215:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.263"

(xi) SEQUENCE DESCRIPTION: SEQ ID NO:215:

```
Lys Ser Lys Val Gly Trp Leu Ile Glu Leu Phe His Lys Lys
1               5                   10
```

(2) INFORMATION FOR SEQ ID NO:216:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.264"

(xi) SEQUENCE DESCRIPTION: SEQ ID NO:216:

```
Lys Ser Lys Val Gly Trp Leu Ile Asp Leu Phe His Lys Lys
1               5                   10
```

(2) INFORMATION FOR SEQ ID NO:217:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.265"

-continued (xi) SEQUENCE DESCRIPTION: SEQ ID NO:217:

Lys Ser Lys Val Gly Trp Leu Ile Lys Leu Phe His Lys Lys
1 5 10

(2) INFORMATION FOR SEQ ID NO:218:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.266"

(xi) SEQUENCE DESCRIPTION: SEQ ID NO:218:

Lys Ser Lys Val Lys Val Leu Ile Gln Leu Phe His Lys Lys
1 5 10

(2) INFORMATION FOR SEQ ID NO:219:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.267"

(xi) SEQUENCE DESCRIPTION: SEQ ID NO:219:

Lys Ser Lys Val Lys Trp Ala Ile Gln Leu Phe His Lys Lys
1 5 10

(2) INFORMATION FOR SEQ ID NO:220:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.268"

(xi) SEQUENCE DESCRIPTION: SEQ ID NO:220:

Lys Ser Lys Val Gly Val Ala Ile Gln Leu Phe His Lys Lys
1 5 10

(2) INFORMATION FOR SEQ ID NO:221:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.269"

(xi) SEQUENCE DESCRIPTION: SEQ ID NO:221:

Lys Ser Lys Val Lys Val Ala Ile Gln Leu Phe His Lys Lys

-continued 1 5 10

(2) INFORMATION FOR SEQ ID NO:222:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.277"

(ix) FEATURE:
(A) NAME/KEY: Modified-site
(B) LOCATION: 2
(C) OTHER INFORMATION: /label= Substituted-Ala
/note= "The alanine at position 2 is
beta-1-naphthyl-substituted."

(xi) SEQUENCE DESCRIPTION: SEQ ID NO:222:

Lys Ala Lys Ala Gln Phe Arg Phe Leu Lys Lys Ser Lys Val Gly Trp
1 5 10 15

Leu Ile Leu Leu Phe His Lys Lys
20

(2) INFORMATION FOR SEQ ID NO:223:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.278"

(xi) SEQUENCE DESCRIPTION: SEQ ID NO:223:

Ile Lys Ile Ser Gly Lys Trp Lys Ala Ala Trp Arg Phe Leu Lys
1 5 10 15

(2) INFORMATION FOR SEQ ID NO:224:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.279"

(ix) FEATURE:
(A) NAME/KEY: Modified-site
(B) LOCATION: 10
(C) OTHER INFORMATION: /label= Substituted-Ala
/note= "The alanine at position 10 is
beta-1-naphthyl-substituted."

(xi) SEQUENCE DESCRIPTION: SEQ ID NO:224:

Ile Lys Ile Ser Gly Lys Trp Lys Ala Ala Phe Arg Phe Leu Lys
1 5 10 15

(2) INFORMATION FOR SEQ ID NO:225:

-continued (i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.280"

(xi) SEQUENCE DESCRIPTION: SEQ ID NO:225:

```
Ile Lys Ile Ser Gly Lys Trp Lys Ala Ala Phe Arg Phe Leu Lys
1               5                   10                  15
```

(2) INFORMATION FOR SEQ ID NO:226:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.281"

(ix) FEATURE:
(A) NAME/KEY: Modified-site
(B) LOCATION: 10
(C) OTHER INFORMATION: /label= Substituted-Ala
/note= "The alanine at position 10 is
beta-1-naphthyl-substituted."

(xi) SEQUENCE DESCRIPTION: SEQ ID NO:226:

```
Ile Lys Ile Ser Gly Lys Trp Lys Ala Ala Ala Arg Phe Leu Lys
1               5                   10                  15
```

(2) INFORMATION FOR SEQ ID NO:227:

(i) SEQUENCE CHARACTERISTICS:
(A) LENGTH: 12 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.170"

(xi) SEQUENCE DESCRIPTION: SEQ ID NO:227:

```
Lys Trp Lys Ala Gln Lys Arg Phe Leu Lys Met Ser
1               5                   10
```

(2) INFORMATION FOR SEQ ID NO:228:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "LBP-10"

(xi) SEQUENCE DESCRIPTION: SEQ ID NO:228:

```
GAGATCGATA GTTTCGCCGA C                                              21
```

(2) INFORMATION FOR SEQ ID NO:229:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "LBP-11"

(xi) SEQUENCE DESCRIPTION: SEQ ID NO:229:

ACTATCGATC TCTGTTGTAA 20

(2) INFORMATION FOR SEQ ID NO:230:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "LBP-BSM"

(xi) SEQUENCE DESCRIPTION: SEQ ID NO:230:

GAATGCAGCC AACCCCGGCT TGGTCGCCA 29

(2) INFORMATION FOR SEQ ID NO:231:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "LBP-8"

(xi) SEQUENCE DESCRIPTION: SEQ ID NO:231:

CTGGCTAACC GTGGGACG 18

(2) INFORMATION FOR SEQ ID NO:232:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "BPI-63"

(xi) SEQUENCE DESCRIPTION: SEQ ID NO:232:

AAAATCGATT CTGTGGCTGG 20

(2) INFORMATION FOR SEQ ID NO:233:

-continued (i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "BPI-64"

(xi) SEQUENCE DESCRIPTION: SEQ ID NO:233:

AGAATCGATT TTGGTCATTA 20

(2) INFORMATION FOR SEQ ID NO:234:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "BPI-40"

(xi) SEQUENCE DESCRIPTION: SEQ ID NO:234:

TGATCTGAAG CTGGGCAG 18

(2) INFORMATION FOR SEQ ID NO:235:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: misc_feature
(D) OTHER INFORMATION: "BPI-7"

(xi) SEQUENCE DESCRIPTION: SEQ ID NO:235:

GAACTTGGTT GTCAGTCG 18

(2) INFORMATION FOR SEQ ID NO:236:

(i) SEQUENCE CHARACTERISTICS:
(A) LENGTH: 27 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "LBP Peptide 1-2"

(xi) SEQUENCE DESCRIPTION: SEQ ID NO:236:

```
Gly Gln Gly Leu Ser Leu Ser Ile Ser Asp Ser Ser Ile Arg Val Gln
1               5                   10                  15

Gly Arg Trp Lys Val Arg Lys Ser Phe Phe Lys
            20                  25
```

(2) INFORMATION FOR SEQ ID NO:237:

-continued

```
    (i) SEQUENCE CHARACTERISTICS:
          (A) LENGTH: 22 amino acids
          (B) TYPE: amino acid
          (D) TOPOLOGY: linear

   (ii) MOLECULE TYPE: peptide

   (ix) FEATURE:
          (A) NAME/KEY: misc_feature
          (D) OTHER INFORMATION: "LBP Peptide 2-1"

   (xi) SEQUENCE DESCRIPTION: SEQ ID NO:237:

Asp Val Glu Val Asp Met Ser Gly Asp Leu Gly Trp Leu Leu Asn Leu
1               5                   10                  15

Phe His Asn Gln Ile Glu
            20
```

ANTI-GRAM-POSITIVE BACTERIAL METHODS AND MATERIALS

This is a Continuation of U.S. application Ser. No. 08/758,116, filed Nov. 25, 1996, now U.S. Pat. No. 5,783,561, which is a continuation of U.S. application Ser. No. 08/372,783, filed Jan. 13, 1995, now U.S. Pat. No. 5,578,572, which is a continuation-in-part of U.S. patent application Ser. No. 08/274,299 filed Jul. 11, 1994, now abandoned, which is a continuation-in-part of U.S. patent application Ser. No. 08/209,762 filed Mar. 11, 1994, now U.S. Pat. No. 5,733,872, which is a continuation-in-part of U.S. patent application Ser. No. 08/183,222 filed Jan. 14, 1994, now abandoned, all of which are incorporated herein by reference.

BACKGROUND OF THE INVENTION

The present invention relates generally to methods and materials for treating gram-positive bacterial infections by administration of bactericidal/permeability-increasing (BPI) protein products alone, or in combination with antibiotic substances. Also disclosed are analogous methods and materials involving use of lipopolysaccharide binding protein (LBP) derivatives.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood,* 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 69 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.,* 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.,* 174:649 (1991).] An N-terminal BPI fragment of approximately 23 kD, referred to as "$rBPI_{23}$," has been produced by recombinant means and also retains antibacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates, eds. Gallin et al., Chapter* 30, Raven Press, Ltd. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^{-6}$ M or 160 $\mu$g/ml had no toxic effect, when tested at a pH of either 7.0 or 5.5, on the gram-positive organisms *Staphylococcus aureus* (four strains), *Staphlococcus epidermidis, Streptococcus faecalis, Bacillus subtilis, Micrococcus lysodeikticus,* and *Listeria monocytogenes.* BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research,* ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.,* 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organisms and which may be situated at the cytoplasmic membrane (Mannion et al., *J. Clin. Invest.* 86: 631–641 (1990). Specific investigation of this possibility has shown that on a molar basis BPI is at least as inhibitory of cytoplasmic membrane vesicle function as polymyxin B (Int'l Veld et al., *Infection and Immunity* 56: 1203–1208 (1988)) but the exact mechanism as well as the relevance of such vesicles to studies of intact organisms has not yet been elucidated.

BPI is also capable of neutralizing the endotoxic properties of LPS to which it binds. Because of its bactericidal properties for gram-negative organisms and its ability to neutralize LPS, BPI can be utilized for the treatment of mammals suffering from diseases caused by gram-negative bacteria, such as bacteremia or sepsis.

U.S. Pat. No. 5,198,541 discloses recombinant genes encoding and methods for expression of BPI proteins, including BPI holoprotein and fragments of BPI. It also describes the use of N-terminal fragments of BPI protein for co-treatment of gram-negative bacterial diseases with certain antibiotics, specifically penicillin, cephalosporins, rifampicin and actinomycin D.

Antibiotics are natural chemical substances of relatively low molecular weight produced by various species of microorganisms, such as bacteria (including Bacillus species), actinomycetes (including Streptomyces) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, caphalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicyclic acid. Some agents may have more than one primary mechanism of action, especially at high concentrations. In addition, secondary changes in the structure or metabolism of the bacterial cell often occur after the primary effect of the antimicrobial drug.

The penicillins have a characteristic double-ring system composed of a β-lactam ring, which provides the antibacterial activity, and a thiazolidene ring. The penicillins are differentiated by a single side chain that is unique for each penicillin. The compounds are bactericidal and act by inhibiting bacterial transpepidase, an enzyme involved in synthesis of the bacterial cell wall. Because of their mechanism of action, penicillin are generally active against growing, but not resting, cells. Penicillins, especially penicillin G, have largely gram-positive activity; the relative insensitivity of gram-negative rods to penicillin G and several other penicillins is probably due to the permeability barrier of the outer membrane of gram-negative bacteria. Ampicillin, carbenicillin, ticarcillin, and some other penicillins are active against gram-negative bacteria because they can pass through this outer membrane. Penicillins have relatively few adverse effects, the most important of which are the hypersensitivity (allergic) reactions. These compounds are widely distributed in the body, but do not enter cells and do not usually accumulate in CSF.

Bacterial resistance to the penicillins is by production of the enzyme β-lactamase, which catalyzes hydrolysis of the β-lactam ring. The percentage of bacteria resistant to penicillin has risen to about 80%. Several penicillins, including methicillin, oxacillin, cloxacillin, dicloxacillin and nafcillin, are not affected by the β-lactamase of staphylococci. These antibiotics are useful against most β-lactamase-producing species of Staphlococcus. However, a small number of species are resistant even to these penicillins. Some penicillins, amoxicillin and ticarcillin, are marketed in combination with clavulanic acid, which is a β-lactamase inhibitor that covalently binds to the enzyme and prevents it from hydrolyzing the antibiotics. Another inhibitor, sulbactam, is marketed in combination with ampicillin.

The cephalosporins are characterized by a β-lactam ring, like the penicillins, but have an adjacent dihydrothiazine ring instead of a thiazolidene ring. For convenience, these compounds are generally classified by generations. The first generation includes cephalothin, cephapirin, cefazolin, cephalexin, cephradine and cefadroxil. These drugs generally have excellent gram-positive activity except for enterococci and methicillin-resistant staphylococci, and have only modest gram-negative coverage. The second generation includes cefamandole, cefoxitin, ceforanide, cefuroxime, cefuroxime axetil, cefaclor, cefonicid and cefotetan. This generation generally loses some gram-positive activity by weight and gains limited gram-negative coverage. The third generation includes cefotazime, moxalactam, ceftizoxime, ceftriaxone, cefoperazone and ceftazidime. These compounds generally sacrifice further gram-positive activity by weight but gain substantial gram-negative coverage against Enterobacter and sometimes are active against Pseudomonas. The cephalosporins bind to penicillin-binding proteins with varying affinity. Once binding occurs, protein synthesis is inhibited. Cephalosporins are usually well tolerated; adverse effects include hypersensitivity reactions and gastrointestinal effects. Cephalosporins may interact with nephrotoxic drugs, particularly aminoglycosides, to increase toxicity. Resistance to cephalosporins is mediated by several mechanisms, including production of β-lactamase, although some strains that do not produce β-lactamase are nevertheless resistant.

Imipenem is a N-formimidoyl derivative of the mold product thienamycin. It contains a β-lactam ring and somewhat resembles penicillin except for differences in the second ring. It has activity against both gram-positive and gram-negative organisms and is resistant to most β-lactamases, although not those from Pseudomonas. It is marketed in combination with cilastin, a compound that inhibits inactivation of imipenem in the kidney by renal dihydropeptidase I enzyme. Cilastin increases the concentration of imipenem in urine, although not in blood.

Aztreonam is the first of a new group of antibiotics referred to as the monobactams. These agents have a β-lactam ring but lack the second ring characteristic of the penicillins and cephalosporins. It acts by binding to penicillin-binding proteins, and produces long, filamentous bacterial shapes that eventually lyse. Aztreonam is active only against aerobic gram-negative bacteria, is susceptible to inactivation by some β-lactamases, and has few adverse effects.

The aminoglycosides contain amino sugars linked to an aminocyclitol ring by glycosidic bonds. They have similar mechanisms of action and properties, but differ somewhat in spectrum of action, toxicity, and susceptibility to bacterial resistance. The compounds are bactericidal, with activity against both gram-positive and gram-negative organisms, and act by binding to proteins on the 30S ribosome of bacteria and inhibiting protein synthesis. The aminoglycosides also bind to isolated LPS and have a very weak outer membrane permeabilizing effect. [Taber et al., *Microbiological Reviews* 53: 439–457 (1987)); Kadurugamuwa et al., *Antimicrobial Agents and Chemotherapy,* 37: 715–721 (1993); Vaara, *Microbiological Reviews* 56: 395–411 (1992)]. This class of antibiotics includes amidacin, gentamicin, kenamycin, neomycin, netilmycin, paromomycin and tobramycin. The aminoglycosides are usually reserved for more serious infections because of severe adverse effects including ototoxicity and nephrotoxicity. There is a narrow therapeutic window between the concentration required to produce a therapeutic effect, e.g., 8 μg/ml for gentamicin, and the concentration that produces a toxic effect, e.g., 12 μg/ml for gentamicin. Neomycin in particular is highly toxic and is never administered parenterally.

Tetracyclines have a common four-ring structure and are closely congeneric derivatives of the polycyclic naphthacenecarboxamide. The compounds are bacteriostatic, and inhibit protein synthesis by binding to the 30S subunit of microbial ribosomes and interfering with attachment of aminoacyl tRNA. The compounds have some activity against both gram-positive and gram-negative bacteria; however, their use if limited because many species are not relatively resistant. Adverse effects include gastrointestinal effects, hepatotoxicity with large doses, and nephrotoxicity in some patients. This antibiotic class includes tetracycline, chlortetracycline, demeclocycline, doxycycline, methacycline, minocycline and oxytetracycline.

The sulfamides are derivatives of sulfanilamide, a compound similar in structure to para-aminobenzoic acid (PABA), which is an essential precursor for bacterial synthesis of folic acid. The compounds are generally bacteriostatic, and act by competitively inhibiting incorporation of PABA into tetrahydrofolic acid, which is a required cofactor in the synthesis of thymidines, purines and DNA. Sulfonamides have a wide range of activity against gram-positive and gram-negative bacteria, but their usefulness has diminished with increasingly high prevalence of bacterial resistance. The sulfonamide class of antibiotics includes sulfacytine, sulfadiazine, sulfamethiozole, sulfisoxazole, sulfamethoxazole, sulfabenzamide and sulfacetamide. Adverse effects include hypersensitivity reactions and occasional hematological toxicity.

Trimethoprim is an inhibitor of the dihydrofolate reductase enzyme, which converts dihydrofolic to tetrahydrofolic acid, a required factor for DNA synthesis. Adverse effects include gastrointestinal distress and rare hematological toxicity. Trimethoprim is also available in combination with sulfamethoxazole (also known as co-trimoxazole). The combination is usually bactericidal, although each agent singly is usually bacteriostatic. The combination is the drug of choice for Salmonella infections, some Shigella infections, *E. coli* traveler's diarrhea and *Pneumocystis carinii* pneumonia.

The fluoroquinolones and quinolones are derivatives of nalidixic acid, a naphthyridine derivative. These compounds are bactericidal, and impair DNA replication, transcription and repair by binding to the DNA and interfering with DNA gyrase, an enzyme which catalyzes negative supercoiling of DNA. The fluoroquinolones, which include norfloxacin, ciprofloxacin, and ofloxacin, and the quinolones, which include cinoxacin, have abroad spectrum of antimicrobial activity against gram-negative and gram-positive organisms. These compounds distribute widely through extravascular tissue sites, have a long serum half-life, and present few adverse effects. Because of their effect on DNA, the drugs are contraindicated in pregnant patients and in children whose skeletal growth is incomplete.

Vancomycin is a glycopeptide, with a molecular weight of about 1500, produced by a fungus. It is primarily active against gram-positive bacteria. The drug inhibits one of the final steps in synthesis of the bacterial cell wall, and is thus effective only against growing organisms. It is used to treat serious infections due to gram-positive cocci when penicillin G is not useful because of bacterial resistance or patient allergies. Vancomycin has two major adverse effects, ototoxicity and nephrotoxicity. These toxicities can be potentiated by concurrent administration of another drug with the same adverse effect, such as an aminoglycoside.

The macrolides are bacteriostatic and act by binding to the 50S subunit of 70S ribosomes, resulting in inhibition of protein synthesis. They have a broad spectrum of activity against gram-positive and gram-negative bacteria and may be bacteriostatic or bactericidal, depending on the concentration achieved at sites of infection. The compounds distribute widely in body fluids. Adverse effects include gastrointestinal distress and rare hypersensitivity reactions. The most common macrolide used is erythromycin, but the class includes other compounds such as clarithromycin and azithromycin.

The polymyxins are a group of closely related antibiotic substances produced by strains of *Bacillus polymyxa.* These drugs, which are cationic detergents, are relatively simple, basic peptides with molecular weights of about 1000. Their antimicrobial activity is restricted to gram-negative bacteria. They interact strongly with phospholipids and act by penetrating into and disrupting the structure of cell membranes. Polymyxin B also binds to the lipid A portion of endotoxin and neutralizes the toxic effects of this molecule. Polymyxin B has sever adverse effects, including nephrotoxicity and neurotoxicity, and should not be administered concurrently with other nephrotoxic or neurotoxic drugs. The drug thus has limited use a therapeutic agent because of high systemic toxicity, but may be used for severe infections, such as *Pseudomonas aeruginosa* meningitis, that respond poorly to other antibiotics.

Chloramphenicol inhibits protein synthesis by binding to the 50S ribosomal subunit and preventing binding of aminoacyl tRNA. It has a fairly wide spectrum of antimicrobial activity, but is only reserved for serious infections, such as meningitis, typhus, typhoid fever, and Rocky Mountain spotted fever, because of its severe and fatal adverse hematological effects. It is primarily bacteriostatic, although it may be bactericidal to certain species.

Lincomycin and clindamycin are lincosamide antimicrobials. They consist of an amino acid linked to an amino sugar. Both inhibit protein synthesis by binding to the 50S ribosomal subunit. They complete with erythromycin and chloramphenicol for the same binding site but in an overlapping fashion. They may be bacteriostatic or bactericidal, depending on relative concentration and susceptibility. Gastrointestinal distress is the most common side effect. Other adverse reactions include cutaneous hypersensitivity, transient hematological abnormalities, and minor elevations of hepatic enzymes. Clindamycin is often the drug of choice for infections caused by anaerobic bacteria or mixed aerobic/anaerobic infections, and can also be used for susceptible aerobic gram-positive cocci.

Some drugs, e.g. aminoglycosides, have a small therapeutic window. For example, 2 to 4 μg/ml of gentamicin or tobramycin may be required for inhibition of bacterial growth, but peak concentrations in plasma above 6 to 10 μg/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or cancomycin, require particular caution because reduced elimination can lead to increased plasma concentrations, which in turn may cause increased toxicity. Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function.

Antibiotic resistance in bacteria is an increasingly troublesome problem. The accelerating development of antibiotic-resistant bacteria, intensified by the widespread use of antibiotics in farm animals and overprescription of antibiotics by physicians, has been accomplished by declining research into new antibiotics with different modes of action. [*Science,* 264: 360–374 (1994).] Antibiotic resistance, once acquired, can be rapidly spread to other bacteria, including bacteria of a different species. There are some species of bacteria that are resistant to all but one antibiotic; it may be only a matter of time before the appearance of bacterial strains that are resistant to all antibiotics.

Bacteria acquire resistance to antibiotics through several mechanisms: (1) production of enzymes that destroy or inactivate the antibiotic [Davies, *Science,* 264: 375–381 (1994)]; (2) synthesis of new of altered target sites on or within the cell that are not recognized by the antibiotic [Spratt, *Science,* 264:388–393 (1994)]; (3) low permeability to antibiotics, which can be reduced even further by altering cell wall proteins, thus restricting access of antibiotics to the bacterial cytoplasmic machinery; (4) reduced intracellular transport of the drug; and (5) increased removal of antibiotics from the cell via membrane-associated pumps [Nikaido, *Science,* 264:382–387 (1994)].

The susceptibility of a bacterial species to an antibiotic is generally determined by two microbiological methods. A rapid but crude procedure uses commercially available filter paper disks that have been impregnated with a specific quantity of the antibiotic drug. These disks are placed on the surface of agar plates that have been streaked with a culture of the organisms being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organisms will successfully cure the subject. While an organism may literally be susceptible to a high concentration of an antibiotic in vitro, the organism may in fact be resistant to that antibiotic at physiologically realistic concentrations. If the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

There continues to exist a need in the art for new antimicrobial, and especially anti-gram-positive microbial, methods and materials. Products and methods responsive to this need would ideally involve substantially non-toxic compounds available in large quantities by means of synthetic or recombinant methods. Ideal compounds would have bactericidal or bacteriostatic activity when administered or applied as the sole anti-microbial agent. Such compounds ideally would also be useful in combinative therapies with other anti-microbial agents, particularly where potentiating effects are provided.

SUMMARY OF THE INVENTION

The present invention provides methods and compositions for treating gram-positive bacterial infections, including conditions associated therewith or resulting therefrom (for example, sepsis or bacteremia), in a subject by administering a BPI protein product alone, or concurrently with an antibiotic. The invention is based upon the discovery that BPI protein products surprisingly have direct bactericidal and growth inhibitory effects on some gram-positive organisms, and that BPI protein products unexpectedly have the ability to increase the antibiotic susceptibility of gram-positive bacteria, including the ability to reverse in many instances the antibiotic resistance of gram-positive bacteria. The invention is also based upon the finding that BPI protein products and antibiotics provide additive and synergistic bactericidal/growth inhibitory effects when administered concurrently.

According to one aspect of the invention, a method is provided of treating a gram-positive bacterial infection comprising the steps of administering to a subject suffering from a gram-positive bacterial infection a BPI protein product in an amount sufficient for monotherapeutic effectiveness. This method may be practiced when any BPI-susceptible gram-positive bacterial species is involved in the infection.

A second aspect of the invention provides a method of treating gram-positive bacterial infection by concurrently administering to a subject suffering from a gram-positive bacterial infection a BPI protein product in an amount sufficient for combinative therapeutic effectiveness and one or more antibiotics in amounts sufficient for combinative therapeutic effectiveness. This method is effective even for gram-positive organisms that are not susceptible to the direct bactericidal/growth inhibitory effects of BPI.

For concurrent administration with antibiotics, the BPI protein product may be administered in an amount effective to increase the antibiotic susceptibility of a gram-positive bacterial species involved in the infection, or to potentiate the effects of the antibiotic. The BPI protein product may also be administered in an amount effective to reverse the antibiotic resistance of a gram-positive bacterial species involved in the infection. The BPI protein product and the antibiotics may each be administered in amounts that would be sufficient for monotherapeutic effectiveness upon administration alone or may be administered in less than monotherapeutic amounts.

Another aspect of the invention provides a method of treating gram-positive bacterial infection by concurrently administering to a subject suffering from a gram-positive bacterial infection a BPI protein product and one or more antibiotics, in synergistically effective amounts.

In addition, the invention provides a method of killing or inhibiting growth of gram-positive bacteria comprising contacting the bacteria with a BPI protein product alone, or in combination with another antibacterial agent. This method can be practiced in vivo or in a variety of in vitro uses such as use in food preparation, to decontaminate fluids and surfaces or to sterilize surgical and other medical equipment and implantable device, including prosthetic joints. These methods can correspondingly be used for in situ sterilization of indwelling invasive devices such as intravenous lines and catheters, which are often foci of infection, or for sterilization of in vitro tissue culture media.

The invention further provides a method of killing or inhibiting growth of gram-positive bacteria with disrupted cell walls, including L-phase variants, by contacting such bacteria with a BPI protein product alone, or in conjunction with another antibacterial agent. This method can also be practiced on organisms that lack cell walls, such as Mycoplasma or Ureaplasma.

The invention further provides the use of BPI protein product for the manufacture of a medicament for treatment of gram-positive bacterial infections, and the use of a BPI protein product in combination with an antibiotic for manufacture of a medicament for treatment of gram-positive bacterial infections.

Numerous additional aspects and advantages of the invention will become apparent to those skilled in the art upon consideration of the following detailed description of the invention which describes presently preferred embodiments thereof.

DETAILED DESCRIPTION

Figure 1:
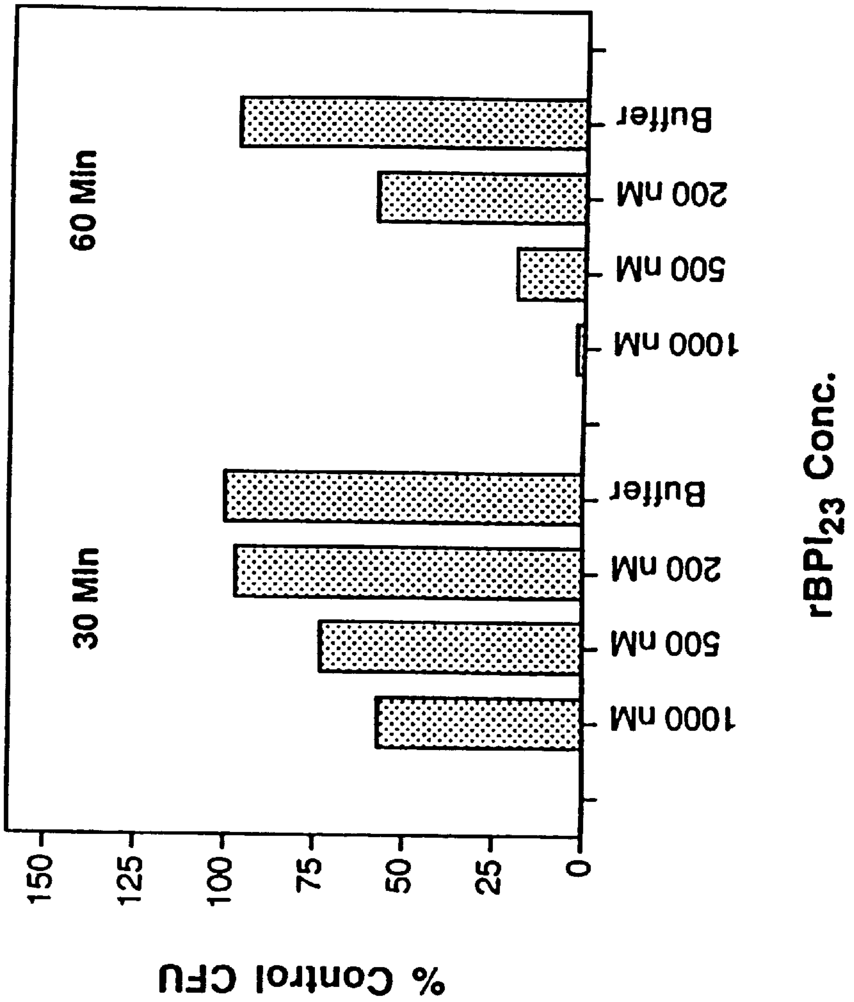
FIG. 1 relates to plate assays of the bactericidal effect of $rBPI_{23}$ on *Bacillus subtilis.*

The present invention relates to methods and materials for treating subjects suffering from gram-positive bacterial infections. "Gram-positive bacterial infection," as used herein, encompasses conditions associated with or resulting from gram-positive bacterial infection (e.g., sequelae). These conditions include gram-positive sepsis and one or more of the conditions associated therewith, including bacteremia, fever, hypotension, shock, metabolic acidosis, disseminated intravascular coagulation and related clotting disorders, anemia, thrombocytopenia, leukopenia, adult respiratory distress syndrome and related pulmonary disorders, renal failure and related renal disorders, hepotobiliary disease and central nervous system disorders. These conditions also include translocation of gram-negative bacteria from the intestines and concomitant release of endotoxin. Gram-positive bacteria include bacteria from the following species: Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, and Corynebacterium.

A variety of gram-positive organisms are capable of causing sepsis. The most common organisms involved in sepsis are *Staphylococcus aureus, Streptococcus pneumoniae,* coagulase-negative staphylococci, beta-hemolytic streptococci, and enterococci, but any gram-positive organism may be involved. [Bone, *J. Critical Care,* 8:51–59 (1993).]

According to one aspect of the invention, BPI protein product alone, in an amount sufficient for monotherapeutic effectiveness, may be administered to a subject suffering from infection involving a BPI-susceptible gram-positive bacteria. When used to described administration of BPI protein product alone, the term "amount sufficient for monotherapeutic effectiveness" means an amount of BPI protein product that provides bactericidal or growth inhibitory effects when administered as a monotherapy. The invention utilizes any of the large variety of BPI protein products known to the art including natural BPI protein, recombinant BPI protein, BPI fragments, BPI analogs, BPI variants, and BPI-derived peptides.

This aspect of the invention is based on the discovery that BPI protein products have direct bactericidal or growth inhibitory activity against some gram-positive organisms. BPI protein products are also shown herein to have direct bactericidal or growth inhibitory effects on L-phase variants of a variety of gram-positive organisms; these L-phase variants lack the cell walls of the normal bacterial form. BPI protein products are also expected to exert direct bactericidal/growth inhibitory effects on the cell wall-less Mycoplasma and Ureaplasma, organisms involved clinically in respiratory and urogenital infections. Mycoplasma is also a major contaminant of in vitro tissue cultures.

According to a second aspect of the invention, a subject suffering from a gram-positive bacterial infection may be treated by concurrent administration of a BPI protein product in an amount sufficient for combinative therapeutic effectiveness and one or more antibiotics in amounts sufficient for combinative therapeutic effectiveness. This aspect of the invention contemplates concurrent administration of BPI protein product with any antibiotic or combinations of antibiotics, including β-lactam antibiotics with and without β-lactamase inhibitors, aminoglycosides, tetracyclines, sulfonamides and trimethoprim, vancomycin, macrolides, fluoroquinolones and quinolones, polymyxins and other antibiotics.

This aspect of the invention is based on the discovery that administration of BPI protein products improves the therapeutic effectiveness of antibiotics, e.g., by increasing the antibiotic susceptibility of gram-positive organisms to a reduced dosage of antibiotics providing benefits in reduction of cost of antibiotic therapy and/or reduction of risk of toxic responses to antibiotics. BPI protein products are shown herein to lower the minimum concentration of antibiotic therapy and/or reduction of risk of toxic responses to antibiotics. BPI protein products are shown herein to lower the minimum concentration of antibiotics needed to inhibit in vitro growth of gram-positive organisms at 24 hours. In cases where BPI protein product did not affect growth at 24 hours, BPI protein product was shown to potentiate the early bactericidal effect of antibiotics in vitro at 0–7 hours. The BPI protein products exert these effects even on gram-positive organisms that are not susceptible to the direct bactericidal or growth inhibitory effects of BPI protein product alone.

This aspect of the invention is correlated to the additional discovery that administration of a BPI protein product can effectively reverse the antibiotic resistance of a gram-positive organism. BPI protein products are shown herein to reduce the minimum inhibitory concentration of antibiotics from a level within the clinically resistant range to a level within the clinically susceptible range. BPI protein products thus can convert normally antibiotic-resistant organisms into antibiotic-susceptible organisms.

According to this second aspect of the invention, the BPI protein product and antibiotics are concurrently administered in amounts sufficient for combinative therapeutic effectiveness. When used to described administration into antibiotic-susceptible organisms.

According to this second aspect of the invention, the BPI protein product and antibiotics are concurrently administered in amounts sufficient for combinative therapeutic effectiveness. When used to described administration of a BPI protein product in conjunction with an antibiotic, the term "amount sufficient for combinative therapeutic effectiveness" with respect to the BPI protein product means at least an amount effective to increase the susceptibility of the organism to the antibiotic, and the term "amount sufficient for combinative therapeutic effectiveness" with respect to an antibiotic means at least an amount of the antibiotic that produces bactericidal or growth inhibitory effects when administered in conjunction with that amount of BPI protein product. Either the BPI protein product or the antibiotic, or both, may be administered in an amount below the level required for monotherapeutic effectiveness against a gram-positive bacterial infection. The BPI protein product may be administered in an amount which is not sufficient for monotherapeutic effectiveness but which provides increased antibiotic susceptibility or potentiates the effects of the antibiotic, or which reverses the resistance of the gram-positive organism to an antibiotic.

A further aspect of the invention relates to the discovery that concurrent administration of BPI protein products with antibiotics provides synergistic bactericidal or growth inhibitory effects beyond the individual bactericidal or growth inhibitory effects of the BPI protein product or the antibiotic. Some methods for evaluating the effect of antimicrobial combinations are described in Eliopoulos and Moellering In *Antibiotics in Laboratory Medicine,* 3rd ed. (Lorian, V., Ed.) pp. 432–492, Williams and Wilkins, Baltimore, Md. (1991). There is general agreement on qualitative definition of synergism; the combined effect of the drugs being examined is significantly greater than the expected result based on independent effects of the drugs when used separately. In a checkerboard assay, the combination of BPI protein product with antibiotics may be shown to result in a "synergistic" fractional inhibitory concentration index (FIC). The checkerboard method is based on additivity, which assumes that the result observed with multiple drugs is the sum of the separate effects of the drugs being tested; according to this system a FIC of less than 0.5 is scored as synergy, 1 is scored as additive, and greater than 1 but less than 2 is scored as indifferent. In contrast, kinetic assays are based on the idea that only one metabolic pathway at a time can be growth rate-limiting for an organism; according to this system, the combined effect of drugs that do not interact with one another (autonomous or indifferent) is simply the effect of the most active drug alone.

According to this aspect of the invention, "effective synergy" or potentiation upon concurrent administration of BPI protein product with one or more antibiotics an be obtained in a number of ways. A BPI protein product may convert an antibiotic-resistant organism into an antibiotic-susceptible organism or otherwise improve the antibiotic susceptibility of the organism. Conversely, a BPI-potentiating antibiotic, such as an antibiotic that acts on the cell wall or cell membrane of bacteria, may convert a BPI-resistant organism into a BPI-susceptible organism. Alternatively, the BPI protein product and antibiotic may both co-potentiate the other agent's activity. The BPI protein product and antibiotic may have a therapeutic effect when both are given in doses below the amounts sufficient for monotherapeutic effectiveness.

Either the BPI protein product or the antibiotics may be administered systemically or topically. Systemic routes of administration include oral, intravenous, intramuscular or subcutaneous injection (including into a depot for long-term release), intraocular or retrobulbar, intrathecal, intraperitoneal (e.g. by intraperitoneal lavage), transpulmonary using aerosolized or nebulized drug, or transdermal. Topical routes include administration in the form of salves, ophthalmic drops, ear drops, or irrigation fluids (for, e.g., irrigation of wounds).

"Concurrent administration," or co-treatment, as used herein includes administration of the agents, in conjunction or combination, together, or before or after each other. The BPI protein product and antibiotics may be administered by different routes. For example, The BPI protein product may be administered intravenously while the antibiotics are administered intramuscularly, intravenously, subcutaneously, orally or intraperitoneally. Alternatively, the BPI protein product may be administered intraperitoneally while the antibiotics are administered intraperitoneally or intravenously, or the BPI protein product may be administered in an aerosolized or nebulized form while the antibiotics are administered, e.g., intravenously. The BPI protein product and antibiotics are preferably both administered intravenously. The BPI protein product and antibiotics may be given sequentially in the same intravenous line, after an intermediate flush, or may be given in different intravenous lines. The BPI protein product and antibiotics may be administered simultaneously or sequentially, as long as they are given in a manner sufficient to allow both agents to achieve effective concentrations at the site of infection.

Concurrent administration of BPI protein product and antibiotic is expected to provide more effective treatment of gram-positive bacterial infection. Concurrent administration of the two agents may provide greater therapeutic effects in vivo than either agent provides when administered singly. It may permit a reduction in the dosage of one or both agents with achievement of a similar therapeutic effect. Alternatively, the concurrent administration may produce a more rapid or complete bactericidal/bacteriostatic effect than could be achieved with either agent alone.

Therapeutic effectiveness is based on a successful clinical outcome, and does not require that the antimicrobial agent or agents kill 100% of the organisms involved in the infection. Success depends on achieving a level of antibacterial activity at the site of infection that is sufficient to inhibit the bacteria in a manner that tips the balance in favor of the host. When host defenses are maximally effective, the antibacterial effect required may be minimal. Reducing organism load by even one log (a factor of 10) may permit the host's own defenses to control the infection. In addition, augmenting an early bactericidal/bacteriostatic effect can be more important than long-term bactericidal/bacteriostatic effect. These early events are a significant and critical part of therapeutic success, because they allow time for host defense mechanisms to activate. Increasing the bactericidal rate may be particularly important for infections such as meningitis, bone or joint infections. [Stratton, *Antibiotics in Laboratory Medicine,* 3rd ed. (Lorian, V., Ed.) pp. 849–879, Williams and Wilkins, Baltimore, Md. (1991)].

The effect of BPI protein product to improve the therapeutic effectiveness of antibiotics in vivo may be demonstrated in in vivo animal models, or may be predicted on the basis of a variety of in vitro tests, including (1) determinations of the minimum inhibitory concentration (MIC) of an antibiotic required to inhibit growth of a gram-negative organism for 24 hours, (2) determinations of the effect of an antibiotic on the kinetic growth curve of a gram-negative organism, and (3) checkerboard assays of the MIC of serial dilutions of antibiotic alone or in combination with serial dilutions of BPI protein product. Exemplary models or tests are described in Eliopooulos and Moellering In *Antibiotics in Laboratory Medicine,* 3rd ed. (Lorian, V., Ed.) pp. 432–492, Williams and Wilkins, Baltimore, Md. (1991).

Using in vitro determinations of antibiotic MIC at 24 hours, a BPI protein product may be shown to reduce the MIC of the antibiotic. With this result, it is expected that concurrent administration of the BPI protein product in vivo will increase susceptibility of the gram-negative organism to the antibiotic. A BPI protein product may also be shown to reduce the MIC of an antibiotic from the range in which the organism is considered clinically resistant to a range in which the organism is considered clinically susceptible. With this result, it is expected that concurrent administration in vivo of the BPI protein product with the antibiotic will reverse resistance and effectively convert the antibiotic-resistant organism into an antibiotic-susceptible organism.

By measuring the effect of antibiotics on the in vitro growth curves of gram-negative organisms, in the presence or absence of a BPI protein product, the BPI protein product may be shown to enhance the early antibacterial effect of antibiotics at 0–24 hours. Enhancement of early bactericidal/growth inhibitory effects is important in determining therapeutic outcome.

BPI protein product is thought to interact with a variety of host defense elements present in whole blood or serum, including complement, p15 and LBP, and other cells and components of the immune system. Such interactions may result in potentiation of the activities of BPI protein product. Because of these interactions, BPI protein products can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media contain higher than physiological concentrations of Mueller-Hinton has~physiological conclusion as serum magnesium and calcium, which are typically inhibitors of the antibacterial activity of BPI protein products. Furthermore, in the host, BPI protein product is available to neutralize translocation of gram-negative bacteria and concomitant release of endotoxin, a further clinical benefit not seen in or predicted by in vitro tests.

It is also contemplated that the BPI protein product be administered with other products that potentiate the bactericidal activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.,* 265: 15956 (1990) and Levy et al. *J. Biol. Chem.,* 268: 6038–6083 (1993) which address naturally-occurring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, described methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/069,510, filed Jun. 17, 1993, the disclosures of all of which are incorporated herein by reference.

BPI is commonly thought to be non-cytotoxic for many types of gram-positive bacteria. This lack of toxicity may be due primarily to the low affinity of BPI for the gram-positive cell wall and the ability of the cell wall to protect the cytoplasmic membrane from prolonged exposure to and subsequent damage by BPI. Because prokaryotic cytoplasmic membranes from both gram-positive and gram-negative bacteria may have similar structures that are distinct from those of eukaryotic membranes, BPI protein products may also be cytotoxic from gram-positive bacteria if the cell wall is removed or damaged or if the BPI protein products can be targeted to the cell surface with high affinity.

Without being bound by a theory of the invention, it is believed that BPI protein product may have several mechanisms of action. BPI protein product may act directly on the cell walls of gram-positive bacteria by binding to LPS-like molecules such as cell wall peptidoglycans and teichoic acid. If BPI is allowed to reach the inner cytoplasmic membrane, the amphipathic nature of BPI may allow it to penetrate the cytoplasmic membrane and exert a bactericidal effect. Thus, agents that act on or disrupt the cell walls of bacteria such as antibiotics, detergents or surfactants, anti-peptidoglycan antibodies, anti-lipoteichoic acid antibodies and lysozyme, may potentiate the activity of BPI by allowing access to the inner cytoplasmic membrane.

Likewise, BPI's action on the inner sytoplasmic membrane of bacteria may potentiate the action of antibiotics by allowing penetration of the antibiotic through the inner membrane, thus permitting it to affect the bacterial biochemical machinery. Moreover, because gram-positive bacterial infection may cause stress-induced translocation of bowel flora and/or LPS, BPI may also act beneficially by killing the gram-negative bacteria and neutralizing the LPS.

BPI protein product, through its heparin-binding ability, may interfere with the binding of gram-positive bacteria to the extracellular matrix (ECM) and to host cells. It has been previously shown that a number of organisms, including the gram-positive bacteria *Staphylococcus aureus, Streptococcus mutans* and *Streptococcus pyogenes* (Group A strep), express heparin-binding receptors. These heparin-binding receptors are believed to mediate biding of organisms to heparin-like molecules in the ECM and on host cells, e.g., endothelial cells. Heparin may also act as a bridge that mediates adhesion of organisms to host cells that have heparin receptors.

Finally, BPI protein product may bind to gram-positive bacterial cell wall components, such as peptidoglycans of teichoic acid, and thereby neutralize the action of these cell wall components in inducing gram-positive sepsis. These cell wall components are believed to play a role in gram-positive sepsis and septic shock. Both peptidoglycans and teichoic acids can activate the alternate complement pathway. Gram-positive bacterial cell wall components can also elicit production of cytokines involved in sepsis, including TNF, IL-1 and IL-6. [Bone, *J. Critical Care,* 8:51–59 (1993); Bone, *Arch. Intern. Med.,* 154:26–34 (1994).] Highly purified gram-positive bacterial cell wall preparations (in which the covalent linkages and structure of peptidoglycan and teichoic acid chains remain unaltered) have been shown to stimulate the production of TNF-α and IL-6 by human monocytes. [Heumann et al., *Infect. Immun.,* 62:2715–2721 (1994).]

An advantage provided by the present invention is the ability to provide more effective treatment of gram-positive bacterial infections by improving the therapeutic effectiveness of antibiotics against gram-positive organisms. This allows use of lower concentrations of highly toxic or very expensive antibiotics, such as the aminoglycosides, vancomycin, rifampin, lincomycin, chloramphenicol, and the fluoroquinolones, Because the use of some antibiotics is limited by their systemic toxicity or prohibitive cost, lowering the concentration of antibiotic required for therapeutic effectiveness reduces toxicity and/or cost of treatment, and thus allows wider use of the antibiotic. Another advantage is the ability to treat gram-positive organisms that are normally resistant to one or more antibiotics. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

The invention also provides improved methods of in vitro decontamination of fluids and surfaces contaminated with gram-positive bacteria by contacting the bacteria with BPI protein product alone, or in combination with one or more antibiotics. The amounts of BPI protein product and antibiotics used are amounts that are separately sufficient for bactericidal/growth inhibitory effects, or amounts sufficient to have additive or synergistic bactericidal/growth inhibitory effects. These methods can be used in a variety of in vitro applications including sterilization of surgical and other medical equipment and implantable devices, including prosthetic joints. These methods can also be used for in situ sterilization of indwelling invasive devices such as intravenous lines and catheters, which are often foci or infection.

The invention further provides pharmaceutical compositions for treatment of gram-positive bacterial infection comprising BPI protein product in combination with an antibiotic lacking gram-negative bactericidal activity, such as lincomycin and vancomycin. The pharmaceutical composition can optionally comprise a pharmaceutically acceptable diluent, adjuvant or carrier. As another aspect of the invention, antiseptic bactericidal compositions are provided which comprise a BPI protein product alone, or in combination with an antibiotic.

"LBP protein derivatives" includes natural, synthetic and recombinantly produced polypeptides comprising a portion of the amino acid sequence of Lipopolysaccharide Binding Protein (LBP) holoprotein, and which are characterized by the ability to bind to LPS but which lack the carboxy terminal-associated immunostimulatory element(s) characteristic of the LBP holoprotein and thus lack the CD14-mediated immunostimulatory activity characteristic of LBP holoprotein. LBP derivative proteins are described in detail in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are incorporated herein by reference. Preferred LBP protein derivatives include N-terminal LBP fragments having a molecular weight of about 25 kD or less. One LBP N-terminal fragment is characterized by the amino acid sequence of the first 197 amino acids of the amino-terminus of LBP set out in SEQ ID NOS: 97 and 98, and is designated $LBP_{25}$. LBP protein derivatives also include polypeptides comprising part or all of one or more of three regions (defined by LBP amino acid sequences 17–45, 65–99 and 141–167) corresponding (by reason of amino acid holology) to LPS binding regions of BPI (comprising amino acid sequences 17–45, 65–99 and 142–169). LBP protein derivatives also include polypeptides comprising a portion of the amino acid sequence of LBP holoprotein, wherein amino acids are added, deleted, or replaced, and wherein the LBP protein derivative maintains LPS-binding activity but lacks CD14-mediated immunostimulatory activity. One such LBP derivative is that wherein the alanine residue at position 131 of the $LBP_{25}$ polypeptide fragment is substituted with a cysteine residue.

LBP derivatives includes LBP derivative hybrid proteins comprising a portion of the amino acid sequence of LBP and a portion of at least one other polypeptide, such as BPI protein or immunoglobulin chain. One such derivative is an LBP/BPI hybrid protein (LBP(1–197)/BPI(200–456)), which comprises amino acid residues 1–197 of LBP followed in sequence by amino acid residues 1–199 of BPI. Other LBP hybrid proteins comprise LBP amino acid sequences into which all or portions of LPS binding domains of other LPS binding proteins (such as BPI) have been inserted or substituted.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as $rBPI_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.,* 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 145 and 146) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in U.S. Pat. No. 5,447,913 and corresponding PCT Application No. PCT/US95/03125 (Int'l Publication No. WO95/24209) the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof. Another example of such a hybrid fusion protein is the recombinant expression product of DNA encoding amino acids 1 through 199 of BPI joined to DNA encoding amino acids 198 through 456 of LBP, designated BPI(1–199)-LBP(198–456) hybrid, is described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are incorporated herein by reference.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 field Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. U.S. Pat. No. 5,447,913 and corresponding PCT Application No. PCT/US95/03125 (Int'l Publication No. WO95/24209), the disclosures of which are incorporated herein by reference.

Other BPI protein products useful according to the methods of the invention are peptides derived from or based on BPI produced by recombinant or synthetic means (BPI-derived peptides), such as those described in co-owned and copending PCT Application No. US94/10427 filed Sep. 15, 1994, which corresponds to U.S. patent application Ser. No. 08/306,473 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. A preferred pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another preferred pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Suitable antibiotics, and therapeutically effective concentrations thereof when administered with BPI protein products, may be determined in in vivo models or according to in vitro tests, for example, the in vitro minimum inhibitory concentration (MIC) and in vivo mouse peritonitis or rabbit bacteremia assays taught herein. Suitable antibiotics are antibiotics that act on the bacterial cell wall, cell membrane, protein metabolism or nucleic acid metabolism. These would include antibiotics or combinations of antibiotics from the following classes: β-lactam antibiotics with or without β-lactamase inhibitors, aminoglycosides, tetracyclines, sulfonamides and trimethoprim, vancomycin, macrolides, fluoroquinolones and quinolones, polymyxins, and other antibiotics. Dosage and administration of suitable antibiotics are known in the art, and briefly summarized below.

PENICILLINS

When a BPI protein product is concurrently administered with a penicillin, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The penicillin is generally given in doses ranging from 1 μg /kg to 750 mg/kg daily, preferably not to exceed 24 grams daily for adults (or 600 mg/kg daily for children), and is preferably administered as follows:

Penicillin G is preferably administered parenterally to adults in doses ranging from 600,000 to 1,000,000 units per day. In conventional administration, it is effective largely against gram-positive organisms. For treatment of pneumococcal meningitis, penicillin G is administered in doses of 20–24 million units daily, in divided doses every 2 or 3 hours. For children, the preferred parenteral dose of penicillin G is 300,000 to 1,000,000 units per day. One unit of penicillin G contains 0.6 μg of pure sodium penicillin G (i.e., 1 mg is 1667 units).

Amoxicillin may be administered parenterally to adults in doses ranging from 750 mg to 1.5 grams per day, in 3 equally divided doses. For children, preferred parenteral doses of amoxicillin range from 20 to 40 mg/kg per day in 3 equally divided doses. Amoxicillin is also available in combination with clavulanic acid, a β-lactamase inhibitor. A 250 mg dose of the combination drug amoxicillin/clavulanate will contain 250 mg of amoxicillin and either 125 or 62.5 mg of clavulanic acid. The combination is preferably administered to adults orally in doses of 750 mg per day divided into 3 equal doses every 8 hours, with a preferred dose of 1.5 grams per day for severe infections, given in 3 equally divided doses. In children, the preferred oral dose is 20 to 40 mg/kg per day in 3 equally divided doses.

Ampicillin is preferably administered parenterally to adults in doses of 6 to 12 grams per day for severe infections, in 3 to 4 equally divided doses. In children, the preferred parenteral dose of ampicillin is 50 to 200 mg/kg per day in 3 to 4 equally divided doses. Larger doses of up to 400 mg/kg per day, for children, or 12 grams per day, for adults, may be administered parenterally for treatment of meningitis. Ampicillin is also available in combination with sulbactam, a β-lactamase inhibitor. Each 1.5 gram dose of ampicillin/sulbactam contains 1 gram of ampicillin and 0.5 grams of sulbactam. The combination is preferably administered parenterally to adults in doses of 6 to 12 grams per day divided into 4 equal doses every 6 hours, not to exceed a total of 12 grams per day.

Azlocillin is preferably administered parenterally to adults in doses of 8 to 18 grams per day, given in 4 to 6 equally divided doses.

Carbenicillin is preferably administered parenterally to adults in doses of 30 to 40 grams per day, given by continuous infusion or in 4 to 6 equally divided doses. Daily doses of up to 600 mg/kg have been used to treat children with life-threatening infections.

Mezlocillin is preferably administered to adults parenterally in doses of 100 to 300 mg/kg per day, given in 4 to 6 equally divided doses. The usual dose is 16 to 18 grams per day; for life threatening infections, 350 mg/kg per day may be administered, but in doses not to exceed 24 grams per day given in 6 equally divided doses every 4 hours. For children, the preferred parenteral dose of mezlocillin is 150 to 300 mg/kg per day.

Nafcillin is preferably administered intravenously to adults in doses of 3 grams per day, given in 6 equally divided doses every 4 hours, with doubled doses for very severe infections. In conventional administration, it is effective largely against gram-positive organisms. In children, the preferred parenteral dose is 20 to 50 mg/kg per day, in 2 equally divided doses every 12 hours. The preferred oral dose for nafcillin ranges from 1 gram per day to 6 grams per day in 4 to 6 divided doses.

Oxacillin is preferably administered parenterally to adults in doses of 2 to 12 grams per day, in 4 to 6 equally divided doses. In conventional administration, it is effective largely against gram-positive organisms. In children, oxacillin is preferably administered in doses of 100 to 300 mg/kg per day.

Piperacillin is preferably administered parenterally to adults in doses ranging from 100 mg/kg, or 6 grams per day, in 2 to 4 equally divided doses, up to a maximum of 24 grams per day, in 4 to 6 equally divided doses. Higher doses have been used without serious adverse effects.

Ticarcillin is preferably administered parenterally to adults in doses ranging from 4 grams per day to 18 grams per day administered in 4 to 6 equally divided doses. The usual dose is 200 to 300 mg/kg per day. For children, the preferred parenteral dose of ticarcillin ranges from 50 mg/kg per day to 300 mg/kg per day, given in 3, 4 or 6 equally divided doses. The combination ticarcillin/clavulanate is preferably administered parenterally to adults in doses of 200 to 300 mg/kg per day (based on ticarcillin content), in 4 to 6 equally divided doses. For adults, the usual dose is 3.1 grams (which contains 3 grams of ticarcillin and 100 mg of clavulanic acid) every 4 to 6 hours. The combination is also available in a dose of 3.2 grams, which contains 3 grams of ticarcillin and 200 mg of clavulanic acid.

In general, it is desirable to limit each intramuscular injection of a penicillin or cephalosporin to 2 grams; larger doses should be administered by multiple injections in different large muscle masses.

CEPHALOSPORINS

When a BPI protein product is concurrently administered with a cephalosporin, for treatment of a gram-negative bacterial infection, the BPI protein product is generally given parenterally in doses ranging from 1 $\mu$g/kg to 100 mg/kg daily, and preferably at doses ranging from 1 mg/kg to 20 mg/kg daily. The cephalosporin is generally given in doses ranging from 1 $\mu$g/kg to 500 mg/kg daily, preferably not to exceed 16 grams daily, and is preferably administered as follows:

Cefamandole is preferably administered parenterally to adults in doses ranging from 1.5 grams per day, given in 3 equally divided doses every 8 hours, to 12 grams per day for life-threatening infections, given in 6 equally divided doses every 4 hours. In children, cefamandole is preferably administered in doses ranging from 50 to 50 mg/kg per day, in 3 to 6 equally divided doses, not to exceed a total of 12 grams per day.

Cefazolin is preferably administered parenterally to adults in doses of 750 mg per day, given in 3 equally divided doses every 8 hours. In severe, life-threatening infections, it may be administered at doses of 6 grams per day divided into 4 equal doses every 6 hours; in rare instances, up to 12 grams per day have been used. In children, the preferred parenteral dose of cefazolin is 20 to 50 mg/kg per day, divided into 3 to 4 equal doses, with 100 mg/kg per day administered for severe infections.

Cefonicid is preferably administered parenterally to adults in doses ranging from 500 mg once daily, to 2 grams once daily for life-threatening infections. For intramuscular administration, a 2 gram dose should be divided into two 1-gram injections.

Cefoperazone is preferably administered parenterally to adults in doses ranging from 2 grams per day, given in 2 equally divided doses every 12 hours, to 12 grams per day for severe infections, given in 2, 3 or 4 equally divided doses. Doses up to 16 grams per day have been administered without complications.

Cefotetan is preferably administered parenterally to adults in doses of 1 to 4 grams per day, in 2 equally divided doses every 12 hours. Cefotetan may be administered in higher doses for life-threatening infections, not to exceed a total dose of 6 grams per day.

Cefotaxime is preferably administered parenterally to adults in doses ranging from 1 to 12 grams per day, not to exceed 12 grams per day (2 grams every 4 hours) for life-threatening infections. In children, the parenteral dose of cefotaxime is preferably 50 to 180 mg/kg, divided into 4 to 6 equal doses.

Cefoxitin is preferably administered parenterally to adults in doses ranging from 3 to 12 grams per day, given in 3, 4, or 6 equally divided doses. In children, cefoxitin is preferably administered parenterally in doses of 80 to 160 mg/kg per day, given in 4 or 6 equally divided doses, not to exceed a total dose of 12 grams per day.

Ceftazidime is preferably administered parenterally to adults in doses ranging from 500 mg per day, given in 2 to 3 equally divided doses (every 8 or 12 hours), up to a maximum of 6 grams per day. In children, ceftazidime is preferably administered intravenously in doses of 30 to 50 mg/kg, to a maximum of 6 grams per day.

Cefizoxime is preferably administered parenterally to adults in doses ranging from 1 gram per day, given in 2 equally divided doses every 12 hours, to 12 grams per day for life-threatening infections, given in 3 equally divided doses every 8 hours. The usual adult dose is 1 to 2 grams every 8 or 12 hours. For children, the preferred parenteral dose is 50 mg/kg every 6 or 8 hours, for a total daily dose of 200 mg/kg.

Ceftriaxone is preferably administered parenterally to adults in doses ranging from 1 to 2 grams per day, given in 2 equally divided doses every 12 hours. It may be given in higher doses, not to exceed a total of 4 grams per day. In children, the preferred parenteral dose of ceftriaxone is 50 to 75 mg/kg per day, not to exceed 2 grams per day. In meningitis, ceftriaxone may be administered in doses of 100 mg/kg per day, not to exceed 4 grams per day.

Cefuroxime is preferably administered parenterally to adults in doses ranging from 2.25 to 4.5 grams per day, in 3 equally divided doses every 8 hours. For life-threatening infections, 6 grams per day may be administered in 4 equally divided doses every 6 hours, and for meningitis, 9 grams per day may be administered in 3 equally divided doses every 8 hours. For children, the preferred parenteral dose of cefuroxime is 50 to 150 mg/kg per day in 3 to 4 equally divided doses, or 240 mg/kg per day for meningitis.

Cephalexin is formulated for oral administration, and is preferably administered orally to adults in doses ranging from 1 to 4 grams per day in 2 to 4 equally divided doses. For children, the preferred dose is 20 to 50 mg/kg per day in divided doses, with doses being doubled for severe infections.

Cephalothin is usually administered parenterally to adults in doses of 8 to 12 grams per day.

OTHER BETA-LACTAMS

When a BPI protein product is concurrently administered with an imipenem antibiotic, for treatment of a gram-negative bacterial infection, the BPI protein product is generally given parenterally in doses ranging from 1 $\mu$g/kg to 100 mg/kg daily, and preferably at doses ranging from 1 mg/kg to 20 mg/kg daily. The imipenem is generally given in doses ranging from 1 $\mu$g/kg to 100 mg/kg daily, and is preferably administered as follows:

Imipenem is available in combination with cilastatin, an inhibitor of the renal dipeptidase enzyme that rapidly inactivates imipenem. The combination is preferably administered intramuscularly to adults in doses of 1 to 1.5 grams per day, given in 2 equally divided doses every 12 hours. Intramuscular doses exceeding 1.5 grams per day are not recommended. The combination is preferably administered intravenously in doses ranging from 1 to 4 grams per day, in 4 equally divided doses every 6 hours; doses exceeding 50 mg/kg per day, or 4 grams per day, are not recommended.

When a BPI protein product is concurrently administered with a monobactam antibiotic, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The monobactam is generally given in doses ranging from 1 μg/kg to 200 mg/kg daily, and is preferably administered as follows:

Aztreonam is preferably administered parenterally to adults in doses ranging from 1 gram per day, given in 2 equally divided doses every 12 hours, up to a maximum recommended dose of 8 grams per day in cases of life-threatening infection, given in 3 or 4 equally divided doses.

AMINOGLYCOSIDES

When a BPI protein product is concurrently administered with an aminoglycoside, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The aminoglycoside is generally given in doses ranging from 1 μg/kg to 20 mg/kg daily, preferably not to exceed 15 mg/kg daily, and is preferably administered as follows:

When administering aminoglycosides, it is desirable to measure serum peak and tough concentrations to ensure the adequacy and safety of the dosage. Dosages should generally be adjusted to avoid toxic peak and trough concentrations. Amikacin is preferably administered parenterally to adults and children in doses of 15 mg/kg per day, divided into two or three equal doses every 8 or 12 hours, and not to exceed a total dose of 1.5 grams per day. For uncomplicated infections, a dose of 500 mg amikacin per day, in 2 equally divided doses, may be administered. Dosages should be adjusted to avoid prolonged serum peak concentrations of amikacin above 35 μg/ml and prolonged trough concentrations greater than 10 μg/ml.

Gentamicin is preferably administered parenterally to adults in doses of 3 mg/kg per day, in three equally divided doses every 8 hours. For life-threatening infections, up to 5 mg/kg per day in 3 to 4 equally divided doses may be administered, but this dosage should be reduced to 3 mg/kg per day as soon as clinically indicated. For children, gentamicin is preferably administered parenterally in doses of 6 to 7.5 mg/kg per day. Dosages should be adjusted to avoid prolonged serum peak concentrations of gentamicin above 12 μg/ml and prolonged trough concentrations greater than 2 μg/ml.

Netilmicin may be administered parenterally to adults in doses ranging from 3 mg/kg per day, in 2 equally divided doses every 12 hours, to 6.5 mg/kg per day for serious systemic infection, in 2 or 3 equally divided doses. In children, the preferred parenteral dose is 5.5 to 8 mg/kg per day, in 2 or 3 equally divided doses. Dosages should be adjusted to avoid prolonged serum peak concentrations of netilmicin above 16 μg/ml and prolonged serum trough concentrations above 4 μg/ml.

Tobramycin is preferably administered parenterally to adults in doses of 3 mg/kg per day, given in three equally divided doses every 8 hours. For life-threatening infections, tobramycin may be administered in doses up to 5 mg/kg per day, in 3 or 4 equally divided doses, but this dosage should be reduced to 3 mg/kg per day as soon as clinically indicated. In children, tobramycin is preferably administered parenterally in doses of 6 to 7.5 mg/kg per day. Prolonged serum concentrations of tobramycin above 12 μg/ml should be avoided, and rising trough levels above 2 μg/ml may indicate tissue accumulation, which may contribute to toxicity.

Concurrent administration of BPI protein product with the aminoglycosides, including amikacin, gentamicin, netilmicin and tobramycin, may permit a lowering of the dose of these toxic antibiotics necessary to achieve a therapeutic effect.

TETRACYCLINES

When a BPI protein product is concurrently administered with a tetracycline, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The tetracycline is generally given in doses ranging from 1 μg/kg to 50 mg/kg daily, and is preferably administered as follows:

The tetracycline antibiotics are generally administered to adults in doses of 1 to 2 grams per day. An exception is doxycycline, which is preferably administered intravenously to adults in doses of 100 to 200 mg per day, and to children in doses of 2 mg/lb per day. Tetracycline may be administered parenterally to adults in doses of 0.5 to 2 grams per day, in 2 equally divided doses, and to children in doses of 10 to 20 mg/kg per day.

SULFONAMIDES

When a BPI protein products is concurrently administered with a sulfonamide or trimethoprim, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The sulfonamide or trimethoprim is generally given in doses ranging from 1 μg/kg to 150 mg/kg daily, preferably not to exceed a combination dose of 960 mg trimethoprim/4.8 g sulfamethoxazole daily, and is preferably administered as follows:

The combination trimethoprim/sulfamethoxazole is available in a formulation containing a 1:5 ratio of trimethoprim and sulfamethoxazole (e.g., 16 mg trimethoprim and 80 mg sulfamethoxazole). The combination is preferably administered intravenously to adults or children in doses of 8 to 10 mg/kg (based on the weight of the trimethoprim component) per day, in 2 to 4 equally divided doses. For *Pneumocystis carinii* infection, the combination can be administered in doses of 20 mg/kg (based on the weight of the trimethoprim component) per day, in 3–4 equally divided doses, to a maximum recommended dose of 960 mg trimethoprim/4.8 g sulfamethoxazole per day. Trimethoprim alone is preferably administered orally to adults in doses of 200 mg per day. Sulfamethoxazole alone is preferably administered orally to adults in doses of 2 to 3 grams per day, and to children orally in doses of 50 to 60 mg/kg per day.

FLUOROQUINOLONES

When a BPI protein product is concurrently administered with a fluoroquinolone or quinolone, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The fluoroquinolone or quinolone is generally given in doses ranging from 1 μg/kg to 50 mg/kg daily, preferably not to exceed 1 gram daily, and is preferably administered as follows:

Norfloxacin is preferably administered orally to adults in doses from 400 to 800 mg daily, divided into two doses every 12 hours. Cinoxacin is preferably administered orally to adults in doses of 1 gram per day, given in 2 or 4 equally divided doses. Ciprofloxacin is preferably administered to adults intravenously in doses from 400 to 800 mg daily, or orally in doses from 500 to 1500 mg daily, divided into two doses every 12 hours. Ofloxacin is preferably administered to adults intravenously in doses from 400 to 800 mg daily, or orally in doses from 400 to 800 mg daily, divided into two doses every 12 hours.

VANCOMYCIN

When a BPI protein product is concurrently administered with vancomycin, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The vancomycin is generally given in doses ranging from 1 mg/kg to 50 mg/kg daily, and is preferably administered parenterally to adults in doses of 2 grams per day, divided into 2 or 4 doses every 6 or 12 hours. In children it is preferably administered in doses of 40 mg/kg, given in 4 equally divided doses every 6 hours. In conventional administration, vancomycin is effective largely against gram-positive organisms.

MACROLIDES

When a BPI protein product is concurrently administered with a macrolide, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The macrolide is generally given in doses ranging from 1 μg/kg to 100 mg/kg daily, and is preferably administered as follows:

Erythromycin is preferably administered intravenously to adults and children in doses of 15 to 20 mg/kg per day, given by continuous infusion or in 4 equally divided doses every 6 hours. Erythromycin can be administered at doses up to 4 grams per day in cases of very severe infection.

Clarithromycin is preferably administered orally to adults in doses of 500 mg to 1 gram daily, in equally divided doses every 12 hours.

Azithromycin is preferably administered orally to adults at a dose of 500 mg on the first day of treatment followed by 250 mg once daily for 4 days, for a total dose of 1.5 grams.

OTHERS

When a BPI protein product is concurrently administered with other antibiotics, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily.

Polymyxin B is generally given in doses ranging from 1 unit/kg to 45,000 units/kg daily, and is preferably administered intravenously to adults and children in doses of 15,000 to 25,000 units/kg per day, divided into 2 equal doses every 12 hours. It may be administered intramuscularly in doses of 25,000 to 30,000 units/kg per day, although these injections are very painful. Doses of polymyxin B as high as 45,000 units/kg per day have been used in limited clinical studies to treat neonates for *Pseudomonas aeruginosa* sepsis. Polymyxin B is the treatment of choice for *P. aeruginosa* meningitis, and is preferably administered intrathecally to adults and older children in doses of 50,000 units once daily for 3 to 4 days, followed by 50,000 units every other day; in children under two years old, it is administered intrathecally in doses of 20,000 daily for 3 to 4 days, followed by 25,000 units every other day.

Chloramphenicol is preferably administered intravenously to adults in doses of 50 mg/kg per day, in 4 equally divided doses; in exceptional cases, it can be administered in doses up to 100 mg/kg per day. In children, chloramphenicol is preferably administered intravenously in doses of 25 mg/kg per day, although up to 100 mg/kg per day can be administered in cases of severe infection.

Clindamycin is preferably administered parenterally to adults in doses ranging from 600 mg to 4.8 grams per day, given in 2, 3 or 4 equally divided doses. It is recommended that the dose in each intramuscular injection not exceed 600 mg. For children, clindamycin is preferably administered parenterally in doses of 15–40 mg/kg per day, given in 3 or 4 equally divided doses.

Dosages of all antimicrobial agents should be adjusted in patients with renal impairment or hepatic insufficiency, due to the reduced metabolism and/or excretion of the drugs in patients with these conditions. Doses in children should also be reduced, generally according to body weight. Those skilled in the art can readily optimize effective dosages and administration regimens for the BPI protein product and the antibiotics in concurrent administration.

Other aspects and advantages of the present invention will be understood upon consideration of the following illustrative examples. Example 1 addresses plate assays of the bactericidal effect in vitro of a BPI protein product on the gram-positive organism *Bacillus subtilis*. Example 2 relates to plate assays of the in vitro growth inhibitory effect of a BPI protein product on the gram-positive organism *Staphylococcus aureus* and its L-phase variant. Example 3 evaluates the in vitro bactericidal and growth inhibitory effects of a variety of BPI protein products on *Staphlococcus aureus*, penicillin-treated *S. aureus*, and the L-phase variant, as measured in radial diffusion assays, plate assays, protein synthesis assays, and broth growth inhibition assays. Examples 4 and 5 evaluate the in vitro growth inhibitory effects of a variety of BPI protein products on L-phase variants of *Streptococcus pneumoniae* and *Enterococcus faecalis*, respectively. Example 6 examines the effect of a variety of BPI protein products on the mycoplasma *Acholeplasma laidlawii*. Example 7 examines the in vitro growth inhibitory effect of an LBP-BPI hybrid on a variety of gram-positive L-phase variants. Example 8 relates to radial diffusion assays measuring the growth inhibitory effect of a variety of BPI synthetic peptides on *S. aureus*. Examples 9–17 address large-scale screening of the bactericidal/growth inhibitory effect and the antibiotic susceptibility-increasing effect of BPI protein products on a variety of gram-positive organisms: *S. pneumoniae* (Example 9), *Streptococcus pyogenes* (Group A strep) (Example 10), *Streptococcus agalactia* (Group B step) (Example 11), *Streptococcus bovis* (Example 12), *E. faecalis* (Example 13), *Enterococcus faecium* (Example 14), a variety of *Enterococcus species* (Example 15), *S. aureus* (Example 16), *Staphlococcus epidermidis* (Example 17), and various coagulase-negative Staphylococcus species (Example 18). Example 19 examines the early in vitro bactericidal effect of BPI and selected antibiotics on *Streptococcus pneumoniae, Staphlyococcus aureus* and *Enterococcus faecalis*. Example 20 evaluates the effect of a BPI protein product, alone or with antibiotics, on *Streptococcus pneumoniae* (especially penicillin-resistant strains), *Staphylococcus aureus* (especially methicillin-resistant strains), Enterococcus (especially multiply resistant strains), and Corynebacteria.

Example 22 evaluates the in vivo effects of BPI protein products alone or in combination with antibiotics in animal models.

EXAMPLE 1

In Vitro Bactericidal Effects of a BPI Protein Product on Bacillus Subtilis

A plate assay was used to determine the effects of a BPI protein product on the gram-positive organism *Bacillus subtilis* (ATCC Accession No. 6633). The cells were incubated overnight at 37° C. in Brain Heart Infusion (BHI) broth (Difco, Detroit, Mich.), after which the optical density of the cell suspension was adjusted with additional BHI broth to $A_{600}$=~1.0 (equivalent to about $5\times10^8$ CFU/ml). The cells were washed twice with 0.9% NaCl and resuspended in D-PBS, pH 7.4, to a cell density of approximately $1–2\times10^4$ CFU/ml. The cells were diluted at a ratio of 1:10 in Earl's MEM medium (GIBCO, Grand Island, N.Y.) and 190 μl of the diluted cells (200–400 cells per well) added to low protein-binding 96 well plates (Corning, N.Y.). The $rBPI_{23}$ at varying concentrations was added to the wells to achieve final concentrations ranging from 200 to 1,000 nM in a total volume of 200 μl in each well, and the plates were incubated at 37° C. for 30 minutes or 60 minutes. After incubation, 100 μl from each well was plated on brain heart infusion agar plates. After 24 hours of incubation at 37° C., the number of colonies on each agar plate was counted.

In multiple experiments, $rBPI_{23}$ displayed clear and reproducible bactericidal activity at concentrations as low as 200 nM (about 4.5 μg/ml). The results of a representative experiment are displayed in FIG. 1, which shows that the bactericidal effects of $rBPI_{23}$ were dose-dependent. The bactericidal effects of $rBPI_{23}$ were more pronounced after 60 minutes of incubation than after 30 minutes.

EXAMPLE 2

In Vitro Effects of a BPI Protein Product on Staphylococcus Aureus and ITS L-Phase Variant in a Plate Assay A plate assay was conducted to test the effect of a BPI protein product on the gram-positive organism *Staphylococcus aureus* (ATCC Accession No. 19636) and its L-phase variant (ATCC Accession No. 19640). An L-phase variant (also called an L-form) lacks a cell wall and must be grown in the presence of osmotically protective media containing serum (usually 5 to 10% horse serum).

*S. aureus*, or *Escherichia coli* J5 as a control were grown overnight in heart infusion (HI) broth and tryptone yeast extract (TYE) broth (both broths from Difco, Detroit, Mich.), respectively, then diluted 1:100 in the same broth and grown to mid-log phase ($A_{600}$=~0.5). The *S. aureus* L-phase variant cells were grown on agar plates containing HI broth supplemented with 3.5% NaCl and 10% horse serum, and colonies were resuspended in 4 ml of HI broth supplemented with 3.5% NaCl to an $A_{600}$ of approximately 0.2 to 0.5. The cell suspensions were spread on agar plates containing HI broth supplemented with 3.5% NaCl and 5% horse serum. $rBPI_{21}$ was spotted on the surface of the plates in amounts varying from 0.75 to 3 μg, in 2 μl. No growth inhibition zones were observed on the *S. aureus* plates, but for the L-phase variant, a clear zone of growth inhibition was observed at 3 μg $rBPI_{21}$, and partial clear zones at 1.5 and 0.75 μg $rBPI_{21}$. In the control *E. coli* plate, clear zones were observed at 1.0 and 0.5 μg of $rBPI_{21}$. No zones of growth inhibition were observed for plates on which buffer alone was spotted. The results indicate that in the absence of a cell wall, growth of the gram-positive bacterium *S. aureus* is affected by BPI protein products.

EXAMPLE 3

In Vitro Effects of Various BPI Protein Products on Staphylococcus Aureus, Penicillin-Treated S. Aureus, and S. Aureus L-Phase Variant A. Evaluation in Radial Diffusion Assays Radial diffusion assays were performed to determine the effect of various BPI protein products on *S. aureus* (ATCC Accession No. 19636) and penicillin-treated *S. aureus* or natural L-phase variants (ATCC Accession No. 19640) grown in osmotically protective media. Because penicillin inhibits peptidoglycan synthesis, cells that have been contacted with penicillin lose their cell walls once growth is initiated. If osmotic protection is provided, a certain percentage of the cells survive and grow as L-phase variants. This example was directed towards determining whether penicillin-treated cells or L-phase variants would be susceptible to BPI protein products because the protective barrier of the cell wall was absent.

Figure 2:
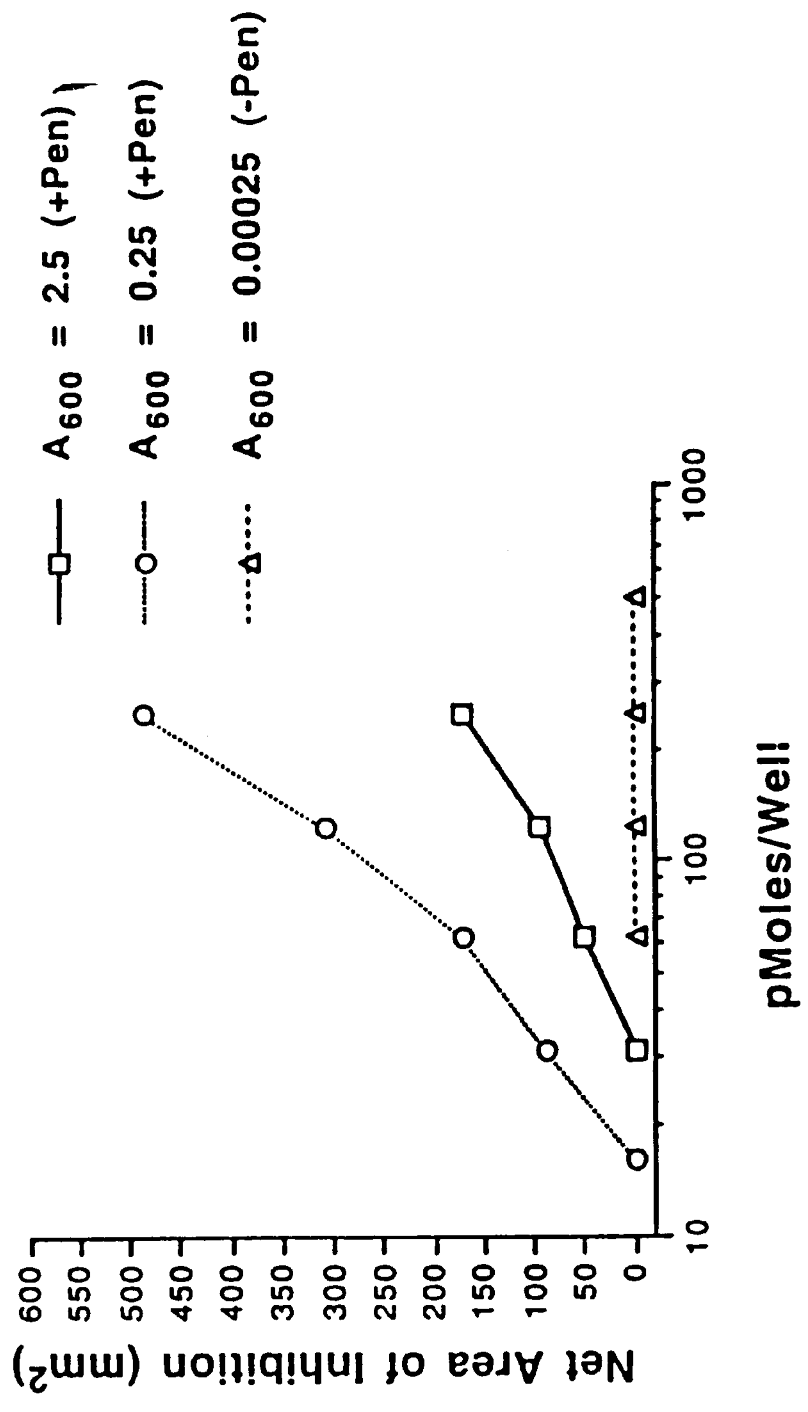
FIG. 2 shows results from radial diffusion assays of the growth inhibitory effect of $rBPI_{21}$ on *Staphylococcus aureus* with or without penicillin.

*S. aureus* cells were grown overnight to mid-log phase in HI broth and were adjusted using the same broth to an optical density of $A_{600}$=~0.25 (equivalent to about $2.5\times10^8$ cells/ml) or 2.5 (equivalent to about $2.5\times10^9$ cells/ml). 80 μl of the cell suspension was added to 8 ml of molten agar medium containing 0.8% agarose, HI broth supplemented with 3.5% NaCl, and 1,000 units/ml penicillin G (Sigma, St Louis, Mo.). The agar was poured into 90 mm plates and allowed to solidify. As a control, the same *S. aureus* cells were adjusted to an optical density of $A_{600}$=0.25, 0.025, 0.0025 or 0.00025, and added to the same agar medium, but without penicillin. Holes, or wells, of 3 mm diameter were prepared in the 90 mm plates, and 5 μl of two-fold serial dilutions of $rBPI_{21}$ were added to each well. For the penicillin-treated cells, 240, 120, 60, 30, 15 and 7.5 picomoles (pmol) per well of $rBPI_{21}$ were tested, and the plates were incubated for 48 hours at 37° C. in a $CO_2$ incubator. For the control cells (not grown on penicillin G-containing plates), 400, 200, 100 and 50 pmol/well of $rBPI_{21}$ were tested, and the plates were incubated for 24 hours. The plates were then examined for zones of inhibition. The results, shown below in FIG. 2, demonstrate that the BPI protein product inhibited bacterial growth in a dose-dependent manner; $rBPI_{21}$ at levels as low as 30 pmol per well was able to inhibit growth of the penicillin-treated *S. aureus* cells. In contrast, even the highest concentration of $rBPI_{21}$ (400 pmol) had no effect on the control *S. aureus* cells grown without penicillin.

These results show that, while the normal bacterial form of *S. aureus* is not susceptible to BPI protein products, it can be rendered susceptible by penicillin treatment that causes loss of the cell wall due to inhibition of cell wall synthesis. This indicates that gram-positive bacteria are susceptible to BPI protein products if the cell wall is removed and the cytoplasmic membrane is exposed.

Additional radial diffusion assays were conducted on the natural *S. aureus* L-phase variant to confirm the above results. The cells were grown overnight in HI broth supplemented with 3.5% NaCl, 10 mM $CaCl_2$ and 1000 units/ml penicillin G, to an $A_{600}$=~0.3. The cells were used either undiluted or as a 1:10 dilution. 80 μl of the cell suspension was added to 8 ml of molten HI agar medium containing HI broth supplemented with 3.5% NaCl and 0.8% agarose. The agar was poured into 90 mm plates and allowed to solidify.

Figure 3:
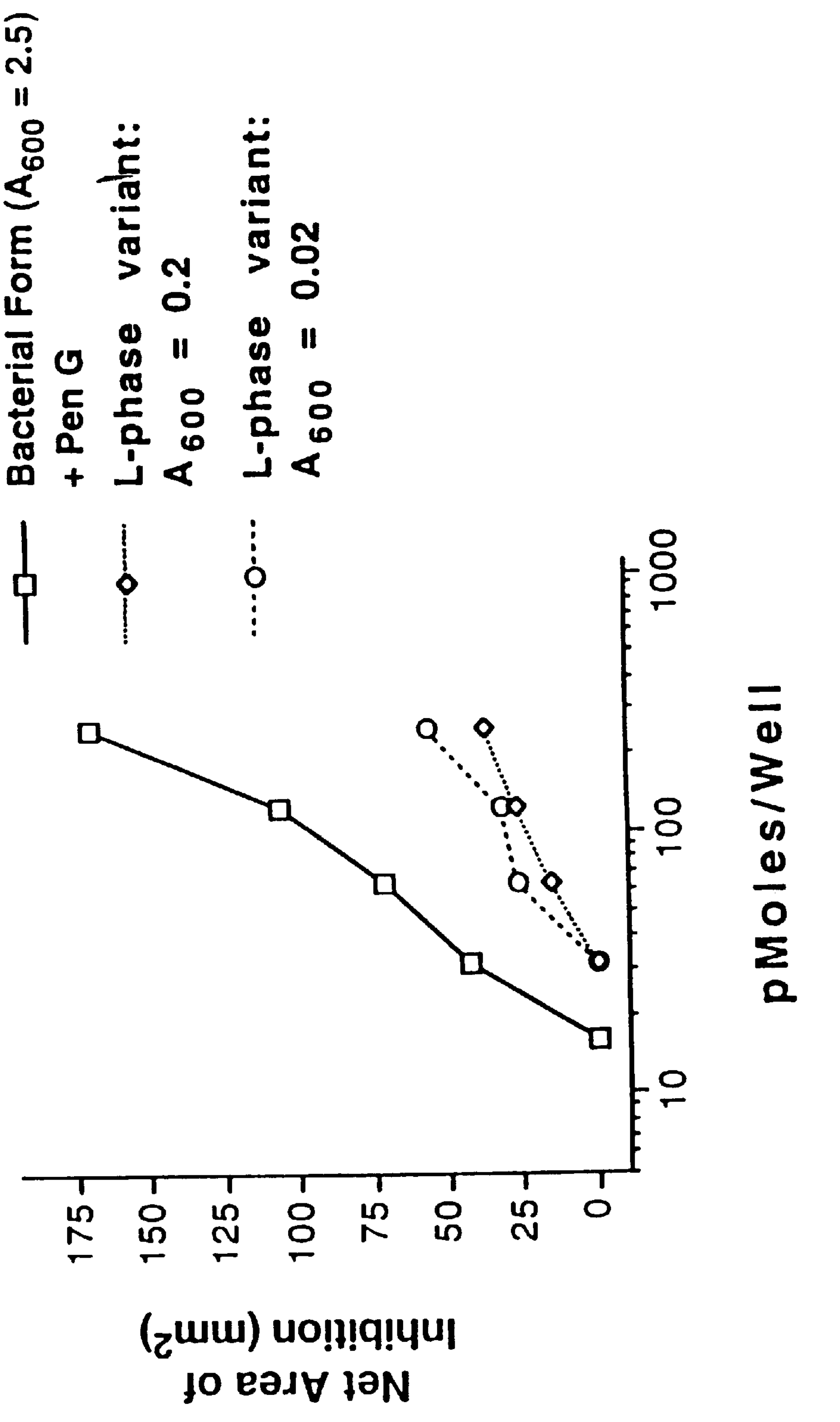
FIG. 3 depicts results from radial diffusion assays of the effect of $rBPI_{21}$ on penicillin-treated *S. aureus* and L-phase variants.

As a control, a plate using the same medium was also prepared using 80 $\mu$l of normal *S. aureus* cells adjusted to $A_{600}$=2.5 with HI broth supplemented with 3.5% NaCl, 10 mM $CaCl_2$, and 1000 $\mu$/ml penicillin G. Holes, or wells, or 3 mm diameter were prepared in the 90 mm plates, and 5 $\mu$l of $rBPI_{21}$ in two-fold serial dilutions, starting at 5 $\mu$g/5 $\mu$l (or 240 pmol/5 $\mu$l), was added to the wells. The plates were incubated for 48 hours and then examined for zones of growth inhibition. The results of this experiment, shown in FIG. 3, demonstrate that the L-phase variant is also susceptible to BPI protein products.

Figure 4:
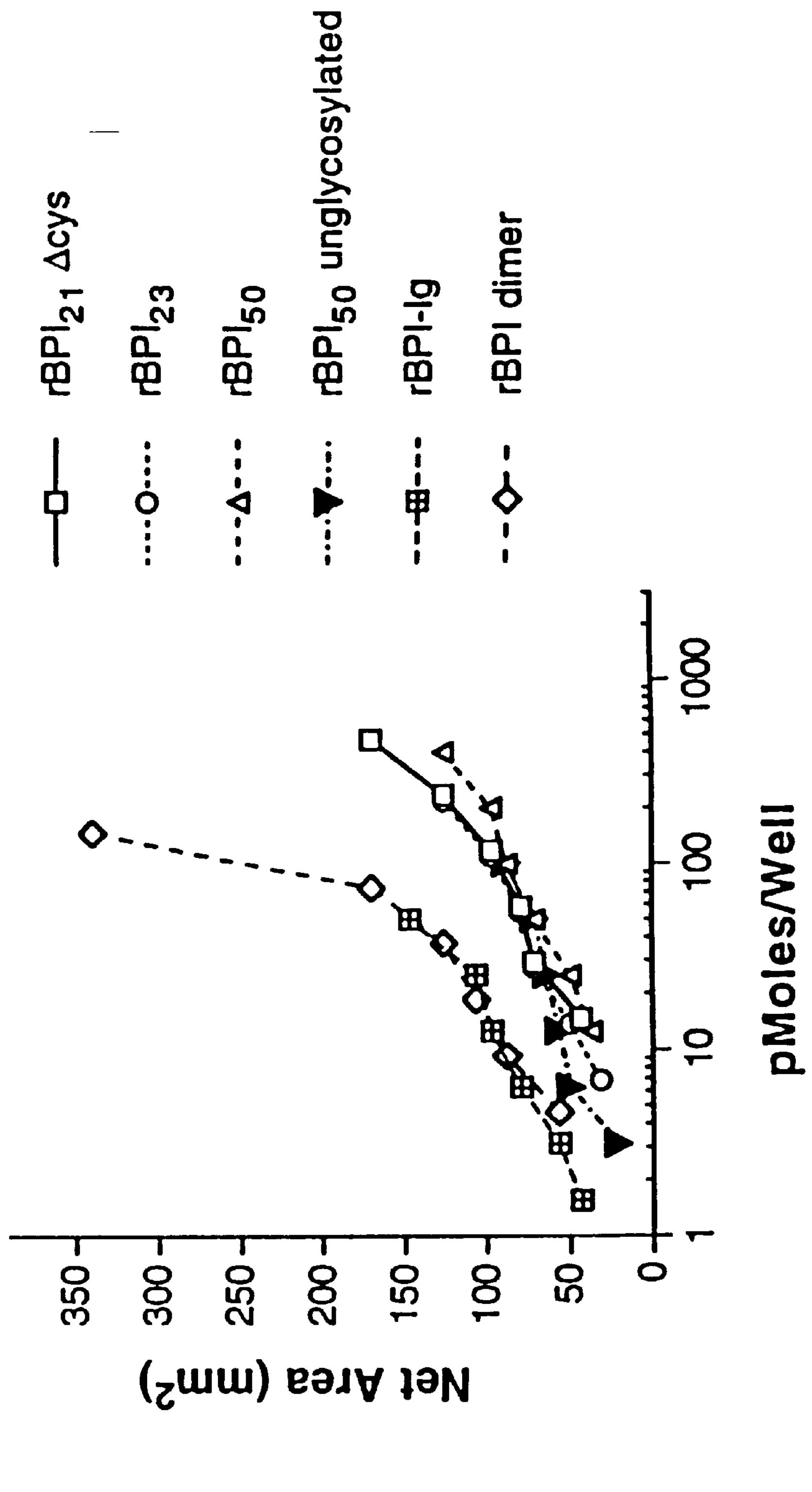
FIG. 4 shows the effect of various BPI protein products on penicillin-treated *S. aureus* in a radial diffusion assay.

Further radial diffusion assays were conducted to evaluate the effect of various BPI protein products, $rBPI_{23}$, $rBPI_{21}$, $rBPI_{50}$, BPI-Immunoglobulin fusion (the expression product of 1.c "p"ING4512 described in Theofan, et al., U.S. application Ser. No. 07/885,911 filed May 19, 1992 and 08/064,693 filed May 19, 1993) and $rBPI_{42}$ dimer (the dimeric form of N-terminal (1-193) BPI, described in Amons, et al., U.S. application Ser. No. 08/212,132 filed Mar. 11, 1994) on penicillin-treated *S. aureus. S. aureus* were grown to log phase in HI broth supplemented with 3.5% NaCl, 5 mM $CaCl_2$ and 100 units/ml penicillin G, and was adjusted to $A_{600}$=~0.025. The cell suspension was added in a 1:100 dilution to molten HI agar medium containing HI broth supplemented with 3.5% NaCl, 0.8% agarose, and 1000 units/ml penicillin G, which was then allowed to solidify. Serial 2-fold dilutions of each BPI protein product in 5 $\mu$l were added to 3-mm wells prepared in the plates. After 24 hours of incubation, the plates were examined for zones of growth inhibition. The results of these assays, shown in FIG. 4, demonstrate that these BPI protein products are all effective in inhibiting growth of penicillin-treated *S. aureus*, with BPI-Immunoglobulin fusion and $rBPI_{42}$ dimer being the most potent.

When these experiments were repeated using other species of bacteria, *Staphylococcus epidermidis* (ATCC Accession No. 35983), *Enterococcus faecalis* (ATCC Accession No. 4200), and *Streptococcus pneumoniae* (ATCC Accession No. 35088), using the BPI protein products $rBPI_{23}$ (5 $\mu$g/well), $rBPI_{21}$ (10 $\mu$g/well), $rBPI_{42}$ dimer (5 $\mu$g/well), $rBPI_{50}$ (20 $\mu$g/well) and rBPI-Ig fusion (5 $\mu$g/well), no growth inhibition was observed for any of these BPI protein products. These results indicate that in this assay, the normal bacterial forms of these species of bacteria are also not susceptible to the BPI protein products when used at the concentrations indicated. Higher concentrations of these BPI protein products may produce different susceptibility results.

Figure 5:
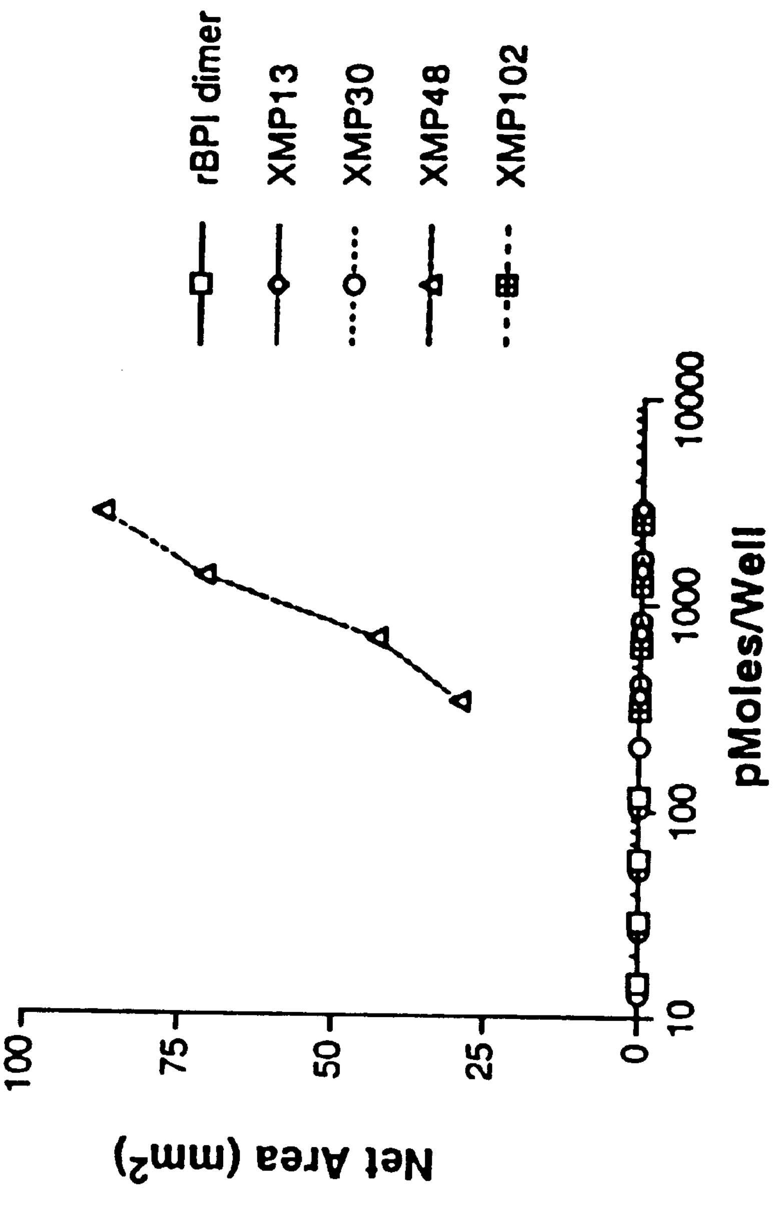
FIGS. 5, 6, 7 and 8 show the effect of various BPI protein products, including BPI-derived peptides, on the *S. aureus* bacterial form and L-phase variant in a radial diffusion assay.
Figure 6:
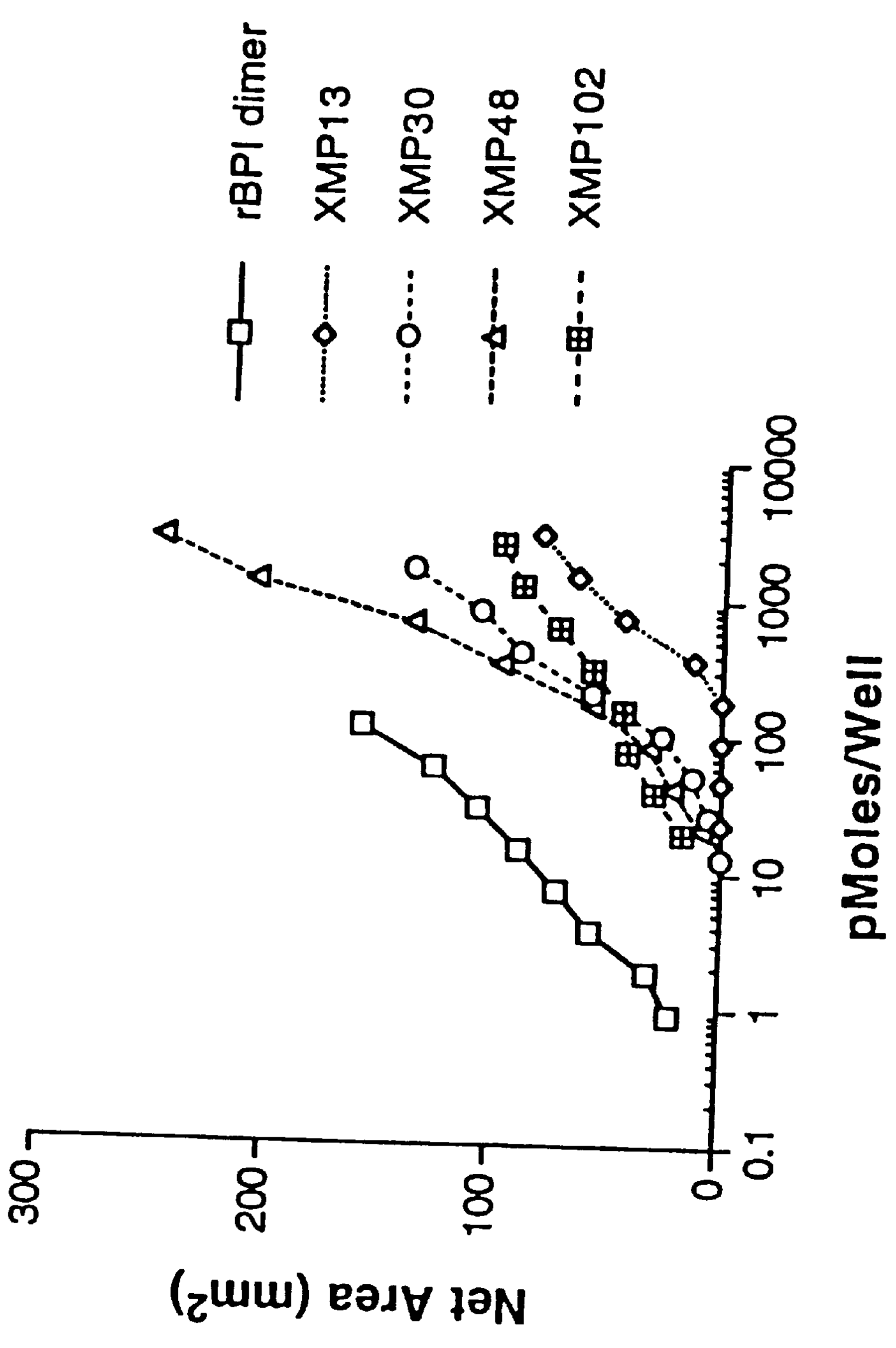

The effects of additional BPI protein products, BPI-derived peptides, on the *S. aureus* bacterial form (ATCC No. 19636) and its corresponding L-phase variant (ATCC No. 19640) were also evaluated in this radial diffusion assay. The cells were grown to log phase in either HI broth (for the bacterial forms) or HI broth supplemented with 3.5% NaCl, 5 mM $CaCl_2$ and 1000 U/mL penicillin G (for the L-phase variants). $rBPI_{42}$ dimer and the BPI-derived peptides XMP.13. XMP.30, XMP.48 and XMP.102 (as described in Example 8 and Table 1 infra) were dissolved at ~2 mg/mL in PBS (without calcium and magnesium) and the corrected concentration determined by comparing absorbance at 280 nM with that predicated by the extinction coefficient. The bacteria were incorporated into agarose, 5 $\mu$l aliquots of various concentrations of the peptides or $rBPI_{42}$ dimer were added to each well, and the plates were incubated at 37° C. for 24 hours (bacterial form) or 48 hours (L-phase variants). The results, shown in FIGS. 5 and 6, indicate that XMP.48 was active against the bacterial form and that all of the peptides tested were active against the L-phase variants. The $rBPI_{42}$ dimer appeared to be about ten-fold more active on a molar basis than any of the peptides, while XMP.13 appeared to be the least potent.

Figure 7:
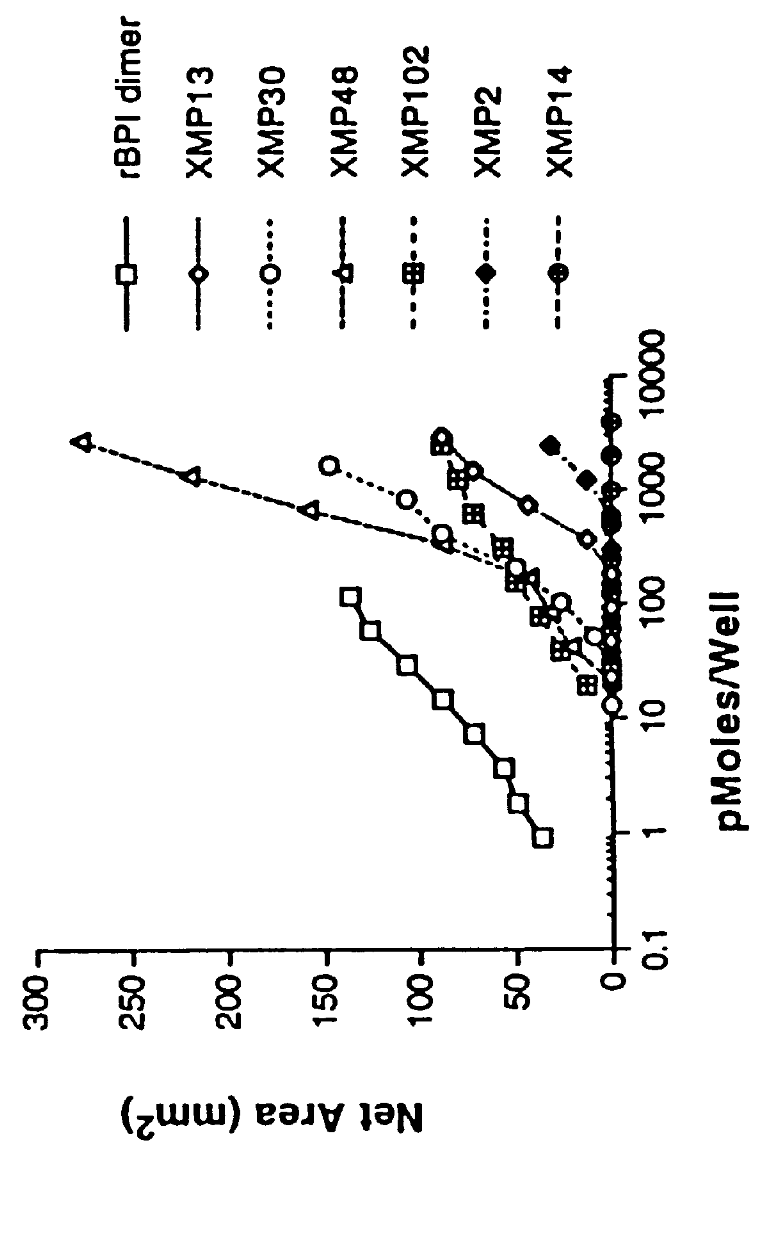
Figure 8:
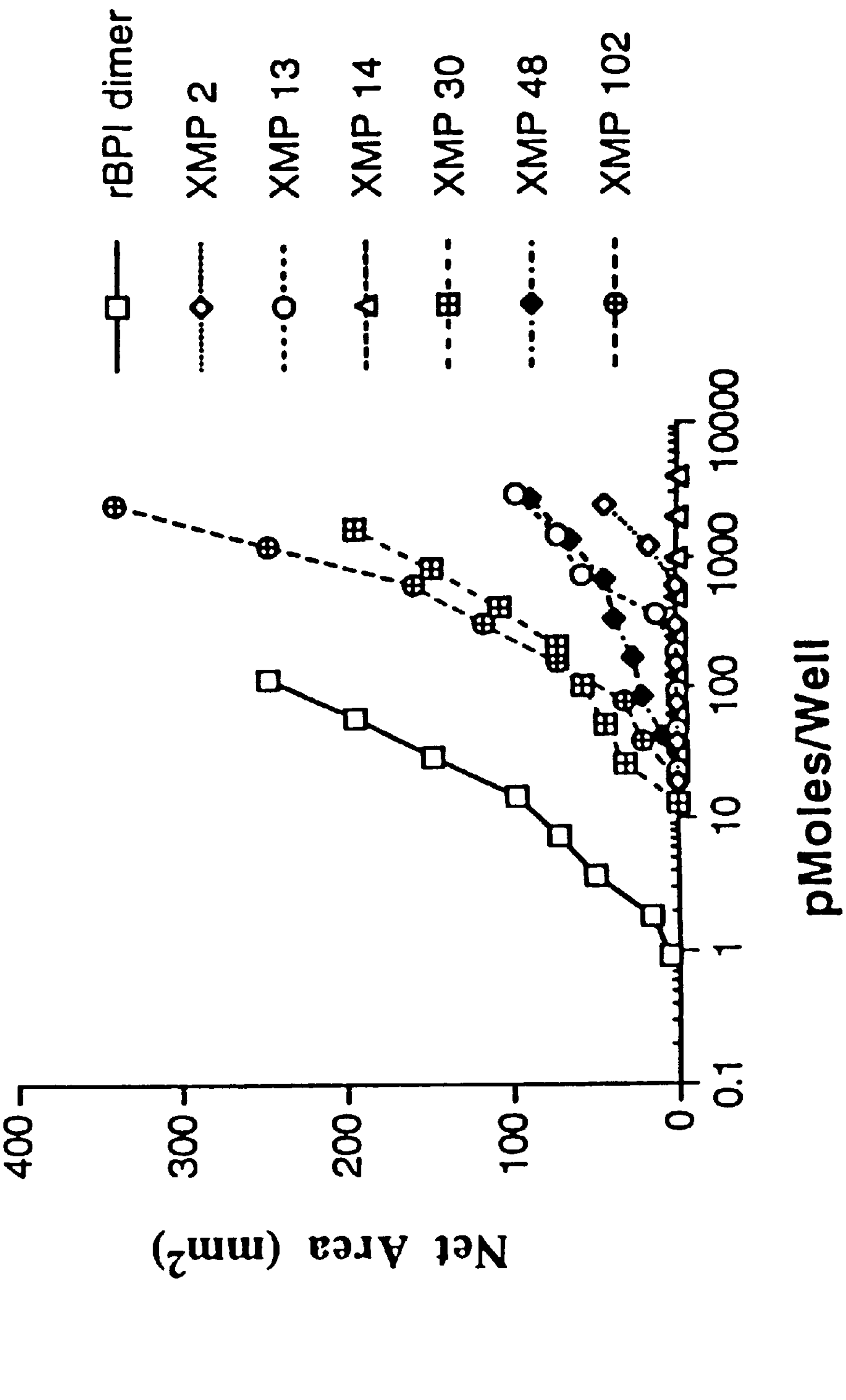

The experiment was repeated with BPI-derived peptides XMP.14, XMP.2, XMP.13, XMP.30, XMP.48 and XMP.102 on the L-phase variant and penicillin-treated bacterial form of *S. aureus*. The results, shown in FIGS. 7 and 8, establish that XMP.14 was completely inactive against the L-phase variant and XMP.2 was less active than XMP.13 on both the L-phase variant and the penicillin-treated bacterial form.

B. Evaluation in a Plate Assay and a Protein Synthesis Assay with S. Aureus L-Phase Variant Plate assays were performed to confirm the relative potency of $rBPI_{42}$ dimer and examine the time course of its bactericidal effects. Cells were grown to $A_{600}$=0.3 (~3x$10^8$ cells/mL) in HI broth supplemented with NaCl to 0.4M and 5 mM $CaCl_2$, diluted 1:100 into NaCl-supplemented PBS, incubated with $rBPI_{21}$, $rBPI_{50}$, $rBPI_{42}$ dimer or buffer, and plated on HI agar supplemented with NaCl and 1% horse serum. The results showed that $rBPI_{42}$ dimer caused up to a 75% reduction in colony forming units (CFUs) relative to buffer-treated cells at 2 hours. Incubation of cells with either buffer or 50 $\mu$g/mL $rBPI_{42}$ dimer for up to 5 hours before being plated produced optimal killing by dimer at 3 hours. In these assays, $rBPI_{42}$ dimer was consistently and significantly more potent than either of the monomeric forms, $rBPI_{50}$ or $rBPI_{21}$. To further extend these studies, the effect of these BPI protein products on protein synthesis of the *S. aureus* L-phase variant was examined. In these experiments, cells were grown to $A_{600}$=0.5 (~5x$10^8$ cells/mL) in HI broth supplemented with NaCl to 0.4M and 5 mM $CaCl_2$, diluted 1:100 into NaCl-supplemented HI broth and incubated with BPI protein product. Following incubation at 37° C., 0.4 $\mu$L of $^{14}$C-amino acids was added and incubation was continued for 30 min. at 37° C. Incorporation of the $^{14}$C-amino acids was linear for at least 30 min. Cells were treated with 3 mL cold 10% TCA to arrest protein synthesis and release free $^{14}$C-amino acids from the cells. The cells were then applied to 0.45 $\mu$m-pore size HA Millipore filters (Millipore, Bedford, Mass.), washed once with 3 mL 10% TCA and then with 5 mL water. The filters were dried and counted, and the percentage of $^{14}$C-amino acids incorporated relative to the control was calculated. An initial experiment to establish the optimum incubation time with 50 $\mu$g/mL $rBPI_{42}$ dimer demonstrated that maximal inhibition of protein synthesis (~90%) was achieved by 2 hours. Incubation of cells for 2 hours with various concentrations of BPI protein product and then with $^{14}$C-amino acids demonstrated that, as in other assays, $rBPI_{42}$ dimer was significantly more potent than the other BPI protein products. The $rBPI_{21}$ appeared to be less potent than $rBPI_{23}$ or $rBPI_{50}$ at inhibiting protein synthesis. Thus, patterns of growth inhibition parallel the patterns of inhibition of protein synthesis, with $rBPI_{42}$ dimer being most potent at inhibiting growth and protein synthesis.

C. Evaluation in a Broth Growth Inhibition Assay with S. Aureus L-Phase Variant

Figure 9:
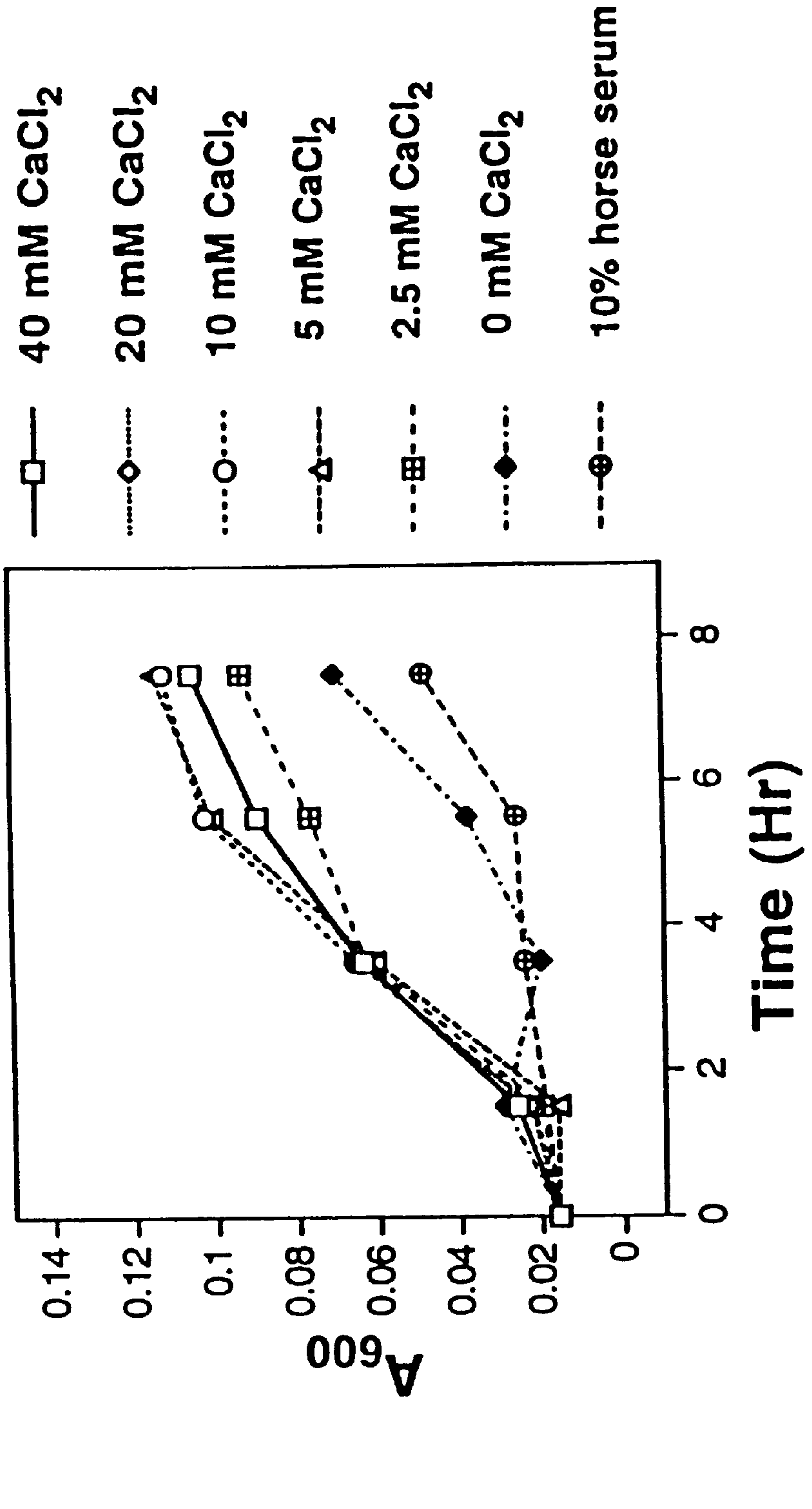
FIG. 9 relates to the effect of $CaCl_2$ concentration on the growth of *S. aureus* L-phase variant in broth.

Broth grown inhibition assays were performed to determine the effect of a BPI protein product on the growth of *S. aureus* L-phase variant cells (ATCC Accession No. 19640). Initial attempts to grow L-phase variant cells in HI broth supplemented with horse serum resulted in poor growth or clumping. The effect of $CaCl_2$ concentration on the growth of L-phase variant cells was tested to determine whether the cells could be readily grown in media supplemented with $CaCl_2$ instead of horse serum. L-phase variant cells were inoculated from an overnight culture into 2 ml of HI broth supplemented with 3.5% NaCl, 1,000 units/ml penicillin G and various concentrations of calcium chloride. The cells were incubated at 37° C. on a rotary shaker and the optical density ($A_{600}$) was measured at set time points. The results, depicted in FIG. 9, show that 5–10 mM $CaCl_2$ maintains an optimal rate of cell growth. These results show that $CaCl_2$ can be substituted for serum to allow growth of the L-phase variants in broth.

Figure 10:
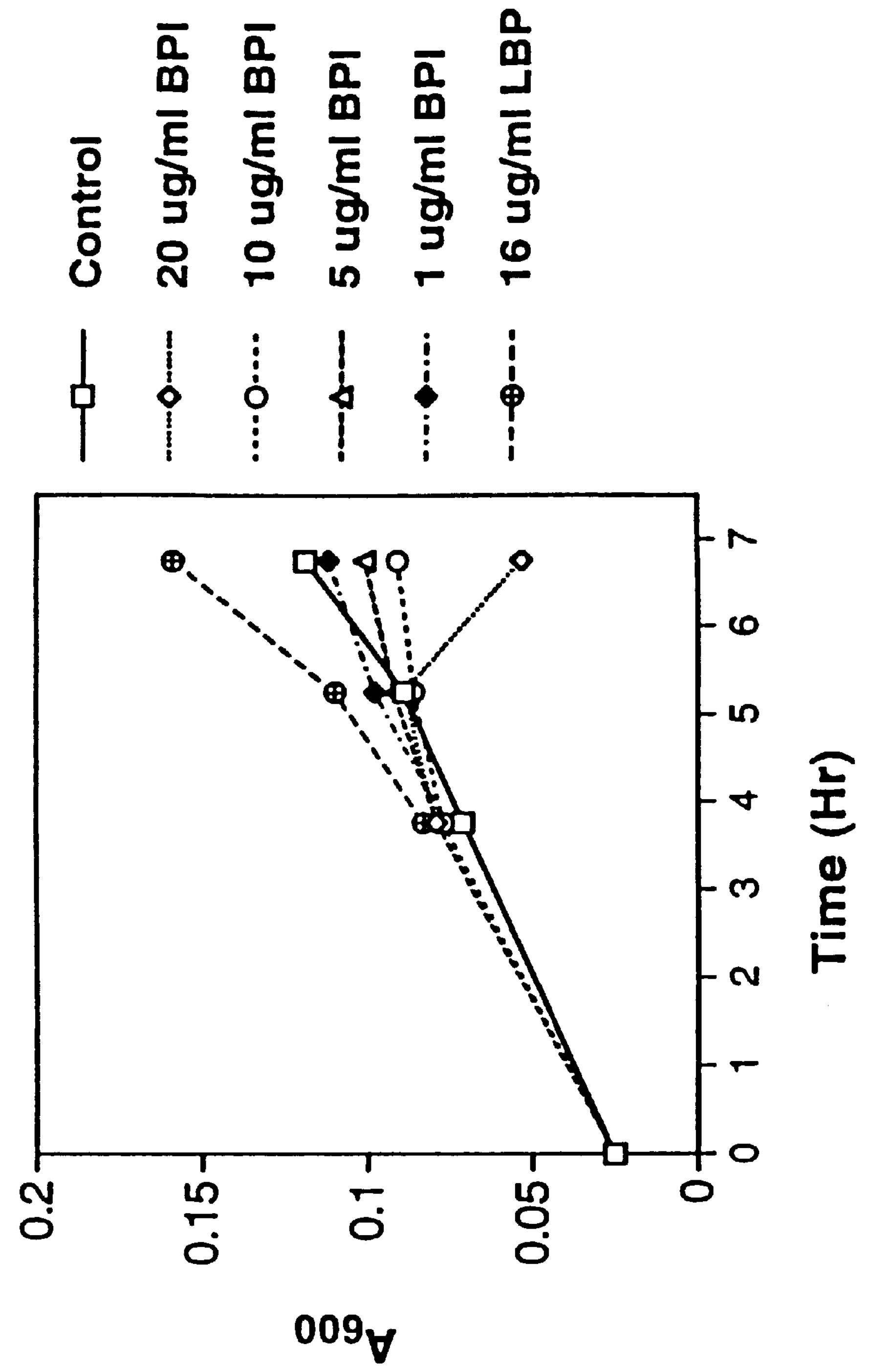
FIG. 10 depicts results from a broth growth inhibition assay of the effect of $rBPI_{21}$ on *S. aureus* L-phase variant.

L-phase variant cells of *S. aureus* were cultured overnight in HI broth supplemented with 3.5% NaCl, 10 mm $CaCl_2$ and 1,000 units/ml penicillin G. The cells were adjusted to an optical density of $A_{600}$=~0.025 (equivalent to ~$2.5\times10^7$ cells/ml) in the same broth and 150 μl of cells was added to each well of a 96 well plate. Varying concentrations of $rBPI_{21}$, diluted in buffer containing 5 mM citrate and 150 mM NaCl to a total volume of 2.5 μl, were added to the wells. Control wells contained cells with dilution buffer only (no BPI protein product) or with 16 μg/ml lipopolysaccharide binding protein (LBP). The cells were incubated at 37° C. on a rotary shaker and cell growth ($A_{600}$) was followed over 7 hours. The results are shown in FIG. 10, which depicts the change in $A_{600}$ over time for varying concentrations of $rBPI_{21}$, LBP or control with no BPI protein product. The open squares indicate the control, the open diamonds indicate 20 μg/ml $rBPI_{21}$, the open circles indicate 10 μg/ml $rBPI_{21}$, the open triangles indicate 5 μg/ml $rBPI_{21}$, the diamonds with a cross inside indicate 1 μg/ml $rBPI_{21}$ and the open circle with a cross inside indicates 16 μg/ml LBP. The results indicate a dose-dependent inhibitory effect on cell growth by 7 hours, with the decrease in turbidity at 20 μg/ml $rBPI_{21}$ suggesting that some cell lysis has occurred.

Figure 11:
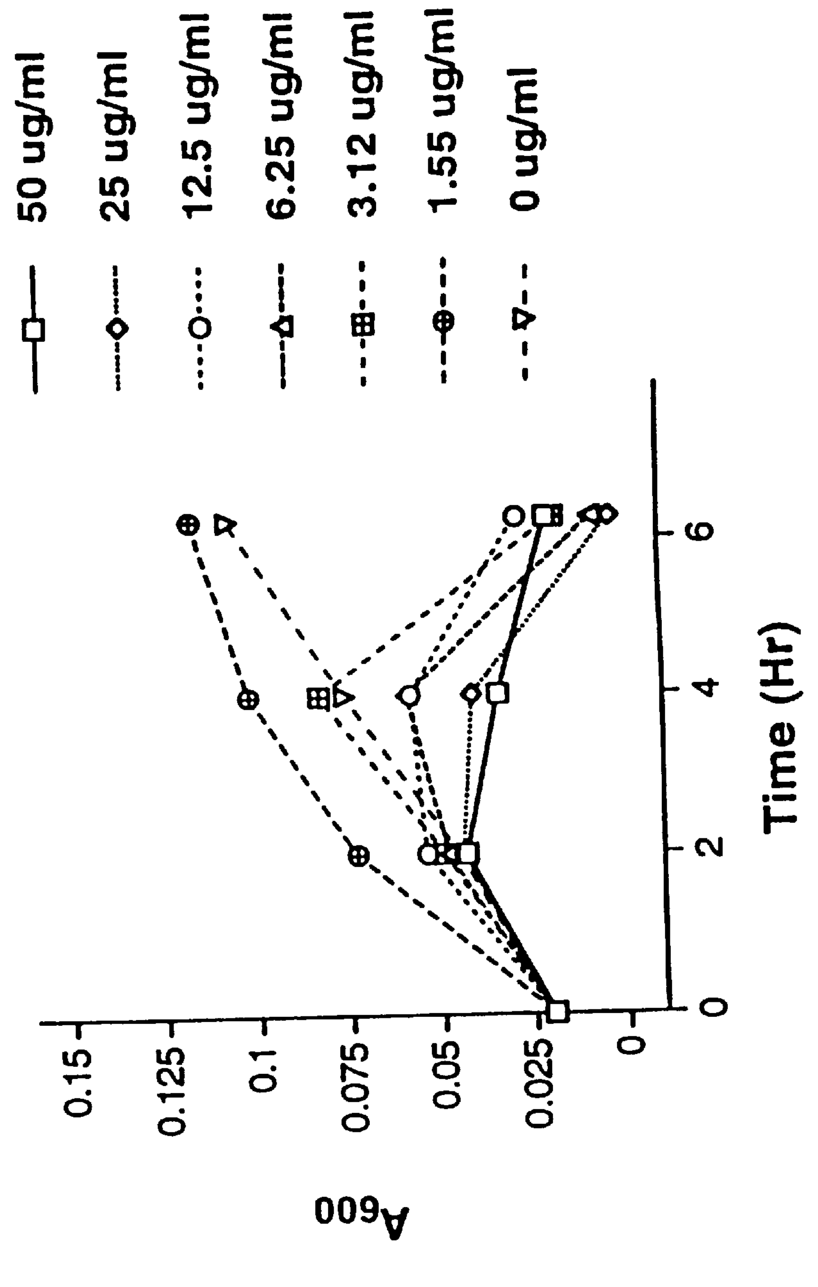
FIGS. 11, 12 and 13 shows results from broth growth inhibition assays of the effect of $rBPI_{21}$ on *S. aureus* L-phase variant, at $CaCl_2$ concentrations of 2.5 mM, 5 mM and 10 mM, respectively.
Figure 12:
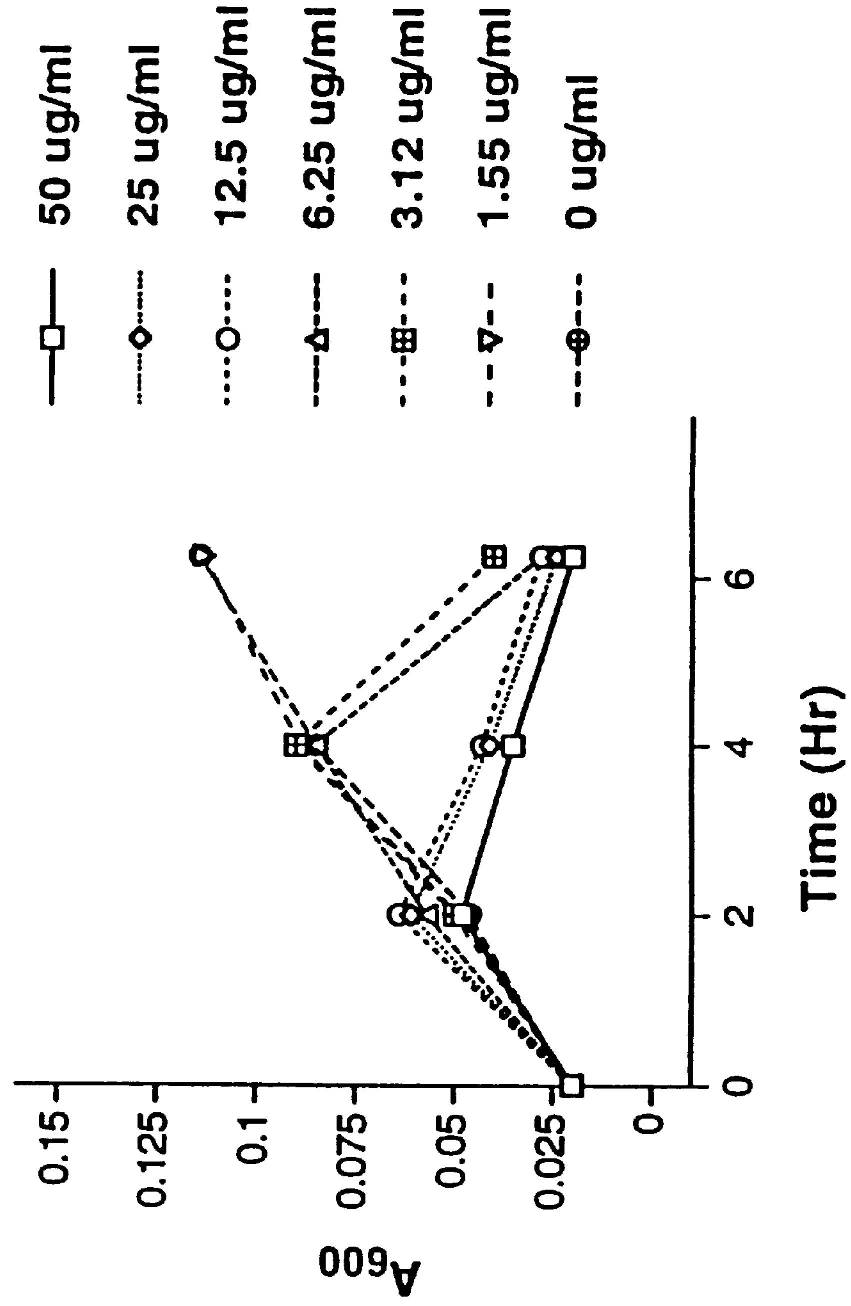
Figure 13:
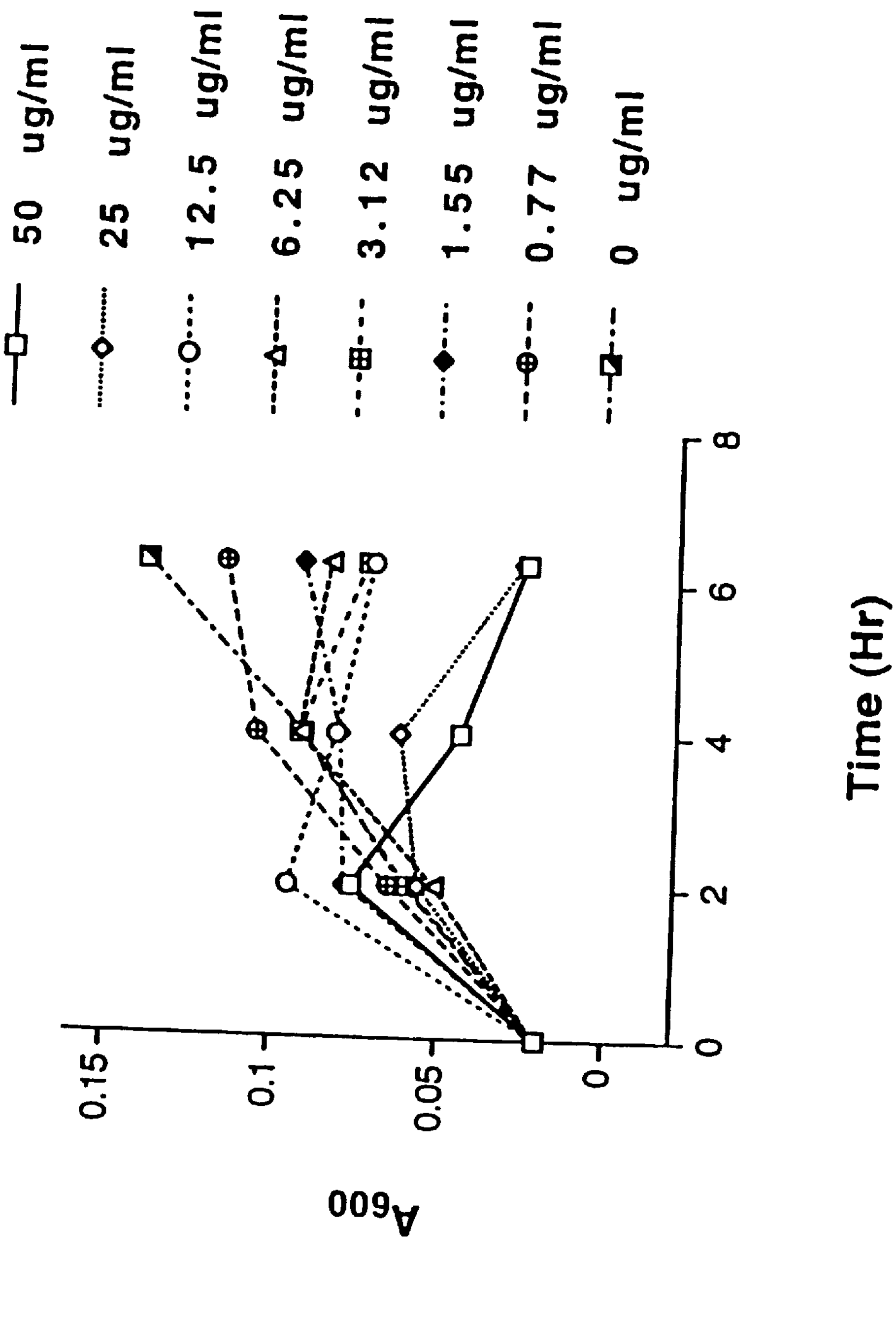
Figure 14:
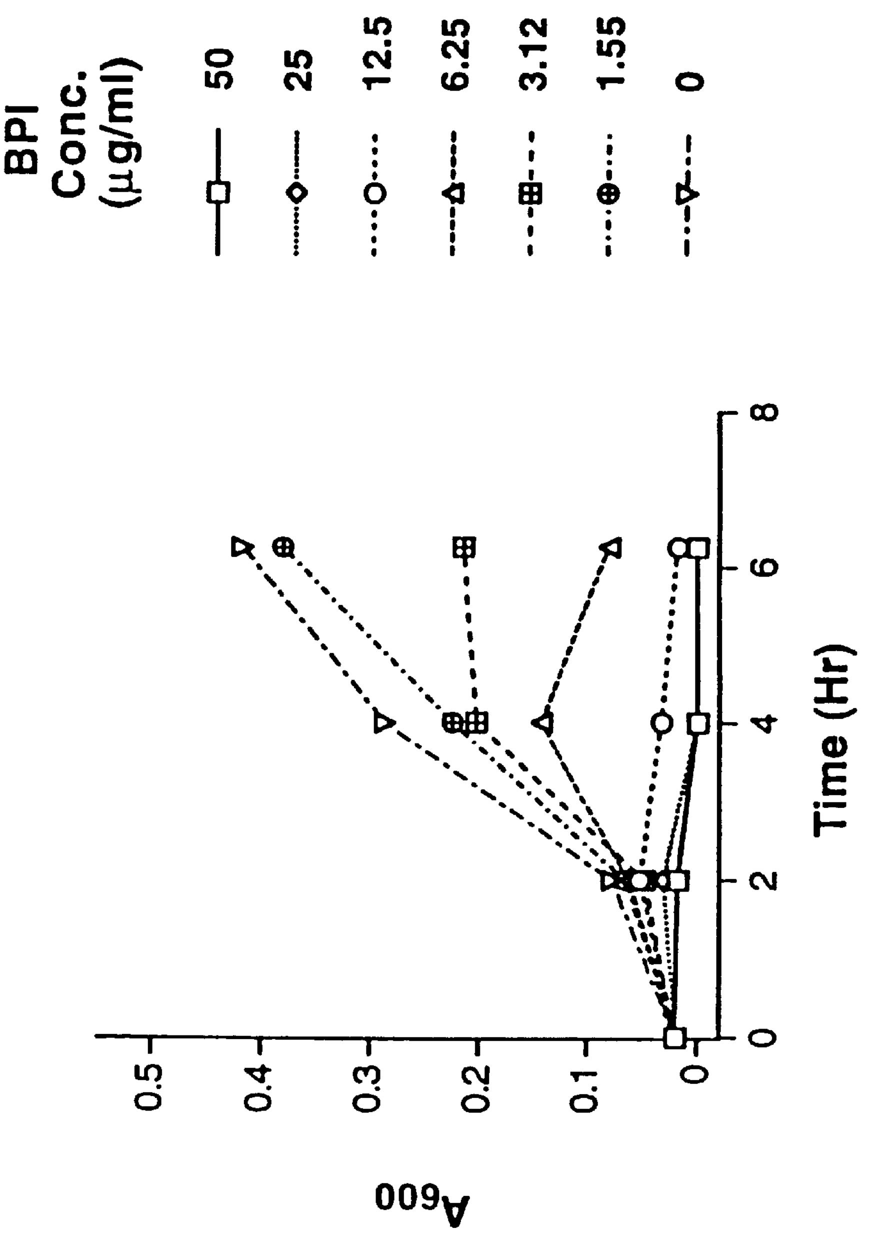
FIG. 14 shows the effect of $rBPI_{21}$ in an *E. coli* broth growth inhibition assay.

Further experiments were performed to confirm this result and to examine the effect of $CaCl_2$ on growth inhibition of *S. aureus* L-phase variants by BPI protein product. The L-phase variant cells were grown overnight in HI broth supplemented with 3.5% NaCl, 10 mM $CaCl_2$ and 1,000 units/ml penicillin G, and were inoculated into 96 well plates to $A_{600}$=~0.02 in 100 μl of the same broth supplemented with 2.5, 5 or 10 mM $CaCl_2$. As a control, the BPI-susceptible gram-negative organism *E. coli* J5 was inoculated from an overnight culture into TYE broth (Difco, Detroit, Mich.). Two-fold serial dilutions of $rBPI_{21}$, diluted in 5 mm citrate and 150 m NaCl to a total volume of 2.5 μl, were added to each well to yield final $rBPI_{21}$ concentrations of 50 to 0.77 μg/ml. The cells were incubated at 37° C. on a rotary shaker and cell growth as measured by $A_{600}$ was followed. The results of these experiments are shown in FIGS. 11, 12 and 13 and confirm that BPI protein product inhibits growth of the L-phase variant beginning at about 4 hours. The greatest inhibitory effect was observed for the cells grown in broth supplemented with 2.5 mM $CaCl_2$. Under these conditions, $rBPI_{21}$ at concentrations as low as 3.12 μg/ml inhibited growth and caused a decrease in absorbance. Higher concentrations of $CaCl_2$ (5 and 10 mM) appeared to inhibit the action of $rBPI_{21}$ on the cells. The results of the control experiment with *E. coli* J5 are shown in FIG. 14. By comparison the *E. coli* J5 cells were immediately inhibited by $rBPI_{21}$, but only at the three highest concentrations (50, 25 and 12.5 μg/ml).

EXAMPLE 4

In Vitro Effects of BPI Protein Products on Streptococcus Species in a Radial Diffusion Assay Radial diffusion assays were conducted to evaluate the effect of the same BPI protein products tested in Example 3, $rBPI_{23}$, $rBPI_{21}$, $rBPI_{50}$, BPI-Immunoglobulin fusion product and $rBPI_{42}$ dimer, on *S. pneumoniae* and *S. pyogenes*. L-phase variants of *S. pneumoniae* (ATCC Accession NO. 35088) were initially isolated by plating log-phase bacterial forms on L-phase variant media (HI broth supplemented with 3.5% NaCl, 10% horse serum, and 1000 units/ml penicillin G). The cells grew optimally on agar plates consisting of 1.3% Bacto-agar (Difco, Detroit, Mich.) and BHI broth supplemented with 2% NaCl and 10% inactivated horse serum. The L-phase variants were subsequently adapted to grow on this BHI medium lacking horse serum. Colonies of L-phase variants from the agar plates were resuspended into BHI broth supplemented with 2% NaCl and adjusted to $A_{600}$=~0.025. The cell suspension was added at a 1:100 dilution to molten BHI agar medium containing 0.8% agarose and BHI broth supplemented with 2% NaCl and 1000 units/ml penicillin G, which was then allowed to solidify. Serial 2-fold dilutions of each BPI protein product in unformulated citrate buffer or formulated citrate buffer were added in 5 μl aliquots to 3-mm wells prepared in the plates. Unformulated citrate buffer was 20 mM citrate, pH 5.0, 150 mM NaCl for $rBPI_{23}$, or 5 mM citrate, pH 5.0, 150 mM NaCl for other BPI protein products. Formulated citrate buffer was 20 mM citrate, pH 5.0, 150 mM NaCl, with 0.1% poloxamer 188 and 0.002% polysorbate 80 for $rBPI_{23}$, or 5 mM citrate, pH 5.0, 150 mM NaCl with 0.2% poloxamer 188 and 0.002% polysorbate 80 for $rBPI_{21}$, or 5 mM citrate, pH 5.0, 150 mM NaCl with 0.1% poloxamer 188 and 0.002% polysorbate 80 for other BPI protein products. The corresponding formulated or unformulated buffer was also added to wells as a control. After 24 hours of incubation at 37° C., the plates were examined for zones of growth inhibition. There were no differences in the activity of BPI protein products in formulated vs. unformulated buffer.

Figure 15:
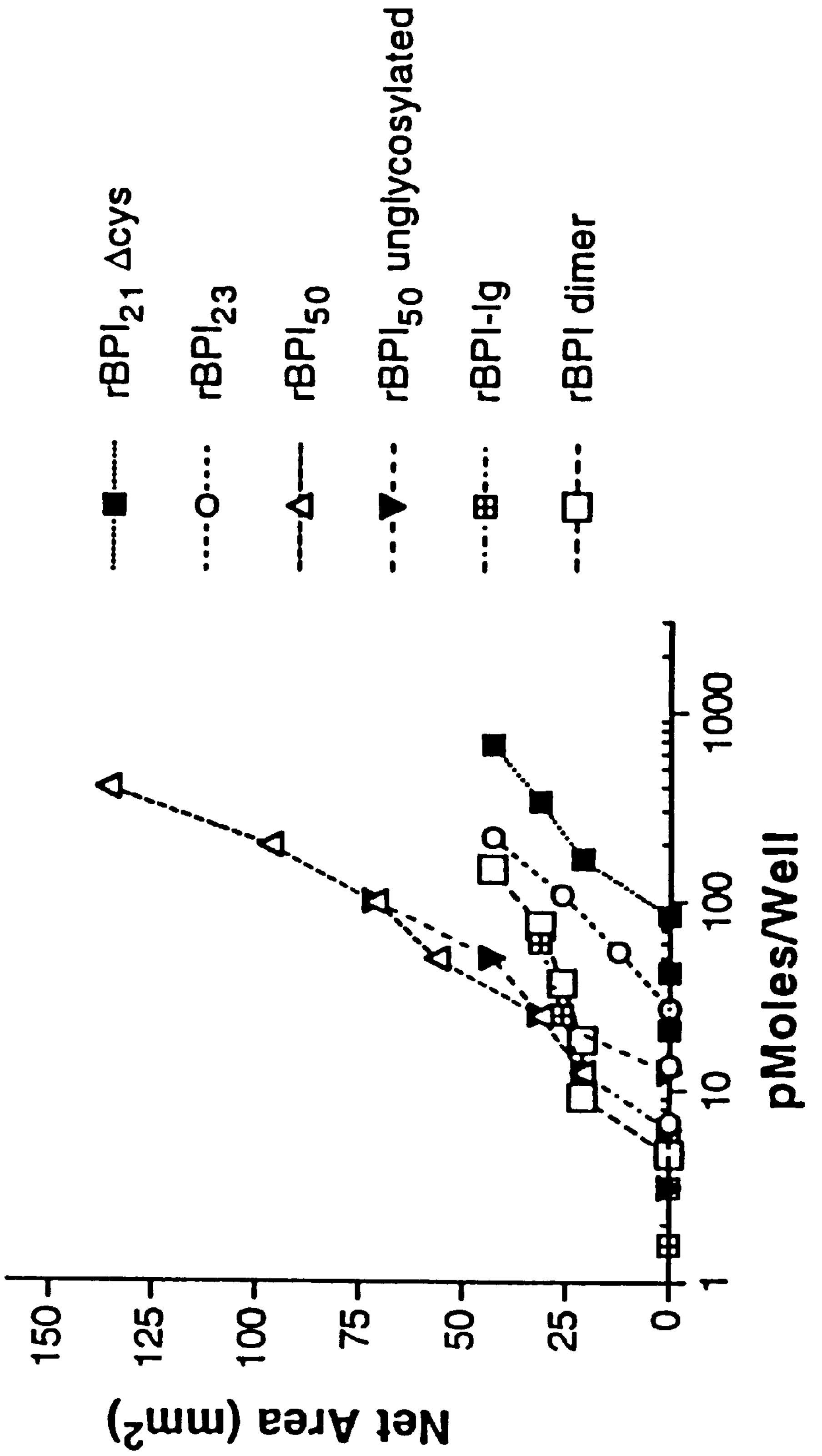
FIG. 15 displays the effect of a variety of BPI protein products on *S. pneumoniae* L-forms in a radial diffusion assay.

The results of one representative assay, shown in FIG. 15, demonstrate that the L-phase variant of *S. pneumoniae* is susceptible to all of these BPI protein products, while the normal bacterial form is not (as shown above in Example 3). In the figure, a closed square signifies $rBPI_{21}$, an open circle indicates $rBPI_{23}$, an open triangle indicates $rBPI_{50}$, a closed inverted triangle indicates unglycosylated $rBPI_{50}$, an open square enclosing a plus-sign indicates BPI-Immunoglobulin fusion, and an open square signifies $rBPI_{42}$ dimer. These data show that $rBPI_{50}$ was the most potent inhibitor of growth, followed by $rBPI_{42}$ dimer and BPI-Immunoglobulin fusion.

Similar results were obtained when the experiment was repeated with penicillin-treated *S. pneumoniae* bacterial forms grown in the presence of osmotic protection. Log-phase cells growing in BHI broth were concentrated to $A_{600}$=~5.0, added to the same BHI agarose medium containing penicillin as above, tested with serial dilutions of the same BPI protein products as above, and incubated for 48–72 hours. These penicillin-treated bacteria were also observed to be susceptible to all tested BPI protein products.

The effects of BPI protein products on the bacterial form (ATCC No. 25663) and L-phase variant (ATCC No. 27080) of *S. pyogenes* were evaluated in this radial diffusion assay. The bacterial form was grown in BHI broth, and the L-phase variant was grown first on ATCC medium No. 608 and later in medium 608 supplemented with penicillin G and 10% heat inactivated horse serum. The cells were incorporated into molten BHI agarose (for the bacterial forms), or molten medium 608 agarose supplemented with penicillin G and 1% heat inactivated horse serum (for the L-phase variants), and various concentrations of $rBPI_{21}$, $rBPI_{23}$, $rBPI_{50}$ and $rBPI_{42}$ dimer were tested. As previously observed for the other bacterial species tested, none of the BPI protein products had an inhibitory effect at the concentrations tested on the *S. pyogenes* bacterial form. The L-phase variant was susceptible to all BPI protein products tested, $rBPI_{21}$, $rBPI_{23}$, $rBPI_{50}$, and $rBPI_{42}$ dimer, with $rBPI_{42}$ dimer and $rBPI_{23}$ being most potent and $rBPI_{50}$ least (this lower potency of $rBPI_{50}$ was not seen with other bacterial species).

Figure 16:
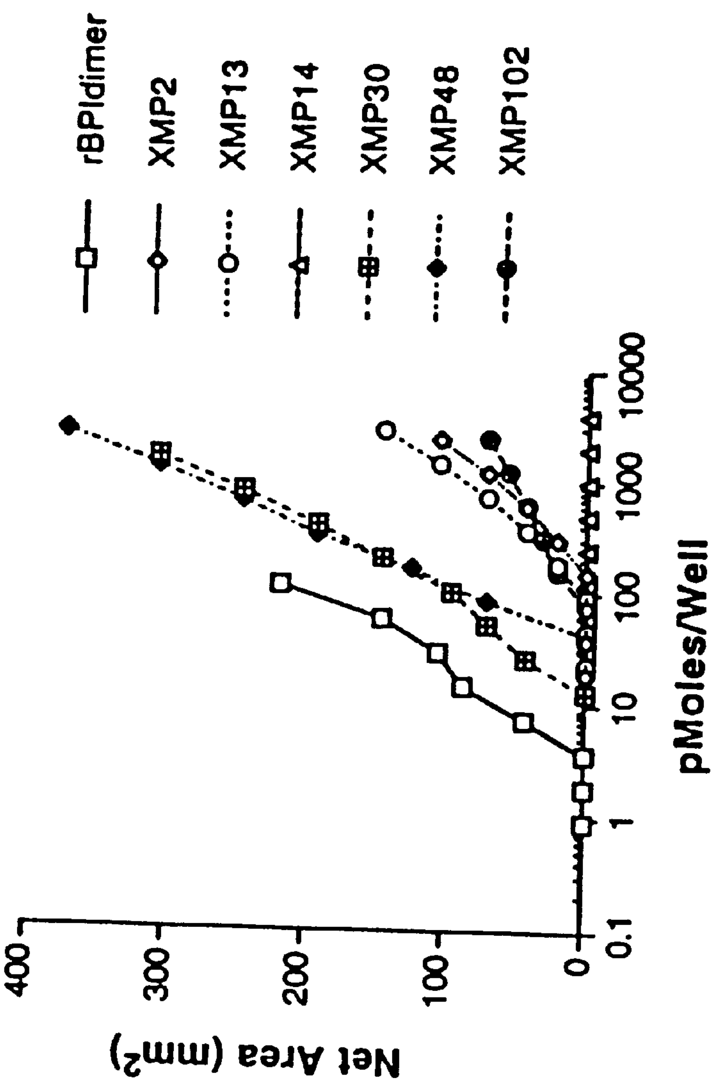
FIGS. 16 and 17 show the effect of BPI protein products, including BPI-derived peptides, on the *S. pneumoniae* bacterial form and L-phase variant in a radial diffusion assay.
Figure 17:
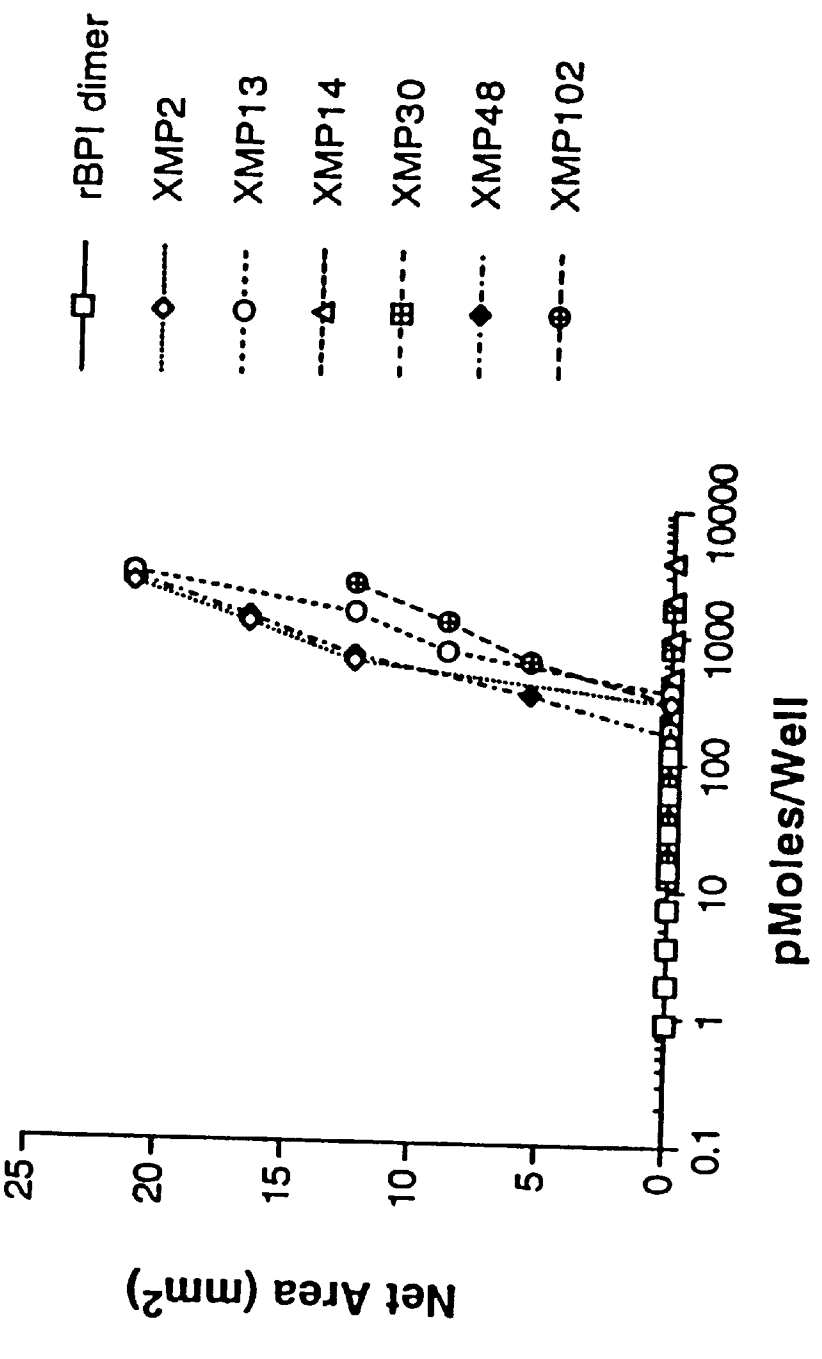
Figure 18:
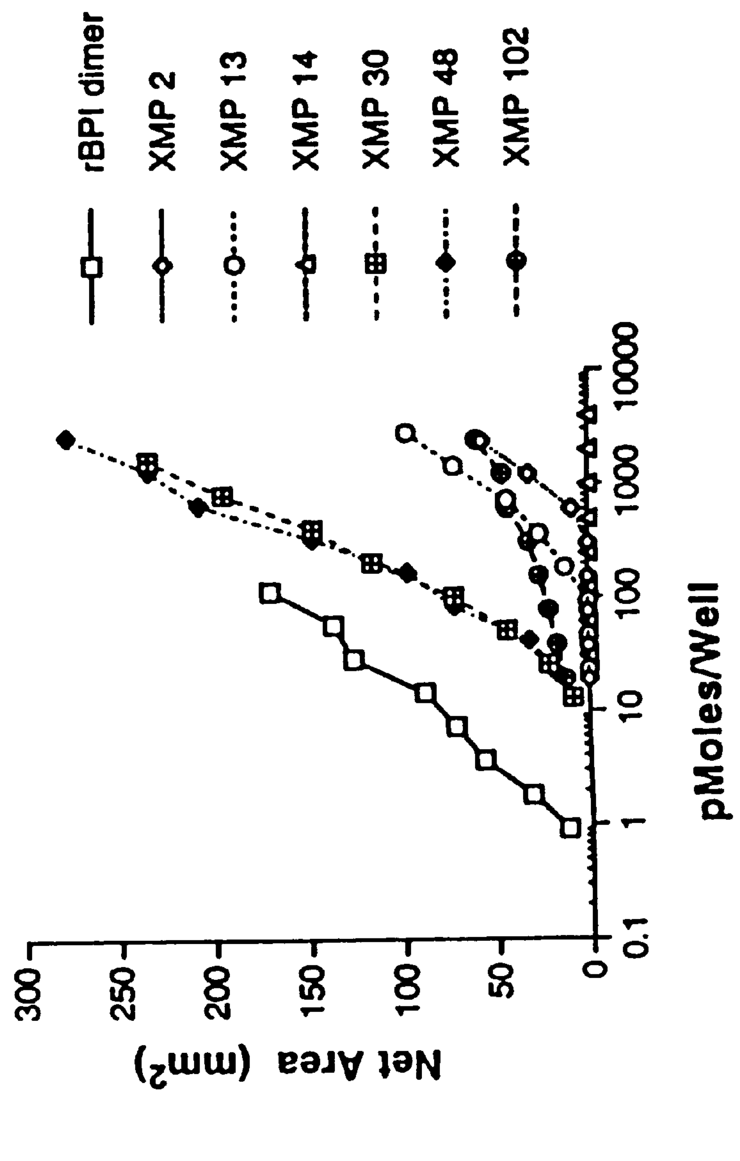
FIGS. 18 and 19 show the effect of BPI protein products, including BPI-derived peptides, on the *S. pyogenes* bacterial form and L-phase variant in a radial diffusion assay.
Figure 19:
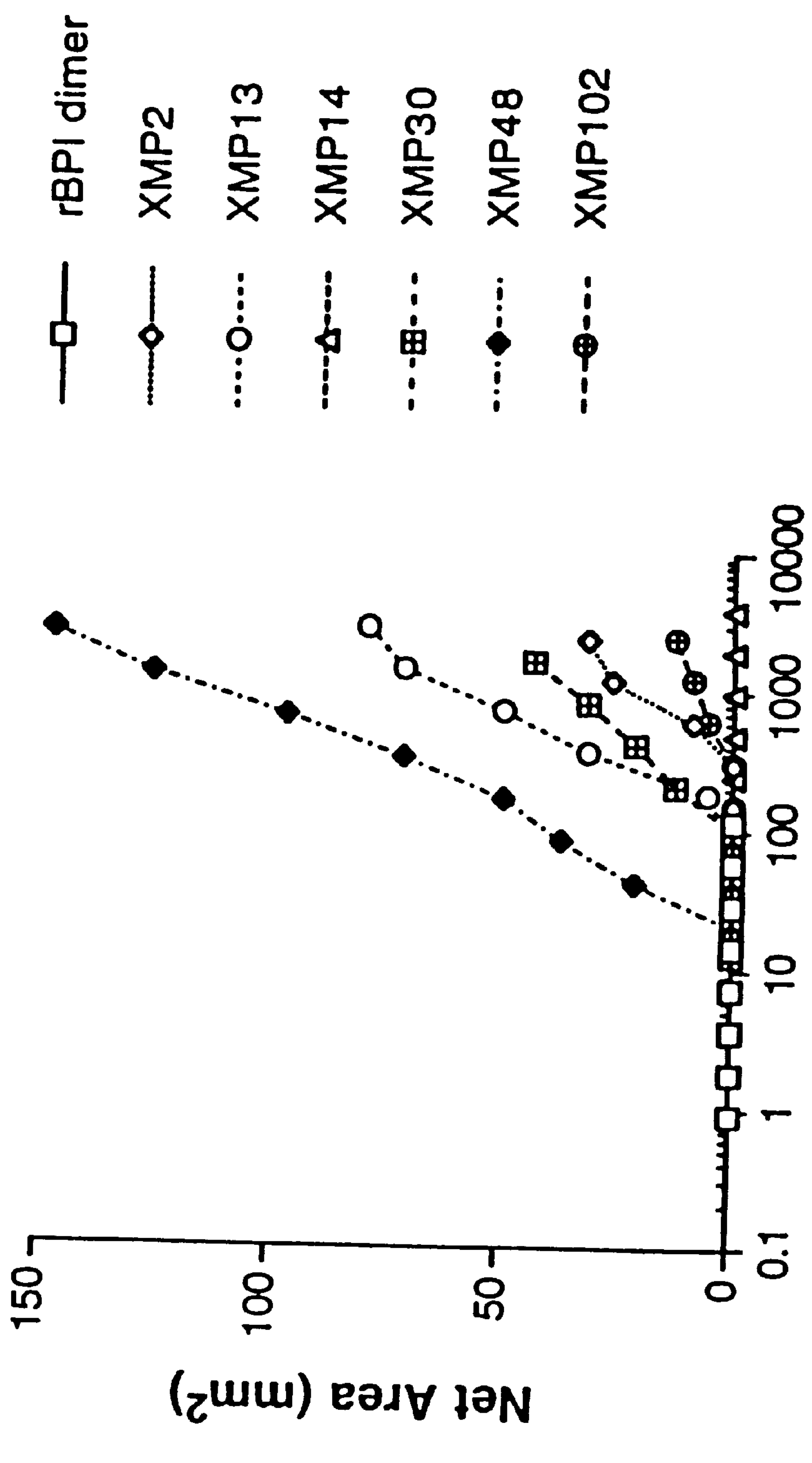

The effects of additional BPI protein products, BPI-derived peptides, on the bacterial and L-phase variants of *S. pneumoniae* (ATCC No. 35088) and *S. pyogenes* (bacterial form ATCC No. 25663; L-phase variant ATCC No. 27080) were also evaluated in this radial diffusion assay. The results, depicted in FIGS. 16 and 17 (for *S. pneumoniae* L-phase variant and bacterial form, respectively) and FIGS. 18 and 19 (for *S. pyogenes* L-phase variant and bacterial form, respectively) demonstrate that, in general, these peptides inhibited growth of the L-phase variant in a similar manner to that observed with the *S. aureus* L-phase variant. Unlike *S. aureus*, the *S. pyogenes* bacterial form was susceptible to XMP.2, XMP.13, XMP.30 and XMP.102 as well as to XMP.48, while the *S. pneumoniae* bacterial form also appeared to be slightly susceptible to high concentrations of XMP.2, XMP.13, XMP.48 and XMP.102, but not XMP.30. However, when the experiment was repeated with XMP.13 and XMP.30, the *S. pneumoniae* bacterial form appeared to be susceptible to XMP.30. As previously observed, only the L-phase variants were sensitive to $rBPI_{42}$ dimer.

EXAMPLE 5

Figure 20:
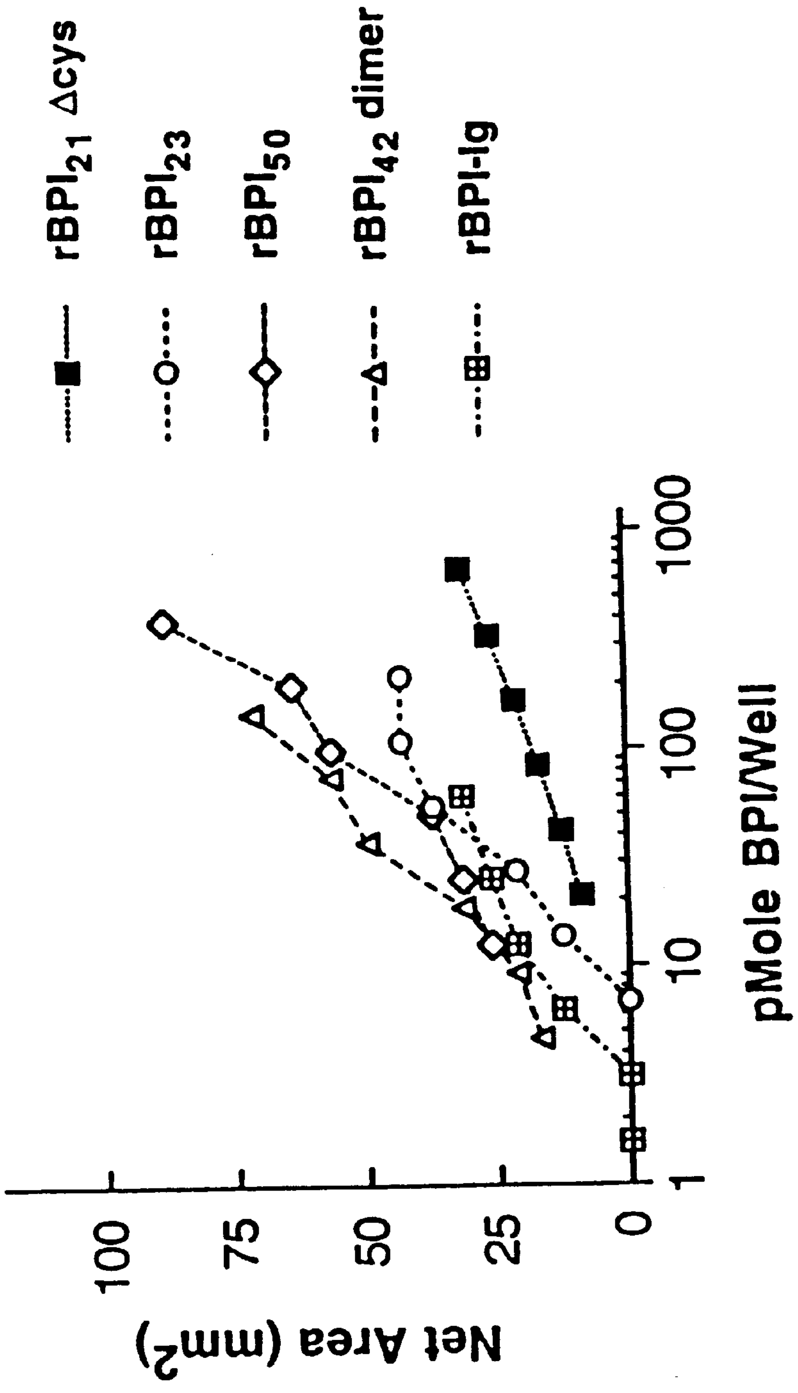
FIG. 20 shows the effect of a variety of BPI protein products on *E. faecalis* L-forms in a radial diffusion assay.

In Vitro Effects of BPI Protein Products on Enterococcus Faecalis L-Phase Variants in a Radial Diffusion Assay Radial diffusion assays were conducted to evaluate the effect of the same BPI protein products, used in Example 3, $rBPI_{23}$, $rBPI_{21}$, $rBPI_{50}$, BPI-Immunoglobulin fusion product and $rBPI_{42}$ dimer, on *E. faecalis* L-phase variants. L-phase variants of *E. faecalis* (ATCC Accession No. 4200) were initially isolated by plating log-phase bacterial forms on agar medium consisting of 1.3% Bacto-agar (Difco, Detroit, Mich.) and BHI broth supplemented with 0.5% yeast extract, 0.93% NaCl, 9.73% sucrose, 0.025% $MgSO_4$, 10% heat inactivated horse serum and 1000 units/ml penicillin G (Medium 607, ATCC, Rockville, Md.), but also grew well on BHI agar supplemented only with NaCl, sucrose and horse serum. The cells were subsequently adapted to growth on Medium 607 lacking horse serum. Colonies of L-phase variants from the agar plates were resuspended into Medium 607 and adjusted to $A_{600}$=~0.025. The cell suspension was added at a 1:100 dilution to molten BHI agarose medium containing BHI broth, 0.93% NaCl, 9.73% sucrose and 1000 units/ml penicillin G, which was then allowed to solidify. Serial 2-fold dilutions of each BPI protein product in 5 $\mu$l were added to 3-mm wells prepared in the plates. After 24 hours of incubation, the plates were examined for zones of growth inhibition. The results of one representative assay, shown in FIG. 20, demonstrate that the L-phase variant of *E. faecalis* is susceptible to all of these BPI protein products, while the normal bacterial form is not (as shown above in Example 3). In the figure, a closed square signifies $rBPI_{21}$, an open circle indicates $rBPI_{23}$, an open triangle indicates $rBPI_{42}$ dimer, an open square enclosing a plus-sign indicates BPI-Immunoglobulin fusion, and an open diamond signifies $rBPI_{50}$ Unglycosylated $rBPI_{50}$ behaved in an identical manner to $rBPI_{50}$.
These data show that $rBPI_{42}$ dimer and $rBPI_{50}$ were the most potent inhibitors of growth.

Similar results were obtained when the experiment was repeated with penicillin-treated *E. faecalis* bacterial forms grown in the presence of osmotic protection. Log-phase cells growing in BHI broth were concentrated to $A_{600}$=~5.0, added to the same BHI agarose medium (consisting of medium 607 with penicillin G but without horse serum as in the radial diffusion assay described above, tested with serial dilutions of $rBPI_{21}$, $rBPI_{23}$, BPI-Immunoglobulin fusion and $rBPI_{42}$ dimer, and incubated for 48–72 hours. These penicillin-treated bacteria were also observed to be susceptible to all tested BPI protein products. In this experiment there were greater differences in activity, with $rBPI_{42}$ dimer and BPI-Immunoglobulin fusion being the most potent inhibitors of growth.

EXAMPLE 6

In Vitro Effects of BPI Protein Products on Mycoplasma in Radial Diffusion Assays Mycoplasmas are prokaryotes that lack a cell wall. Many members of this group are naturally-occurring, non-pathogenic inhabitants of humans. *Mycoplasma pneumoniae,* however, is a major cause of primary atypical pneumonia. The susceptibility of L-phase variants to BPI protein products predicts that mycoplasmas also are susceptible.

Figure 21:
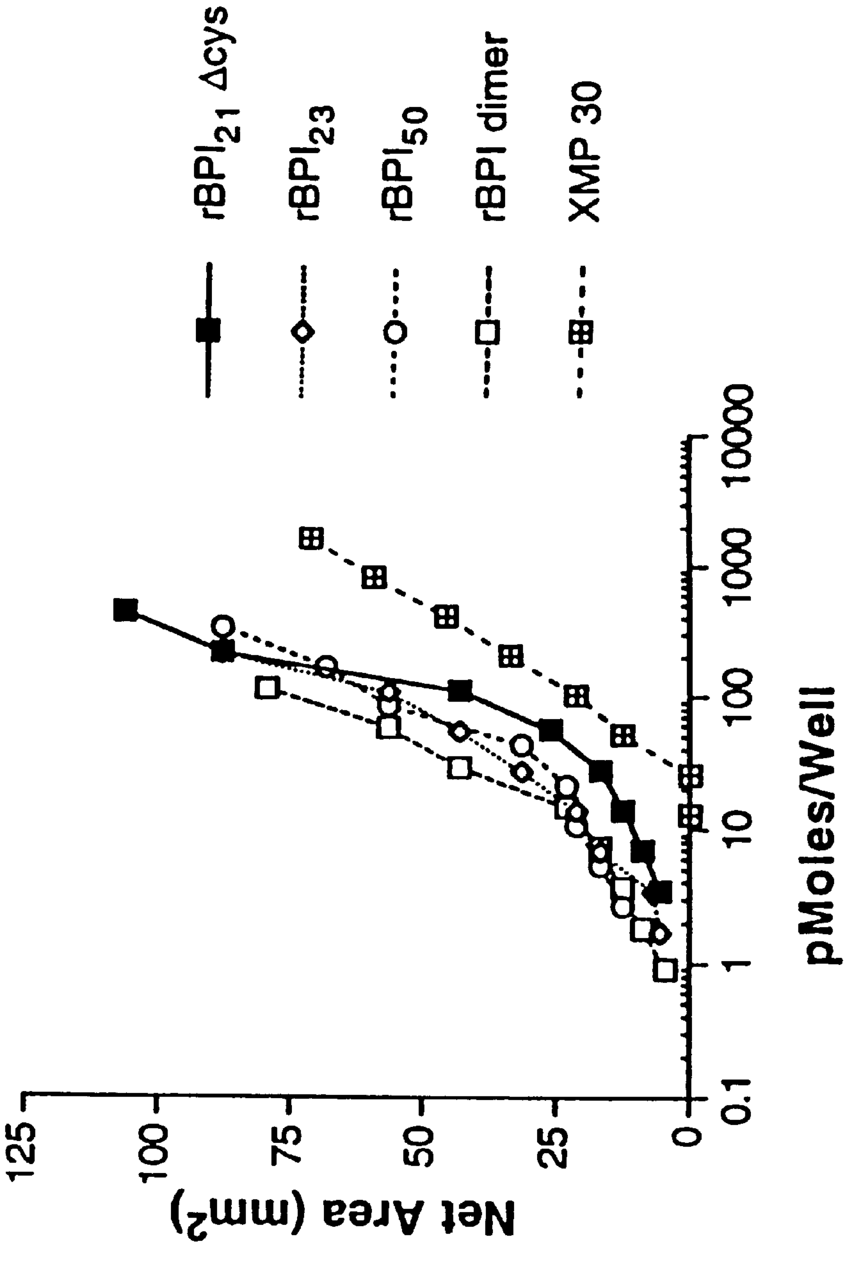
FIGS. 21 and 22 show the effect of BPI protein products, including BPI-derived peptides, on the mycoplasma *Acholeplasma laidlawii* in a radial diffusion assay.

Experiments were performed to evaluate the effects of BPI protein products on the mycoplasma *Acholeplasma laidlawaii,* which is relatively unfastidious and does not require a $CO_2$-enriched atmosphere to grow. Cells were grown overnight in HI broth supplemented with 1% PPLO serum fraction (Difco, Detroid, Mich.), incorporated into the same medium containing agarose, and used in radial diffusion assays as described above for L-phase variants. BPI protein products ($rBPI_{23}$, $BPI_{21}$, $BPI_{50}$, $rBPI_{42}$ dimer and purified XMP.30) were added to the wells and the plates were incubated at 37° C. for 2 days. The results, shown in FIG. 21, demonstrate that all of the BPI forms tested were effective against the Acholeplasma. For $rBPI_{23}$ and $rBPI_{21}$, a second zone of reduced growth was observed outside of the zone of complete inhibition.

Figure 22:
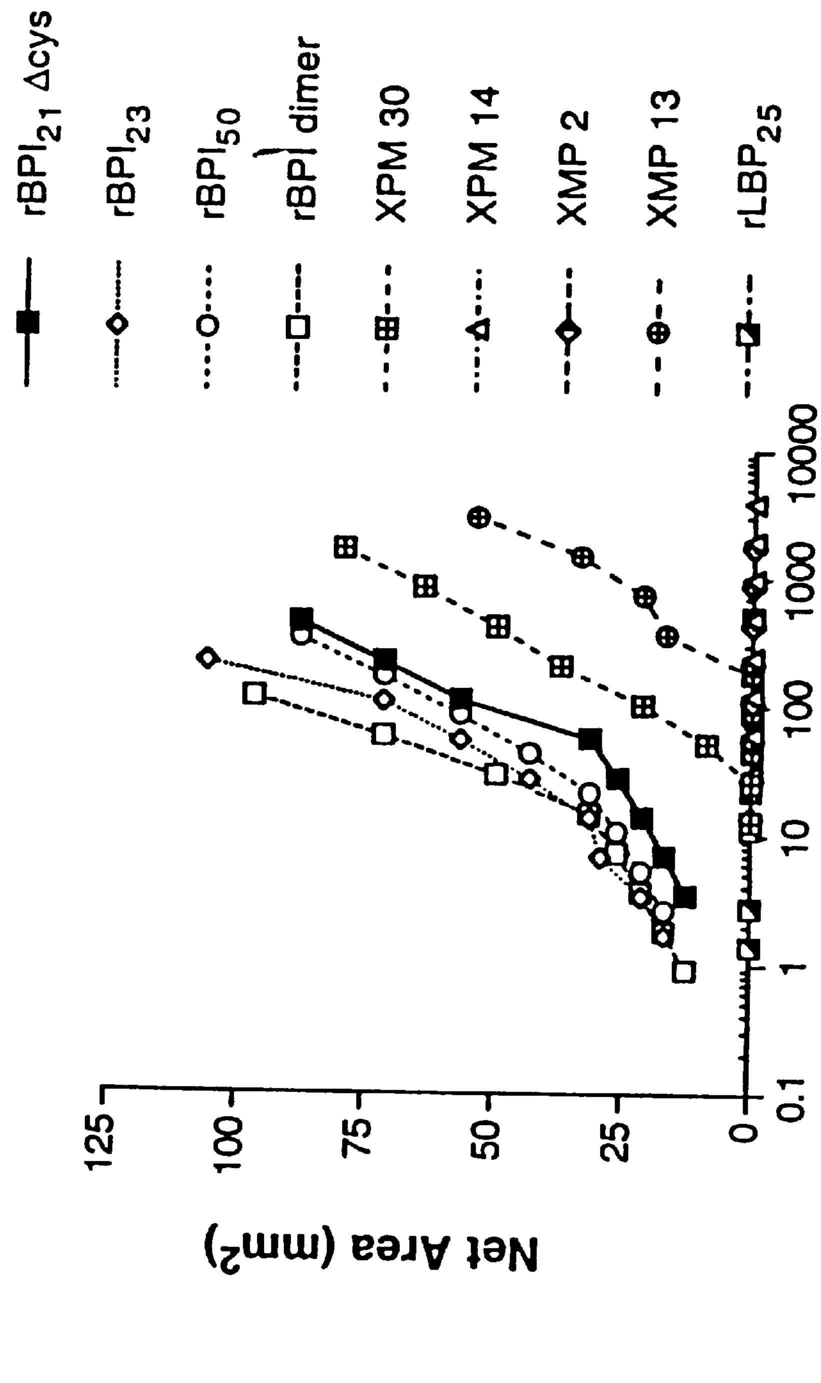

The experiment was repeated with the same BPI protein products and XMP.13, XMP.2 and XMP.14. The results, depicted in FIG. 22, showed that XMP.13 and XMP.30 formed inhibition zones while XMP.2 and XMP.14 were not active at the concentrations tested. Additional experiments can be performed with this Acholeplasma species as well as other mycoplasma species.

EXAMPLE 7

In Vitro Effects of LBP Derivatives on L-Phase Variants of *S. aureus, S. pneumoniae* and *E. faecalis* in a Radial Diffusion Assay BPI protein products and LBP protein derivatives were evaluated in the radial diffusion assays described above for their effect on the growth of L-phase variants of various bacterial species, including *S. aureus, S. pneumoniae* and *E. faecalis.* The compounds evaluated were $rBPI_{50}$, $rBPI_{23}$, $rBPI_{21}$, mature LBP protein ($LBP_{50}$), $LBP_{25}$, LBP(1–197)/BPI(200–456) hybrid and BPI(1–199)/LBP(198–456) hybrid.

A plasmid encoding the LBP(1–197) BPI(200–456) hybrid was constructed by combining appropriate portions of the two molecules via a ClaI restriction site engineered into homologous locations in the DNA encoding the two molecules. The first step necessary for the construction of the mammalian expression vector pING4160 was the construction of two intermediate plasmids to introduce a ClaI restriction site by overlap extension PCR mutagenesis at the Ile-Asp at positions 197–198 in LBP (to generate plasmid pML127) and the Ile-Asp at positions 199–200 in BPI (to generate plasmid pML126). These were silent mutations which changed the nucleotide sequence only and not the amino acid sequence. The next step was to combine the amino terminal portion of LBP from pML127 with the carboxyl terminal of BPI from pML126 at the homologous ClaI sites to generate the intermediate plasmid pML128. The final step was then to subclone the LBP-BPI insert from pML126 into a mammalian expression vector to generate pING4160.

To construct plasmid pML127 (LBP with ClaI at 197–198), overlapping primers were designed to incorporate the changes necessary to encode a ClaI recognition site at the desired location. The template was pML125, a plasmid containing an insert encoding full length LBP. The printers were LBP-10, SEQ. ID. NO: 228, facing downstream, and LBP-11, SEQ. ID. NO: 229, facing upstream. Two separate PCR reactions were carried out with primer pairs LBP-Bsm, SEQ. ID. NO: 230, facing downstream, and LBP-11, to generate a 600 bp fragment that was then digested with StuI and ClaI to generate a 389 bp fragment, and primer pairs LBP-10 and LBP-8, SEQ. ID. NO: 231, facing upstream, to generate a 328 bp fragment that was then digested with ClaI and Bsu36I to generate a 148 bp fragment. The two resulting fragments were then ligated to the Bsu36I-StuI vector fragment from pML125 to generate the plasmid pML127.

To construct plasmid pML126 (BPI with ClaI at 199–200), overlapping primers were designed to incorporate the changes necessary to encode a ClaI recognition site at the desired location. The template was pML124, a plasmid containing an insert encoding full length BPI protein. The primers were BPI-63, SEQ. ID. NO: 232, facing downstream, and BPI-64, SEQ. ID. NO: 233, facing upstream. Two separate PCR reactions were carried out with primer pairs BPI-40, SEQ. ID. NO: 234, facing downstream, and BPI-64, to generate a 260 bp fragment that was then digested with PmlI and ClaI to generate a 170 bp fragment, and primer pairs BPI-7, SEQ. ID. NO: 235, facing upstream, and BPI-63, to generate a 296 bp fragment that was then digested with ClaI and BstXI to generate a 215 bp fragment. The two resulting fragments were then ligated to the BstXI-PmlI vector fragment from pML124 to generate the plasmid pML126.

To construct pML128, the intermediate plasmid encoding the LBP(1–197)BPI(200–456) hybrid, the 620 bp HindIII-ClaI fragment encoding the amino terminal region of BPI in the plasmid pML126 was replaced with the corresponding HindIII-ClaI fragment from pML127 encoding the amino terminal region of LBP. To construct the mammalian expression vector pING4160, the 623 bp FspI-Bsu361 fragment of pML128 was ligated to the 361 bp SalI-FspI fragment from pING4539 (described in Gassano-Santaro et al., U.S. application Ser. No. 08/261,660 filed Jun. 17, 1994), which includes the LBP signal sequence, and the approximately 8630 bp Bsu36I-SalI fragment from pING4321. The latter fragment includes sequences encoding part of the carboxyl terminus of BPI and all the vector sequences, which include the CMV promoter and the light chain 3' transcription termination sequences (as described in Ammons et al., U.S. application Ser. No. 08/212,132, filed Mar. 11, 1994).

A plasmid encoding the BPI(1–199) LBP(198–456) hybrid was constructed by combining appropriate portions of the two molecules via a ClaI restriction site engineering into homologous locations in the DNA encoding the two molecules. The intermediate plasmid encoding the BPI (1–199)LBP(198–456) hybrid, pML129, was constructed by replacing the 620 bp HindIII-ClaI fragment encoding the amino terminal region of LBP in the plasmid pML127 with the corresponding HindIII-ClaI fragment from pML126 encoding the amino terminal region of BPI protein.

To construct the mammalian expression vector pING4161, the 881 bp BstBI-SstII/T4 fragment of pML129, including part of the BPI and all of the LBP insert sequence, was ligated to the approximately 8755 XhoI/T4-BstBI fragment of pING4147 (described in Gazzano-Santaro et al., U.S. application Ser. No. 08/261,660 filed Jun. 17, 1994). The latter fragment includes sequences encoding the signal sequence and part of the amino terminus of BPI and all the vector sequences, which include the CMV promoter and the light chain 3' transcription termination sequences.

To obtain the desired hybrid proteins, beads co-cultured with CHO-K1 cells transfected with pING4160 or pING4161 as described in U.S. patent application Ser. No. 08/072,063 filed May 19, 1993, were washed with approximately 600 mls of 20 mM sodium acetate, pH 4.0 mM NaCl and then 600 mls of the same buffer containing 600 mM NaCl. Protein was eluted in two steps of 20 mM sodium acetate; the first with 1.0 M NaCl and the second with 1.5 M NaCl, with the majority of the desired protein eluting from the S-Sepharose in the 1.0 M step. Fractions containing the protein were then pooled and diluted to a final NaCl concentration of 300 mM with the addition of MES buffer, to a final concentration of 20 mM MES, pH 5.0. The diluted material recovered from all cell harvests was combined, yielding a final volume of approximately 6.5 liters. This pooled eluate was applied to two columns arranged in a tandem fashion, the first being a 100 ml Q-Sepharose column and the second a 12 ml CM-Spherodex column. The flow through material, which contained the desired protein, was adjusted to pH 4.0 and loaded in three batches on to a 15 ml S-Sepharose column. Each time the column was washed with 20 mM MES, pH 4.0 200 mM NaCl and the bound protein recovered with a step elution of 20 mM MES, pH 5.5, 1.2 M NaCl. The volume of the recovered protein was approximately 40 mls. This material was then run on a S-100 size exclusion column in 5 mM sodium citrate, pH 5.0, 150 mM NaCl. Column fractions were assayed using Coommassie stained SDS-PAGE and Western analysis using an anti-LBP primary antibody, and fractions containing the desired protein were pooled.

Figure 23:
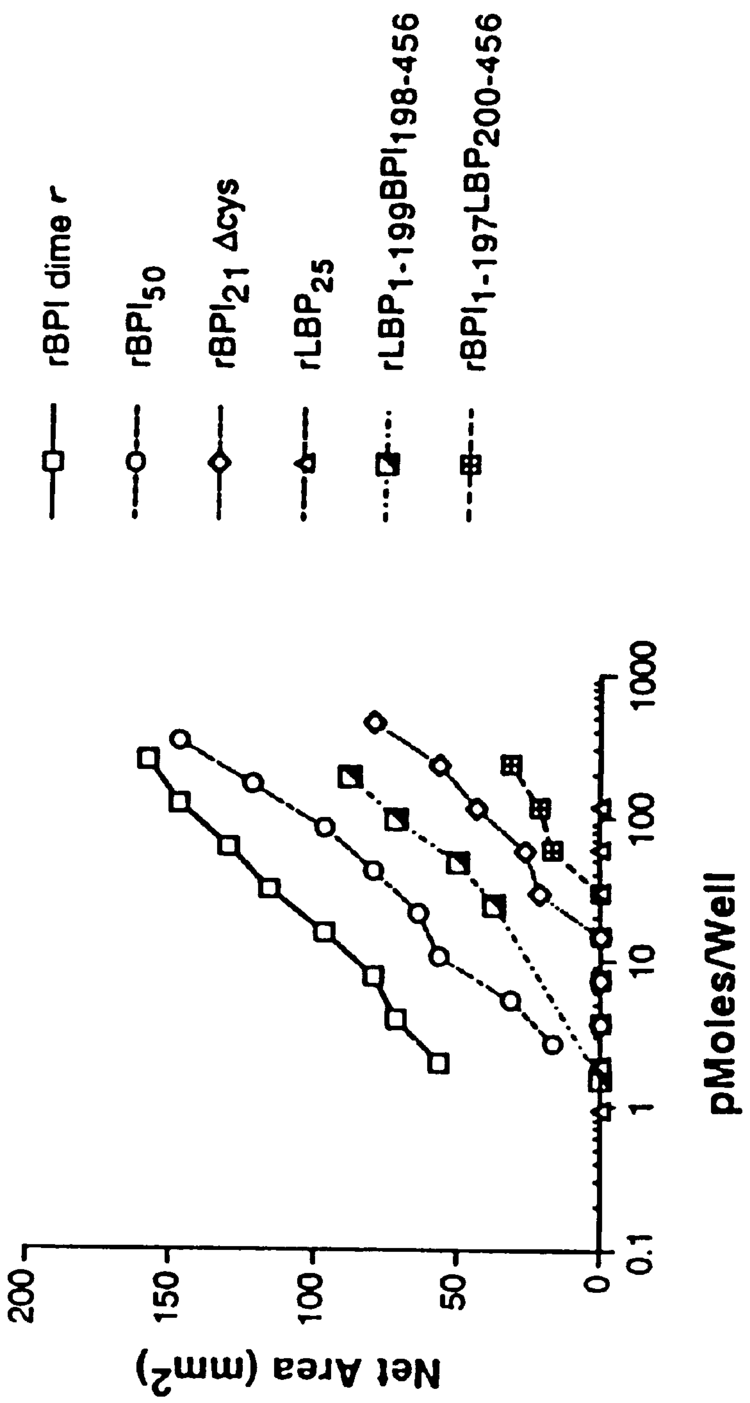
FIGS. 23, 24 and 25 display the effect of BPI protein products and LBP derivatives on *S. aureus* L-forms and *S. pneumoniae* L-forms in radial diffusion assays.

Radial diffusion assays on L-phase variants of *S. pneumoniae* (ATCC Accession No. 35088) and *E. faecalis* (ATCC Accession No. 4200) and the natural L-variant of *S. aureus* (ATCC Accession No. 19640) were performed as described above in Examples 3, 5 and 6, using varying concentrations of $rBPI_{50}$, $LBP_{50}$, LBP-BPI hybrid, and thaumatin as a control. LBP-BPI hybrid inhibited growth of *S. aureus* and *S. pneumoniae* L-phase variants, but not growth of *E. faecalis* L-phase variant. The LBP-BPI hybrid was especially potent against *S. pneumoniae,* with activity close to that of $rBPI_{50}$. Results of one representative assay on *S. aureus* L-phase variant using $rBPI_{23}$, $rBPI_{50}$, $rBPI_{21}$, $rLBP_{25}$, $rLBP_{50}$, LBP-BPI hybrid and BPI-LBP hybrid are displayed in FIG. 23. The LBP-BPI hybrid was bactericidal while $rLBP_{50}$ and $rLBP_{25}$ had little or no activity. The BPI-LBP hybrid was also active against the L-phase variant but less so than the LBP-BPI hybrid. As usual, $rBPI_{42}$ dimer was the most potent molecule against the L-phase variant. These results suggest that the presence of the BPI carboxyl terminus has enhanced the activity of $rLBP_{25}$ on prokaryotic membranes.

Figure 24:
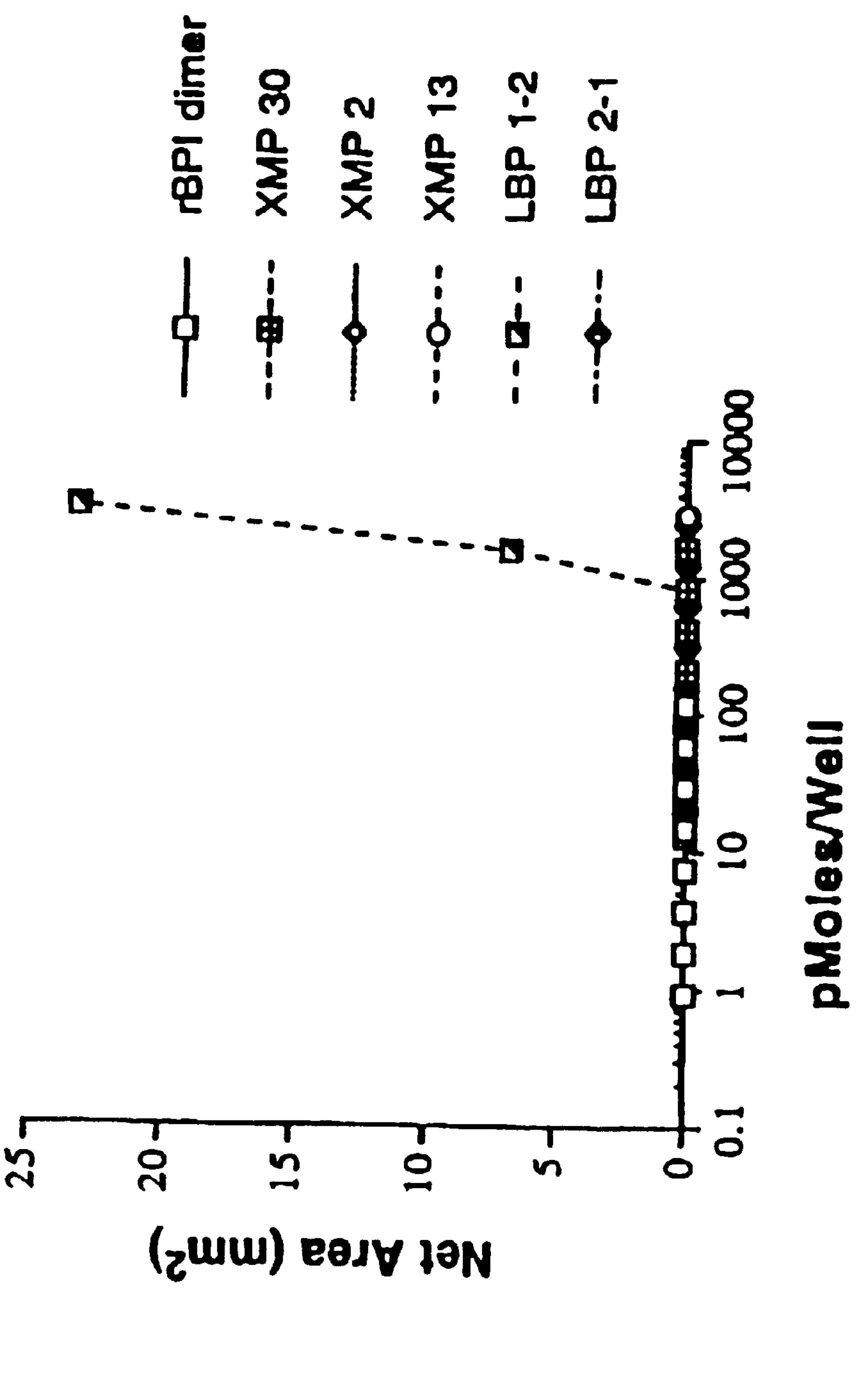
Figure 25:
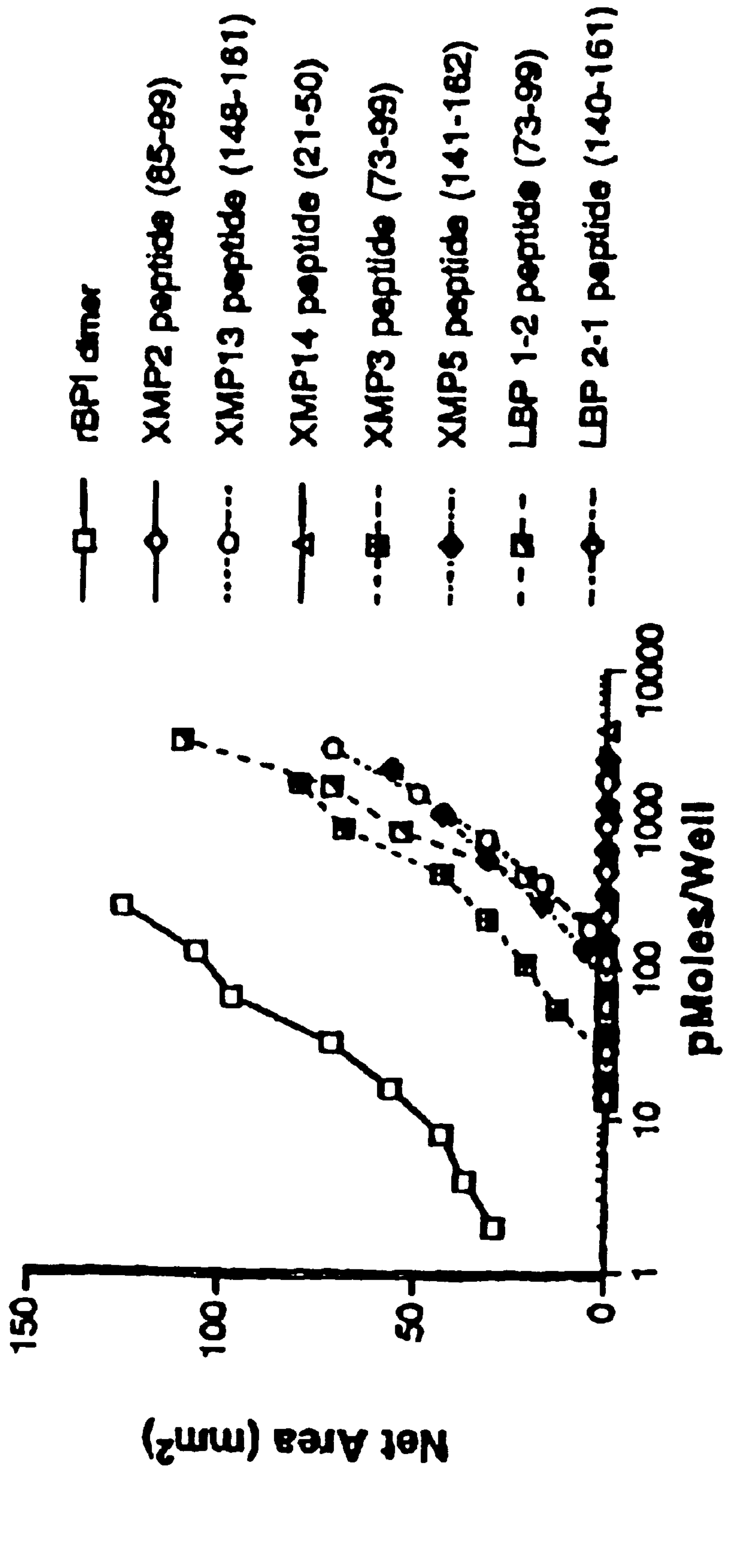

Further radial diffusion assays on these three organisms were conducted with LBP derivatives. LBP peptide 1–2, SEQ. ID NO: 236, and LBP peptide 2–1, SEQ. ID NO: 237, and with other BPI protein products, $rBPI_{42}$ dimer, XMP.2, XMP.13, XMP.14, XMP.3 and XMP.5. Results of representative assays on the *S. aureus* bacterial form and L-phase variant are displayed in FIGS. 24 and 25. At high concentrations, LBP peptide 1–2 had some bactericidal activity against the bacterial form. For the L-phase variant, LBP peptide 2–1 (amino acids 73–99 from domain II of LBP) was as potent as XMP.3 (amino acids 73–99 from domain II of BPI protein). XMP.5, XMP.13 and $rBPI_{42}$ dimer also displayed bactericidal activity against the L-phase variant, with $rBPI_{42}$ dimer being the most potent of all molecules tested. Additional assays were performed to evaluate the activity of LBP peptide 1–2 and LBP peptide 2–1 and other BPI protein products on the *E. faecalis* bacterial form, the *S. pyogenes* L-phase variant of Example 4, and the *S. pneumoniae* bacterial form and L-phase variant. LBP peptide 1–2 displayed some bactericidal activity against the two bacterial forms at high concentrations (300 pmol/well or more). LBP peptide 1–2 was as potent as $rBPI_{42}$ dimer against the *S. pneumoniae* L-phase variant, and was intermediate in potency between $rBPI_{42}$ dimer and XMP.13 for the *S. pyogenes* L-phase variant. LBP peptide 2–1 had no bactericidal activity against the tested bacterial forms or L-phase variants.

EXAMPLE 8

In Vitro Effects of BPI-Derived Peptides on *S. aureus* in a Radial Diffusion Assay This example addresses in vitro screening of BPI protein products, specifically BPI-derived peptides, for antimicrobial activity in a radial diffusion assay. The peptides tested were all prepared according to the procedures described in parent U.S. patent application Ser. Nos. 08/209,762 and 08/183,222. Briefly summarized, peptides were prepared by solid phase peptide synthesis according to the methods of Merrifield, *J. Am Chem. Soc.* 85: 2149 (1963) and Merrifield et al. *Anal. Chem.,* 38: 1905–1914 (1966) using an Applied Biosystems, Inc. Model 432 peptide synthesizer. Peptide design was based in principal part on the discovery of three functional domains present in the $NH_2$-terminal region of the BPI holoprotein domain I comprising BPI amino acids from about position 17 to about position 45 (SEQ ID NO: 1); domain II comprising BPI amino acids from about position 65 to about 99 (SEQ ID NO: 6); and domain III comprising BPI amino acids from about position 142 to about position 169 (SEQ ID NO: 12). Peptides included sequences and subsequences of the domain sequences and variants thereof including linear and branched chain combination peptides with and without single or multiple amino acid (including atypical amino acid) substitutions as well as cyclized peptides and interdomain sequence peptides. Table 1 below sets out peptides derived from or based on BPI sequences, as identified by the peptide number with a prefix XMP or BPI (e.g., XMP.1 or BPI.1, XMP.2 or BPI.2, etc.), SEQ ID NO:, amino acid sequence based on reference to position within BPI and designation of amino acid substitutions and additions. Also set out in Table 1 are mass spectroscopy and HPLC estimates of purity of the peptides.

Overnight *S. aureus* cultures were diluted 1:50 into fresh tryptic soy broth and incubated for 3 hours at 37° C. to attain log phase. Bacteria were pelleted at 3,000 rpm (1500×g) for 5 minutes in a Beckman J-6M centrifuge. 5 ml of 10 mM sodium phosphate buffer, pH 7.4, was added and the suspension was recentrifuged. Supernatant was decanted and 5 ml of fresh buffer was added for an $OD_{570}$ determination. An $OD_{570}$ of 1.0 was considered equivalent to $5\times10^8$ CFU/ml. Ten mL of molten underlayer agarose comprising 3% tryptic soy broth, 1% agarose (Pharmacia, Piscataway, N.J.), 0.02% Tween 20, and 10 mM sodium phosphate, at pH 7.4 was added to polystyrene tubes and maintained in a 56° C. water bath until the addition of bacteria. Tubes were cooled to approximately 45° C., bacteria were added to give a final concentration of $1\times10^6$ CFU/ml, and the tubes were mixed again by inverting. The contents were poured into level square petri dishes and distributed evenly. The agarose solidified in less than 30 seconds and had a uniform thickness of about 1 mm. A series of wells were punched into the hardened agarose using a sterile 3 mm punch attached to a vacuum apparatus.

Peptides to be screened were 2-fold serially diluted in Dulbecco's PBS (D-PBS) starting from a concentration of approximately 1 mg/mL. Five $\mu$L of each dilution was added to each well and the plates were incubated at 37° C. for 3 hours. An overlayer of 10 mL of molten agarose comprising 6% tryptic soy broth; 1% agarose, and 10 mM sodium phosphate, pH 7.4, (at approximately 45° C.) was then added and plates were incubated overnight at 37° C. Following this overnight incubation, a dilute Coomassie solution was poured into the plates and allowed to stain for 24 hours.

Clear zones of growth inhibition around each well were measured with calipers. The actual area of growth inhibition ($mm^2$) was calculated by subtracting the area of the well. Table 1 below sets out the results of the radial diffusion assays for tested peptides in terms of the number of $\mu$g or picomoles (pmol) of peptide required to establish a 30 $mm^2$ area of growth inhibition.

Peptides XMP.221 through XMP.281 (SEQ ID NOs: 166 through 226) are prepared and tested for anti-bacterial activity as described above.

TABLE 1

| Peptide # (Seq. ID No.) | Protein AA Segment | MS % Purity | HPLC % Purity | *S. aureus* $\mu$g/ 30 $mm^2$ zone | *S. aureus* pmol/ 30 $mm^2$ zone |
|---|---|---|---|---|---|
| XMP.1 (4) | 19–33 | — | 2 Peaks | N | N |
| XMP.2 (7) | 85–99 | 64 | 37.2 | N | N |
| XMP.3 (11) | 73–99 | — | 17 | X | X |
| XMP.4 (3) | 25–46 | — | No Peak | N | N |
| XMP.5 (67) | 142–163 | — | 18 | X | X |
| XMP.7 (54) | (90–99) x 2 | 69 | 27 | >5.00 | >1,891 |
| XMP.8 (8) | 90–99 | 79 | Mixtures | X | X |

TABLE 1-continued

| Peptide # (Seq. ID No.) | Protein AA Segment | MS % Purity | HPLC % Purity | *S. aureus* μg/ 30 $mm^2$ zone | *S. aureus* pmol/ 30 $mm^2$ zone |
|---|---|---|---|---|---|
| XMP.9 (51) | 95–99, 90–99 | — | 29 | X | X |
| XMP.10 (55, 65) | 94–99, 90–99, 90–99 and 95–99, 90–99, 90–99 | — | Mixture | X | X |
| XMP.11 (13) | 148–151,153–161 | — | 76 | X | X |
| XMP.12 (14) | 141–169 | — | 26 | X | X |
| XMP.13 (15) | 148–161 | 78 | 69 | >5.00 | >2,924 |
| XMP.13P (15) | 148–161 | 100 | 98 | X | X |
| XMP.14 (2) | 21–50 | — | — | X | X |
| XMP.15 (16) | 85–99, A @ 85 (I) | 66 | 57.6 | X | X |
| XMP.16 (17) | 85–99, A @ 86 (K) | — | 84.1 | X | X |
| XMP.17 (18) | 85–99, A @ 87 (I) | 86 | 77,67 | X | X |
| XMP.18 (19) | 85–99. A @ 88 (S) | 66 | 70 | X | X |
| XMP.19 (20) | 85–99, A @ 89 (G) | — | 69 | X | X |
| XMP.20 (21) | 85–99, A @ 90 (K) | — | 66 | X | X |
| XMP.21 (22) | 85–99, A @ 91 (W) | 68 | 66.8 | X | X |
| XMP.22 (23) | 85–99, A @ 92 (K) | — | 66 | X | X |
| XMP.23 (24) | 85–99, A @ 94 (Q) | — | 69 | X | X |
| XMP.24 (25) | 85–99, A @ 95 (K) | — | 67 | X | X |
| XMP.25 (26) | 85–99, A @ 96 (R) | — | 73 | X | X |
| XMP.26 (27) | 85–99, A @ 97 (F) | — | 73 | X | X |
| XMP.27 (28) | 85–99, A @ 98 (L) | — | 65 | X | X |
| XMP.28 (29) | 85–99, A @ 99 (K) | — | 80 | X | X |
| XMP.29 (56) | (148–161) × 2 | — | 26 | >5.00 | >1,469 |
| XMP.30 (52) | 90–99,148–161 | — | 21 | 3.68 | 1,216 |
| XMP.30-P (52) | 90–99,148–161 | 95 | 98 | X | X |
| XMP.31 (33) | 148–161, A @ 148 (K) | — | 68 | X | X |
| XMP.32 (34) | 148–161, A @ 149 (S) | — | 70 | X | X |
| XMP.33 (35) | 148–161, A @ 150 (K) | — | 58 | X | X |
| XMP.34 (36) | 148–161, A @ 151 (V) | — | 51 | X | X |
| XMP.35 (37) | 148–161, A @ 152 (G) | — | 72 | X | X |
| XMP.36 (38) | 148–161, A @ 153 (W) | — | 64 | X | X |
| XMP.37 (39) | 148–161, A @ 154 (L) | — | 51 | X | X |
| XMP.38 (40) | 148–161, A @ 155 (I) | — | 70 | X | X |
| XMP.39 (41) | 148–161, A @ 156 (Q) | — | 53 | X | X |
| XMP.40 (42) | 148–161, A @ 157 (L) | — | 53 | X | X |
| XMP.41 (43) | 148–161, A @ 158 (F) | — | 63 | X | X |
| XMP.42 (44) | 148–161, A @ 159 (H) | — | 59 | X | X |
| XMP.43 (45) | 148–161, A @ 160 (K) | — | 53 | X | X |
| XMP.44 (46) | 148–161, A @ 161 (K) | — | 70 | X | X |
| XMP.45 (31) | 85–99, A @ 94(Q)&95(K) | 71 | 46 | >5.00 | >1,697 |
| XMP.46 (57) | (90–99) × 2, A @ 1st 94(Q)&95(K) | 67 | 47 | >5.00 | >1,811 |
| XMP.47 (58) | (90–99) × 2, A @ 2d 94(Q)&95(K) | 57 | 34 | >5.00 | >2,461 |
| XMP.48 (59) | (90–99) × 2, A @ both 94(Q)&95(K) | 68 | 33 | >5.00 | >1,390 |
| XMP.54 (5) | 21–35 | — | — | X | X |
| XMP.55 (61) | 152–172 | — | 28 | >5.00 | >1,592 |
| XMP.56 (47) | 85–99, K @ 94 (Q) & Q @ 95(K) | — | 55 | N | N |
| XMP.57 (99) | Cys 85–99 Cys | 50 | Mixture | N | N |
| XMP.58 (9) | Cys-85–99 | 49 | 25.7 | N | N |
| XMP.59 (30) | 85–99, A @ 90(K)&92(K) | 56 | 30 | N | N |
| XMP.60 (32) | 85–99, A @ 86(K)&99(K) | 57 | 78 | N | N |
| XMP.61 (48) | 85–99, F @ 91(W) | 60 | 60 | N | N |
| XMP.63 (53) | 85–99, 148–161 | 38 | 31.0 | >5.00 | >1,006 |
| XMP.65 Rd (68) | Cys-85–99-Cys | 41 | 22, 34 | N | N |
| XMP.65 Ox (10) | Cys-85–99-Cys | — | No Peak | >5.00 | >3,118 |
| XMP.66 (49) | 85–99, $W_D$ @ 91(W) | — | 70 | N | N |
| XMP.67 (50) | 85–99, β-(1-naphthyl)-A @ 91 | 65 | 52 | N | N |
| XMP.69 (60) | [90–99, A @ 94 (Q) & 95 (K)] × 3 | 44 | 54, 40 | 3.83 | 1,058 |
| XMP.70 (63) | 85–99, β-(3-pyridyl)-A @ 91 | 66 | 54 | N | N |
| XMP.71 (64) | $A_D$-$A_D$-85–99 | — | 60 | N | N |
| XMP.72 (66) | 85–99, β-(3-pyridyl)-A @ 97 (F) | — | 52 | N | N |
| XMP.73 (62) | 85–99, F @ 95 (K) | — | 44, 39 | >5.00 | >1,811 |
| XMP.74 (70) | 148–161, 90–99 | — | 29 | >5.00 | >2,148 |
| XMP.75 (100) | IKKRAISFLGKKWQK (2-mixed) | — | 32 | >5.00 | >2,031 |
| XMP.76 (71) | 85–99, $F_D$ @ 95 (K) | 53 | 39 | N | N |
| XMP.77 (72) | 85–99, W @ 95 (K) | — | 38 | 3.15 | 1,684 |
| XMP.79 (73) | 85–99, K @ 94 (Q) | — | 48 | N | N |
| XMP.80 (74) | 85–99, β-(1-naphthyl)-A @ 95 (K) | 71 | 44 | 4.82 | 2,533 |
| XMP.81 (75) | 85–99, F @ 94 (Q) | 44 | 33, 35 | >5.00 | >2,345 |

TABLE 1-continued

| Peptide # (Seq. ID No.) | Protein AA Segment | MS % Purity | HPLC % Purity | *S. aureus* μg/ 30 $mm^2$ zone | *S. aureus* pmol/ 30 $mm^2$ zone |
|---|---|---|---|---|---|
| XMP.82 (76) | 148–161, W @ 158 (F) | 82 | 58 | >5.00 | >1,198 |
| XMP.83 (77) | 148–161, β(1-naphthyl)-A @ 153 (W) | 85 | 63 | >5.00 | >2,034 |
| XMP.84 (78) | 85–99, β-(1-naphthyl) A @ 91 (W) & F @ 95 (K) | 64 | 50 | >5.00 | >2,017 |
| XMP.85 (79) | 148–161, L @ 152 (G) | 79 | 74 | >5.00 | >1,881 |
| XMP.86 (80) | 148–161, L @ 156 (Q) | 69 | 51 | >5.00 | >2,048 |
| XMP.87 (81) | 148–161, L @ 159 (H) | 79 | 63 | >5.00 | >1,536 |
| XMP.88 (82) | 85–99, F @ 94 (Q) & 95 (K) | 62 | 50 | >5.00 | >2,380 |
| XMP.89 (84) | 85–99, β-(1-naphthyl) A @ 91 (W) & F @ 94 (Q) | 66 | 50 | >5.00 | >1,882 |
| XMP.90 (85) | 85–99, β-(1-naphthyl) A @ 91 (W), F @ 94 (Q) & 95 (K) | 70 | 63 | >5.00 | >1,863 |
| XMP.91 (86) | 148–161, F @ 156 (Q) | — | 31 | N | N |
| XMP.92 (87) | 148–161, K @ 156 (Q) | — | 50 | N | N |
| XMP.93 (88) | 85–99 148–161 β-(1-naphthyl) A @ 91 (W), F @ 95 (K) | 72 | 38 | >5.00 | >980 |
| XMP.94 (89) | 148–161, F @ 159 (H) | — | 59 | >5.00 | >922 |
| XMP.95 (90) | 148–161, F @ 152 (G) | — | 57 | N | N |
| XMP.96 (101) | 148–161, F @ 161 (K) | — | 60 | >5.00 | >2,048 |
| XMP.97 (92) | 148–161, K @ 152 (G) | — | 67 | N | N |
| XMP.98 (83) | 90–99, β-(1-naphthyl) A @ 91 (W), F @ 95 (K) + 148–161 F @ 156 (Q) | 69 | 31 | N | N |
| XMP.99 (93) | [90–99, W @ 95 (K)] × 3 | — | — | >5.00 | >1,064 |
| XMP.100 (94) | 148–161, K @ 152 (G) & 156 (Q) | — | 61 | N | N |
| XMP.101 (95) | (148–161) × 2[K @ 152(G) & 156(Q), F @ 159(H) & 161(K)] | — | 16 | >5.00 | >993 |
| XMP.102 (96) | 90–99 (F @ 95(K)) + 148–161 L @ 156 (Q) | — | 16 | N | N |
| XMP.103 (102) | 85–99, W @ 94 (Q) | — | 28 | >5.00 | >2,703 |
| XMP.104 (103) | 148–161, S @ 156 (Q) | — | 34 | >5.00 | >5,569 |
| XMP.105 (104) | 85–99, β-(1-naphthyl)-A @ 94 (Q) | 58 | 43 | >5.00 | >1,843 |
| XMP.106 (105) | 148–161, T @ 156 (Q) | — | 26 | N | N |
| XMP.107 (106) | 148–161, W @ 159 (H) | — | 55 | N | N |
| XMP.108 (107) | 148–161, W @ 161 (K) | — | 50 | >5.00 | >3,219 |
| XMP.109 (108) | 148–161, β(1-naphthyl) - A @ 158 (F) | — | 41 | N | N |
| XMP.110 (109) | 148–161, β(1-naphthyl) - A @ 159 (H) | — | 56 | N | N |
| XMP.111 (110) | 148–161, β(1-naphthyl) - A @ 161 (K) | — | 73 | >5.00 | >2,809 |
| XMP.112 (111) | 85–99, β(1-naphthyl)A @ 91 (W) & 95 (K) | — | 56 | N | N |
| XMP.113 (112) | 148–161, F @ 157 (L) | — | 46 | N | N |
| XMP.114 (113) | KWQLRSKGKIKIFKA | — | 17 | N | N |
| XMP.116 (114) | 148–161, K @ 152 (G), β(1-naphthyl)A @ 153 (W) | — | 72 | N | N |
| XMP.119 (115) | 85–99, β(1-naphthyl)A @ 91 (W) & 94 (K) | — | 77 | >5.00 | >2,617 |
| XMP.120 (116) | 85–99, K @ 97 (F) | — | 52 | N | N |
| XMP.121 (117) | 85–99, β(1-naphthyl)A @ 94 (Q) & 95 (K) | 65 | 35 | >5.00 | >2,540 |
| XMP.122 (118) | 85–99, β(1-naphthyl)A @ 91 (W), 94(Q) & 95 (K) | — | 46 | >5.00 | >2,526 |
| XMP.123 (119) | 148–161, p-Amino-F @ 156 (Q) | — | 64 | N | N |
| XMP.124 (120) | 148–161,K @ 152(G), W @ 158 (F) | — | 67 | N | N |
| XMP.125 (121) | 148–161, Y @ 156 (Q) | — | 54 | N | N |
| XMP.126 (122) | 148–161, $W_D$ @ 153 (W) | 66 | 54 | N | N |
| XMP.127 (123) | 148–161, F @ 153 (W) | 65 | 63 | N | N |
| XMP.128 (124) | 148–161 $F_D$ @ 153 (W) | 63 | 51 | N | N |
| XMP.129 (125) | 148–161, 1-β(1-naphthyl)$A_D$ @ 153 (W) | 24 | 28 | N | N |
| XMP.130 (126) | 148–161, 2-β(1-naphthyl)A @ 153 (W) | 55 | 80 | N | N |
| XMP.131 (127) | 148–161, 2-β(1-naphthyl)$A_D$ @ 153 (W) | 75 | 60 | N | N |
| XMP.132 (128) | 148–161, Pyr-A @ 153 (W) | 49 | 50 | N | N |
| XMP.133 (129) | 148–161, p-Amino-F @ 153 (W) | 63 | 47 | N | N |
| XMP.134 (130) | 148–161, p-Amino-F @ 152 (G) | — | 68 | N | N |

TABLE 1-continued

| Peptide # (Seq. ID No.) | Protein AA Segment | MS % Purity | HPLC % Purity | *S. aureus* μg/ 30 mm$^2$ zone | *S. aureus* pmol/ 30 mm$^2$ zone |
|---|---|---|---|---|---|
| XMP.135 (131) | 148–161, K @ 153 (W) | — | 70 | N | N |
| XMP.136 (132) | 85–99, E @ 95 (K) | — | 50 | N | N |
| XMP.137 (133) | Cys-148–161-Cys | — | 28 | X | X |
| XMP.138 (134) | 148–161, K @ 152 (G), F @ 153 (W) | — | 61 | N | N |
| XMP.139 (135) | 148–161, Y @ 153 (W) | — | 60 | N | N |
| XMP.140 (136) | 90–99 β(1 naphthyl)A @ 94 (Q) & 95 (K) + 104 | — | 26 | >5.00 | >1,601 |
| XMP.141 (137) | 85–99, W @ 97 (F) | — | 50 | N | N |
| XMP.142 (138) | 148–161, W @ 157 (L) | — | 57 | N | N |
| XMP.143 (139) | 148–161, β(1-naphthyl)A @ 157 (L) | — | 65 | N | N |
| XMP.144 (140) | 148–161, Cyclohexyl-A @ 153 (W) | — | 60 | N | N |
| XMP.145 (141) | 90–99, β(1-naphthyl)A @ 94(Q) & 95(K) + 148–161 | — | 20 | X | X |
| XMP.146 (142) | 148–161, β(1-naphthyl)A @ 159(H) & 161(K) | — | 53 | N | N |
| XMP.147 (143) | 85–99 K @ 96 (R) | — | 55 | N | N |
| XMP.148 (144) | 148–161, β(1-naphthyl)A @ 153 (W) & 159 (H) | — | 62 | N | N |
| XMP.149 (147) | KWKVFKKIEK + 148–161 | — | 27 | N | N |
| XMP.150 (148) | KWAFAKKQKKRLKRQWLKKF | — | Mixture | N | N |
| XMP.151 (55) | 94–99, 90 99, 90–99 | — | 14 | N | N |
| XMP.152 (65) | 95–99, 90–99, 90–99 | — | 21 | N | N |
| XMP.153 (149) | (90–99) x 3 | — | 17 | N | N |
| XMP.154 (150) | (90–99) x 2, β(1-naphthyl) A @ 1st 94 (Q) & 95 (K) | — | 31 | >5.00 | >1,796 |
| XMP.155 (151) | (90–99) x 2, β(1-naphthyl) A @ 2nd 94 (Q) & 94 (K) | — | 23 | >5.00 | >1,796 |
| XMP.156 (152) | (90–99) x 2, β(1-naphthyl) A @ both 94 (Q) & 95 (K) | — | 38 | N | N |
| XMP.157 (153) | (90–99, β(1-naphthyl) A @ 94 (Q) & 95 (K)) x 3 | — | 38 | N | N |
| 0XMP.158 (154) | 85–99, 148–161, β(1-naphthyl) A @ 94 (Q) & 95 (K) | — | 16 | N | N |
| XMP.159 (155) | (90–99, β(1-naphthyl) A @ 91 (W) & 95 (K)) + 82 | — | 23 | >5.00 | >1,590 |
| XMP.160 (156) | (90–99) x 2, β(1-naphthyl) A @ both 91 (W) & 95 (K) | — | 32 | >5.00 | >1,782 |
| XMP.161 (157) | 148–161, K @ 152 (G) & A @ 153 (W) | — | 75 | >5.00 | >2,999 |
| XMP.162 (158) | 90–99, 148–161, W @ 95 (K) | — | 21 | N | N |
| XMP.163 (159) | (90–99) x 2, W @ both 95 (K) | — | Mixture | >5.00 | >1,810 |
| XMP.164 (160) | (90–99) x 2, β (1-naphthyl) A @ both 94 (Q) | — | 46 | >5.00 | >1,796 |
| XMP.165 (161) | (90–99, β (1-naphthyl A @ 91 (W) & F @ 95 (K)) x 2 | — | 72 | >5.00 | >1,847 |
| XMP.166 (162) | 148–161, V @ 153 (W) | — | 68 | N | N |
| XMP.167 (163) | 90–97 | — | 56 | N | N |
| XMP.168 (164) | C- 90–101-C | — | 13 | N | N |
| XMP.l69 (165) | C-90–97-C | — | 20 | >5.00 | >4,974 |
| XMP.170 (227) | 90–101 | — | 69 | N | N |

X = Not tested
N = No detectable activity up to 5 μg/well

EXAMPLE 9

In Vitro Effects of a Variety of BPI Protein Products Alone or in Combination with Antibiotics on Strains of *Streptococcus pneumoniae*

This experiment evaluated the in vitro growth inhibitory effects of a variety of BPI protein products, alone or in combination with antibiotics, on clinical isolates of *Streptococcus pneumoniae* (from Baxter Microscan® library, Sacramento, Calif.). The BPI protein products' direct growth inhibitory effect and effect on the antibiotic susceptibility of the organisms was determined using Microscan® panel plates (Baxter Diagnostics, Inc., Deerfield, Ill.) that allow simultaneous determination of minimum inhibitory concentrations for a number of different antibiotics. Any other antimicrobial panel systems known in the art, such as the Pasco (DIFCO, Detroit, Mich.) and Alamar (Alamar, Sacramento, Calif.) systems, may be used instead of the Microscan® system to assay for activity. Control assays performed with the Microscan® panel plates confirmed that the formulation buffer for $rBPI_{21}$ (without $rBPI_{21}$) had no effect on the antibiotic susceptibility of a variety of organism: *S. pneumoniae* (Microscan library no. 31573), *S. pyogenes* (Group A) (30403), *S. bovis* (008-010), *S. aureus* (052-106) and *E. faecalis* (011-066).

The antimicrobial susceptibility tests performed on the Microscan® panel plates are miniaturizations of the broth dilution susceptibility test. Antimicrobial agents are serially diluted in Mueller-Hinton broth (supplemented with calcium and magnesium, or with sodium chloride for oxacillin, or with thymidine phosphorylase for trimethoprim, sulfamethoxazole and trimethoprim/sulfamethoxazole) to concentrations bridging the range of clinical interest. One well on the 96-well Microscan® plate is a growth control well that contains dehydrated broth only. The remaining wells contain dehydrated broth and antibiotic (or broth and biochemical reagent indicator), which is rehydrated to the desired concentration by inoculation of a standardized suspension of test organism. The chromogenic biochemical agent indicators are used to identify and characterize the species of bacteria based on detection of pH changes and substrate utilization. After incubation overnight, the minimum inhibitory concentration (MIC) of an antibiotic for the test organism is determined by observing the well with the lowest concentration of the antibiotic that shows inhibition of growth. Two types of panel plates were utilized to test these gram-positive organisms: the Pos Combo Panel Type 6, and the Pos MIC Panel Type 6 (both available from Baxter Diagnostics, Inc., Deerfield, Ill.). The concentrations of antibiotics tested in each panel are shown in Tables 2 and 3 below.

For each experimental run, the following procedure was performed: The organism was streaked onto 5% sheep blood agar plates (Remel, Lenexa, Kans.) and incubated for 18–24 hours overnight. Well-isolated colonies from the plates were emulsified in 3 ml of sterile Inoculum Water (catalog no. B1015-2, MicroScan® system, Baxter Diagnostics, Inc., Deerfield, Ill.) to a final turbidity equivalent to 0.5 McFarland Barium Sulfate standard. This cell suspension was vortexed for 2 to 3 seconds and 100 μl was transferred to glass tubes containing 25 ml of Inoculum Water with Pluronic-D (catalog no. B1015-7, MicroScan® system, Baxter Diagnostics, Inc., Deerfield, Ill.) (hereinafter "Pluronic Inoculum water"), or 25 ml of Pluronic Inoculum water into which the BPI protein product (in formulation buffer) had been diluted to the desired concentration, generally between 0 and 64 μg/mL.

The 25 ml of this inoculum containing the BPI protein product was mixed by inversion and poured into a tray. The inoculum was drawn up into a manual 96-well pipetting system (RENOK™ rehydrator-inoculator system, Baxter

TABLE 2

| Antibiotic Concentrations (μg/mL) Tested in Pos Combo Panel Type 6 Plate | | | | | | | | | |
|---|---|---|---|---|---|---|---|---|---|
| Trimethoprim/Sulfamethoxazole | 2/38 | | | | | | | | |
| Rifampin | 2 | 1 | | | | | | | |
| Imipenem | 8 | 4 | | | | | | | |
| Cephalothin | 16 | 8 | | | | | | | |
| Amoxicillin/K Clavulanate | 16/8 | 8/4 | 4/2 | | | | | | |
| Cefotaxime | 32 | 8 | | | | | | | |
| Ciprofloxacin | 2 | 1 | | | | | | | |
| Norfloxacin | 8 | 4 | | | | | | | |
| Nitrofurantoin | 64 | 32 | | | | | | | |
| Gentamicin | 6 | 4 | 2 | 1 | | | | | |
| Clindamycin | 2 | 1 | 0.5 | 0.25 | | | | | |
| Cefazolin | 16 | 8 | 4 | 2 | | | | | |
| Erythromycin | 4 | 2 | 1 | 0.5 | 0.25 | | | | |
| Vancomycin | 16 | 8 | 4 | 2 | | | | | |
| Penicillin | 8 | 4 | 2 | 1 | 0.5 | 0.25 | 0.12 | 0.06 | 0.03 |
| Ampicillin | 8 | 4 | 2 | 1 | 0.5 | 0.25 | 0.12 | | |
| Oxacillin | 4 | 2 | 1 | 0.5 | | | | | |
| Tetracycline | 128 | 8 | 4 | 2 | | | | | |

TABLE 3

| Antibiotic Concentrations (μg/mL) Tested in Pos MIC Panel Type 6 Plate | | | | | | | | | |
|---|---|---|---|---|---|---|---|---|---|
| Erythromycin | 4 | 2 | 1 | 0.5 | 0.25 | | | | |
| Vancomycin | 16 | 8 | 4 | 2 | | | | | |
| Clindamycin | 2 | 1 | 0.5 | 0.25 | | | | | |
| Cefazolin | 16 | 8 | 4 | 2 | | | | | |
| Cephalothin | 16 | 8 | 4 | 2 | | | | | |
| Cefuroxime | 16 | 8 | 4 | 2 | | | | | |
| Ceftriaxone | 32 | 16 | 8 | 4 | | | | | |
| Chloramphenicol | 16 | 8 | 4 | | | | | | |
| Cefotaxime | 32 | 16 | 8 | 4 | | | | | |
| Ticarcillin/K Clavulanate | 8 | 4 | 2 | 1 | | | | | |
| Imipenem | 8 | 4 | 2 | 1 | | | | | |
| Gentamicin | 6 | 4 | 2 | 1 | | | | | |
| Amoxicillin/K Clavulante | 16/8 | 8/4 | 4/2 | | | | | | |
| Ampicillin/Sulbactam | 16/8 | 8/4 | | | | | | | |
| Rifampin | 2 | 1 | | | | | | | |
| Trimethoprim/Sulfamethoxazole | 2/38 | | | | | | | | |
| Norfloxacin | 8 | 4 | | | | | | | |
| Penicillin | 8 | 4 | 2 | 1 | 0.5 | 0.25 | 0.12 | 0.06 | 0.03 |
| Ampicillin | 8 | 4 | 2 | 1 | 0.5 | 0.25 | 0.12 | | |
| Oxacillin | 4 | 2 | 1 | 0.5 | | | | | |
| Tetracycline | 128 | 8 | 4 | 2 | | | | | |
| Nitrofurantoin | 64 | 32 | | | | | | | |
| Ciprofloxacin | 2 | 1 | | | | | | | |
| Amikacin | 32 | 16 | | | | | | | |
| Sulfamethoxazole | 256 | | | | | | | | |

Health Care Corporation, West Sacramento, Calif.) designed for use with the Microscan® panel plates, and 110 μl of the inoculum was delivered to each well of a Microscan® Pos Combo Panel Type 6 or Pos MIC Panel Type 6 plate. When added to the wells, this inoculum achieves a final bacterial concentration of $4\times10^5$ to $7\times10^5$ CFU/ml. The panel plates were then incubated at 35° C. for 15–24 hours and read visually for cell growth.

No growth was defined as a slight whiteness in the well or a clear broth. Growth appeared as turbidity which could take the form of a white haze throughout the well, a white button in the center of the well, or a fine granule growth throughout the well. All wells were read against a black indirectly lighted background. Visual results of the biochemical reactions were read into a database for bacterial identification. The MICs for each antibiotic tested were determined by identifying the lowest concentration of antibiotic which inhibited visible growth.

Table 4 below displays a summary of the results of the antibiotic screening panels, reported for each strain tested as the MIC of the tested antibiotics at varying concentrations of $rBPI_{21}$. Results are only reported where $rBPI_{21}$ altered the antibiotic susceptibility. The antibiotic susceptibility standards (interpretation of an MIC as clinically resistant, intermediate or susceptible according to NCCLS standards) applicable to the organisms tested appear in Table 4A. Stars after the antibiotic name in the "antibiotic tested" column indicate whether $rBPI_{21}$ reversed the resistance of that organism to the antibiotic tested (two stars) or converted an indifferent MIC into a susceptible MIC (one star). These data show the $rBPI_{21}$ converted one ampicillin-resistant strain of *S. pneumoniae* into ampicillin-susceptible (the other tested strains were already sensitive to ampicillin) and increased the susceptibility of other *S. pneumoniae* strains to amikacin, ampicillin, gentamicin and penicillin.

Table 4 also shows the presence or absence of bacterial growth in the growth control wells, which contained varying concentrations of $rBPI_{21}$ alone without antibiotic. A "G" signifies growth at the tested concentration, while "NG" signifies no growth. These results indicate that *S. pneumoniae* is a BPI-susceptible organism; $rBPI_{21}$ was directly bactericidal/growth inhibitory for all tested isolates of *S. pneumoniae* at a concentration of 2 μg/ml.

Additional screening of *S. pneumoniae* strains was conducted with a variety of BPI protein products, $rBPI_{21}$, $rBPI_{23}$, $rBPI_{50}$ and $rBPI_{42}$ dimer. Table 4X below displays a summary of the results of the antibiotic screening panels, reported for each strain tested as the MIC of the tested antibiotics at varying concentrations of the indicated BPI protein product. Results are only reported if antibiotic susceptibility was altered.

TABLE 4

EFFECTS OF $rBPI_{21}$ ± ANTIBIOTICS ON *Streptococcus pneumoniae*

| Microscan Library ID No. | Antibiotic Tested | Minimum Inhibitory Concentration of Antibiotic (μg/mL) With 0 μg/mL $rBPI_{21}$ | With 0.5 μg/mL $rBPI_{21}$ | With 2 μg/mL $rBPI_{21}$ | With 8 μg/mL $rBPI_{21}$ | With 16 μg/mL $rBPI_{21}$ |
|---|---|---|---|---|---|---|
| 31573 | — | G | G | NG | NG | NG |
| | Ampicillin** | 8 | <0.12 | <0.12 | <0.12 | <0.12 |
| | Penicillin* | 0.5 | <0.03 | <0.03 | <0.03 | <0.03 |
| | Gentamicin* | 6 | 2 | <1 | <1 | <1 |
| 31582 | — | G | — | NG | NG | NG |
| | Ampicillin* | 0.5 | — | <0.12 | <0.12 | <0.12 |
| | Penicillin | 0.06 | — | <0.03 | <0.03 | <0.03 |
| | Gentamicin | <1 | — | <1 | <1 | <1 |
| 15972 | — | G | G | NG | NG | NG |
| | Ampicillin | <0.12 | <0.12 | <0.12 | <0.12 | <0.12 |
| | Penicillin | <0.03 | <0.03 | <0.03 | <0.03 | <0.03 |
| | Gentamicin | 4 | 2 | <1 | <1 | <1 |
| | Amikacin* | 32 | — | — | — | <16 |
| 015-035 | — | G | G | NG | NG | NG |
| | Ampicillin | <0.12 | <0.12 | <0.12 | <0.12 | <0.12 |
| | Penicillin | <0.03 | <0.03 | <0.03 | <0.03 | <0.03 |
| | Gentamicin | 4 | <1 | <1 | <1 | <1 |
| 015-034 | — | G | — | NG | NG | NG |
| | Ampicillin | <0.12 | — | <0.12 | <0.12 | <0.12 |
| | Penicillin | <0.03 | — | <0.03 | <0.03 | <0.03 |
| | Gentamicin | <1 | — | <1 | <1 <1 | |

| Organism Name (Microscan ® ID No.) | Antibiotic Tested | Minimum Inhibitory Concentration of Antibiotic (μg/mL) With 0 μg/mL $rBPI_{21}$ | With 4 μg/mL $rBPI_{21}$ | With 16 μg/mL $rBPI_{21}$ |
|---|---|---|---|---|
| *S. pneumoniae* 1293 | — | G | NG | NG |
| | Erythromycin* | 1 | <.25 | <.25 |
| | Clindamycin** | >2 | <.25 | <.25 |
| | Cefuroxime | 4 | <2 | <2 |
| | Penicillin* | 1 | <.03 | <.03 |
| | Chloramphenicol* | 16 | <4 | <4 |
| | Gentamicin | 4 | <1 | <1 |
| | Ampicillin | 1 | <.12 | <.12 |
| | Norfloxacin** | >8 | <4 | <4 |
| | Ciprofloxacin* | 2 | <1 | <1 |
| | Amikacin* | 32 | <16 | <16 |
| *S. pneumoniae* 130 | — | G | NG | NG |
| | Penicillin | .06 | <.03 | <.03 |
| | Gentamicin* | 6 | <1 | <1 |
| | Trimethoprim/ Sulfamethoxazole** | >2 | <2 | <2 |
| | Amikacin** | >32 | <16 | <16 |
| *S. pneumoniae* 145 | — | G | NG | NG |
| | Cephalothin | 4 | <2 | <2 |
| | Penicillin* | 0.5 | <.03 | <.03 |
| | Gentamicin | 4 | <1 | <1 |
| | Ampicillin | 1 | <.12 | <.12 |
| | Trimethoprim/ Sulfamethoxazole** | >2 | <2 | <2 |
| *S. pneumoniae* 152 | — | G | NG | NG |
| | Gentamicin | 4 | <1 | <1 |
| | Amikacin* | 32 | <16 | <16 |
| *S. pneumoniae* 154 | — | G | G | NG |
| | Erythromycin* | 1 | <.25 | <.25 |
| | Cefuroxime | 4 | <2 | <2 |
| | Penicillin* | 1 | .12 | <.03 |
| | Chloramphenicol* | 16 | 8 | <4 |
| | Gentamicin | 4 | <1 | <1 |
| | Ampicillin | 2 | 0.5 | <.12 |

*BPI protein product reversed antibiotic indifference
**BPI protein product reversed antibiotic resistance

TABLE 4A

Susceptibility ranges for *S. pneumoniae*

| Antibiotic | MIC (μg/mL) Resistant | Intermediate | Susceptible |
|---|---|---|---|
| Amikacin | >32 | 32 | ≦16 |
| Ampicillin | ≧4 | 0.25–2 | ≦0.12 |

TABLE 4A-continued

| Susceptibility ranges for *S. pneumoniae* | | | |
|---|---|---|---|
| | MIC (μg/mL) | | |
| Antibiotic | Resistant | Intermediate | Susceptible |
| Gentamicin | >6 | 6 | ≦4 |
| Penicillin | ≧2 | 0.12–1 | ≦0.06 |

TABLE 4X

EFFECTS OF BPI PROTEIN PRODUCTS ± ANTIBIOTICS

| | | Minimum Inhibitory Concentration of Antibiotic (μg/mL) With: | | | | | | | | |
|---|---|---|---|---|---|---|---|---|---|---|
| Organism Name (Micro-scan ® ID No.) | Antibiotic Tested | 0 μg/mL BPI | 4 μg/mL $rBPI_{23}$ | 4 μg/mL $rBPI_{21}$ | 4 μg/mL $BPI_{50}$ | 4 μg/mL $rBPI_{42}$ dimer | 16 μg/mL $rBPI_{23}$ | 16 μg/mL $rBPI_{21}$ | 16 μg/mL $rBPI_{50}$ | 16 μg/mL $rBPI_{42}$ dimer |
| *S. pneumoniae* 1293 | — | G | G | NG | G | G | G | NG | G | NG |
| | Erythromycin* | 1 | <0.25 | <0.25 | <0.25 | <0.25 | <0.25 | <0.25 | <0.25 | <0.25 |
| | Clindamycin** | >2 | <0.25 | <0.25 | <0.25 | <0.25 | <0.25 | <0.25 | <0.25 | <0.25 |
| | Cefuroxime | 4 | <2 | <2 | 4 | <2 | <2 | <2 | <2 | <2 |
| | Penicillin* | 1 | 0.12 | <0.03 | 0.5 | <0.03 | 0.5 | <0.03 | 0.5 | <0.03 |
| | Chloramphenicol | 16 | <4 | <4 | 8 | <4 | 8 | <4 | <4 | <4 |
| | Gentamicin | 4 | <1 | <1 | 2 | <1 | 4 | <1 | 2 | <1 |
| | Ampicillin | 1 | <0.12 | <0.12 | 2 | 0.5 | 1 | <0.12 | 1 | 1 |
| | Norfloxacin | >8 | <4 | <4 | <4 | <4 | <4 | <4 | <4 | <4 |
| | Trimethoprim/ Sulfamethoxazole | >2 | <2 | <2 | >2 | <2 | >2 | <2 | <2 | <2 |
| | Ciprofloxacin | 2 | <1 | <1 | 2 | <1 | <1 | <1 | <1 | <1 |
| | Amikacin | 32 | <16 | <16 | <16 | <16 | <16 | <16 | <16 | <16 |
| *S. pneumoniae* 130 | — | G | NG | NG | G | NG | G | NG | NG | NG |
| | Penicillin | 0.06 | <0.03 | <0.03 | <0.03 | <0.03 | <0.03 | <0.03 | <0.03 | <0.03 |
| | Gentamicin | 6 | <1 | <1 | 6 | <1 | 4 | <1 | <1 | <1 |
| | Trimethoprim/ Sulfamethoxazole | >2 | <2 | <2 | <2 | <2 | >2 | <2 | <2 | <2 |
| | Amikacin | >32 | <16 | <16 | >32 | <16 | 32 | <16 | <16 | <16 |
| *S. pneumoniae* 145 | — | G | G | NG | G | NG | G | NG | G | NG |
| | Cefazolin | <2 | <2 | <2 | <2 | <2 | 4 | <2 | <2 | <2 |
| | Cephalothin | 4 | <2 | <2 | <2 | <2 | 4 | <2 | <2 | <2 |
| | Penicillin* | 0.5 | 0.06 | <0.03 | 0.5 | 1 | 1 | <0.03 | <0.03 | 1 |
| | Gentamicin | 4 | <1 | <1 | 2 | <1 | 2 | <1 | <1 | <1 |
| | Ampicillin | 1 | 0.25 | <0.12 | 0.5 | 0.5 | 2 | <0.12 | <0.12 | 2 |
| | Trimethoprim/ Sulfamethoxazole | >2 | <2 | <2 | <2 | <2 | >2 | <2 | <2 | >2 |
| *S. pneumoniae* 152 | — | G | G | NG | G | G | G | NG | G | NG |
| | Gentamicin | 4 | 4 | <1 | <1 | 2 | 4 | <1 | <1 | <1 |
| | Amikacin* | 32 | <16 | <16 | 32 | <16 | <16 | <16 | <16 | <16 |
| *S. pneumoniae* 154 | — | G | G | G | G | NG | G | NG | G | G |
| | Erythromycin* | 1 | <0.25 | <0.25 | 0.5 | <0.25 | <0.25 | <0.25 | 1 | <0.25 |
| | Cefuroxime | 4 | <2 | <2 | 4 | <2 | <2 | <2 | <2 | <2 |
| | Penicillin* | 1 | 0.25 | 0.12 | 1 | <0.03 | 0.5 | <0.03 | 0.5 | 0.25 |
| | Chloram-phenicol* | 16 | 8 | 8 | 8 | <4 | 8 | <4 | 8 | <4 |
| | Gentamicin | 4 | 2 | <1 | 2 | <1 | 4 | <1 | 4 | 2 |
| | Ampicillin** | 2 | 0.5 | 0.5 | 1 | <0.12 | 2 | <0.12 | 2 | <0.12 |
| | Amikacin | 32 | <16 | <16 | 32 | <16 | <16 | <16 | <16 | <16 |
| *S. pneumoniae* 141 | Penicillin | 0.12 | <0.03 | <0.03 | 0.12 | 0.06 | 0.06 | 0.06 | 0.12 | <.03 |
| | Gentamicin | >6 | >6 | 6 | >6 | >6 | >6 | >6 | >6 | 6 |
| | Trimethoprim/ Sulfametho-xazole** | >2 | <2 | <2 | >2 | <2 | <2 | <2 | <2 | <2 |
| | Amikacin | >32 | >32 | >32 | >32 | >32 | >32 | >32 | >32 | 32 |

TABLE 4X-continued

EFFECTS OF BPI PROTEIN PRODUCTS ± ANTIBIOTICS

| Organism Name (Micro-scan ® ID No.) | Antibiotic Tested | Minimum Inhibitory Concentration of Antibiotic (μg/mL) With: 0 μg/mL BPI | 4 μg/mL $rBPI_{23}$ | 4 μg/mL $rBPI_{21}$ | 4 μg/mL $BPI_{50}$ | 4 μg/mL $rBPI_{42}$ dimer | 16 μg/mL $rBPI_{23}$ | 16 μg/mL $rBPI_{21}$ | 16 μg/mL $rBPI_{50}$ | 16 μg/mL $rBPI_{42}$ dimer |
|---|---|---|---|---|---|---|---|---|---|---|
| *S. pneumoniae* 145 | Cefazolin | 4 | <2 | <2 | 4 | <2 | <2 | <2 | 4 | <2 |
| | Cephalothin | 4 | <2 | <2 | 4 | <2 | 4 | <2 | 4 | <2 |
| | Penicillin* | 0.5 | <0.03 | <0.03 | 0.5 | <0.03 | 1 | <0.03 | 0.5 | <0.03 |
| | Gentamicin | 4 | 4 | <1 | 4 | <1 | 6 | <1 | 6 | <1 |
| | Ampicillin** | 1 | <0.12 | <0.12 | 2 | <0.12 | 2 | <0.12 | 2 | <0.12 |
| | Trimethoprim/Sulfametho-xazole** | >2 | <2 | <2 | >2 | <2 | >2 | <2 | >2 | <2 |
| | Amikacin* | 32 | <16 | <16 | <16 | <16 | 32 | <16 | 32 | <16 |

EXAMPLE 10

In Vitro Effects of BPI Protein Product Alone or in Combination with Antibiotics on Strains of the Gram-Positive Organism *Streptococcus pyogenes* (Group A)

The direct growth inhibitory effect of a BPI protein product, $rBPI_{21}$, on various strains of *Streptococcus pyogenes,* also known as Group A strep, was evaluated using the Microscan® screening assay of Example 9. The effect of $rBPI_{21}$ on the antibiotics susceptibility of these strains was also evaluated in the same assay. Assays were conducted on clinical isolates of *S. pyogenes* (from Baxter Microscan® library, Sacramento, Calif.).

A summary of the results of the BPI protein product and antibiotic screening panels, reported as MICs (μg/ml) of the tested antibiotic at varying concentrations of $rBPI_{21}$ (μg/ml), is shown in Table 5 below. Results are only reported where $rBPI_{21}$ altered the antibiotic susceptibility or growth. The antibiotic susceptibility standards (interpretation of an MIC as clinically resistant, intermediate or susceptible according to NCCLS standards) applicable to the organism tested appear in Table 5A. Table 5 also shows the presence or absence of bacterial growth ("G" or "NG") in the control well, which contains varying concentrations of $rBPI_{21}$ alone without antibiotic.

These results indicate that $rBPI_{21}$ alone had a direct bactericidal/growth inhibitory effect on one strain of *S. pyogenes* (Group A) at a concentration as low as 2 μg/ml, on three of the strains at 8 μg/ml, and on the remaining strain at 32 μg/ml. The data also show that BPI protein product increased the antibiotic susceptibility of *Strep. pyogenes* (Group A) strains to norfloxacin and gentamicin.

TABLE 5

EFFECTS OF $rBPI_{21}$ ± ANTIBIOTICS ON *Streptococcus pyogenes* (Group A)

| Microscan Library ID No. | Antibiotic Tested | Minimum Inhibitory Concentration of Antibiotic (μg/mL) With 0 μg/mL $rBPI_{21}$ | With 0.5 μg/mL $rBPI_{21}$ | With 2 μg/mL $rBPI_{21}$ | With 8 μg/mL $rBPI_{21}$ | With 16 μg/mL $rBPI_{21}$ | With 32 μg/mL $rBPI_{21}$ |
|---|---|---|---|---|---|---|---|
| 30847 | — | G | G | G | NG | NG | NG |
| | Norfloxacin | <4 | <4 | <4 | <4 | <4 | <4 |
| | Gentamicin | 2 | 2 | <1 | <1 | <1 | <1 |
| 002-002 | — | G | G | G | G | G | NG |
| | Norfloxacin | <4 | <4 | <4 | <4 | <4 | <4 |
| | Gentamicin | 2 | <1 | <1 | <1 | <1 | <1 |
| 19035 | — | G | G | G | NG | G | NG |
| | Norfloxacin | <4 | <4 | <4 | <4 | <4 | <4 |
| 30403 | — | G | G | NG | NG | NG | NG |
| | Norfloxacin* | 8 | <4 | <4 | <4 | <4 | <4 |
| 30413 | — | G | G | G | NG | G | NG |
| | Norfloxacin* | 8 | <4 | <4 | <4 | <4 | <4 |

*BPI protein product reversed antibiotic indifference

TABLE 5A

Susceptibility ranges for *S. pyogenes* (Group A)

| Antibiotic | MIC (μg/mL) Resistant | Intermediate | Susceptible |
|---|---|---|---|
| Gentamicin | >6 | 6 | ≦4 |
| Norfloxacin | >8 | 8 | ≦4 |

EXAMPLE 11

In Vitro Effects of BPI Protein Product Alone or in Combination with Antibiotics on Strains of the Gram-Positive Organism *Streptococcus agalactiae* (Group B)

The effect of a BPI protein product, $rBPI_{21}$, on the antibiotic susceptibility of various strains of *Streptococcus agalactiae,* also known as Group B strep, was evaluated using the Microscan® antibiotic susceptibility screening assay of Example 9. The direct growth inhibitory effect of $rBPI_{21}$ on these strains was also evaluated in the same assay. Assays were conducted on clinical isolates of *S. agalactiae* (from Baxter Microscan® library, Sacramento, Calif.).

A summary of the results of the antibiotic screening panels, reported as MICs (μg/ml) of the antibiotic tested, is shown in Table 6 below. Results are only reported where $rBPI_{21}$ altered the antibiotic susceptibility. The antibiotic susceptibility standards (interpretation of an MIC as clinically resistant, intermediate or susceptible according to NCCLS standards) applicable to the organism tested appear in Table 6A. These results show that BPI protein product reversed the resistance of one strain to gentamicin, and increased the susceptibility of other strains to ciprofloxacin, gentamicin, norfloxacin. These strains were not susceptible to BPI protein product alone, without antibiotic.

TABLE 6

EFFECTS OF $rBPI_{21}$ ± ANTIBIOTICS ON *Streptococcus agalactiae* (Group B)

| | | Minimum Inhibitory Concentration of Antibiotic (μg/mL) | | | | |
|---|---|---|---|---|---|---|
| Microscan Library ID No. | Antibiotic Tested | With 0 μg/mL $rBPI_{21}$ | With 0.5 μg/mL $rBPI_{21}$ | With 2 μg/mL $rBPI_{21}$ | With 8 μg/mL $rBPI_{21}$ | With 16 μg/mL $rBPI_{21}$ |
| 003-044 | Gentamicin* | >6 | 6 | 4 | 6 | 6 |
| | Ciprofloxacin | <1 | <1 | <1 | <1 | <1 |
| | Norfloxacin | <4 | <4 | <4 | <4 | <4 |
| 003-049 | Gentamicin** | >6 | 4 | 4 | 4 | 4 |
| | Ciproflo-xacin* | 2 | 2 | <1 | <1 | <1 |
| | Norfloxacin | 8 | 8 | 8 | 8 | 8 |
| 30851 | Gentamicin | 4 | <1 | 2 | 2 | <1 |
| | Ciprofloxacin | <1 | <1 | <1 | <1 | <1 |
| | Norfloxacin* | 8 | <4 | <4 | <4 | <4 |
| 31947 | Gentamicin | 2 | 4 | <1 | <1 | <1 |
| | Ciprofloxacin* | 2 | <1 | <1 | <1 | <1 |
| | Norfloxacin | 8 | 8 | 8 | 8 | 8 |
| 30911 | Gentamicin | 4 | <1 | 4 | <1 | <1 |
| | Ciprofloxacin | <1 | <1 | <1 | <1 | <1 |
| | Norfloxacin | <4 | <4 | <4 | <4 | <4 |

*BPI protein product reversed antibiotic indifference
**BPI protein product reversed antibiotic resistance

TABLE 6A

Susceptibility ranges for *S. agalactiae* (Group B)

| | MIC (μg/mL) | | |
|---|---|---|---|
| Antibiotic | Resistant | Intermediate | Susceptible |
| Ciprofloxacin | >2 | 2 | ≦1 |
| Gentamicin | >6 | 6 | ≦4 |
| Norfloxacin | >8 | 8 | ≦4 |

EXAMPLE 12

In Vitro Effects of BPI Protein Products Alone or in Combination with Antibiotics on Strains of the Gram-Positive Organism *Streptococcus bovis*

The effect of a BPI protein product, $rBPI_{21}$, on the antibiotic susceptibility of various trains of *Streptococcus bovis* was evaluated using the Microscan® antibiotic susceptibility screening assay of Example 9. The direct growth inhibitory effect of $rBPI_{21}$ on these strains was also evaluated in the same assay. Assays were conducted on clinical isolates of *S. bovis* (from Baxter Microscan® library, Sacramento, Calif.).

A summary of the results of the antibiotic screening panels, reported as MICs (μg/ml) of the antibiotic tested, is shown in Table 7 below. Results are only reported where $rBPI_{21}$ altered the antibiotic susceptibility. The antibiotic susceptibility standards (interpretation of an MIC as clinically resistant, intermediate or susceptible according to NCCLS standards) applicable to the organism tested appear in Table 7A. These results show that the BPI protein product reversed the resistance of one strain to ciprofloxacin, three strains to norfloxacin, and two strains to tetracycline. The results show the BPI protein product also increased the susceptibility of some strains to ciprofloxacin, gentamicin, norfloxacin, and tetracycline. These strains were not susceptible to BPI protein product alone, without antibiotic.

TABLE 7

EFFECTS OF $rBPI_{23}$ ± ANTIBIOTICS ON *Streptococcus bovis*

| Micro-scan Library ID No. | Antibiotic Tested | Minimum Inhibitory Concentration of Antibiotic (μg/mL) With 0 μg/mL $rBPI_{21}$ | With 0.5 μg/mL $rBPI_{21}$ | With 2 μg/mL $rBPI_{21}$ | With 8 μg/mL $rBPI_{21}$ | With 16 μg/mL $rBPI_{21}$ |
|---|---|---|---|---|---|---|
| ATCC #49147 | Tetracycline* | 128 | 8 | 8 | 4 | 8 |
| | Gentamicin | 2 | 2 | <1 | <1 | <1 |
| | Ciprofloxacin | <1 | <1 | <1 | <1 | <1 |
| | Norfloxacin* | 8 | <4 | <4 | <4 | <4 |
| 008-009 | Tetracycline** | 128 | 4 | 8 | 4 | <2 |
| | Gentamicin | 2 | 2 | 2 | <1 | <1 |
| | Ciprofloxacin* | 2 | <1 | <1 | <1 | <1 |
| | Norfloxacin** | >8 | 8 | 8 | 8 | <4 |
| 008-010 | Tetracycline** | 128 | 128 | 128 | 8 | 4 |
| | Gentamicin | 4 | 4 | 2 | 2 | <1 |
| | Ciprofloxacin* | 2 | 2 | <1 | <1 | <1 |
| | Norfloxacin** | >8 | 8 | >8 | <4 | <4 |
| 008-011 | Tetracycline | <2 | <2 | <2 | <2 | <2 |
| | Gentamicin | 2 | 2 | <1 | <1 | <1 |
| | Ciprofloxacin* | 2 | <1 | 2 | <1 | <1 |
| | Norfloxacin** | >8 | 8 | 8 | 8 | <4 |
| 008-012 | Tetracycline | 128 | 128 | 128 | 128 | 8 |
| | Gentamicin | 4 | 2 | <1 | 2 | <1 |
| | Cipro-floxacin** | >2 | 2 | <1 | 2 | <1 |
| | Norfloxacin | >8 | 8 | 8 | 8 | 8 |

*BPI protein product reversed antibiotic indifference
**BPI protein product reversed antibiotic resistance

TABLE 7A

Susceptibility ranges for *S. bovis*

| Antibiotic | MIC (μg/mL) Resistant | Intermediate | Susceptible |
|---|---|---|---|
| Ciprofloxacin | >2 | 2 | ≦1 |
| Gentamicin | >6 | 6 | ≦4 |
| Norfloxacin | >8 | 8 | ≦4 |
| Tetracycline | ≦128 | 8 | ≦4 |

EXAMPLE 13

In Vitro Effects of BPI Protein Products Alone or in Combination with Antibiotics on Strains of the Gram-Positive Organism *Enterococcus faecalis*

The effect of a BPI protein product, $rBPI_{21}$, on the antibiotic susceptibility of various strains of *Enterococcus faecalis* was evaluated using the Microscan® antibiotic susceptibility screening assay of Example 9. The direct growth inhibitory effect of $rBPI_{21}$ on these strains was also evaluated in the same assay. Assays were conducted on clinical isolates of *E. faecalis* (from Baxter Microscan® library, Sacramento, Calif.).

A summary of the results of the antibiotic screening panels, reported as MICs (μg/ml) of the antibiotic tested, is shown in Table 8 below. Results are only reported where $rBPI_{21}$ altered the antibiotic susceptibility. The antibiotic susceptibility standards (interpretation of an MIC as clinically resistant, intermediate or susceptible according to NCCLS standards) applicable to the organism tested appear in Table 8A. These results show the BPI protein product reversed the resistance of three strains to ciprofloxacin and two strains to norfloxacin. The BPI protein product also increased the susceptibility of some *E. faecalis* strains to ampicillin, ciprofloxacin, erythromycin, norfloxacin, penicillin, rifampin, and tetracycline. These strains were not susceptible to BPI protein product alone, without antibiotic.

TABLE 8

EFFECTS OF $rBPI_{21}$ ± ANTIBIOTICS ON *Enterococcus faecalis*

| Microscan Library ID No. | Antibiotic Tested | Minimum Inhibitory Concentration of Antibiotic (μg/mL) With 0 μg/mL $rBPI^{21}$ | With 2 μg/mL $rBPI_{21}$ | With 8 μg/mL $rBPI_{21}$ | With 32 μg/mL $rBPI_{21}$ |
|---|---|---|---|---|---|
| 011-070 | Penicillin | 2 | 2 | 1 | 1 |
| | Tetracycline | 128 | 128 | 128 | 8 |
| 16967 | Rifampin | >2 | >2 | >2 | 2 |
| | Ciprofloxacin** | >2 | 2 | 2 | <1 |
| | Norfloxacin** | >8 | 8 | 8 | <4 |
| | Penicillin | 2 | 2 | 2 | 1 |
| | Erythromycin | 4 | 2 | 2 | 2 |
| 19010 | Penicillin | 8 | 8 | 8 | 4 |
| | Ampicillin | 4 | 4 | 4 | 2 |
| 011-028 | Penicillin | 8 | 8 | 8 | 4 |
| | Ciprofloxacin* | 2 | <1 | <1 | <1 |
| | Ampicillin | 1 | <0.5 | <0.5 | <0.5 |
| 011-001 | Ciprofloxacin** | >2 | <1 | <1 | <1 |
| | Norfloxacin | <4 | <4 | <4 | <4 |
| 011-002 | Penicillin | 2 | 1 | 1 | 1 |
| | Ampicillin | 2 | 0.5 | 0.5 | 0.5 |
| 011-003 | Rifampin | >2 | >2 | >2 | 2 |
| | Penicillin | 2 | 2 | 2 | 1 |
| | Norfloxacin* | 8 | 8 | 8 | <4 |
| | Ampicillin | 1 | 1 | 0.5 | 0.5 |
| 011-004 | Penicillin | 8 | 8 | 8 | 4 |
| | Ampicillin | 4 | 4 | 2 | 2 |
| 011-005 | Penicillin | 2 | 2 | 2 | 1 |
| | Ampicillin | 1 | 0.5 | 0.5 | 0.5 |
| 011-006 | Penicillin | 2 | 2 | 2 | 1 |
| | Ampicillin | 1 | 1 | 1 | 0.5 |
| 011-066 | Ciprofloxacin** | >2 | <1 | <1 | <1 |
| | Norfloxacin** | >8 | <4 | <4 | <4 |
| | Ampicillin | 1 | 1 | 0.5 | 0.5 |

*BPI protein product reversed antibiotic indifference
**BPI protein product reversed antibiotic resistance

TABLE 8A

Susceptibility ranges for *E. faecalis*

| Antibiotic | MIC (μg/mL) Resistant | Intermediate | Susceptible |
|---|---|---|---|
| Ampicillin | >8 | | ≦8 |
| Ciprofloxacin | >2 | 2 | ≦1 |
| Erythromycin | >4 | 1–4 | ≦0.5 |
| Norfloxacin | >8 | 8 | ≦4 |
| Penicillin | >8 | | ≦8 |
| Rifampin | >2 | 2 | ≦1 |
| Tetracycline | >128 | 8 | ≦4 |

EXAMPLE 14

In Vitro Effects of BPI Protein Products Alone or in Combination with Antibiotics on Strains of the Gram-Positive Organism *Enterococcus faecium*

The effect of a variety of BPI protein products on the antibiotic susceptibility of various strains of *Enterococcus faecium* was evaluated using the Microscan® antibiotic susceptibility screening assay of Example 9. The direct growth inhibitory effect of the BPI protein products on these strains was also evaluated in the same assay. Assays were conducted on clinical isolates of *E. faecium* (from Baxter Microscan® library, Sacramento, Calif.).

A summary of the results of the antibiotic screening panels, reported as MICs (μg/ml) of the antibiotic tested at varying concentrations of $rBPI_{21}$, is shown in Table 9 below. Results are only reported where $rBPI_{21}$ altered the antibiotic susceptibility. The antibiotic susceptibility standards (interpretation of an MIC as clinically resistant, intermediate or susceptible according to NCCLS standards) applicable to the organism tested appear in Table 9A. These results show the $rBPI_{21}$ reversed the resistance of five strains to amoxicillin/K clavulanate, two strains to cefazolin, two strains to ciprofloxacin, two strains to erythromycin, one strain to norfloxacin, two strains to oxacillin, two strains to rifampin, one strain to tetracycline, and one strain to vancomycin. The $rBPI_{21}$ also increased the susceptibility of some *E. faecium* strains to amoxicillin/K clavulanate, cefotaxime, ciprofloxacin, erythromycin, penicillin, rifampin, and vancomycin. These strains were not susceptible to BPI protein product alone, without antibiotic.

Additional screening of an *E. faecium* strain (Microscan® ID no. 15773) was conducted with a variety of BPI protein products, $rBPI_{21}$, $rBPI_{23}$, $rBPI_{50}$ and $rBPI_{42}$ dimer. Table 9X below displays a summary of the results of the antibiotic screening panels, reported as the MIC of the tested antibiotics at varying concentrations of the indicated BPI protein product. Results are only reported if antibiotic susceptibility was altered.

TABLE 9

EFFECTS OF $rBPI_{21}$ ± ANTIBIOTICS ON *Enterococcus faecium*

| | | Minimum Inhibitory Concentration of Antibiotic (μg/mL) | | | |
|---|---|---|---|---|---|
| Microscan Library ID No. | Antibiotic Tested | With 0 μg/mL $rBPI^{21}$ | With 2 μg/mL $rBPI_{21}$ | With 8 μg/mL $rBPI_{21}$ | With 32 μg/mL $rBPI_{21}$ |
| 17611 | Rifampin** | >2 | >2 | 2 | <1 |
| | Ciprofloxacin** | >2 | 2 | 2 | <1 |
| | Augmentin* | >16 | 16 | 16 | 16 |
| 16866 | Ciprofloxacin* | 2 | 2 | <1 | <1 |
| | Tetracycline** | 128 | 128 | 128 | 4 |
| 20076 | Rifampin** | >2 | 2 | 2 | <1 |
| | Erythromycin* | 4 | 2 | 1 | <0.25 |
| | Augmentin*** | 16 | 8 | 8 | <4 |
| | Oxacillin** | >4 | <0.5 | <0.5 | <0.5 |
| 012-048 | Rifampin | >2 | >2 | 2 | 2 |
| | Ciprofloxacin** | >2 | >2 | <1 | <1 |
| | Penicillin | 0.25 | 0.25 | 0.25 | 0.12 |
| | Cefotaxime* | 32 | <8 | <8 | <8 |
| | Cefazolin** | >16 | 16 | 8 | 8 |
| 15773 | Rifampin* | 2 | 2 | <1 | <1 |
| | Ciprofloxacin* | 2 | <1 | <1 | <1 |
| | Erythromycin** | >4 | <0.25 | <0.25 | <0.25 |
| | Augmentin*** | 16 | <4 | <4 | <4 |
| | Vancomycin | 4 | 4 | <2 | <2 |
| 012-001 | Rifampin | >2 | 2 | >2 | 2 |
| | Augmentin[a]** | 16 | 8 | 8 | 8 |
| 012-002 | Rifampin | >2 | >2 | >2 | 2 |
| | Oxacillin** | >4 | 1 | <0.5 | <0.5 |
| | Vancomycin** | >16 | >16 | >16 | <2 |
| | Norfloxacin** | >8 | <4 | <4 | <4 |
| | Cefazolin** | >16 | >16 | >16 | 8 |
| 012-003 | Rifampin | <1 | <1 | <1 | <1 |
| | Augmentin*** | 16 | 8 | 8 | 8 |
| 012-004 | Rifampin* | 2 | 2 | <1 | <1 |
| | Ciprofloxacin* | 2 | <1 | <1 | <1 |
| | Augmentin*** | 16 | <4 | <4 | <4 |
| | Vancomycin | 4 | 4 | <2 | <2 |
| | Erythromycin** | >4 | 0.5 | <0.25 | <0.25 |

[a]Augmentin is Amoxicillin K/Clavulanate
*BPI protein product reversed antibiotic indifference
**BPI protein product reversed antibiotic resistance

TABLE 9A

Susceptibility ranges for *E. faecium*

| | MIC (μg/mL) | | |
|---|---|---|---|
| Antibiotic | Resistant | Intermediate | Susceptible |
| Amoxicillin K/Clavulanate | ≧16/8 | | ≦8/4 |
| Cefazolin | >16 | 16 | ≦8 |
| Cefotaxime | >32 | 16–32 | ≦8 |
| Ciprofloxacin | >2 | 2 | ≦1 |
| Erythromycin | >4 | 1–4 | ≦0.5 |
| Norfloxacin | >8 | 8 | ≦4 |
| Oxacillin (staph only) | ≦4 | | ≦2 |
| Penicillin | >8 | | ≦8 |
| Rifampin | >2 | 2 | ≦1 |

TABLE 9A-continued

| Susceptibility ranges for *E. faecium* | | | |
|---|---|---|---|
| | MIC (μg/mL) | | |
| Antibiotic | Resistant | Intermediate | Susceptible |
| Tetracycline | ≧128 | 8 | ≦4 |
| Vancomycin | >16 | 8–16 | ≦4 |

*casseliflavus,* BPI protein product increased susceptibility to ampicillin, penicillin, oxacillin, cephalothin, and cefazolin. For *E. durans,* BPI protein product increased susceptibility to ampicillin and rifampin. For *E. avium,* BPI protein product increased susceptibility to ampicillin, penicillin, cefotaxime and ciprofloxacin, and oxacillin. These Enterococcus species were not susceptible to BPI protein product alone, without antibiotic.

TABLE 9X

EFFECTS OF BPI PROTEIN PRODUCTS ± ANTIBIOTICS

| | | Minimum Inhibitory Concentration of Antibiotic (μg/mL) With: | | | | | | | | |
|---|---|---|---|---|---|---|---|---|---|---|
| Organism Name (Microscan ® ID No.) | Antibiotic Tested | 0 μg/mL BPI | 4 μg/mL $rBPI_{21}$ | 4 μg/mL $rBPI_{23}$ | 4 μg/mL $rBPI_{50}$ | 4 μg/mL $rBPI_{42}$ dimer | 16 μg/mL $rBPI_{21}$ | 16 μg/mL $rBPI_{23}$ | 16 μg/mL $rBPI_{50}$ | 16 μg/mL $rBPI_{42}$ dimer |
| *E. faecium* 15773 | Erythromycin** | >4 | 1 | <0.25 | >4 | >4 | <0.25 | <0.25 | >4 | <0.25 |
| | Vancomycin | 4 | 4 | 4 | 4 | 4 | <2 | 4 | 4 | <2 |
| | Cefotaxime | >32 | >32 | >32 | >32 | >32 | >32 | 32 | >32 | >32 |
| | Ticarcillin/K Clavulanate | >8 | >8 | >8 | >8 | >8 | >8 | 8 | >8 | >8 |
| | Gentamicin** | >6 | 4 | 4 | >6 | >6 | 6 | 6 | >6 | 4 |
| | Amoxicillin/K Clavulanate | 16 | 8 | <4 | 16 | 8 | <4 | <4 | 8 | <4 |
| | Ampicillin/ Sulbactam | 16 | <8 | <8 | 16 | <8 | <8 | <8 | <8 | <8 |
| | Rifampin | >2 | 2 | 2 | >2 | 2 | <1 | <1 | >2 | <1 |
| | Ciprofloxacin* | 2 | <1 | <1 | 2 | <1 | <1 | <1 | <1 | <1 |
| | Amikacin* | 32 | <16 | <16 | 32 | 32 | <16 | 32 | 32 | <16 |
| | Sulfamethoxazole** | >256 | <256 | <256 | >256 | >256 | <256 | >256 | >256 | <256 |

EXAMPLE 15

In Vitro Effects of BPI Protein Products Alone or in Combination with Antibiotics on Other Gram-Positive Enterococcus Species The effect of a BPI protein product, $rBPI_{21}$, on the antibiotic susceptibility of a variety of Enterococcus species was evaluated using the Microscan® antibiotic susceptibility screening assay of Example 9. The direct growth inhibitory effect of $rBPI_{21}$ on these species was also evaluated in the same assay. Assays were conducted on clinical isolates of Enterococcus species (from Baxter Microscan® library, Sacramento, Calif.).

A summary of the results of the antibiotic screening panels, reported as MICs (μg/ml) of the antibiotic tested, is shown in Table 10 below. Results are only reported where $BPI_{21}$ altered the antibiotic susceptibility. The antibiotic susceptibility standards (interpretation of an MIC as clinically resistant, intermediate or susceptible according to NCCLS standards) applicable to the organism tested appear in Table 10A. These results show that for *E. gallinarum,* BPI protein product reversed resistance to cephalothin, cefazolin, ciprofloxacin and norfloxacin, and increased susceptibility to ampicillin, penicillin and rifampin. For *E. raffinosus,* BPI protein product reversed resistance to ampicillin and increased susceptibility to imipenem. For *E.*

TABLE 10

EFFECTS OF $rBPI_{21}$ ± ANTIBIOTICS ON Enterococcus SPECIES

| | | Minimum Inhibitory Concentration of Antibiotic (μg/mL) | | | |
|---|---|---|---|---|---|
| Microscan Library ID No. | Antibiotic Tested | With 0 μg/mL $rBPI^{21}$ | With 2 μg/mL $rBPI_{231}$ | With 8 μg/mL $rBPI_{21}$ | With 32 μg/mL $rBPI_{21}$ |
| 031-009 (*E. gallinarum*) | Ampicillin | 1 | 1 | 0.5 | 0.5 |
| | Penicillin | 1 | 0.5 | 0.5 | 0.25 |
| | Rifampin | >2 | >2 | >2 | 2 |
| | Cephalothin** | >16 | <8 | <8 | <8 |
| | Cefazolin** | >16 | 8 | 8 | 4 |
| | Ciprofloxacin** | >2 | 2 | <1 | <1 |
| | Norfloxacin** | >8 | 8 | 8 | <4 |
| 16206 (*E. raffinosus*) | Ampicillin** | >8 | >8 | >8 | 8 |
| | Imipenem | >8 | >8 | >8 | 8 |
| 030-008 and 030-001[a] (*E. casseliflavus*) | Ampicillin | 1 | 0.5 | 0.25 | 0.25 |
| | Penicillin | 1 | 0.25 | 0.25 | 0.12 |
| | Oxacillin | >4 | >4 | >4 | 4 |
| | Cephalothin* | 16 | <8 | <8 | <8 |
| | Cefazolir* | 16 | 8 | 4 | 4 |
| 17543 (*E. durans*) | Ampicillin | 1 | 0.5 | 0.5 | 0.5 |
| | Rifampin | >2 | 2 | 2 | 2 |
| 31413 | Ampicillin | 0.5 | 0.5 | 0.5 | <0.12 |

TABLE 10-continued

EFFECTS OF $rBPI_{21}$ ± ANTIBIOTICS ON Enterococcus SPECIES

| Microscan Library ID No. | Antibiotic Tested | Minimum Inhibitory Concentration of Antibiotic (μg/mL) With 0 μg/mL $rBPI^{21}$ | With 2 μg/mL $rBPI_{231}$ | With 8 μg/mL $rBPI_{21}$ | With 32 μg/mL $rBPI_{21}$ |
|---|---|---|---|---|---|
| (*E. avium*) | Penicillin | 1 | 1 | 1 | 0.5 |
| | Oxacillin** | >4 | >4 | 4 | 0.5 |
| | Cefotaxime* | 32 | <8 | <8 | <88 |
| | Ciprofloxacin* | 2 | <1 | <1 | <1 |

[a]Two strains of *E. casseliflavus* were tested; both strains gave identical results.

TABLE 10A

Susceptibility ranges for Enterococcus species

| Antibiotic | MIC (μg/mL) Resistant | Intermediate | Susceptible |
|---|---|---|---|
| Ampicillin | >8 | | ≦8 |
| Cefazolin | >16 | 16 | ≦8 |
| Cefotaxime | >32 | 16–32 | ≦8 |
| Cephalothin | >16 | 16 | ≦8 |
| Ciprofloxacin | >2 | 2 | ≦1 |
| Imipenem | >8 | 8 | ≦4 |
| Norfloxacin | >8 | 8 | ≦4 |
| Oxacillin | ≧4 | | ≦2 |
| Penicillin | >8 | | ≦8 |
| Rifampin | >2 | 2 | ≦1 |

EXAMPLE 16

In Vitro Effects of BPI Protein Products Alone or in Combination with Antibiotics on Strains of the Gram-Positive Organism *Staphylococcus aureus*

The effect of BPI protein products on the antibiotic susceptibility of a variety of *S. aureus* species was evaluated using the Microscan® antibiotic susceptibility screening assay of Example 9. The direct growth inhibitory effect of BPI protein products on these species was also evaluated in the same assay. Assays were conducted on the following clinical isolates of *S. aureus* (from Baxter Microscan® library, Sacramento, Calif.): 052-066, 052-106, 052-107, 052-108, 052-184, 052-219, 052-230, 14288, 20720, 29213 (ATCC No.), 32075 and 32073.

These strains of *S. aureus* were tested to determine the $MIC_{90}$ for each antibiotic in the panel at varying concentrations of $rBPI_{21}$. The $MIC_{90}$ is defined as the lowest concentration of antibiotic that inhibits the growth of 90% of all *S. aureus* isolates tested. Results are reported in Table 11 below, and applicable antibiotic susceptibility standards (interpretation of an MIC as clinically resistant, intermediate or susceptible according to NCCLS standards) appear in Table 11A.

The data show that $rBPI_{21}$ was able to reduce the *S. aureus* $MIC_{90}$ values for eight of twenty-five antibiotics evaluated: amoxicillin/K clavulanate (Augmentin), cefotaxime, ceftriaxone, cefuroxime, cephalothin, chloramphenicol, imipenem and sulfamethoxazole. Dashes in Table 11 indicate that no concentration of antibiotic tested was able to inhibit growth of 90% of all tested strains. None of the *S. aureus* strains tested were susceptible to $rBPI_{21}$ alone without antibiotic.

Comparable results obtained from testing of the BPI protein product $rBPI_{21}$ on *S. aureus* (Microscan® ID no. 052-106) in the Pasco system confirm the effect of BPI protein products on the antibiotic susceptibility of gram-positive organisms.

Additional screening of this *S. aureus* strain (Microscan® ID no. 052-106) was conducted with a variety of BPI protein products, $rBPI_{21}$, $rBPI_{23}$, $rBPI_{50}$ and $rBPI_{42}$ dimer. Table 11X below displays a summary of the results of the antibiotic screening panels, reported as the MIC of the tested antibiotics at varying concentrations of the indicated BPI protein product. Results are only reported if antibiotic susceptibility was altered.

TABLE 11

Effect of $rBPI_{21}$ on $MIC_{90}$ of Antibiotics for *Staphylococcus aureus*

| Antibiotic Tested | $MIC_{90}$ With 0 μg/mL (n = 38)[a] | $MIC_{90}$ With 0.5–8 μg/mL (n = 31)[a] | $MIC_{90}$ With 16–64 μg/mL (n = 25)[a] |
|---|---|---|---|
| Amikacin | 16 | 16 | 16 |
| Amox/K Clav | 16 | 16 | 8 |
| Amp/Sulbactam | 8 | 8 | 8 |
| Ampicillin | — | — | — |
| Cefazolin | — | — | — |
| Cefotaxime | 32 | 8 | 4 |
| Ceftriaxone | — | 32 | 8 |
| Cefuroxime | — | — | 16 |
| Cephalothin | 8 | 4 | 4 |
| Chloramphenicol | 8 | 8 | 4 |
| Ciprofloxacin | 1 | 1 | 1 |
| Clindamycin | — | — | — |
| Erythromycin | — | — | — |
| Gentamicin | — | — | — |
| Imipenem | — | — | 8 |
| Nitrofurantoin | 32 | 32 | 32 |
| Norfloxacin | 4 | 4 | 4 |
| Oxacillin | — | — | — |
| Penicillin | — | — | — |
| Rifampin | 1 | 1 | 1 |
| Sulfamethoxazole | — | — | 256 |
| Tetracycline | 128 | 128 | 128 |
| Ticarcillin/K Clav | — | — | — |
| Trimethy/Sulfa | 2 | 2 | 2 |
| Vancomycin | 2 | 2 | 2 |

[a]Number of runs; 12 strains tested

TABLE 11A

Susceptibility ranges for *S. aureus*

| Antibiotic | MIC (μg/mL) Resistant | Intermediate | Susceptible |
|---|---|---|---|
| Amikacin | >32 | 32 | ≦16 |
| Amoxicillin/K Clav. | ≦8/4 | | ≦4/2 |
| Ampicillin/Sulbactam | >16/8 | 16/8 | ≦8/4 |
| Ampicillin | ≧0.5 | | ≦0.25 |
| Cefazolin | >16 | 16 | ≦8 |
| Cefotaxime | >32 | 16–32 | ≦8 |
| Ceftriaxone | >32 | 16–32 | ≦8 |
| Cefuroxime | >16 | 16 | ≦8 |
| Cephalothin | >16 | 16 | ≦8 |
| Chloramphenicol | >16 | 16 | ≦8 |
| Ciprofloxacin | >2 | 2 | ≦1 |
| Clindamycin | >2 | 1–2 | ≦0.5 |
| Erythromycin | >4 | 1–4 | ≦0.5 |
| Gentamicin | >6 | 6 | ≦4 |
| Imipenem | >8 | 8 | ≦4 |
| Nitrofurantoin | >64 | 64 | ≦32 |
| Norfloxacin | >8 | 8 | ≦4 |
| Oxacillin | ≧4 | | ≦2 |

TABLE 11A-continued

Susceptibility ranges for *S. aureus*

| Antibiotic | MIC ($\mu$g/mL) Resistant | Intermediate | Susceptible |
|---|---|---|---|
| Penicillin | ≧0.25 | | ≦0.12 |
| Rifampin | >2 | 2 | ≦1 |
| Sulfamethoxazole | >256 | | ≦256 |
| Tetracycline | ≧128 | 8 | ≦4 |
| Ticarcillin/K Clav. | ≧8 | | ≦4 |
| Trimethoprim/ Sulfamethoxazole | >2/38 | | ≦2/38 |
| Vancomycin | >16 | 8–16 | ≦4 |

TABLE 11X

EFFECTS OF BPI PROTEIN PRODUCTS ± ANTIBIOTICS

| Organism Name (Microscan ® ID No.) | Antibiotic Tested | Minimum Inhibitory Concentration of Antibiotic ($\mu$g/mL) With: 0 $\mu$g/mL BPI | 4 $\mu$g/mL $rBPI_{21}$ | 4 $\mu$g/mL $rBPI_{23}$ | 4 $\mu$g/mL $RBPI_{50}$ | 4 $\mu$g/mL $rBPI_{42}$ dimer | 16 $\mu$g/mL $rBPI_{21}$ | 16 $\mu$g/mL $rBPI_{23}$ | 16 $\mu$g/mL $rBPI_{50}$ | 16 $\mu$g/mL $rBPI_{42}$ dimer |
|---|---|---|---|---|---|---|---|---|---|---|
| *S. aureus* 052-106 | Cephalothin | 8 | 4 | 4 | 4 | 8 | 4 | 4 | 4 | 4 |
| | Cefuroxime** | >16 | 16 | 16 | 16 | >16 | 8 | 8 | 8 | 8 |
| | Ceftriaxone* | 16 | 8 | 8 | 8 | 16 | 8 | 8 | 8 | 8 |
| | Chloramphenicol | 8 | 8 | 8 | 8 | 8 | <4 | <4 | 16 | <4 |
| | Trimethoprim/ Sulfamethoxazole** | >2 | <2 | <2 | <2 | <2 | <2 | <2 | <2 | <2 |
| | Ciprofloxacin | <1 | <1 | <1 | <1 | <1 | <1 | <1 | >2 | <1 |
| | Sulfamethoxazole** | >256 | >256 | >256 | >256 | >256 | <256 | >256 | >256 | <256 |

EXAMPLE 17

In Vitro Effects of BPI Protein Products Alone or in Combination with Antibiotics on Strains of the Gram-Positive Organism *Staphylococcus epidermidis*

The effect of a BPI protein product, $rBPI_{21}$, on the antibiotic susceptibility of a variety of *Staphylococcus epidermidis* species was evaluated using the Microscan® antibiotic susceptibility screening assay of Example 9. The direct growth inhibitory effect of $rBPI_{21}$ on these species was also evaluated in the same assay. Assays were conducted on the following clinical isolates of *S. epidermidis* (from Baxter Microscan® library, Sacramento, Calif.): 055051, 055155, 19776, 20778, 20959, 055125, 055129, 055126, 32086 and 32085. *S. epidermidis* is a coagulase-negative staphylococcus that is a major agent of nosocomial (hospital-acquired) sepsis in oncology and neonatal sections, and accounts for about 40% of all prosthetic joint infections.

These strains of *S. epidermidis* were tested to determine the $MIC_{90}$ for each antibiotic in the panel at varying concentrations of $rBPI_{21}$. Results are reported in Table 12 below, and applicable antibiotic susceptibility standards (interpretation of an MIC as clinically resistant, intermediate or susceptible according to NCCLS standards) appear in Table 12A.

The data show that the BPI protein product was able to reduce the *S. epidermidis* $MIC_{90}$ values for thirteen of twenty-five antibiotics evaluated: amikacin, amoxicillin/K clavulanate (augmentin), ampicillin, cefazolin, cefotaxime, ceftriaxone, cefuroxime, chloramphenicol, penicillin, sulfamethoxazole, tetracylcine, ticarcillin/K clavulanate and trimethoprim/sulfamethoxazole. None of the *S. epidermidis* strains tested were susceptible to BPI protein product alone, without antibiotic.

TABLE 12

Effect of $rBPI_{21}$ on $MIC_{90}$ of Antibiotics for *Staphylococcus epidermidis*

| Antibiotic Tested | $MIC_{90}$ With 0 $\mu$g/mL $rBPI_{21}$ (n = 35)[a] | $MIC_{90}$ With 8 $\mu$g/mL $rBPI_{21}$ (n = 10)[a] | $MIC_{90}$ With 32 $\mu$g/mL $rBPI_{21}$ (n = 9)[a] |
|---|---|---|---|
| Amikacin | 32 | NT | 16 |
| Amoxicillin/K Clav | 8 | 8 | 4 |
| Ampicillin/Sulbactam | 8 | NT | 8 |
| Ampicillin | — | — | 4 |

TABLE 12-continued

Effect of $rBPI_{21}$ on $MIC_{90}$ of Antibiotics for *Staphylococcus epidermidis*

| Antibiotic Tested | $MIC_{90}$ With 0 $\mu$g/mL $rBPI_{21}$ (n = 35)[a] | $MIC_{90}$ With 8 $\mu$g/mL $rBPI_{21}$ (n = 10)[a] | $MIC_{90}$ With 32 $\mu$g/mL $rBPI_{21}$ (n = 9)[a] |
|---|---|---|---|
| Cefazolin | 4 | 4 | 2 |
| Cefotaxime | — | — | 8 |
| Ceftriaxone | — | NT | 4 |
| Cefuroxime | — | NT | 2 |
| Cephalothin | 8 | 8 | 8 |
| Chloramphenicol | — | NT | 4 |
| Ciprofloxacin | 1 | 1 | 1 |
| Clindamycin | — | — | — |
| Erythromycin | — | — | — |
| Gentamicin | — | — | — |
| Imipenem | — | — | — |
| Nitrofurantoin | 32 | 32 | 32 |
| Norfloxacin | 4 | 4 | 4 |
| Oxacillin | — | — | — |
| Pencillin | | — | 8 |
| Rifampin | 1 | 1 | 1 |
| Sulfamethoxazole | — | NT | 256 |
| Tetracycline | 128 | 128 | 8 |
| Ticarcillin/K Clav | — | NT | 1 |
| Trimeth/Sulfa | — | 2 | 2 |
| Vancomycin | 2 | 2 | 2 |

[a]Number of runs.

TABLE 12A

| Susceptibility ranges for *S. epidermidis* | | | |
|---|---|---|---|
| | MIC (μg/mL) | | |
| Antibiotic | Resistant | Intermediate | Susceptible |
| Amikacin | >32 | 32 | ≦16 |
| Amoxicillin/K Clav. | ≧8/4 | | ≦4/2 |
| Ampicillin/Sulbactam | >16/8 | 16/8 | ≦8/4 |
| Ampicillin | ≧0.5 | | ≦0.25 |
| Cefazolin | >16 | 16 | ≦8 |
| Cefotaxime | >32 | 16–32 | ≦8 |
| Ceftriaxone | >32 | 16–32 | ≦8 |
| Cefuroxime | >16 | 16 | ≦8 |
| Cephalothin | >16 | 16 | ≦8 |
| Chloramphenicol | >16 | 16 | ≦8 |
| Ciprofloxacin | >2 | 2 | ≦1 |
| Clindamycin | >2 | 1–2 | ≦0.5 |
| Erythromycin | >4 | 1–4 | ≦0.5 |
| Gentamicin | >6 | 6 | ≦4 |
| Imipenem | >8 | 8 | ≦4 |
| Nitrofurantoin | >64 | 64 | ≦32 |
| Norfloxacin | >8 | 8 | ≦4 |
| Oxacillin | ≧4 | | ≦2 |
| Penicillin | ≧0.25 | | ≦0.12 |
| Rifampin | >2 | 2 | ≦1 |
| Sulfamethoxazole | >256 | | ≦256 |
| Tetracycline | ≧128 | 8 | ≦4 |
| Ticarcillin/K Clav | ≧8 | | ≦4 |
| Trimethoprim/ Sulfamethoxazole | >2/38 | | ≦2/38 |
| Vancomycin | >16 | 8–16 | ≦4 |

EXAMPLE 18

In Vitro Effects of BPI Protein Products Alone or in Combination with Antibiotics on Species of the Gram-Positive Organism Staphylococcus The effect of a BPI protein product, $rBPI_{21}$, on the antibiotic susceptibility of a variety of other coagulase-negative Staphylococcus species was evaluated using the Microscan® antibiotic susceptibility screening assay of Example 9. The direct growth inhibitory effect of $rBPI_{21}$ on these species was also evaluated in the same assay. Assays were conducted on clinical isolates of Staphylococcus species (from Baxter Microscan® library, Sacramento, Calif.). In the last decade there has been a marked increase in clinical infections caused by the coagulase-negative staphylococci. These organisms are also significant opportunistic pathogens.

A summary of the results of the antibiotic screening panels, reported as MICs (μg/ml) of the antibiotic tested, is shown in Table 13 below. The antibiotic susceptibility standards (interpretation of an MIC as clinically resistant, intermediate or susceptible according to NCCLS standards) applicable to the organism tested appear in Table 13A.

These results shown that BPI protein product reversed resistance to penicillin for one *S. hominis* strain, and reversed resistance to trimethoprim/sulfamethoxazole for one *S. haemolyticus* strain and the *S. intermedius* strain. BPI protein product increased susceptibility of *S. hominis* strains to ampicillin and penicillin, the *S. sciuri* strain to clindamycin and penicillin, the *S. saprophyticus* strain to erythromycin, *S. haemolyticus* strains to erythromycin, and the *S. hyicus* strain to clindamycin and erythromycin, the *S. intermedius* strain to erythromycin, and the *S. simulans* strain to erythromycin. None of these tested strains were susceptible to $BPI_{21}$ alone at the concentrations tested.

TABLE 13

| Effects of $rBPI_{21}$ on Staphylococcus Species | | | | |
|---|---|---|---|---|
| | | Minimum Inhibitory Concentration (μg/ml) | | |
| Microscan Library ID No.[a] | Antibiotic Tested[b] | With 0 μg/ml $rBPI_{21}$ | With 4 μg/ml $rBPI_{21}$ | With 16 μg/ml $rBPI_{21}$ |
| (*S. hominis*) | Ampicillin | 0.25 | <0.12 | <0.12 |
| 057-003 | Penicillin** | 0.5 | 0.06 | 0.06 |
| (*S. hominis*) | Ampicillin | 0.25 | 0.25 | <0.12 |
| 057-001 | Penicillin | 0.25 | 0.12 | 0.06 |
| (*S. hominis*) | AMpicillin | 0.25 | 0.5 | 0.25 |
| 057-024 | Penicillin | 0.5 | 0.5 | 0.5 |
| (*S. scirui*) | Pencillin | 0.06 | 0.06 | <0.03 |
| 060-016 | Clindamycin* | 1 | 1 | 0.5 |
| (*S. saprophyticus*) | Erythromycin | 0.5 | 0.5 | <0.25 |
| 059-003 | | | | |
| (*S. haemolyticus*) | Trim/Sulfa** | >2 | <2 | <2 |
| 19770 | Erythromycin | >4 | 4 | 4 |
| (*S. haemolyticus*) | Ampicllin | 0.5 | 1 | 0.5 |
| 056-042 | Penicillin | 0.25 | 0.5 | 0.25 |
| (*S. hyicus*) | Erythromycin | 0.5 | <0.25 | <0.25 |
| 10377 | Clindamycin | 0.5 | <0.25 | <0.25 |
| (*S. intermedius*) | Trim/Sulfa** | >22 | <2 | <2 |
| 10254 | Erythromycin | 0.5 | <0.25 | <0.25 |
| (*S. simulans*) | Erythromycin | 0.5 | 0.5 | <0.25 |
| 061-001 | | | | |

[a]Two strains of *S. lugdunensis* (Microscan library ID Nos. 19782 and 11130) were also tested but were susceptible to all antibiotics tested.
[b]Strains were susceptible to all other antibiotics that were tested but are not shown here.

TABLE 13A

| Susceptibility ranges for Staphylococcus species | | | |
|---|---|---|---|
| | MIC (μg/mL) | | |
| Antibiotic | Resistant | Intermediate | Susceptible |
| Ampicillin | ≦0.5 | | ≦0.25 |
| Clindamycin | >2 | 1–2 | ≦0.5 |
| Erythromycin | >4 | 1–4 | ≦0.5 |
| Penicillin | ≧0.25 | | ≦0.12 |
| Trimethoprim/ Sulfamethoxazole | >2/38 | | ≦2/38 |

EXAMPLE 19

Early in Vitro Bactericidal Effects of BPI Protein Product Alone or in Combination with Antibiotics on *S. aureus, S. pneumoniae,* and *E. faecium*

The effect of a BPI protein product, $rBPI_{21}$, on the killing curves of selected antibiotics was determined for selected organism. Microscan® panel plates were prepared for a methicillin-resistant *S. aureus* (Microscan library ID no. 052-106), *S. pneumoniae* (Microscan library ID no. 31573), and *E. faecium* (Microscan library ID no. 15773), according to Example 9. Cell suspensions were added to 25 ml Pluronic Inoculum Water containing 0 or 16 μg/ml $rBPI_{21}$. After inoculation, the panel plates were incubated at 35° C. for 24 hours. At 0, 4, 7 and 24 hours after inoculation, 5 μl samples were removed from each growth control well (containing culture media without antibiotic) and from each well containing: 8 μg/ml penicillin, 2 μg/ml ciprofloxacin, 256 μg/ml sulfamethoxazole, 32 μg/ml cefotaxime, 16 μg/ml chloramphenicol, or 16 μg/ml vancomycin. These 5 μl samples were diluted in sterile water and inoculated onto Trypticase Soy agar plates (Remel, Lenaxa, Kans.) or blood agar plates (Remel, Lenexa, Kans.) for *S. pneumoniae*. After 48 hours of incubation at 35° C., the plates were counted and the number of colony forming units of bacteria remaining in the well was calculated.

The results are shown below in FIGS. 26 through 32. In all of the figures, the growth in the presence of antibiotic alone (without $rBPI_{21}$) is indicated for: *S. aureus* (a filled square), *S. pneumoniae* (a filled diamond) or *E. faecium* (a filled triangle). Also, in all figures, the growth in the presence of antibiotic with $rBPI_{21}$ is indicated for: *S. aureus* (an open square), *S. pneumoniae* (an open diamond) or *E. faecium* (an open triangle).

Figure 26:
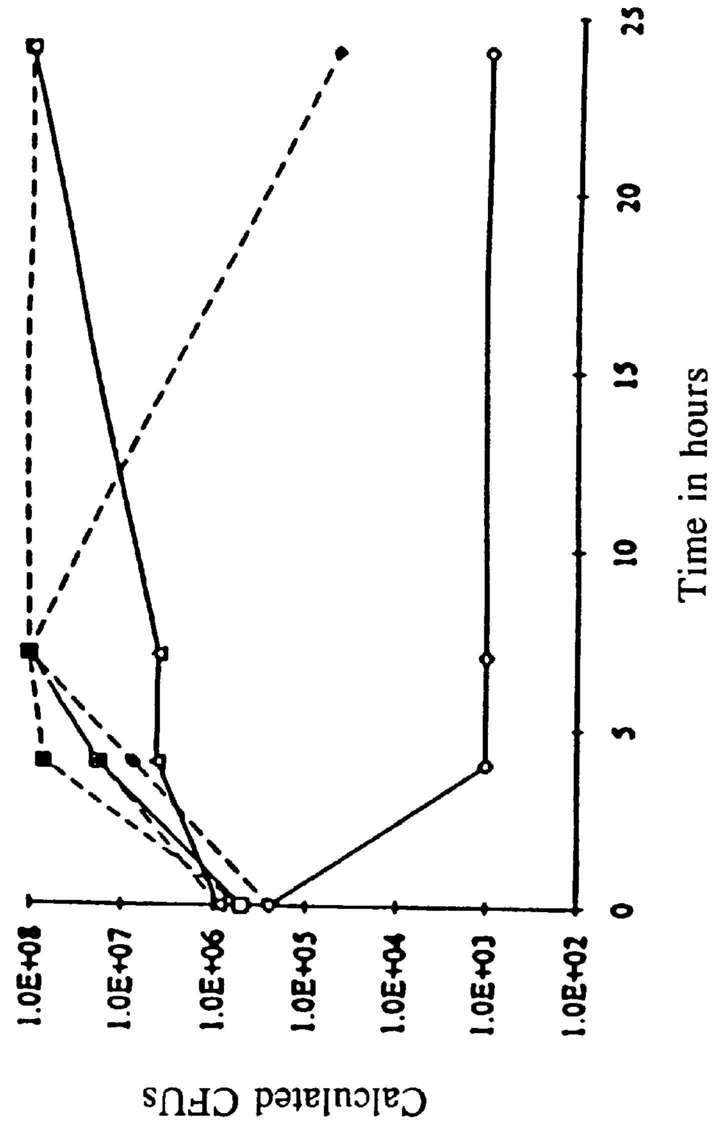
FIGS. 26 through 32 displays $rBPI_{21}$ potentiation of the early bactericidal effect of various antibiotics on *S. pneumoniae, S. aureus* and *E. faecalis.*

FIG. 26 shows the growth curve of organisms with $rBPI_{21}$ (and without antibiotic) and without $rBPI_{21}$ (and without antibiotic). In FIG. 26, the growth curves for *S. aureus* with $rBPI_{21}$ (open squares) and *E. faecium* without $rBPI_{21}$ (filled triangles) overlap at 7 and 24 hours. The results show that BPI protein product has a dramatic bactericidal effect on *S. pneumoniae* that continues through 24 hours, and a moderate early inhibitory effect on growth of *E. faecium* that is not sustained after 10 hours.

Figure 27:
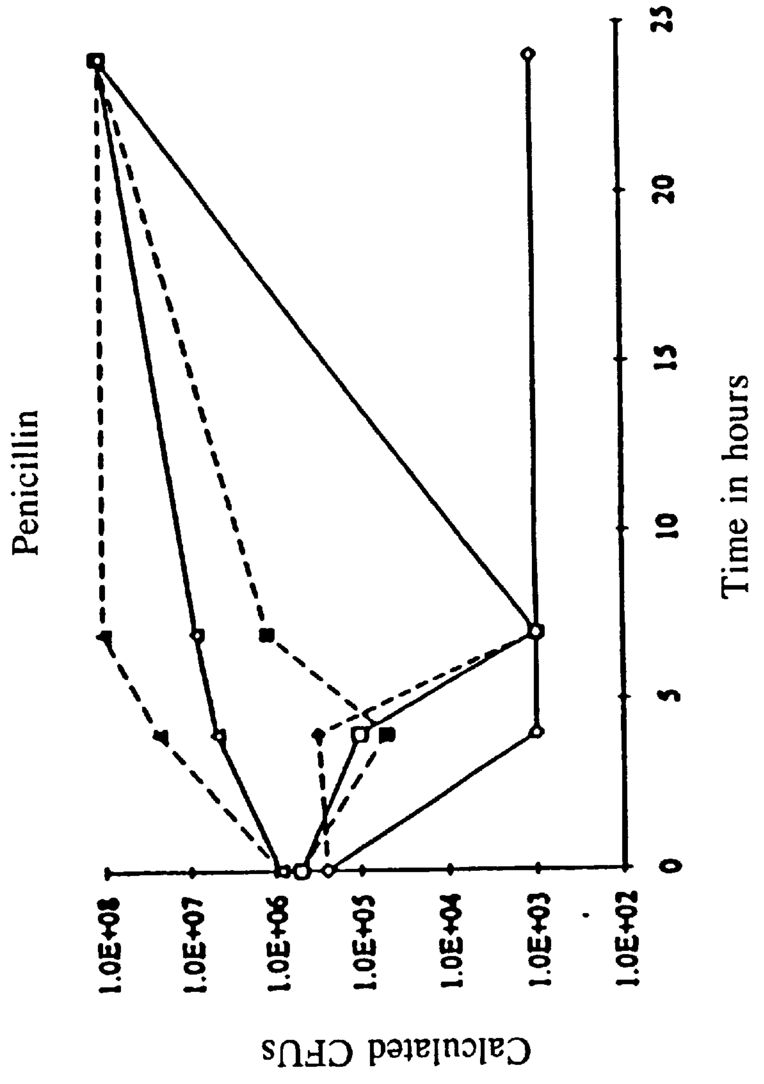

In FIG. 27, the growth curves for *S. pneumoniae* with $rBPI_{21}$ (open diamonds) and *S. pneumoniae* without $rBPI_{21}$ (filled diamonds) overlap at 7 and 24 hours. FIG. 27 shows that the BPI protein product enhanced the early bactericidal effect of penicillin on all three organisms at 0–10 hours.

Figure 28:
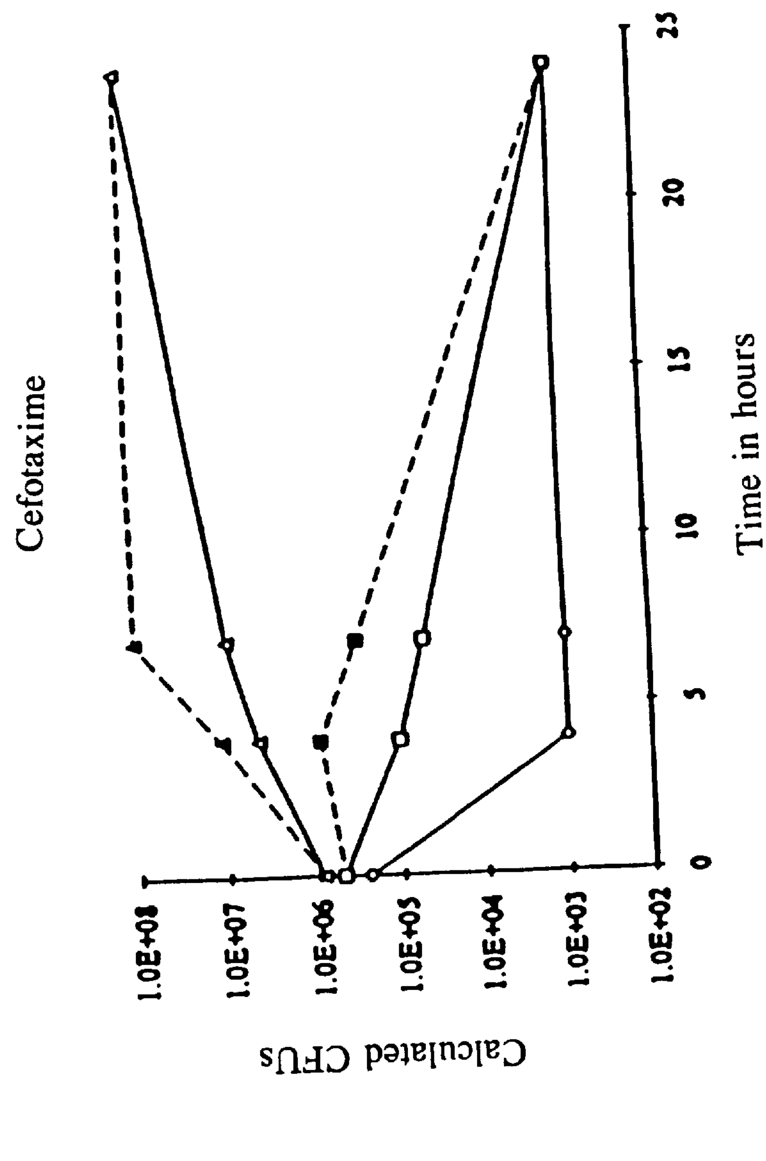

In FIG. 28, the growth curves for *S. pneumoniae* with $rBPI_{21}$ (open diamonds) and *S. pneumoniae* without $rBPI_{21}$ (filled diamonds) overlap completely. FIG. 28 shows that BPI protein product enhanced the early bactericidal activity of cefotaxime for *S. aureus* and *E. faecium* at 0–10 hours.

Figure 29:
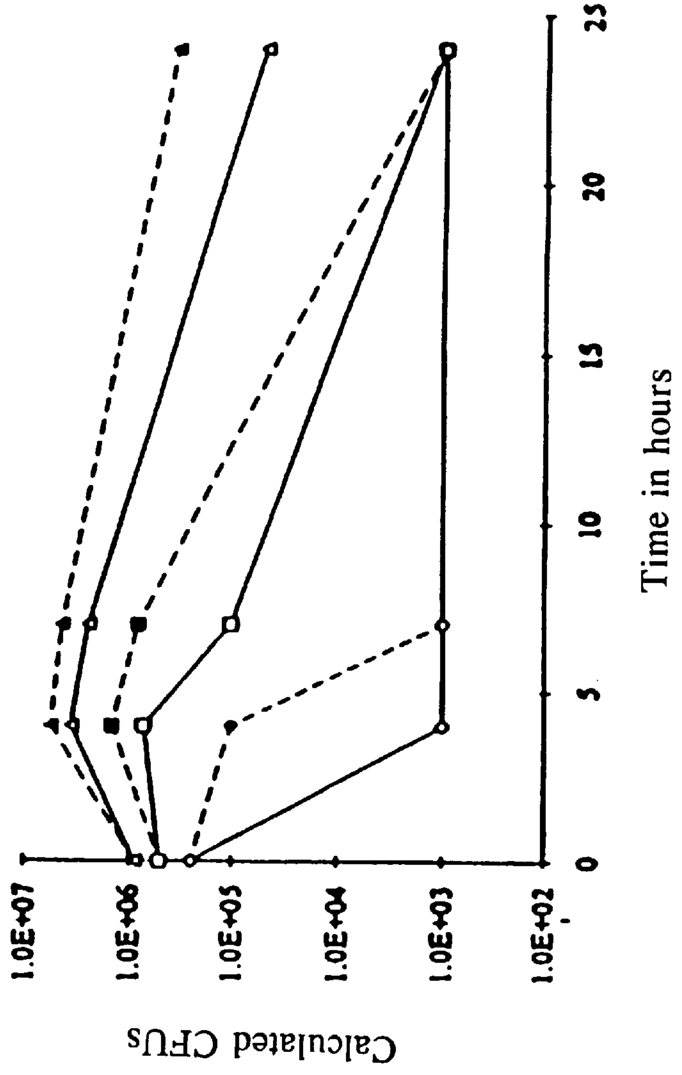

FIG. 29 shows that BPI protein product enhanced the early bactericidal activity of chloramphenicol for all three organisms at 0–10 hours.

Figure 30:
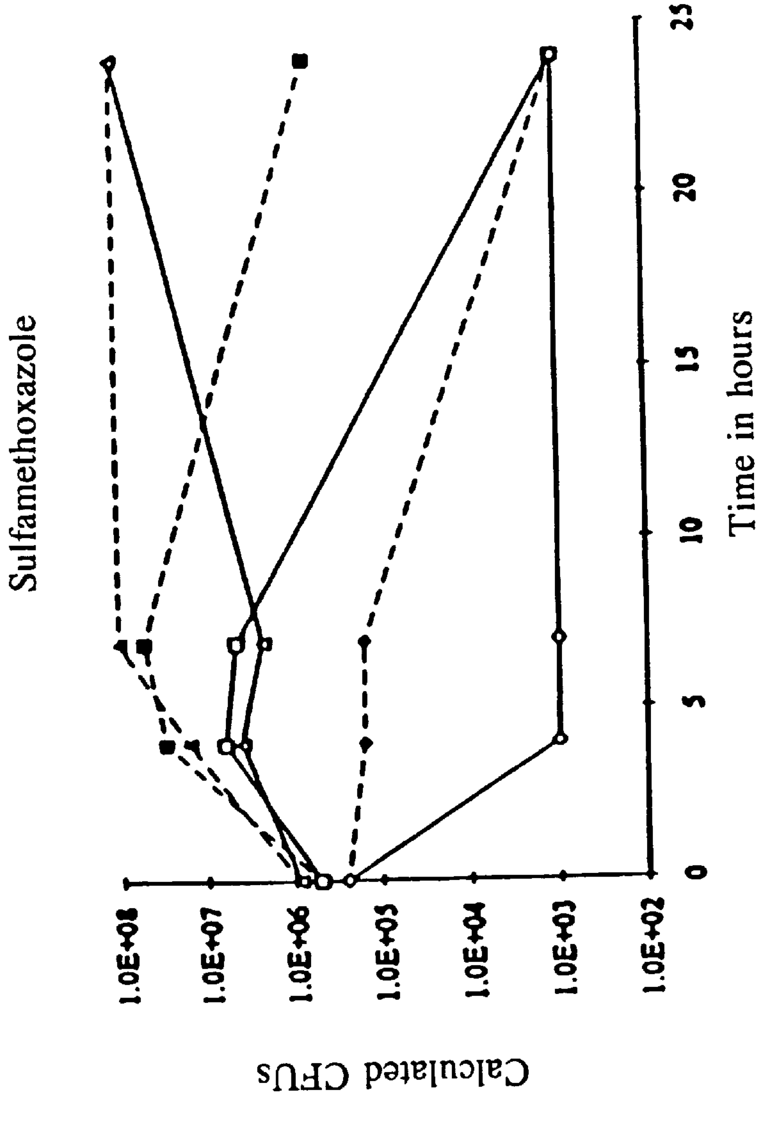

FIG. 30 shows the BPI protein product enhanced the early bactericidal activity of sulfamethoxazole for all three organisms at 0–10 hours.

Figure 31:
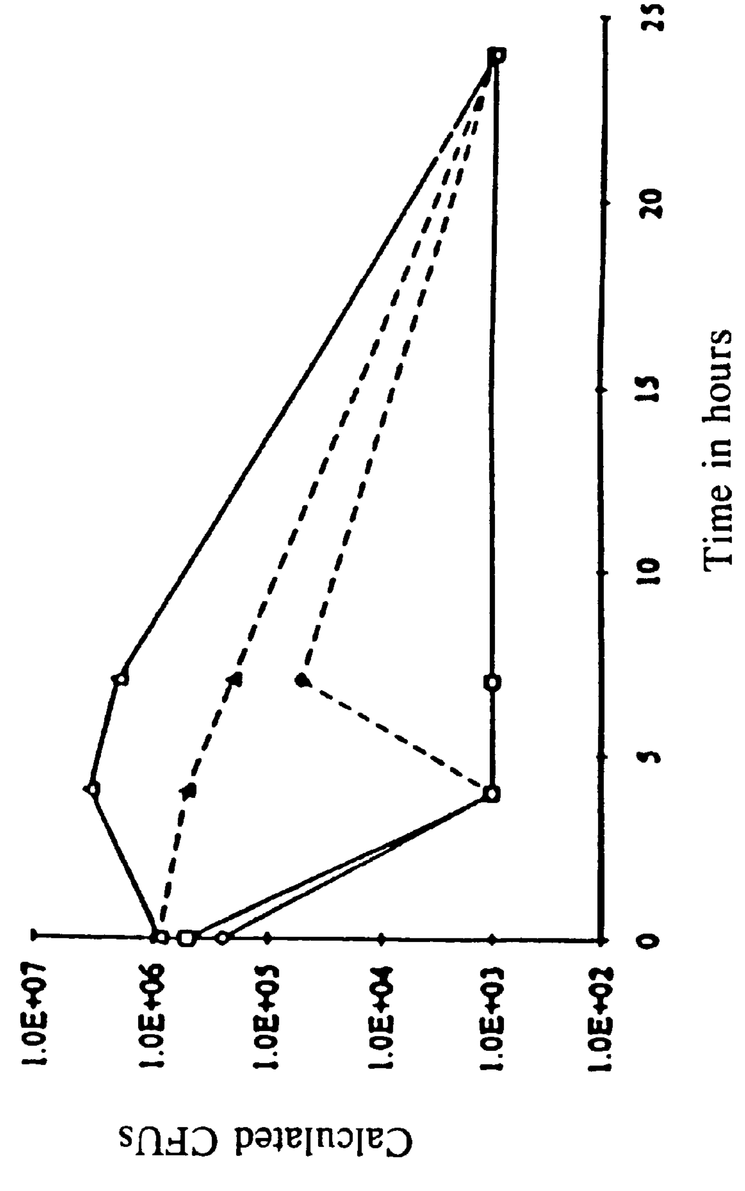

In FIG. 31, the growth curves for *S. aureus* with $rBPI_{21}$ (open squares), *S. aureus* without $rBPI_{21}$ (filled squares) and *S. pneumoniae* without $rBPI_{21}$ (filled diamonds) overlap almost completely. FIG. 31 shows that BPI protein product enhanced the early bactericidal activity of ciprofloxacin for *S. pneumoniae* and *E. faecium* at 0–10 hours.

Figure 32:
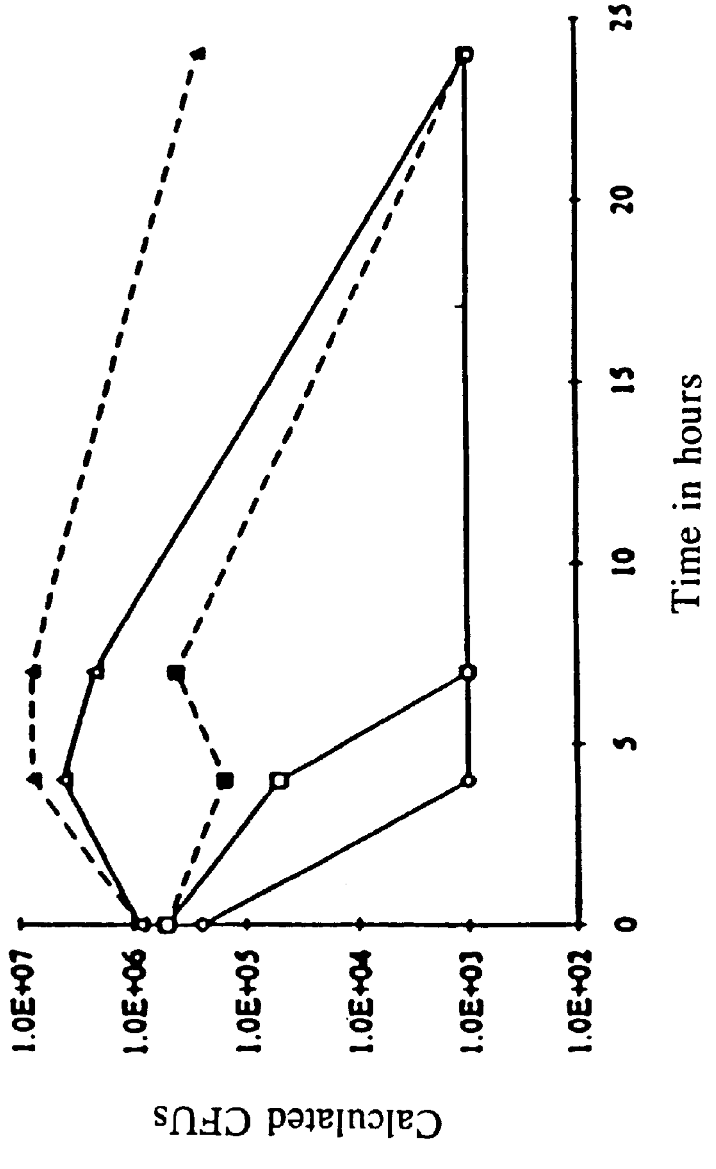

In FIG. 32, the growth curves for *S. pneumoniae* with $rBPI_{21}$ (open diamonds) and *S. pneumoniae* without $rBPI_{21}$ (filled diamonds) overlap completely. FIG. 32 shows that BPI protein product enhanced the early bactericidal effect of vancomycin for *S. aureus* and *E. faecium* at 0–10 hours.

The early time course of the bactericidal activity of BPI protein product was studied for three clinical isolates (methicillin-resistant *S. aureus, S. pneumoniae,* and *E. faecium*). Approximately 4 to 10 colonies of each bacterial species, from 18 to 24 hour growth on either trypticase soy agar plates (for *S. aureus* and *E. faecium*) or 5% sheep blood agar plates (for *S. pneumoniae*) (Remel, Lenexa, Kans.), were emulsified in sterile water to a density equivalent to an 0.5 McFarland standard; 100 $\mu$L of this bacterial inoculum was transferred to glass tubes containing 25 mL Microscan® Pluronic Inoculum Water, such that the final concentration of organisms was ~4 to $7\times10^5$ cells/mL, and $rBPI_{21}$ was added to a final concentration of 16 $\mu$g/mL. The tubes were mixed by inversion, and a control and BPI sample were immediately removed and diluted 1:100 in sterile water for colony counts. Similar samples were taken at 7.5, 15, 30, 60, 90 and 120 minutes. The plates were incubated at 35° C., to 37° C., for 15 to 24 hours and the CFUs/mL were measured by direct counts.

Some bactericidal activity was observed for all isolates after 15 minutes of incubation at room temperature. However, the strain considered susceptible to the direct bactericidal effects of BPI protein product (*S. pneumoniae*) was immediately reduced to 0 CFU at 7.5 minutes, while the killing curves for "resistant" strains (*S. aureus* and *E. faecium*) were prolonged. There was at least a three-log reduction in the number of organisms after the BPI treatment; however, 0 CFU was never reached. CFU data is summarized in Table 14 below.

TABLE 14

| | Calculated CFUs/mL | | | | | | |
|---|---|---|---|---|---|---|---|
| | 0 mins | 7.5 mins | 15 mins | 30 mins | 60 mins | 90 mins | 120 mins |
| *S. pneumoniae* control | 179000 | 173000 | 153000 | 187000 | 169000 | 168000 | 143000 |
| *S. pneumoniae* with $rBPI_{21}$ | 6000 | 2 | 0 | 0 | 0 | 686 | 0 |
| *S. aureus* control | 488000 | 615000 | 440000 | 640000 | 480000 | 720000 | 410000 |
| *S. aureus* with $rBPI_{21}$ | 650000 | 5000 | 300 | 260 | 510 | 530 | 510 |
| *E. faecium* control | 276000 | 193000 | 265000 | 277000 | 265000 | 301000 | 212000 |
| *E. faecium* with $rBPI_{21}$ | 131000 | 129000 | 41000 | 3340 | 990 | 700 | 570 |

To determine if the reason *S. aureus* organisms had survived the initial BPI treatment was due to resistance to BPI protein product, colonies recovered after 90 minutes of incubation with 16 $\mu$g/mL $rBPI_{21}$ were grown for 24 hours, prepared as previously described and incubated with an additional 16 $\mu$g/mL $rBPI_{21}$. Control *S. aureus* that had not been previously exposed to BPI protein product were also incubated with 16 $\mu$g/mL $rBPI_{21}$. After 30 minutes of incubation, the survivors and controls were plated and counted. As seen in Table 15 below, the survivors from an initial treatment with $rBPI_{21}$ were not resistant to BPI protein product.

TABLE 15

| | Control | 16 $\mu$g/mL $rBPI_{21}$ |
|---|---|---|
| *S. aureus* | $5\times10^3$ CFU/mL | $3\times10^2$ CFU/mL |
| *S. aureus* recovered after 90 min. incubation with 16 $\mu$g/mL $rBPI_{21}$ | $4\times10^3$ CFU/mL | $2\times10^2$ CFU/mL |

In another experiment, *S. aureus* organisms were incubated for 30 minutes in 16 $\mu$g/mL $rBPI_{21}$, and an aliquot was removed, plated and counted. Half of the BPI-treated cell suspension was incubated with an additional 16 $\mu$g/mL $rBPI_{21}$. Incubation continued for both cell suspensions for an additional 30 minutes. The additional $rBPI_{21}$ treatment decreased the relative number of survivors over the untreated control (84% reduction/30 min. vs 34% control reduction/30 min.).

It should be noted that incubation in Mueller-Hinton broth inhibited the complete killing of *S. pneumoniae* between 0 and 7.5 minutes. In additional experiments conducted to explore this phenomenon, it was determined that the addition of calcium chloride to the incubation medium appeared to reduce the effectiveness of $rBPI_{21}$ as measured by increased CFUs. A preliminary experiment indicating the NaCl may also reduce the effectiveness of $rBPI_{21}$ (i.e., increased CFUs) suggests that osmolality may be a factor.

EXAMPLE 20

In Vitro Effect of BPI Protein Products Alone or in Combination with Antibiotics on Gram-Positive Organisms BPI protein products are evaluated, using a multiwell antibiotic susceptibility screening assay, for their effects alone or in combination with penicillin, ampicillin or ciprofloxacin on a culture of *Streptococcus pneumoniae* (especially penicillin-resistant organisms). BPI protein products are also evaluated alone or in combination with the antibiotics vancomycin, rifampin, ciprofloxacin, cefazolin, vancomycin/gentamicin and ciprofloxacin/pep eracillin for their effects on the organism *Staphylococcus aureus* (especially methicillin resistant organisms). BPI protein products are evaluated alone or in combination with penicillin, ampicillin, vancomycin, ciprofloxacin, penicillin/gentamicin, or azithromycin for their effects on Enterococcus (multiply resistant strains). The effect of BPI protein products alone or in combination with vancomycin or clindamycin on Corynebacteria are evaluated.

EXAMPLE 21

In Vitro Enhancement of the Bactericidal Activity of BPI Protein Products by Selected Poloxamers The anti-bacterial activity of therapeutic compositions comprising a BPI protein product and a variety of different poloxamer surfactants was evaluated as described in co-owned, co-pending U.S. patent application Ser. No. 08/372,104, the disclosure of which is herein incorporated by reference. Briefly, therapeutic compositions comprising a BPI protein product and a poloxamer surfactant at concentrations ranging from 0.005 to 0.1% (weight/volume) were prepared and incubated at 37° C. with gram-positive organisms in water, broth, or varying concentrations of serum. After incubation, the colony forming units (CFU) of bacteria remaining were determined to ascertain enhancement of anti-bacterial activity. Studies were also performed using poloxamer surfactants that had been heat-treated using the following procedure: (1) making a solution of the poloxamer in deionized water, (2) heating the solution to a boil, (3) removing it from heat, (4) allowing it to cool to room temperature, and (5) stirring until the poloxamer is completely solubilized. Alternatively, in the heating step (2), the solution may be boiled for up to 30 minutes or more.

It was observed that poloxamer 333 (heat-treated or not) and poloxamer 403 (heat-treated or not) and poloxamer 335 and heat-treated poloxamer 334 provided enhancement of the anti-bacterial activity of BPI protein products against bacteria.

EXAMPLE 22

In Vivo Effects of BPI Protein Products Alone or with Antibiotics

Preliminary experiments, in which BPI protein products alone or with penicillin were administered to mice challenged intravenously with $5\times10^8$ CFU of the *S. aureus* bacterial form of Example 3 above, did not show an effect on mortality. This outcome was not unexpected in view of the lack of effect of BPI protein products on that bacterial form in the in vitro assays of Examples 2, 3 and 16. No effect on mortality was observed in preliminary experiments in which mice were challenged with $1\times10^5$ CFU of a *S. pneumoniae* bacterial form which appeared in a preliminary experiment to be susceptible to $rBPI_{21}$ alone in the Microscan® system. Additional in vivo experiments will be performed in a variety of other animals models, including using a variety of different BPI protein products alone and in conjunction with a variety of different antibiotics.

A. Evaluation in the Mouse Pneumonia Model

The effect on gram-positive infections of BPI protein products administered alone or in combination with antibiotics is evaluated in a mouse pneumonia model. Pneumonia is induced in mice by intranasal instillation of 3 drops of an undiluted overnight culture of *S. pneumoniae* in trypticase soy broth containing 5% goat serum. The challenge dose is administered under light Metofane anesthesia with a 1-ml tuberculin syringe and a 22-gauge needle. Infected mice are treated 24 hours after infection with a single intravenous dose of BPI protein product alone, antibiotic alone, or the combination of both agents. The mice are sacrificed 48 hours after infection. The lungs are removed aseptically and cultured for the presence of organism by touching a cut surface of the lung to a blood agar plate. Under these conditions, at 48 hours after infection, untreated controls exhibit consolidation of the lungs and heavily positive cultures. Further, in this model, most of the untreated controls die within 96 hours after infection.

B. Evaluation in the Rabbit Endocarditis Model

The effect on gram-positive infections of BPI protein products administered alone or in combination with antibiotics is evaluated in a rabbit endocarditis model. Young New Zealand white rabbits weighing 1 to 2 kg are anesthetized by the intravenous injection of 40 to 60 mg of pentobarbitone. An incision is made parallel to the trachea, approximately 4 cm long and 1 cm to the right of the midline. To produce right-sided endocarditis, the jugular vein is exposed and opened between ligatures. The lower ligature is loosened, and a polyethylene catheter of 0.8 mm external diameter and 0.4 mm internal diameter containing sterile saline is passed toward the heart until resistance and pulsation indicates that it has entered the right atrium or ventricle. The catheter is then secured in place by tightening both ligatures, any excess is cut off, and the distal end is sealed with a heated spatula before the skin is closed over the catheter with silk sutures. For left-sided endocarditis, the right carotid artery can be exposed through a similar incision, opened between ligatures, and a catheter passed toward the heart until pulsation resistance and reflux of arterial blood indicates that it has reached the aortic valve or passed beyond into the left ventricle. It is then secured as described above.

The presence of a catheter in the heart results in the development of sterile vegetations consisting of small, rough whitish nodules 1 to 2 mm in size, usually at points of contact between the catheter and the endocardium. The sterile vegetations are infected by a single injection of bacteria into an ear vein. If *Streptococcus viridans* is used for infection, the infecting inoculum can be prepared by diluting an overnight glucose broth culture and injecting approximately $10^8$ organisms in a volume of 1 ml. Other gram-positive organisms can be used and may include *Micrococcus albus, S. aureus, S. epidermidis,* and other strains. An infecting inoculum can be prepared for these organisms by preparing a 1:10 dilution of an overnight glucose broth culture and injecting 1 mL intravenously. BPI protein product alone, antibiotic alone, or the combination treatment is given intravenously in daily doses. After days, the rabbits are sacrificed and any vegetations found are removed aseptically. The vegetations are weighed and homogenized in glucose broth. Bacterial counts are determined by preparing serial dilutions in glucose broth and incorporating the dilutions into blood agar pour plates. The CFU of organism per g of wet weight is then calculated.

C. Evaluation in the Mouse Intraperitoneal Abscess Model

The effect on gram-positive infections of BPI protein products administered alone or in combination with antibiotics is evaluated in a mouse intraperitoneal abscess mode. *S. aureus* is grown for 24 hours in trypticase soy broth with constant shaking. Cultures are continuously gassed with 100% oxygen to minimize α-hemolysin production. The organisms are harvested by centrifugation, washed in saline containing 1% trypticase soy broth (v/v), and resuspended in the same diluent to approximately $1\times10^{10}$ to $5\times10^{10}$ bacteria per ml. Bacterial counts can be confirmed by plate counts.

Groups of female white Swiss mice weighing 20 to 30 g are inoculated intraperitoneally with 0.5 ml of a suspension containing 1 to $2\times10^9$ bacteria. Beginning at 3 hours and at various intervals thereafter, subgroups of infected animals selected at random are sacrificed, and the clumped organisms or abscesses are aseptically removed from the peritoneal cavities. All clumps or abscesses from a single animal are ground and homogenized in 5 ml of saline containing 1% trypticase soy broth. The suspension is serially diluted and the bacterial population determined by plate counts.

D. Evaluation in the Mouse Thigh Abscess Model

The effect on gram-positive infections of BPI protein products administered alone or in combination with antibiotics is evaluated in a mouse thigh abscess model.

The thigh lesion model provides a nonlethal experimental infection to evaluate the effectiveness of an antimicrobial and allows the measurement of drug-pathogen interaction and drug pharmacokinetics in the infected host. If the animals are made neutropenic, then the high model becomes an excellent system for measuring the drug-microorganism interaction with most of the host defense system eliminated.

Swiss outbred mice, preferably ICR mice, weighing 23 to 27 g are used. The mice are made neutropenic by administering cyclophosphamide (150 and 100 mg/kg i.p.) on days 0 and 3, respectively. By day 4 severe neutropenia is induced (<100 neutrophils/$mm^3$) which lasts for two to three days. The infecting organism is grown in broth to log phase and adjusted to an OD of 0.30 at 580 nm (~$10^6$ to $10^7$ CFU/ml). The mice are infected on day 4 by injecting 0.1 ml of this inoculum into each thigh while the animals are under light ether anesthesia. The infection is allowed to proceed for 2 hours. The antimicrobial is then administered in graded doses subcutaneously to groups of infected mice. Infected, untreated animals serve as controls. Two to four mice from each treatment group are sacrificed every hour for the first 4 hours and every 2 to 4 hours until 16 hours after treatment. Infected, untreated animals are killed at similar times.

The thigh muscles are removed at each sampling period and homogenized immediately in 9 ml of 0.85% NaCl with a Polytron tissue homogenizer. Viable counts are determined after plating duplicate 10μ samples of serial 10-fold dilutions of the homogenates on appropriate media. The log CFU/thigh is determined at each time point for groups of treated and untreated animals.

E. Evaluation in a Rabbit Intraocular Infection Model

The effect on gram-positive infections of BPI protein products administered alone or in combination with antibiotics is evaluated in the following model. The rabbits' eyes, anesthetized locally with 0.5% tetracaine hydrochloride, are sterilized with Metaphen (1:4000) and flushed with normal saline. Using a 26-gauge needle, approximately 0.2 ml containing 300,000 or 5,000 CFU or 0.02 ml containing 700 CFU of *S. aureus* is inoculated into the center of the rabbit cornea, the anterior chamber, or the vitreous of the eye. Cultures are taken at 24, 48, and 72 hours from the corneas and anterior chambers of the rabbits' eyes that received corneal inoculations. All corneas are flushed with Metaphen (1:4000) and saline before culturing to eliminate surface contaminants.

Cultures are taken at the same intervals from the anterior chamber and vitreous of rabbit eyes that were inoculated in the anterior chamber. Vitreous humor is removed with a 19-gauge needle. The irises are also cultured.

The eyes that are inoculated intravitreally are also cultured at 24, 48, and 72 hours. Samples of the vitreous humor and anterior chamber as well as the retina are used to determine the progress of the infection.

When 300,000 CFU in 0.2 ml of broth is inoculated into the corneas, anterior chamber, and vitreous of the rabbit's eyes, a virulent panophthalmitis is generally produced within 24 to 48 hours, and destruction of the eye occurs within 72 hours regardless of the site of inoculation. When 5000 CFU in 0.2 ml is inoculated into the corneas, anterior chambers, and vitreous, a panophthalmitis generally results in 72 hours, with infections being most severe following intravitreal inoculations and less intense when the anterior chamber is the site of inoculation. When 700 CFU in 0.02 ml is used as the inoculum, the infections are generally eliminated in the corneas and anterior chambers within 24 hours but not in the vitreous.

Other models of ocular infection and disease known in the art [see, e.g., Sugar et al., *Arch. Opthalmol.,* 104:1230–1232 (1986) and Moon et al., *Investigative Ophthalmol. Visual Science,* 29:1277–1284 (1988)] may be used for the assessment of BPI protein product effects on ocular conditions associated with bacterial infection, when the BPI protein product is administered alone or in conjunction with antibiotics.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. In a method of treating a subject suffering from a gram-positive bacterial infection by administering one or more antibiotics, said antibiotics selected from the group consisting of penicillins, cephalosporins, imipenem, monobactams, aminoglycosides, tetracyclines, sulfonamides, trimethoprim/sulfonamide, fluoroquinolones, macrolides, vancomycin, polymyxins, chloramphenicol and lincosamides, the improvement comprising concurrently administering a BPI protein product in an amount effective to increase antibiotic susceptibility of a gram-positive bacterial species involved in the infection.

2. The method of claim 1 wherein one of said antibiotics is a penicillin antibiotic.

3. The method of claim 1 wherein one of said antibiotics is a cephalosporin antibiotic.

4. The method of claim 1 wherein one of said antibiotics is imipenem.

5. The method of claim 1 wherein one of said antibiotics is a monobactam antibiotic.

6. The method of claim 1 wherein one of said antibiotics is an aminoglycoside antibiotic.

7. The method of claim 1 wherein one of said antibiotics is a tetracycline antibiotic.

8. The method of claim 1 wherein one of said antibiotics is a sulfonamide or trimethoprim/sulfonamide antibiotic.

9. The method of claim 1 wherein one of said antibiotics is a fluoroquinolone antibiotic.

10. The method of claim 1 wherein one of said antibiotics is a macrolide antibiotic.

11. The method of claim 1 wherein one of said antibiotics is vancomycin.

12. The method of claim 1 wherein one of said antibiotics is a polymyxin antibiotic.

13. The method of claim 1 wherein one of said antibiotics is a chloramphenicol.

14. The method of claim 1 wherein one of said antibiotics is a lincosamide antibiotic.

* * * * *